(12) United States Patent
Angiolini et al.

(10) Patent No.: US 9,682,083 B2
(45) Date of Patent: Jun. 20, 2017

(54) PYRROLO[2,3-D]PYRIMIDINE DERIVATIVES, PROCESS FOR THEIR PREPARATION AND THEIR USE AS KINASE INHIBITORS

(71) Applicant: NERVIANO MEDICAL SCIENCES S.R.L., Nerviano (IT)

(72) Inventors: Mauro Angiolini, Gavirate (IT); Laura Buffa, Rossiglione (IT); Maria Menichincheri, Milan (IT); Ilaria Motto, Nerviano (IT); Paolo Polucci, Cassina Rizzardi (IT); Gabriella Traquandi, Milan (IT); Fabio Zuccotto, Milan (IT)

(73) Assignee: NERVIANO MEDICAL SCIENCES S.R.L., Nerviano (IT)

( * ) Notice: Subject to any disclaimer, the term of this patent is extended or adjusted under 35 U.S.C. 154(b) by 0 days.

(21) Appl. No.: 14/889,987

(22) PCT Filed: May 7, 2014

(86) PCT No.: PCT/EP2014/059342
§ 371 (c)(1),
(2) Date: Nov. 9, 2015

(87) PCT Pub. No.: WO2014/184069
PCT Pub. Date: Nov. 20, 2014

(65) Prior Publication Data
US 2016/0166575 A1 Jun. 16, 2016

(30) Foreign Application Priority Data
May 14, 2013 (EP) .................................... 13167606

(51) Int. Cl.
*A61K 31/519* (2006.01)
*A61K 45/06* (2006.01)
*A61K 31/496* (2006.01)
*C07D 487/04* (2006.01)

(52) U.S. Cl.
CPC .......... *A61K 31/519* (2013.01); *A61K 31/496* (2013.01); *A61K 45/06* (2013.01); *C07D 487/04* (2013.01)

(58) Field of Classification Search
None
See application file for complete search history.

(56) References Cited

U.S. PATENT DOCUMENTS 5,665,721 A * 9/1997 Bhagwat .............. C07D 487/04
514/252.02
2015/0291595 A1* 10/2015 Erra Sola ............. C07D 487/04
514/243

FOREIGN PATENT DOCUMENTS

WO           9640686 A1    12/1996
WO      2005044835 A1     5/2005

OTHER PUBLICATIONS

Database CAPLUS in STN, Acc. No. 2014:665540, Montserrat et al., WO 2014060432 A1 (Apr. 24, 2014) (patent family member of US 20150291595 A1) (abstract).*
Database CAPLUS in STN, Acc. No. 1997:613832, Bhagwat et al., U.S. Pat. No. 5,665,721 A (Sep. 9, 1997) (abstract).*
Arighi E., et al., "RET thyrosine kinase signaling in development and cancer," Cytokine & Growth Factor Reviews 16 (2005) 441-467.
Boulay A., et al., "The Ret receptor tyrosine kinase pathway functionally interacts with ERalpha pathway in breast cancer," Cancer Res 2008:68(10):3743-51.
Diner P. et al. "Preparation of 3-substituted1-isopropyl-1H-pyrazolo[3,4-d]pyrimidin-4-amines as RES kinase inhibitors," J Med Chem 2012,55, 4872-4876.
Futami H, et al., "A novel somatic point mutation of the RET proto-oncogene in tumor tissues and small cell lung cancer patients," JPN J Cancer Res. 86, 1127-1130, Dec. 1995.
Gil Z et al., "Paracrine regulation of pancreatic cancer cell invasion by peripheral nerves," J Natl Cancer Inst 2010;102:107-118.
Greco A., et al., "Molecular pathology of differentiated thyroid cancer," Q J Nucl Med Mol Imaging 2009;53:440-54.
Grieco M., et al., "PTC is a novel rearranged form of the ret proto-oncogene and is frequently detected in vivo in human thyroid papillary carcinomas," Cell, vol. 60, 557-563, Feb. 23, 1990.
Ito Y et al., "Expresssion of glial cell line-derived neurotrophic factor family members and their receptors in pancreatic cancers," Surgery 2005;138:788-94.
Iwahashi N., et al., "Expression of glial cell line-derived neurotrophic factor correlates with perinueural invasion of bile duct carcinoma," Cancer 2002;94:167-74.
Kohno T., et al., "KIF5B-RET fusions in lung adenocarcinoma", Nature Medicine, vol. 18, No. 12 Feb. 2012, 375-377.
Lipson D., et al., "Identification of new AKL and RET gene fusions from colorectal and lung cancer biopsies," Nature Medicine vol. 18, No. 3, Feb. 12, 2012, 382-384.
Matsubara D., et al., "Identification of CCDC6-RET fusion in human lung adenocarcinoma cell line, LC-2/ad," J Thorac Oncol. 2012;7:1872-1876.
Plaza-Menacho i., et al., "Targeting the receptor tyrosine kinase RET sensitizes breast cancer cells to tamoxifen treatment and reveals a role for RET in endocrine resistance," Oncogene (2010) 29, 4648-4657.
Rucci, et al., "Inhibition of protein kinase c-Src as a therapeutic approach for cancer and bone metastases", Anti-Cancer Agents in Medicinal Chemistry, Bentham Science Publishers, LTD, NL, vol. 8, No. 3, Apr. 1, 2008.

(Continued)

*Primary Examiner* — Brian J Davis
(74) *Attorney, Agent, or Firm* — Silvia Salvadori, P.C.; Silvia Salvadori

(57) ABSTRACT

The present invention relates to 6-amino-7-deaza-purine derivatives which modulate the activity of protein kinases and are therefore useful in treating diseases caused by dysregulated protein kinase activity, in particular RET family kinases. The present invention also provides methods for preparing these compounds, pharmaceutical compositions comprising these compounds, and methods of treating diseases utilizing pharmaceutical compositions containing these compounds.

7 Claims, No Drawings

(56) References Cited

OTHER PUBLICATIONS

Schuchardt A, et al., "Defects in the kidney and enteric nervous system of mice lacking the tyrosine kinase receptor Ret," Nature vol. 367, Jan. 27, 1994 380-383.

Seela, et al., "Pyrrolo[2,3-d]pyrimidine nucleosides: synthesis and antitumor activity of 7-substituted 7-deaza-2'-deoxyadenosines", Nucleosides, Nucleotides & Nucleic Acids, vol. 19, No. 1-2, 2000, pp. 237-251.

Seok Ju Y., et al., "A transforming KIF5B and RET gene fusion in lung adenocarcinoma revealed from whole-genome and transcriptome sequencing," Genome Res 22:436-445 2012.

Takeuchi K, et al., "RET, ROS1 and ALK fusions in lung cancer," Nature Medicine,vol. 18, No. 3, Feb. 12, 2012 378-381.

Traxler, et al, "Protein tyrosine kinase inhibitors in cancer treatment", Expert Opinion on Therapeutic Patents Informa Healthcare, GB, vol. 7, No. 6, Jan. 1, 1997.

Wells S., et al., "Targeting the RET pathway in thyroid cancer," Clin Cancer Res 2009;15:7119-7123.

Willem J, et al., "RET as a diagnostic and therapeutic target in sporadic and hereditary endocrine tumors," Endocrine Reviews 27:535-560, 2006.

Wood, D.L, et al., The genomic landscapes of human breast and colorectal cancer, Science vol. 318 Nov. 16, 2007 1108-1113.

Santoro M., et al. "A development of thyroid papillary carcinomas secondary to tissue specific expression of RET PTC1 oncogene in transgenic mice," Oncogene 1996 12:1821-1826.

International Search Report of PCT/EP2014/059342 of Sep. 8, 2014.

* cited by examiner ary PYRROLO[2,3-D]PYRIMIDINE
DERIVATIVES, PROCESS FOR THEIR
PREPARATION AND THEIR USE AS KINASE
INHIBITORS This application is a U.S. national stage of PCT/EP2012/059342 filed on 7 May 2014, which claims priority to and the benefit of European Patent Application No. 13167606.6 filed on 14 May 2013, the contents of which are incorporated herein by reference in their entirety.

The present invention relates to certain substituted 6-amino-7-deazapurine compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

RET is a single-pass transmembrane receptor belonging to the tyrosine kinase superfamily (reviewed in Arighi et al., Cytokine Growth Factor Rev, 2005, 16, 441-67). The extracellular portion of the RET protein contains four calcium-dependent cadherin-like repeats involved in ligand binding and a juxtamembrane cysteine-rich region necessary for the correct folding of RET extracellular domain, while the cytoplasmic portion of the receptor includes two tyrosine kinase subdomains. RET is the signaling component of a multiprotein complex: binding of RET to the glial-derived neurotrophic factor (GDNF) family ligands (GDNF, artemin, neurturin and persephin) through ligand-specific GDNF-family receptor alpha co-receptors (GFRα1-4) induces the formation of active RET dimers and the autophosphorylation of specific tyrosine residues in the cytoplasmic domain. These phosphorylated tyrosines function as docking sites for effector/adaptor proteins such as PLC-γ, PI3K, Shc, Grb2, Src, Enigma, STAT3, which in turn activate downstream signaling pathways, including Ras/Raf/ERK, PI3K/Akt/mTOR and PLC-γ/PKC. During embryogenesis RET signaling is critical for development of the enteric nervous system and for kidney organogenesis (Schuchardt et al., Nature, 1994, 367, 380-3). In adults RET is expressed in neural crest-derived cell types, such as neuroendocrine cells (thyroid parafollicular cells and adrenal medullary cells), peripheral ganglia, urogenital tract cells and spermatogonia.

Aberrant RET expression and/or activity have been demonstrated in different human cancers.

The oncogenic role of RET was firstly described in papillary thyroid carcinoma (PTC) (Grieco et al., Cell, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (reviewed in Greco et al., Q. J. Nucl. Med. Mol. Imaging, 2009, 53, 440-54), therefore driving its ectopic expression in thyroid cells. To date, twelve different fusion partners have been identified, all providing a protein/protein interaction domain that induces ligand-independent RET dimerization and constitutive kinase activity. The role of RET-PTC rearrangements in the pathogenesis of PTC has been confirmed in transgenic mice (Santoro et al., Oncogene, 1996, 12, 1821-6). Recently, a 10.6 Mb pericentric inversion in chromosome 10, where RET gene maps, has been identified in about 2% of lung adenocarcinoma patients, generating different variants of the chimeric gene KIF5B-RET (Ju et al., Genome Res., 2012, 22, 436-45; Kohno et al., 2012, Nature Med., 18, 375-7; Takeuchi et al., Nature Med., 2012, 18, 378-81; Lipson et al., 2012, Nature Med., 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what observed with RET-PTC fusion proteins, KIF5B-RET is constitutively phosphorylated and induces NIH-3T3 transformation and IL-3 independent growth of BA-F3 cells. However other RET fusion proteins have been identified in lung adenocarcinoma patients, such as the CCDC6-RET protein, which has been found to play a key role in the proliferation of the human lung adenocarcinoma cell line LC-2/ad (Journal of Thoracic Oncology, 2012, 7(12):1872-1876).

Besides rearrangements of the RET sequence, gain of function point mutations of RET proto-oncogene are also driving oncogenic events, as shown in medullary thyroid carcinoma (MTC), which arises from parafollicular calcitonin-producing cells (reviewed in: de Groot et al., Endocrine Rev., 2006, 27, 535-60; Wells and Santoro, Clin. Cancer Res., 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., Science, 2007, 318, 1108-13) and small cell lung carcinoma (Jpn. J. Cancer Res., 1995, 86, 1127-30).

RET signaling components have been found to be expressed in primary breast tumors and to functionally interact with estrogen receptor-α pathway in breast tumor cell lines (Boulay et al., Cancer Res. 2008, 68, 3743-51; Plaza-Menacho et al., Oncogene, 2010, 29, 4648-57), while RET expression and activation by GDNF family ligands could play an important role in perineural invasion by different types of cancer cells (Ito et al., Surgery, 2005, 138, 788-94; Gil et al., J Natl Cancer Inst., 2010, 102, 107-18; Iwahashi et al., Cancer, 2002, 94, 167-74).

Very recently the identification of RET rearrangements has been reported in a subset of (patient-derived xenograft) PDX established from colorectal cancer. Although the frequency of such event in colorectal cancer patients remains to be defined, these data suggest a role of RET as a target in this indication (Gozgit at al, AACR Annual Meeting 2014).

Given the relevant role of RET in human cancer, RET tyrosine kinase inhibitors could be of high therapeutic value. Novel 7-(2'-substituted-β-D-ribofuranosyl)-4-amino-5-(substituted-ethyn-1-yl)-pyrrolo[2,3-d]pyrimidine compounds, useful in treating viral infections, have been disclosed in WO2005/044835 in the name of GeneLabs Technologies Inc.

New 9-cyclopentyl-7-deaza-purine derivatives have been disclosed in WO96/40686, in the name of Abbott Laboratories. These compounds are useful for inhibiting adenosine kinase.

Several 3-substituted-1-isopropyl-1H-pyrazolo[3,4-d]pyrimidin-4-amines have been disclosed as RET kinase inhibitors in the article of J. Med. Chem. 2012, 55 (10), 4872-4876, in the name of AstraZeneca and University of Gothenburg.

Despite these developments, there is still need for effective agents for the treatment of diseases as cancer.

The present inventors have now discovered that compounds of formula (I), described below, are kinase inhibitors and are thus useful in therapy as antitumor agents.

Accordingly, a first object of the present invention is to provide a substituted 6-amino-7-deaza-purine compound represented by formula (I)

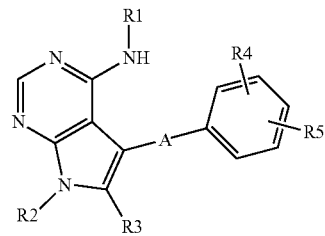

(I)

wherein:

R1 is hydrogen or an optionally substituted group selected from straight or branched $(C_1-C_8)$ alkyl, $(C_3-C_8)$ cycloalkyl and CORE, wherein
R6 is an optionally substituted group selected from straight or branched $(C_1-C_8)$ alkyl and $(C_3-C_8)$ cycloalkyl;

R2 is hydrogen or an optionally substituted group selected from straight or branched $(C_1-C_8)$ alkyl, $(C_2-C_8)$ alkenyl, $(C_2-C_8)$ alkynyl, $(C_3-C_8)$ cycloalkyl, aryl, heteroaryl, a 3- to 4- or a 6- to 7-membered heterocyclyl ring, where one or more carbon atoms are replaced by nitrogen, sulfur or oxygen, and a 5-membered heterocyclyl ring where one or more carbon atoms are replaced by nitrogen or sulfur;

R3 is hydrogen or an optionally substituted group selected from straight or branched $(C_1-C_8)$ alkyl, $(C_2-C_8)$ alkenyl, heterocyclyl, aryl and heteroaryl;

A is C=C or C≡C;

R4 is hydrogen, halogen, hydroxyl or an optionally substituted group selected from straight or branched $(C_1-C_8)$ alkyl, $(C_1-C_8)$ alkoxyl and cyano;

R5 is hydrogen or a group -L-R7, wherein

R7 is hydrogen or an optionally substituted group selected from straight or branched $(C_1-C_8)$ alkyl, $(C_3-C_8)$ cycloalkyl, heterocyclyl, aryl and heteroaryl; and L is —CON(Y)—, —NHCO—, —SO$_2$N(Y)—, —NHSO$_2$—, —NHCON(Y)—, —NHCOCH$_2$—, —CH$_2$CONH—, wherein Y is hydrogen or, taken together with the nitrogen atom to which they are bonded, Y and R7 may form an optionally substituted 3 to 6 membered heterocyclyl, optionally containing one additional heteroatom selected from nitrogen, sulfur or oxygen;

or pharmaceutically acceptable salts thereof, with the provisos that when R1=R2=H, then R5 is different from hydrogen and
when L is —CH$_2$CONH—, then R2 is different from hydrogen.

The present invention also provides methods of preparing the substituted 6-amino-7-deazapurine compounds, represented by formula (I), prepared through a process consisting of standard synthetic transformations.

The present invention also provides a method for treating diseases caused by and/or associated with dysregulated protein kinase activity, particularly RET, RAF family, protein kinase C in different isoforms, Abl, Aurora A, Aurora B, Aurora C, EphA, EphB, FLT3, KIT, LCK, LYN, EGF-R, PDGF-R, FGF-R, PAK-4, P38 alpha, TRKA, TRKB, VEGFR, more particularly RET family kinases, which comprises administering to a mammal in need thereof, more particularly a human, an effective amount of a substituted 6-amino-7-deazapurine compound represented by formula (I) as defined above.

A preferred method of the present invention is to treat a disease caused by and/or associated with dysregulated protein kinase activity selected from the group consisting of cancer, cell proliferative disorders, viral infections, immune-related disorders and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid cancers, such as papillary thyroid carcinoma and medullary thyroid carcinoma, and Kaposi's sarcoma.

Another preferred method of the present invention is to treat specific cellular proliferation disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, comprising the prevention of AIDS development in HIV-infected individuals.

Another preferred method of the present invention is to treat immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis.

Another preferred method of the present invention is to treat neurodegenerative disorders including but not limited to: Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

In addition, the method of the present invention also provides tumor angiogenesis and metastasis inhibition as well as the treatment of organ transplant rejection and host versus graft disease.

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof, as defined above, and at least one pharmaceutically acceptable excipient, carrier and/or diluent.

The present invention further provides a pharmaceutical composition of a compound of the formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Moreover the invention provides an in vitro method for inhibiting the RET family protein activity which comprises contacting the said protein with an effective amount of a compound of formula (I) as defined above.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

Unless otherwise specified, when referring to the compounds of formula (IA) or (IB), per se as well as to any pharmaceutical composition thereof or to any therapeutic treatment comprising them, the present invention includes the compounds of formula (I) wherein A is respectively a triple carbon-carbon bond (IA) or a double carbon-carbon bond (IB).

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

If a stereogenic center or another form of an asymmetric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form. Pharmaceutically acceptable salts of the compounds of formula (I) include the salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines.

With the term "straight or branched ($C_1$-$C_8$) alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched ($C_1$-$C_3$) alkyl", we intend any of the groups such as, for instance, methyl, ethyl, n-propyl, isopropyl.

With the term "($C_3$-$C_8$) cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene. The ($C_3$-$C_8$)

cycloalkyl ring can be optionally further fused or linked to aromatic and non-aromatic carbocyclic and heterocyclic rings.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, tetrahydropyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like. The heterocyclyl ring can be optionally further fused or linked to aromatic and non-aromatic carbocyclic and heterocyclic rings.

With the term "($C_2$-$C_8$) alkenyl" we intend an aliphatic ($C_2$-$C_8$) hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "($C_2$-$C_8$) alkynyl" we intend an aliphatic ($C_2$-$C_8$) hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl, α- or β-tetrahydronaphthalenyl, biphenyl, and indanyl groups. The aryl ring can be optionally further fused or linked to aromatic and non-aromatic carbocyclic and heterocyclic rings.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, thiadiazolyl, isoxazolyl, isothiazolyl, oxadiazolyl, indazolyl, cinnolinyl, benzo[1,3]dioxolyl, benzo[1,4]dioxinyl, benzothiazolyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above R1, R2, R3, R4, R6 and R7 may be optionally substituted, in any of their free positions, by one or more groups, for instance 1 to 6 groups, independently selected from: halogen, nitro, oxo groups (=O), cyano, ($C_1$-$C_8$) alkyl, polyfluorinated alkyl, polyfluorinated alkoxy, ($C_2$-$C_8$) alkenyl, ($C_2$-$C_8$) alkynyl, hydroxyalkyl, aryl, arylalkyl, alkylaryl, heteroaryl, heteroarylalkyl, alkylheteroaryl, heterocyclyl, heterocyclylalkyl, alkylheterocyclyl, alkylheterocyclylalkyl, ($C_3$-$C_8$) cycloalkyl, hydroxy, polyhydroxyalkyl, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, amino, heterocyclylalkyloxycarbonylamino, ureido, alkylamino, aminoalkyl, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term "halogen" we intend a fluorine, chlorine, bromine or iodine atom.

With the term "polyfluorinated alkyl" or "polyfluorinated alkoxy" we intend any of the above straight or branched ($C_1$-$C_8$) alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "hydroxyalkyl" we intend any of the above ($C_1$-$C_8$) alkyl, bearing a hydroxyl group such as, for instance, hydroxymethyl, 2-hydroxyethyl, 3-hydroxypropyl and the like.

From all of the above, it is clear to the skilled person that any group which name is a composite name such as, for instance, "arylamino" has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, ($C_3$-$C_8$) cycloalkyl and heterocyclyl moieties are as above defined.

A preferred class of compounds of formula (I) are the compounds wherein:
R1 is hydrogen, methyl, cyclopropyl or CORE wherein R6 is methyl,
R2 is hydrogen or an optionally substituted group selected from straight or branched ($C_1$-$C_8$) alkyl, ($C_3$-$C_8$) cycloalkyl, aryl, heteroaryl, a 3- to 4- or a 6- to 7-membered heterocyclyl ring, where one or more carbon atoms are replaced by nitrogen, sulfur or oxygen, and a 5-membered heterocyclyl ring where one or more carbon atoms are replaced by nitrogen or sulfur;
R3 is hydrogen, ($C_1$-$C_8$) alkyl, ($C_2$-$C_8$) alkenyl, aryl, heteroaryl or heterocyclyl,
A is C≡C,
R4 is hydrogen, halogen, hydroxyl, cyano or optionally substituted ($C_1$-$C_3$) alkyl,
R5 is a group -L-R7, wherein:
R7 is hydrogen or an optionally substituted group selected from straight or branched ($C_1$-$C_8$) alkyl, ($C_3$-$C_8$) cycloalkyl and aryl, and
L is —CON(Y)—, NHCO—, —CH$_2$CONH—, —NHCOCH$_2$—, —SO$_2$NH—, —NHSO$_2$—, wherein Y is as defined above.

A more preferred class of compounds of formula (I) are the compounds wherein:
R1 and R3 are hydrogen,
R2 is hydrogen or an optionally substituted group selected from straight or branched ($C_1$-$C_8$) alkyl, ($C_3$-$C_8$) cycloalkyl, a 3- to 4- or a 6- to 7-membered heterocyclyl ring, where one or more carbon atoms are replaced by nitrogen, sulfur or oxygen, and a 5-membered heterocyclyl ring where one or more carbon atoms are replaced by nitrogen or sulfur;

R4 is hydrogen, halogen, hydroxyl, cyano or methyl,
R5 is a group -L-R7, wherein:
R7 is hydrogen or an optionally substituted group selected from ($C_3$-$C_8$) cycloalkyl and aryl, and
L is —CON(Y)—, NHCO—, —CH$_2$CONH—, —NHCOCH$_2$—, —SO$_2$NH—, —NHSO$_2$—, wherein Y is as defined above.

Preferred specific compounds (cmpd) of formula (I) or a pharmaceutically acceptable salt thereof are the compounds listed below:

3-[(4-amino-7-methyl-7H-pyrrolo[2,3-d]pyrimidin-5-yl) ethynyl]phenol trifluoroacetate (cmpd 1),
3-[4-(2-Dimethylamino-ethylamino)-7H-pyrrolo[2,3-d]pyrimidin-5-ylethynyl]-phenol (cmpd 2),
N-[3-(4-Amino-7H-pyrrolo[2,3-d]pyrimidin-5-ylethynyl)-phenyl]-benzenesulfonamide (cmpd 3),
N-[3-(4-Amino-7H-pyrrolo[2,3-d]pyrimidin-5-ylethynyl)-phenyl]-methanesulfonamide (cmpd 4),
N-{3-[(4-amino-7H-pyrrolo[2,3-d]pyrimidin-5-yl)ethynyl]phenyl}cyclopropanesulfonamide (cmpd 5),
3-[(4-amino-7H-pyrrolo[2,3-d]pyrimidin-5-yl)ethynyl]-N-cyclopropylbenzenesulfonamide (cmpd 6),
3-[(4-amino-7H-pyrrolo[2,3-d]pyrimidin-5-yl)ethynyl]-N-methylbenzenesulfonamide (cmpd 7),
3-[(4-amino-7H-pyrrolo[2,3-d]pyrimidin-5-yl)ethynyl]-N-phenylbenzenesulfonamide (cmpd 8),
N-{3-[(4-amino-7H-pyrrolo[2,3-d]pyrimidin-5-yl)ethynyl]phenyl}benzamide (cmpd 9),
N-{3-[(4-amino-7-methyl-7H-pyrrolo[2,3-d]pyrimidin-5-yl)ethynyl]phenyl}benzamide (cmpd 10),
N-[3-(4-Amino-7H-pyrrolo[2,3-d]pyrimidin-5-ylethynyl)-phenyl]-2-(3-trifluoromethyl-phenyl)-acetamide (cmpd 11),
2-[3-(4-Amino-7H-pyrrolo[2,3-d]pyrimidin-5-ylethynyl)-phenyl]-N-[4-(4-ethyl-piperazin-1-ylmethyl)-3-trifluoromethyl-phenyl]-acetamide (cmpd 12),
N-{3-[(4-amino-7H-pyrrolo[2,3-d]pyrimidin-5-yl)ethynyl]phenyl}cyclopropanecarboxamide (cmpd 13),
N-{3-[(4-amino-7H-pyrrolo[2,3-d]pyrimidin-5-yl)ethynyl]phenyl}acetamide (cmpd 14),
3-[(4-amino-7H-pyrrolo[2,3-d]pyrimidin-5-yl)ethynyl]-N-cyclopropylbenzamide (cmpd 15),
3-[(4-amino-7H-pyrrolo[2,3-d]pyrimidin-5-yl)ethynyl]-N-phenylbenzamide (cmpd 16),
3-[(4-amino-7H-pyrrolo[2,3-d]pyrimidin-5-yl)ethynyl]-N-methylbenzamide (cmpd 17),
3-[(4-amino-7H-pyrrolo[2,3-d]pyrimidin-5-yl)ethynyl]benzamide (cmpd 18),
3-(4-Amino-7H-pyrrolo[2,3-d]pyrimidin-5-ylethynyl)-N-[4-(4-ethyl-piperazin-1-ylmethyl)-3-trifluoromethyl-phenyl]-benzamide (cmpd 19),
3-[(4-amino-7H-pyrrolo[2,3-d]pyrimidin-5-yl)ethynyl]-N-tert-butylbenzamide (cmpd 20),
3-[(4-amino-7H-pyrrolo[2,3-d]pyrimidin-5-yl)ethynyl]-N-cyclopentylbenzamide (cmpd 21),
{3-[(4-amino-7H-pyrrolo[2,3-d]pyrimidin-5-yl)ethynyl]phenyl}(pyrrolidin-1-yl)methanone (cmpd 22),
3-[(4-amino-7H-pyrrolo[2,3-d]pyrimidin-5-yl)ethynyl]-N-(propan-2-yl)benzamide (cmpd 23),
N-{3-[(4-amino-7H-pyrrolo[2,3-d]pyrimidin-5-yl)ethynyl]phenyl}-3-(trifluoromethyl)benzamide (cmpd 24),
N-{3-[(4-amino-7H-pyrrolo[2,3-d]pyrimidin-5-yl)ethynyl]phenyl}-4-(trifluoromethyl)benzamide (cmpd 25),
N-{3-[(4-amino-7H-pyrrolo[2,3-d]pyrimidin-5-yl)ethynyl]phenyl}-3-fluorobenzamide (cmpd 26),
N-{3-[(4-amino-7H-pyrrolo[2,3-d]pyrimidin-5-yl)ethynyl]phenyl}-4-fluorobenzamide (cmpd 27),
N-{3-[(4-amino-7H-pyrrolo[2,3-d]pyrimidin-5-yl)ethynyl]phenyl}-3-chlorobenzamide (cmpd 28),
N-{3-[(4-amino-7H-pyrrolo[2,3-d]pyrimidin-5-yl)ethynyl]phenyl}-4-chlorobenzamide (cmpd 29),
N-{3-[(4-amino-7H-pyrrolo[2,3-d]pyrimidin-5-yl)ethynyl]phenyl}-3-methylbenzamide (cmpd 30),
N-{3-[(4-amino-7H-pyrrolo[2,3-d]pyrimidin-5-yl)ethynyl]phenyl}-4-methylbenzamide (cmpd 31),
N-{3-[(4-amino-7H-pyrrolo[2,3-d]pyrimidin-5-yl)ethynyl]phenyl}-3-methoxybenzamide (cmpd 32),
N-{3-[(4-amino-7H-pyrrolo[2,3-d]pyrimidin-5-yl)ethynyl]phenyl}-4-methoxybenzamide (cmpd 33),
N-{3-[(4-amino-7H-pyrrolo[2,3-d]pyrimidin-5-yl)ethynyl]phenyl}-3-(trifluoromethoxy)benzamide (cmpd 34),
N-{3-[(4-amino-7H-pyrrolo[2,3-d]pyrimidin-5-yl)ethynyl]phenyl}-1,3-benzodioxole-5-carboxamide (cmpd 35),
3-{[4-amino-7-(2,2,2-trifluoroethyl)-7H-pyrrolo[2,3-d]pyrimidin-5-yl]ethynyl}-N-cyclopropylbenzamide (cmpd 36),
3-{[4-amino-7-(2-hydroxyethyl)-7H-pyrrolo[2,3-d]pyrimidin-5-yl]ethynyl}-N-cyclopropylbenzamide (cmpd 37),
3-{[4-amino-7-(2-aminoethyl)-7H-pyrrolo[2,3-d]pyrimidin-5-yl]ethynyl}-N-cyclopropylbenzamide (cmpd 38),
3-({4-amino-7-[(1-methylpiperidin-4-yl)methyl]-7H-pyrrolo[2,3-d]pyrimidin-5-yl}ethynyl)-N-cyclopropylbenzamide (cmpd 39),
3-{[4-amino-7-(propan-2-yl)-7H-pyrrolo[2,3-d]pyrimidin-5-yl]ethynyl}-N-cyclopropylbenzamide (cmpd 40),
5-[(4-amino-7H-pyrrolo[2,3-d]pyrimidin-5-yl)ethynyl]-N-cyclopropyl-2-methylbenzamide (cmpd 41),
3-[(4-amino-7H-pyrrolo[2,3-d]pyrimidin-5-yl)ethynyl]-N-cyclopropyl-4-methylbenzamide (cmpd 42),
3-[(4-amino-7H-pyrrolo[2,3-d]pyrimidin-5-yl)ethynyl]-N-cyclopropyl-4-fluorobenzamide (cmpd 43),
5-[(4-amino-7H-pyrrolo[2,3-d]pyrimidin-5-yl)ethynyl]-N-cyclopropyl-2-fluorobenzamide (cmpd 44),
3-[(4-amino-7H-pyrrolo[2,3-d]pyrimidin-5-yl)ethynyl]-N-cyclopropyl-5-fluorobenzamide (cmpd 45),
3-{[4-amino-7-(1-methylpiperidin-4-yl)-7H-pyrrolo[2,3-d]pyrimidin-5-yl]ethynyl}-N-cyclopropylbenzamide (cmpd 46),
3-{[4-amino-7-(tetrahydro-2H-pyran-4-yl)-7H-pyrrolo[2,3-d]pyrimidin-5-yl]ethynyl}-N-cyclopropylbenzamide (cmpd 47),
3-{[4-amino-7-(2-methoxyethyl)-7H-pyrrolo[2,3-d]pyrimidin-5-yl]ethynyl}-N-cyclopropylbenzamide (cmpd 48),
3-({7-[2-(acetylamino)ethyl]-4-amino-7H-pyrrolo[2,3-d]pyrimidin-5-yl}ethynyl)-N-cyclopropylbenzamide (cmpd 49),
3-{[4-amino-7-(2-amino-2-oxoethyl)-7H-pyrrolo[2,3-d]pyrimidin-5-yl]ethynyl}-N-cyclopropylbenzamide (cmpd 50),
3-{[4-amino-7-(propan-2-yl)-7H-pyrrolo[2,3-d]pyrimidin-5-yl]ethynyl}-N-cyclopropyl-4-methylbenzamide (cmpd 51),
3-{[4-amino-7-(2,2,2-trifluoroethyl)-7H-pyrrolo[2,3-d]pyrimidin-5-yl]ethynyl}-N-cyclopropyl-4-methylbenzamide (cmpd 52),
3-{[4-amino-7-(propan-2-yl)-7H-pyrrolo[2,3-d]pyrimidin-5-yl]ethynyl}-N-cyclopropyl-4-fluorobenzamide (cmpd 53), 3-{[4-amino-7-(2,2,2-trifluoroethyl)-7H-pyrrolo[2,3-d]pyrimidin-5-yl]ethynyl}-N-cyclopropyl-4-fluorobenzamide (cmpd 54), 3-{[4-amino-7-(2-hydroxyethyl)-7H-pyrrolo[2,3-d]pyrimidin-5-yl]ethynyl}-N-cyclopropyl-4-fluorobenzamide (cmpd 55), 3-{[4-amino-7-(2-aminoethyl)-7H-pyrrolo[2,3-d]pyrimidin-5-yl]ethynyl}-N-cyclopropyl-4-fluorobenzamide (cmpd 56), 3-({4-amino-7-[(1-methylpiperidin-4-yl)methyl]-7H-pyrrolo[2,3-d]pyrimidin-5-yl}ethynyl)-N-cyclopropyl-4-fluorobenzamide (cmpd 57), 3-{[4-amino-7-(propan-2-yl)-7H-pyrrolo[2,3-d]pyrimidin-5-yl]ethynyl}-N-cyclopropyl-5-fluorobenzamide (cmpd 58), 3-{[4-amino-7-(2,2,2-trifluoroethyl)-7H-pyrrolo[2,3-d]pyrimidin-5-yl]ethynyl}-N-cyclopropyl-5-fluorobenzamide (cmpd 59), 3-{[4-amino-7-(2-hydroxyethyl)-7H-pyrrolo[2,3-d]pyrimidin-5-yl]ethynyl}-N-cyclopropyl-5-fluorobenzamide (cmpd 60), 3-{[4-amino-7-(2-aminoethyl)-7H-pyrrolo[2,3-d]pyrimidin-5-yl]ethynyl}-N-cyclopropyl-5-fluorobenzamide (cmpd 61), 3-({4-amino-7-[(1-methylpiperidin-4-yl)methyl]-7H-pyrrolo[2,3-d]pyrimidin-5-yl}ethynyl)-N-cyclopropyl-5-fluorobenzamide (cmpd 62), N-cyclopropyl-3-{[4-(methylamino)-7-(propan-2-yl)-7H-pyrrolo[2,3-d]pyrimidin-5-yl]ethynyl}benzamide (cmpd 63), 3-{[4-(acetylamino)-7-(propan-2-yl)-7H-pyrrolo[2,3-d]pyrimidin-5-yl]ethynyl}-N-cyclopropylbenzamide (cmpd 64), 2-(3-{[4-amino-7-(propan-2-yl)-7H-pyrrolo[2,3-d]pyrimidin-5-yl]ethynyl}phenyl)-N-phenylacetamide (cmpd 65), 3-[(4-amino-7-propyl-7H-pyrrolo[2,3-d]pyrimidin-5-yl)ethynyl]-N-cyclopropylbenzamide (cmpd 66), 3-({4-amino-7-[2-(formylamino)ethyl]-7H-pyrrolo[2,3-d]pyrimidin-5-yl}ethynyl)-N-cyclopropylbenzamide (cmpd 67), 3-{[4-amino-7-(pyridin-3-yl)-7H-pyrrolo[2,3-d]pyrimidin-5-yl]ethynyl}-N-cyclopropylbenzamide (cmpd 68), 3-{[4-amino-7-(pyridin-4-yl)-7H-pyrrolo[2,3-d]pyrimidin-5-yl]ethynyl}-N-cyclopropylbenzamide (cmpd 69), 3-{[4-amino-7-(3-methoxyphenyl)-7H-pyrrolo[2,3-d]pyrimidin-5-yl]ethynyl}-N-cyclopropylbenzamide (cmpd 70), 3-{[4-amino-7-(1-methyl-1H-pyrazol-4-yl)-7H-pyrrolo[2,3-d]pyrimidin-5-yl]ethynyl}-N-cyclopropylbenzamide (cmpd 71), 3-{[4-amino-7-(furan-2-yl)-7H-pyrrolo[2,3-d]pyrimidin-5-yl]ethynyl}-N-cyclopropylbenzamide (cmpd 72), 3-{[4-amino-7-(1-cyclopropylpiperidin-4-yl)-7H-pyrrolo[2,3-d]pyrimidin-5-yl]ethynyl}-N-cyclopropylbenzamide (cmpd 73), 3-({4-amino-7-[1-(propan-2-yl)piperidin-4-yl]-7H-pyrrolo[2,3-d]pyrimidin-5-yl}ethynyl)-N-cyclopropylbenzamide (cmpd 74), 3-({4-amino-7-[1-(2-hydroxyethyl)piperidin-4-yl]-7H-pyrrolo[2,3-d]pyrimidin-5-yl}ethynyl)-N-cyclopropylbenzamide (cmpd 75), 3-{[7-(1-acetylpiperidin-4-yl)-4-amino-7H-pyrrolo[2,3-d]pyrimidin-5-yl]ethynyl}-N-cyclopropylbenzamide (cmpd 76), 3-({4-amino-7-[1-(methylsulfonyl)piperidin-4-yl]-7H-pyrrolo[2,3-d]pyrimidin-5-yl}ethynyl)-N-cyclopropylbenzamide (cmpd 77), ethyl 4-(4-amino-5-{[3-(cyclopropylcarbamoyl)phenyl]ethynyl}-7H-pyrrolo[2,3-d]pyrimidin-7-yl)piperidine-1-carboxylate (cmpd 78), 2-(3-{[4-amino-7-(propan-2-yl)-7H-pyrrolo[2,3-d]pyrimidin-5-yl]ethynyl}phenyl)-N-[3-(trifluoromethyl)phenyl]acetamide (cmpd 79), 2-(3-{[4-amino-7-(propan-2-yl)-7H-pyrrolo[2,3-d]pyrimidin-5-yl]ethynyl}phenyl)-N-[4-(trifluoromethyl)phenyl]acetamide (cmpd 80), 3-{[4-amino-7-(propan-2-yl)-7H-pyrrolo[2,3-d]pyrimidin-5-yl]ethynyl}-N-{4-[(4-ethylpiperazin-1-yl)methyl]-3-(trifluoromethyl)phenyl}-4-methylbenzamide (cmpd 81), 3-{[4-amino-7-(propan-2-yl)-7H-pyrrolo[2,3-d]pyrimidin-5-yl]ethynyl}-N-{4-[(4-ethylpiperazin-1-yl)methyl]-3-(trifluoromethyl)phenyl}benzamide (cmpd 82), 5-{[4-amino-7-(propan-2-yl)-7H-pyrrolo[2,3-d]pyrimidin-5-yl]ethynyl}-N-cyclopropyl-2-fluorobenzamide (cmpd 83), 3-{[4-amino-7-(2-methylpropyl)-7H-pyrrolo[2,3-d]pyrimidin-5-yl]ethynyl}-N-cyclopropylbenzamide (cmpd 84), 3-{[4-amino-7-(butan-2-yl)-7H-pyrrolo[2,3-d]pyrimidin-5-yl]ethynyl}-N-cyclopropylbenzamide (cmpd 85), 3-{[4-amino-7-(2-fluoroethyl)-7H-pyrrolo[2,3-d]pyrimidin-5-yl]ethynyl}-N-cyclopropylbenzamide (cmpd 86), 3-[(4-amino-7-ethyl-6-methyl-7H-pyrrolo[2,3-d]pyrimidin-5-yl)ethynyl]-N-cyclopropylbenzamide (cmpd 87), 3-({4-amino-7-[(3-methyloxetan-3-yl)methyl]-7H-pyrrolo[2,3-d]pyrimidin-5-yl}ethynyl)-N-cyclopropylbenzamide (cmpd 88), 3-{[4-amino-7-(1-methylpyrrolidin-3-yl)-7H-pyrrolo[2,3-d]pyrimidin-5-yl]ethynyl}-N-cyclopropylbenzamide (cmpd 89), 3-{[4-amino-7-(pyridin-4-ylmethyl)-7H-pyrrolo[2,3-d]pyrimidin-5-yl]ethynyl}-N-cyclopropylbenzamide (cmpd 90), 3-{[4-amino-7-(pyridin-3-ylmethyl)-7H-pyrrolo[2,3-d]pyrimidin-5-yl]ethynyl}-N-cyclopropylbenzamide (cmpd 91), 3-{[4-amino-7-(3,3,3-trifluoropropyl)-7H-pyrrolo[2,3-d]pyrimidin-5-yl]ethynyl}-N-cyclopropylbenzamide (cmpd 92), 3-[(4-amino-7-methyl-7H-pyrrolo[2,3-d]pyrimidin-5-yl)ethynyl]-N-cyclopropylbenzamide (cmpd 93), 3-[(4-amino-7-ethyl-7H-pyrrolo[2,3-d]pyrimidin-5-yl)ethynyl]-N-cyclopropylbenzamide (cmpd 94), 3-{[4-amino-7-(cyclobutylmethyl)-7H-pyrrolo[2,3-d]pyrimidin-5-yl]ethynyl}-N-cyclopropylbenzamide (cmpd 95), 3-{[4-amino-7-(cyclohexylmethyl)-7H-pyrrolo[2,3-d]pyrimidin-5-yl]ethynyl}-N-cyclopropylbenzamide (cmpd 96), 3-{[4-amino-7-(2,2,2-trifluoroethyl)-7H-pyrrolo[2,3-d]pyrimidin-5-yl]ethynyl}-N-(cyclopropylmethyl)benzamide (cmpd 97), 4-{[4-amino-7-(2,2,2-trifluoroethyl)-7H-pyrrolo[2,3-d]pyrimidin-5-yl]ethynyl}-N-cyclopropylbenzamide (cmpd 98), 3-{[4-amino-7-(cyclopropylmethyl)-7H-pyrrolo[2,3-d]pyrimidin-5-yl]ethynyl}-N-cyclopropylbenzamide (cmpd 99), 3-{[4-amino-7-(1-methoxypropan-2-yl)-7H-pyrrolo[2,3-d]pyrimidin-5-yl]ethynyl}-N-cyclopropylbenzamide (cmpd 100), 3-[(4-amino-7-cyclohexyl-7H-pyrrolo[2,3-d]pyrimidin-5-yl)ethynyl]-N-cyclopropylbenzamide (cmpd 101), 3-[(4-amino-7-cyclobutyl-7H-pyrrolo[2,3-d]pyrimidin-5-yl)ethynyl]-N-cyclopropylbenzamide (cmpd 102), 3-[(4-amino-7-cyclopropyl-7H-pyrrolo[2,3-d]pyrimidin-5-yl)ethynyl]-N-cyclopropylbenzamide (cmpd 103), 3-{[4-amino-7-(cyanomethyl)-7H-pyrrolo[2,3-d]pyrimidin-5-yl]ethynyl}-N-cyclopropylbenzamide (cmpd 104), 3-({4-amino-7-[2-(dimethylamino)ethyl]-7H-pyrrolo[2,3-d]pyrimidin-5-yl}ethynyl)-N-cyclopropylbenzamide (cmpd 105), 3-{[4-amino-7-(1,1,1-trifluoropropan-2-yl)-7H-pyrrolo[2,3-d]pyrimidin-5-yl]ethynyl}-N-cyclopropylbenzamide (cmpd 106), 3-{[4-amino-7-(4,4,4-trifluorobutan-2-yl)-7H-pyrrolo[2,3-d]pyrimidin-5-yl]ethynyl}-N-cyclopropylbenzamide (cmpd 107), 3-{[4-amino-7-(propan-2-yl)-7H-pyrrolo[2,3-d]pyrimidin-5-yl]ethynyl}-4-cyano-N-cyclopropylbenzamide (cmpd 108), 3-{[4-amino-7-(1-methylpiperidin-3-yl)-7H-pyrrolo[2,3-d]pyrimidin-5-yl]ethynyl}-N-cyclopropylbenzamide (cmpd 109), 3-{[4-amino-7-(propan-2-yl)-7H-pyrrolo[2,3-d]pyrimidin-5-yl]ethynyl}benzamide (cmpd 110), 3-{[4-amino-7-(propan-2-yl)-7H-pyrrolo[2,3-d]pyrimidin-5-yl]ethynyl}-N-cyclopropylbenzenesulfonamide (cmpd 111), 3-[(4-amino-7-cyclopentyl-7H-pyrrolo[2,3-d]pyrimidin-5-yl)ethynyl]-N-cyclopropylbenzamide (cmpd 112) and 2-(3-{[4-amino-7-(2,2,2-trifluoroethyl)-7H-pyrrolo[2,3-d]pyrimidin-5-yl]ethynyl}phenyl)-N-cyclopropylacetamide (cmpd 113).

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

The compounds of every general formula can be further transformed in other compounds of the same general formula according to methods well known in the literature, as reported in the experimental section.

A compound of formula (I) can be prepared according to the general synthetic processes described hereafter in Schemes from 1 to 13.

The general preparation of compounds of formula (IA) and (IB) and the salts thereof, object of the present invention, wherein R1, R2, R3, R4 and R5 are as defined above, is shown in the following Scheme 1.

Scheme 1

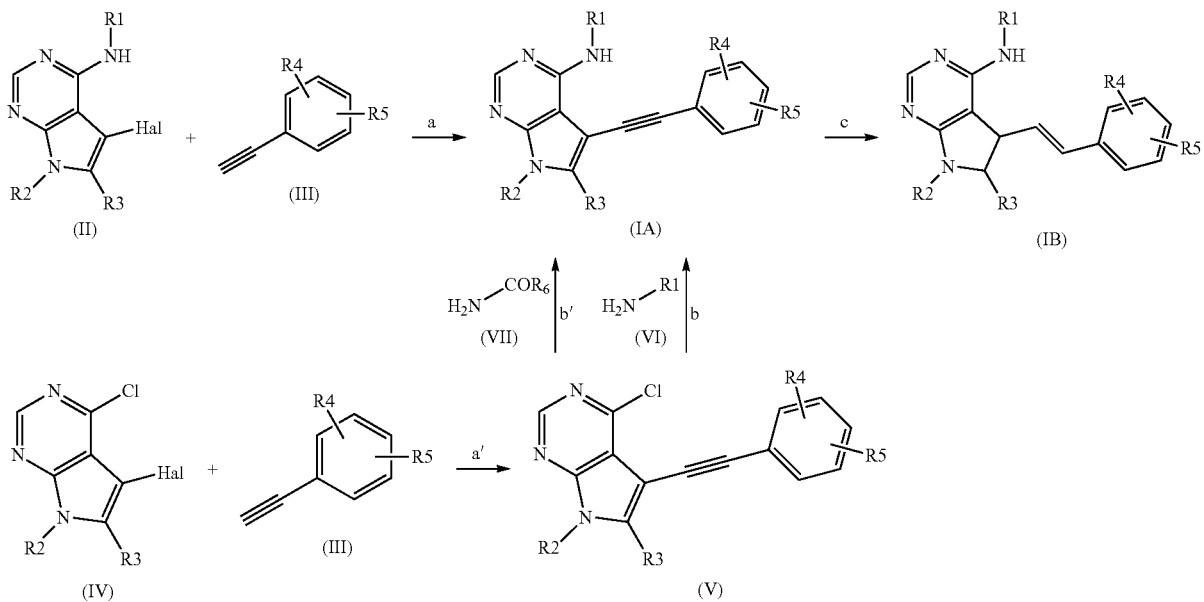

According to the above Scheme 1, a process of the present invention comprises the following steps:

Step a) reaction of a derivative of formula (II), wherein R1, R2 and R3 are as defined above and Hal is iodine or bromine, preferably iodine, with a compound of formula (III), wherein R4 and R5 are as defined above, to obtain a compound of formula (IA), wherein R1, R2, R3, R4 and R5 are as defined above;

alternatively:

Step a') reaction of a compound of formula (IV) wherein R2, R3 and Hal are as defined above, with a compound of formula (III) as defined above, to obtain a compound of formula (V) wherein R2, R3, R4 and R5 are as defined above; and Step b) reaction of the resultant compound of formula (V) with a compound of formula (VI), wherein R1 is hydrogen or an optionally substituted ($C_1$-$C_8$) alkyl or ($C_3$-$C_8$) cycloalkyl, to obtain a compound of formula (IA), wherein R1 is an optionally substituted ($C_1$-$C_8$) alkyl or ($C_3$-$C_8$) cycloalkyl and R2, R3, R4 and R5 are as defined above;

or:

Step b') reaction of the resultant compound of formula (V) with a compound of formula (VII) wherein R6 is as defined above, to obtain a compound of formula (IA) wherein R1, R2, R3, R4 and R5 are as defined above;

afterwards:

Step c) reduction of the resultant compound of formula (IA), obtained through step a) or steps a') and b) or b'), in the corresponding compound of formula (IB), wherein R1, R2, R3, R4 and R5 are as defined above;

optionally converting a compound of formula (IA) or (IB) into another compound of formula (IA) or (IB), and, if desired, converting a compound of formula (IA) or (IB) into a pharmaceutically acceptable salt thereof or converting a salt into the free compound (IA) or (IB).

According to steps a) and a') of Scheme 1, the reaction of a compound of formula (II) or (IV) with a compound of formula (III) can be carried out in a suitable solvent such as acetonitrile, 1,4-dioxane, 1,2-dimethoxyethane or N,N-dimethylformamide in the presence of a base such as triethylamine, with cuprous iodide and with a palladium catalyst, such as bis(triphenylphosphine)palladium(II) dichloride, at a temperature ranging from room temperature to 100° C. in classical thermal conditions or in a microwave apparatus.

According to step b) of Scheme 1 the reaction of a compound of formula (V) with a compound of formula (VI) can be carried out without solvent or in a solvent such as N,N-dimethylformamide, N,N-dimethylacetamide or dimethylsulfoxide at a temperature ranging from 60 to 150° C. for a time ranging from 1 to 24 h in classical thermal conditions or in a microwave apparatus.

According to step b') of Scheme 1 the reaction of a compound of formula (V) with a compound of formula (VII) can be carried out in a suitable solvent such as tetrahydrofuran in the presence of a base such as caesium or sodium or potassium carbonate, in the presence of a catalyst such as palladium acetate and in the presence of a ligand such as Xantphos (4,5-bis(diphenylphosphino)-9,9-dimethylxanthene) in classical thermal conditions at reflux or in a microwave apparatus at a temperature ranging from 50 to 100° C.

According to step c) of Scheme 1, the conversion of a compound of formula (IA) in the corresponding compound of formula (IB) can be carried out by reaction with molecular hydrogen, in the presence of a catalyst such as Lindlar catalyst, palladium on calcium carbonate, barium carbonate, barium sulphate or in the presence of quinoline in a suitable solvent such as methanol, ethanol, 1,4-dioxane, hexane or tetrahydrofuran at room temperature or alternatively by reduction with 1.4-cyclohexadiene in N,N-dimethylformamide, with lithium aluminium hydride in tetrahydrofuran or with Red-Al in diethylether or tetrahydrofuran at a temperature ranging from −78° C. to room temperature.

As indicated above, compounds of formula (IA) or (IB), which are prepared according to the processes object of the present invention, can be conveniently converted into other compounds of formula (IA) or (IB) by operating according to well-known synthetic conditions, the following being examples of possible conversions:

conv.1) converting compounds of formula (IA) or (IB) in other compounds of formula (IA) or (IB) by protecting group removal, as reported in the experimental section (i.e. Example 5);

conv.2) submitting compounds of formula (IA) or (IB) to reductive amination, as reported in the experimental section (i.e. Example 6);

conv.3) submitting compounds of formula (IA) or (IB) to alkylation, as reported in the experimental section (i.e. Example 7).

Alternatively:

the general preparation of compounds of formula (IA) and the salts thereof, object of the present invention, wherein R1, R2, R3, R4 and R5 are as defined above can be carried out as described in the following Scheme 2.

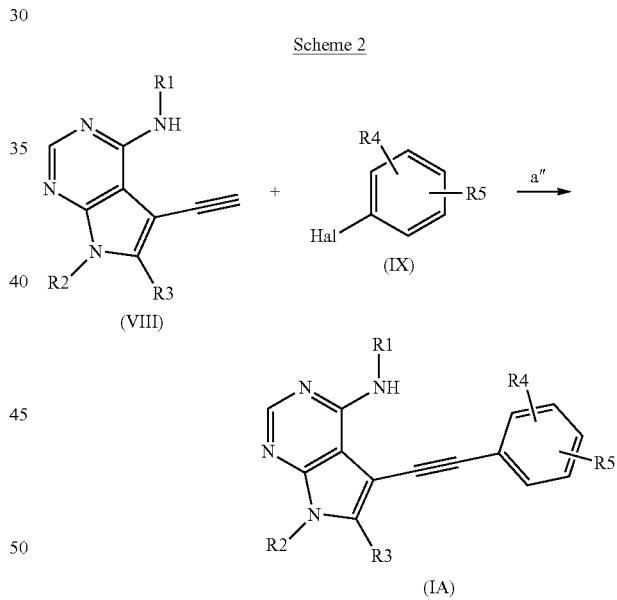

Scheme 2

According to the above Scheme 2, a process of the present invention comprises the step a"):

Step a") reaction of a derivative of formula (VIII), wherein R1, R2 and R3 are as defined above, with a compound of formula (IX), wherein R4 and R5 are as defined above, to obtain a compound of formula (IA), wherein R1, R2, R3, R4 and R5 are as defined above;

According to step a") of Scheme 2, the reaction of a compound of formula (VIII) with a compound of formula (IX) can be carried out in a suitable solvent such as acetonitrile, 1,4-dioxane, 1,2-dimethoxyethane or N,N-dimethylformamide in the presence of a base such as triethylamine, with cuprous iodide and with a palladium catalyst, such as bis(triphenylphosphine)palladium(II) dichloride, at a temperature ranging from room temperature to 100° C. in classical thermal conditions or in a microwave apparatus.

The compounds of formula (II) are known compounds which can be easily obtained according to known methods, for instance as reported in the experimental section.

The following Scheme 3 shows the preparation of the compounds of formula (II), wherein Hal is iodine or bromine, R1 is a group PG, wherein PG is hydrogen or a suitable protecting group such as dimethylaminoimino group, R2 and R3 are hydrogen, as per formula (IIA), and of compounds of formula (II), wherein Hal is iodine or bromine, R1 is a group PG, wherein PG is hydrogen or a suitable protecting group such as dimethylaminoimino group, R3 is hydrogen and R2 is as defined above except hydrogen, as per formula (IIB).

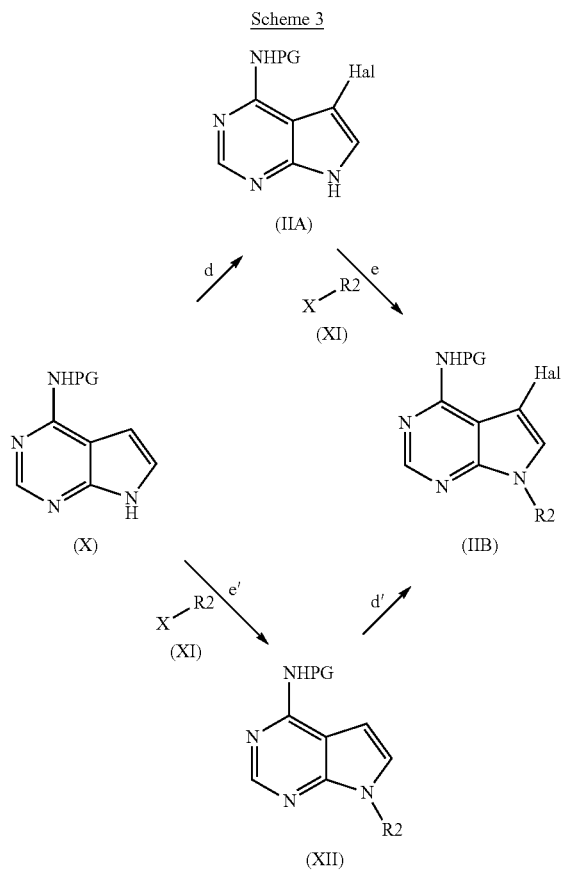

In the above Scheme 3, R2 is as defined above except hydrogen, Hal is iodine or bromine, X is chlorine, bromine, iodine, mesylate, tosylate, triflate, hydroxy, boronic acid or boronate ester and PG is hydrogen or a protecting group suitable to selectively protect amino group, such as dimethylaminoimino group.

According to Scheme 3, the compounds of formula (IIA) can be prepared by halogenation of the compounds of formula (X), wherein PG is hydrogen or a protecting group suitable to selectively protect amino groups, such as dimethylaminoimino group, as depicted in step d).

According to the same Scheme 3, a process for preparation of the compounds of formula (IIB) comprises the following steps:

Step d) halogenation of the compounds of formula (X), wherein PG is hydrogen or a protecting group suitable to selectively protect an amino group, such as dimethylaminoimino group, thus obtaining the compounds of formula (IIA) wherein PG is as defined above and Hal is bromine or iodine;

Step e) reaction of the resulting compounds of formula (IIA), wherein PG and Hal are as defined above, with the compounds of formula (XI), wherein R2 is as defined above except hydrogen and X is chlorine, bromine, iodine, mesylate, tosylate, triflate, hydroxy, boronic acid or boronate ester, thus obtaining the compounds of formula (IIB) wherein R2 is different from hydrogen.

Alternatively, the alkylation step e') can be firstly carried out on compounds of formula (X), thus obtaining the compounds of formula (XII), wherein R2 is as defined above except hydrogen and PG are as defined above, and the halogenation step d') can be secondly carried out on the resulting compounds of formula (XII), thus obtaining the above compounds of formula (IIB), wherein R2 is different from hydrogen.

Compounds wherein PG is a protective group can be prepared from the compounds wherein PG is hydrogen, according to methods well known in the literature.

According to steps d) and d') of the present invention, intermediates (X) or (XII) are submitted to halogenation with N-iodosuccinimide to respectively obtain the compounds of formula (IIA) or (IIB), wherein Hal is iodine, or with N-bromosuccinimide or pyridine hydrobromide perbromide to respectively obtain the compounds of formula (IIA) or (IIB), wherein Hal is bromine. The reactions can be carried out in a suitable solvent such as acetonitrile, N,N-dimethylformamide, chloroform or tetrahydrofuran at a temperature ranging from room temperature to 80° C., operating in classical thermal conditions or in a microwave apparatus. Alternatively, the reaction to obtain the compounds of formula (IIA) or (IIB), wherein Hal is iodine, can be carried out with molecular iodine, with or without the presence of potassium hydrate in a suitable solvent such as N,N-dimethylformamide or mixtures water-methanol, at room temperature, or with molecular iodine with the presence of silver acetate or trifluoroacetate in a suitable solvent such as N,N'-dimethylformamide or dichloromethane at a temperature ranging from room temperature to 70° C. The reaction can be carried out also with iodine monochloride, with or without the presence of sodium or potassium carbonate, in a suitable solvent such as 1,4-dioxane or dichloromethane, at a temperature ranging from room temperature to reflux.

According to steps e) and e') of the present invention, the reaction of compounds (X) or (IIA) with the compounds of formula (XI), wherein X is iodine, bromine, chlorine, mesylate, tosylate or triflate and R2 is as defined above except hydrogen, can be carried out in the presence of a suitable base such as caesium, sodium or potassium carbonate or sodium hydride in a suitable solvent such as 1,4-dioxane, tetrahydrofuran, N,N-dimethylformamide at a temperature ranging from room temperature to 100° C., in classical thermal conditions or in a microwave apparatus. Alternatively, the reaction of compounds (X) or (IIA) with the compounds of formula (XI), wherein X is hydroxyl, can be carried out by Mitsunobu reaction in the presence of diethyl or diisopropyl azodicarboxylate and triphenylphosphine, in a suitable solvent such as tetrahydrofuran or dichloromethane at a temperature ranging from 0° C. to 70° C.

In a further alternative way, the reaction of compounds of formula (X) or (IIA) with the compounds of formula (XI), wherein X is boronic acid or boronate ester, can be carried out in the presence of copper acetate, 2,2'-bipyridyl and sodium carbonate in N,N-dimethylacetamide at a temperature ranging from 70 to 120° C. or with cuprous oxide in methanol at reflux.

Alkyl iodide, bromide, chloride, mesylate, triflate, hydroxyl and aryl, heteroaryl, heterocyclyl boronic derivatives employed as reactants in the above mentioned steps e) and e') are commercially available compounds or can be prepared according to methods described in the literature.

Another embodiment of the present invention is provided in the following Scheme 4 which shows the preparation of the compounds of formula (II), wherein R1 is hydrogen, $(C_1\text{-}C_8)$ alkyl or $(C_3\text{-}C_8)$ cycloalkyl, and R2 and R3 are as defined above.

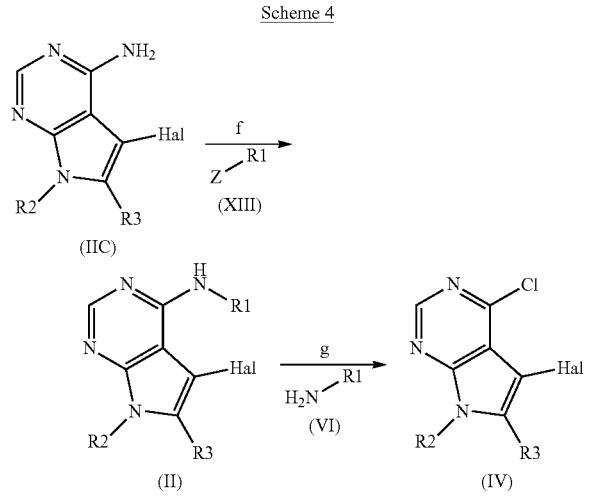

Scheme 4

In the above Scheme 4, R1, R2 and R3 are as defined above, Hal is iodine or bromine. In compounds (XIII) Z is iodine, bromine, chlorine, mesylate, tosylate or triflate and R1 is as defined above, except hydrogen. In compounds (VI) R1 is hydrogen or an optionally substituted group selected from straight or branched $(C_1\text{-}C_6)$ alkyl or $(C_3\text{-}C_6)$ cycloalkyl.

According to Scheme 4, the compounds of formula (II) can be prepared by the following reactions:

Step f) alkylation of the compounds of formula (IIC), wherein R2 and R3 are as defined above and Hal is iodine or bromine, with the compounds of formula (XIII), wherein R1 is $(C_1\text{-}C_8)$ alkyl or $(C_3\text{-}C_8)$ cycloalkyl and Z is iodine, bromine, chlorine, mesylate, tosylate or triflate, thus obtaining the compounds of formula (II), wherein R1, R2, R3 and Hal are as defined above;

alternatively:

Step g) reaction of the compounds of formula (IV) wherein R2 and R3 are as defined above and Hal is iodine or bromine, with the compounds of formula (VI) wherein R1 is as defined above, thus obtaining the compound of formula (II).

According to step f) of the present invention, the reaction can be carried out in the presence of a base such as sodium hydride in a suitable solvent such as tetrahydrofuran, 1,4-dioxane or N,N-dimethylformamide or in the presence of sodium or potassium hydrate in a suitable solvent such as mixtures water-ethanol at a temperature ranging from room temperature to reflux.

According to step g) of the present invention, the reaction can be carried out in a suitable solvent such as 1,4-dioxane at a temperature ranging from 70° C. to reflux, in classical thermal condition or in a microwave apparatus. Another embodiment of the present invention is provided in the reported Scheme 5 which shows the preparation of the compounds of formula (II), wherein R1 is hydrogen or $(C_1\text{-}C_8)$ alkyl or $(C_3\text{-}C_8)$ cycloalkyl, R2 is as defined above, R3 is an optionally substituted straight or branched $(C_1\text{-}C_6)$ alkyl and Hal is iodine or bromine, as per formula (IID). Scheme 5 also shows the preparation of the compounds of formula (IV), reported in the above Scheme 4, starting from the common intermediate (XIV).

Scheme 5

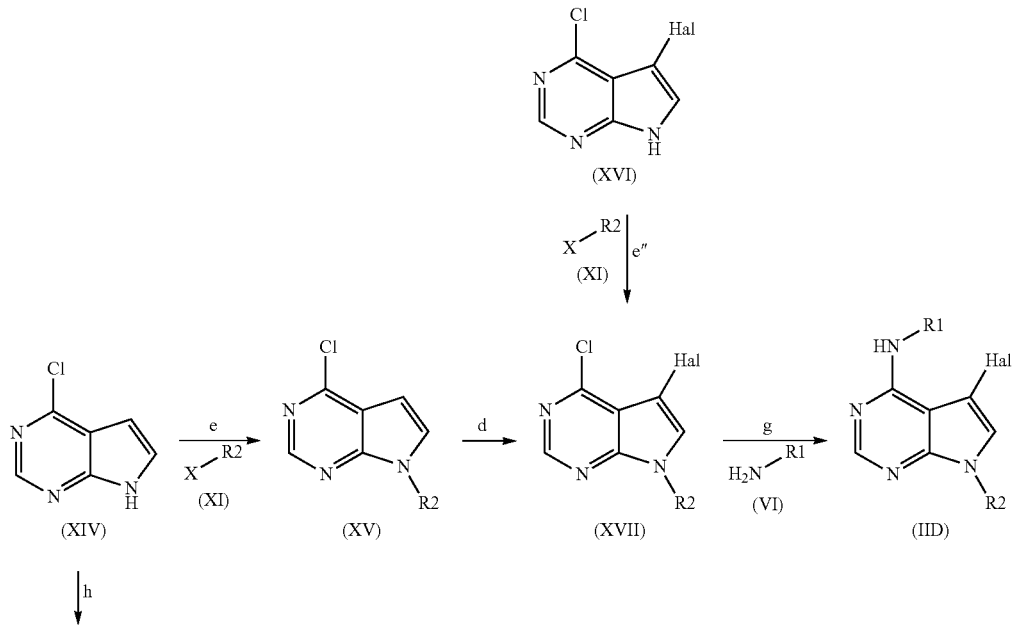

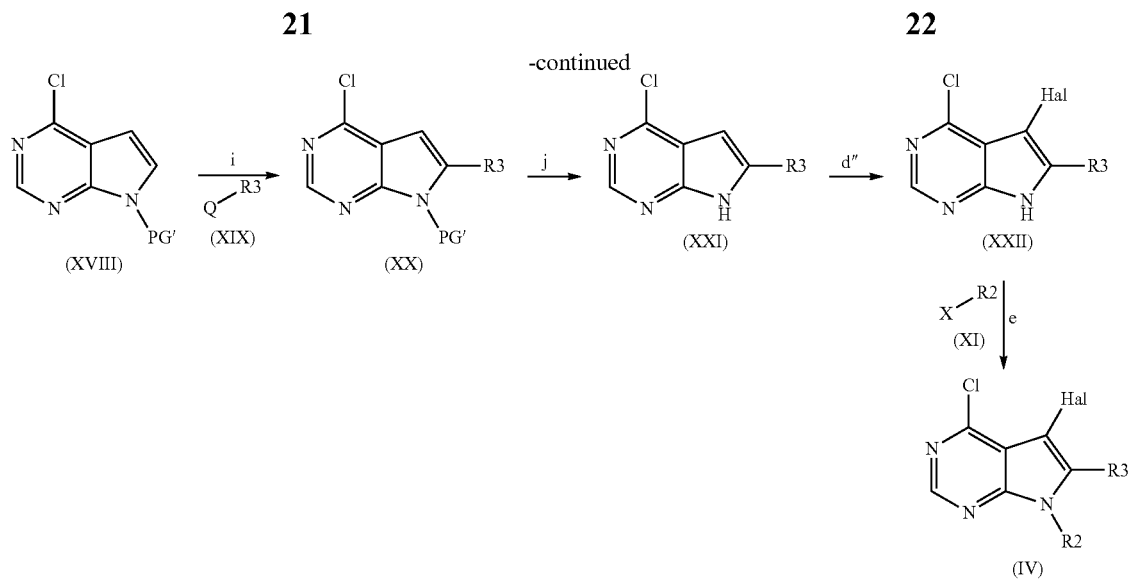

In the above Scheme 5, R1, R2 and R3 are as defined above, Hal is iodine or bromine, PG' is a suitable protective group such as a benzensulfonyl group.

According to Scheme 5, the compounds of formula (IID) can be prepared by the following reactions:

Step e): reaction of the compounds of formula (XIV) with the compounds of formula (XI) to obtain the compounds of formula (XV), wherein R2 is as defined above, and Step d): halogenation of the resultant compounds of formula (XV) to obtain the compounds of formula (XVII), wherein R2 is as defined above.

Alternatively:

Step e"): reaction of the compounds of formula (XVI) with the compounds of formula (XI) to obtain directly the compounds of formula (XVII), as defined above.

Afterwards:

Step g): nucleophilic substitution on the compounds of formula (XVII) with the compounds of formula (VI) to obtain the compounds of formula (IID), wherein R1 and R2 are as defined above.

According to Step e) and to Step e") of the present invention, carried out on compounds of formula (XIV) and (XVI), the reaction can be carried out in the presence of a suitable base such as caesium, sodium or potassium carbonate in a suitable solvent such as 1,4-dioxane, tetrahydrofurane, N,N-dimethylformamide at a temperature ranging from room temperature to 100° C., in classical thermal conditions or in a microwave apparatus. Alternatively, the reaction of compounds (XIV) or (XVI) with the compounds of formula (XI), wherein X is hydroxyl, can be carried out by Mitsunobu reaction in the presence of diethyl or diisopropyl azodicarboxylate and triphenylphosphine, in a suitable solvent such as tetrahydrofuran or dichloromethane at a temperature ranging from 0° C. to 70° C.

In a further alternative way, the reaction of compounds of formula (XIV) or (XVI) with the compounds of formula (XI), wherein X is boronic acid or boronate ester, can be carried out in the presence of copper acetate, 2,2'-bipyridyl and sodium carbonate in N,N-dimethylacetamide at a temperature ranging from 70 to 120° C. or with cuprous oxide in methanol at reflux.

Alkyl iodide, bromide, chloride, mesylate, tosylate, triflate, hydroxyl and aryl, heteroaryl or heterocyclyl boronic derivatives employed as reactants in the above mentioned Step e) are commercially available compounds or can be prepared according to methods described in the literature.

According to Step d) of the present invention, the intermediates (XV) are submitted to halogenation with N-iodosuccinimide to obtain the compounds of formula (XVII) wherein Hal is iodine, or with N-bromosuccinimide or pyridine hydrobromide perbromide to obtain the compounds of formula (XVII), wherein Hal is bromine. The reaction can be carried out in a suitable solvent such as acetonitrile, N,N-dimethylformamide, chloroform or tetrahydrofuran at a temperature ranging from room temperature to 70° C., operating in classical thermal conditions or in a microwave apparatus. Alternatively, the reaction to obtain the compounds of formula (XVII), wherein Hal is iodine, can be carried out with molecular iodine, with or without the presence of potassium hydrate in a suitable solvent such as N,N-dimethylformamide or mixtures water-methanol, at room temperature, or with molecular iodine with the presence of silver acetate or silver trifluoroacetate in a suitable solvent such as N,N'-dimethylformamide or dichloromethane at a temperature ranging from room temperature to 80° C. The reaction can be carried out also with iodine monochloride, with or without the presence of sodium or potassium carbonate, in a suitable solvent such as 1,4-dioxane or dichloromethane, at a temperature ranging from room temperature to reflux.

According to Step g) of the present invention, the reaction can be carried out in a suitable solvent such as 1,4-dioxane at a temperature ranging from 80° C. to reflux, in classical thermal condition or in a microwave apparatus.

According to the above Scheme 5, a process for preparation of the compounds of formula (IV) comprises the following steps:

Step h): introduction of PG' protective group to obtain the compounds of formula (XVIII) wherein PG' is a suitable protective group such as a benzensulfonyl group;

Step i): reaction of the compounds of formula (XVIII) with the compounds of formula (XIX) wherein R3 is an optionally substituted straight or branched ($C_1$-$C_6$) alkyl and Q is iodine, chlorine or bromine, to obtain the compounds of formula (XX), wherein R3 and PG' are as defined above;

Step j): removal of the protective group PG' to obtain the compounds of formula (XXI) wherein R3 is as defined above;

Step d"): halogenation of the compounds of formula (XXI) to obtain the compounds of formula (XXII) wherein R3 and PG' are as defined above and Hal is iodine or bromine;

Step e): reaction of the compounds of formula (XXII) with the compounds of formula (XI) wherein X and R2 are as defined above, to obtain the compounds of formula (IV) wherein R2, R3 and Hal are as defined above.

According to Step h) of the Scheme 5 of the present invention, the reaction can be carried out with a suitable reagent such as benzensulfonyl chloride, in the presence of a suitable base such as caesium carbonate, in a suitable solvent such as N,N'-dimethylformamide, at room temperature.

According to step i) of the present invention, the reaction can be carried out with the suitable reactant such as an alkyl iodide or bromine in the presence of a base such as lithium diisopropylamide, in a suitable solvent such as dry tetrahydrofuran, at a temperature ranging from −78° C. to 0° C.

According to Step j) of Scheme 5, the protective group PG' is hydrolyzed in basic medium, for example with sodium hydrate in a mixture tetrahydrofurane/methanol at room temperature to obtain the compounds of formula (XXI).

According to Step d") of Scheme 5, the intermediates (XXI) are submitted to halogenation with N-iodosuccinimide to obtain the compounds of formula (XVII) wherein Hal is iodine, or with N-bromosuccinimide or pyridine hydrobromide perbromide to obtain the compounds of formula (XXII), wherein Hal is bromine. The reactions can be carried out in a suitable solvent such as acetonitrile, N,N-dimethylformamide, chloroform or tetrahydrofuran at a temperature ranging from room temperature to 80° C., operating in classical thermal conditions or in a microwave apparatus. Alternatively, the reaction to obtain the compounds of formula (XXII), wherein Hal is iodine, can be carried out with molecular iodine, with or without the presence of potassium hydrate in a suitable solvent such as N,N-dimethylformamide or mixtures water/methanol, at room temperature, or with molecular iodine with the presence of silver acetate or silver trifluoroacetate in a suitable solvent such as N,N'-dimethylformamide or dichloromethane at a temperature ranging from room temperature to 80° C. The reaction can be also carried out with iodine monochloride, with or without the presence of sodium or potassium carbonate, in a suitable solvent such as 1,4-dioxane or dichloromethane, at a temperature ranging from room temperature to reflux.

According to Step e) of Scheme 5, the reaction can be carried out in the presence of a suitable base such as caesium, sodium or potassium carbonate in a suitable solvent such as 1,4-dioxane, tetrahydrofurane, N,N-dimethylformamide at a temperature ranging from room temperature to 70° C., in classical thermal conditions or in a microwave apparatus. Alternatively, the reaction of compounds (XXII) with the compounds of formula (XI), wherein X is hydroxyl, can be carried out by Mitsunobu reaction in the presence of diethyl or diisopropyl azodicarboxylate and triphenylphosphine, in a suitable solvent such as tetrahydrofuran or dichloromethane at a temperature ranging from 0° C. to 70° C.

In a further alternative way, the reaction of compounds of formula (XXII) with the compounds of formula (XI), wherein X is boronic acid or boronate ester, can be carried out in the presence of copper acetate, 2,2'-bipyridyl and sodium carbonate in N,N-dimethylacetamide at a temperature ranging from 70 to 120° C. or with cuprous oxide in methanol et reflux.

Alkyl iodide, bromide, chloride, mesylate, triflate, hydroxyl and aryl, heteroaryl, heterocycloalkyl boronic derivatives employed as reactants in the above mentioned step e) are commercially available compounds or can be prepared according to methods described in the literature.

Another embodiment of the present invention is reported in the following Scheme 6 where the preparation of the compounds of formula (II), wherein R1 is alkylcarbonyl, R2, R3 and R6 are as defined above and Hal is iodine or bromine, as per formula (IIE), is shown.

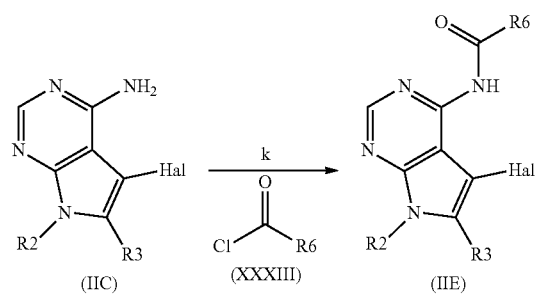

Scheme 6

In the above Scheme 6, R2, R3 and R6 are as defined above and Hal is iodine or bromine.

According to Scheme 6, the compounds of formula (IIE) can be prepared by the following reaction:

Step k) reaction of a compound of formula (IIC), wherein R2 and R3 are as defined above and Hal is iodine or bromine with a compound of formula (XXXIII) wherein R6 is as defined above, to obtain the compound of formula (IIE) wherein R2, R3, R6 and Hal are as defined above.

According to step k) of the present invention, the reaction can be carried out in the presence of a base such as triethylamine, N,N-diisopropyl-N-ethylamine, N-methylmorpholine or pyridine, in a suitable solvent such as dichloromethane, diethylether, tetrahydrofuran, 1,4-dioxane, N,N-dimethylformamide, at a temperature ranging from 0° C. to reflux.

Another embodiment of the present invention provides the preparation of the compounds of formula (II) wherein R1 and R2 are as defined above, R3 is (C₂-C₈) alkenyl, aryl, heteroaryl or heterocyclyl, Hal is iodine or bromine and PG is hydrogen or a suitable protective group, such as dimethylaminoimino group, as per formula (IIF), as shown in the following Scheme 7.

Scheme 7

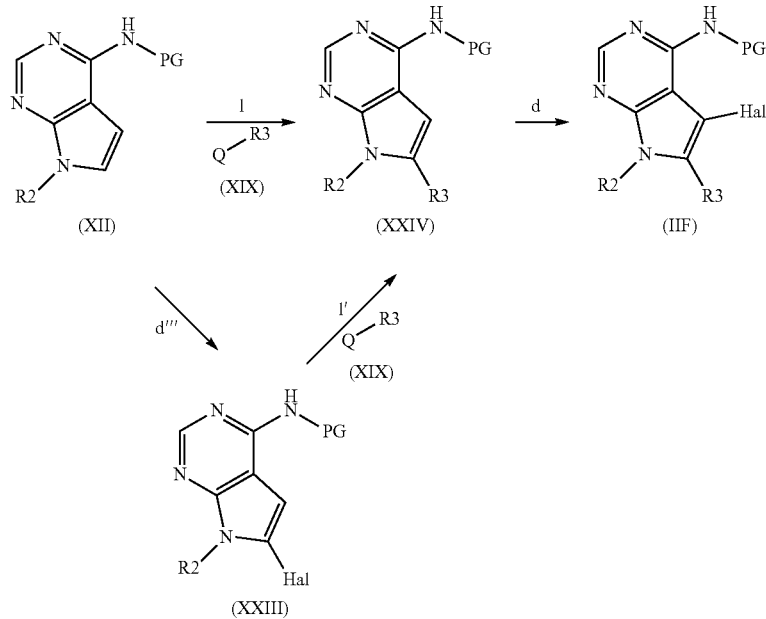

In the above Scheme 7, R2 and R3 are as defined above, Hal is iodine or bromine, Q is chlorine, bromine, iodine, boronic acid or boronate ester when R3 is aryl, heteroaryl or heterocyclyl, or Q is stannane when R3 is ($C_2$-$C_6$) alkenyl, or Q is hydrogen when R3 is ($C_2$-$C_8$) alkenyl, and PG is hydrogen or a suitable protecting group, such as dimethylaminoimino group.

According to Scheme 7, a process for preparation of the compounds of formula (IIF) comprises the following steps:

Step I): reaction of a compound of formula (XII), wherein R2 and PG are as defined above, with a compound of formula (XIX) wherein 0 is chlorine, bromine, iodine, boronic acid or boronate ester, stannane or a ($C_2$-$C_8$) alkenyl, and R3 is ($C_2$-$C_8$) alkenyl, aryl, heteroaryl or heterocyclyl, thus affording the compounds of formula (XXIV) wherein R2 is as defined above, PG is hydrogen or a proper protecting group and R3 is ($C_2$-$C_8$) alkenyl, aryl, heteroaryl or heterocyclyl;

Step d): halogenation of the resultant compound of formula (XXIV), defined above, thus affording a compound of formula (IIF), wherein R2 is as defined above, R3 is ($C_2$-$C_8$) alkenyl, aryl, heteroaryl or heterocyclyl, PG is hydrogen or a suitable protecting group, such as dimethylaminoimino group, and Hal is bromine or iodine;

alternatively:

Step d"): halogenation of the compounds of formula (XII) defined above, thus affording a compound of formula (XXIII) wherein PG and R2 are as defined above and Hal is iodine or bromine;

Step I'): reaction of a compound of formula (XXIII), wherein R2 and PG are as defined above and Hal is iodine or bromine, with a compound of formula (XIX) wherein Q is chlorine, bromine, iodine, boronic acid or boronate ester, stannane, and R3 is ($C_2$-$C_8$) alkenyl, aryl, heteroaryl or heterocyclyl, or Q is hydrogen when R3 is ($C_2$-$C_8$) alkenyl, thus affording the compounds of formula (IIF) wherein R2 is as defined above, PG is hydrogen or a proper protecting group and R3 is ($C_2$-$C_8$) alkenyl, aryl, heteroaryl or heterocyclyl.

According to steps I) and I') of the present invention, when Q is chlorine, bromine or iodine, the reaction can be carried out in the presence of a base such as caesium acetate, potassium carbonate, potassium phosphate, and with or without the presence of silver oxide and in the presence of a catalyst such as palladium acetate or Pd(thd)$_2$ (thd=2,2,6,6-tetramethyl-3,5-heptandione) or Pd2(isopropyl-3-(CO-pyrrolidino)-imidazol-2-ylidene)(PPh$_3$), with or without the presence of triphenylphosphine in a suitable solvent such as N-methylpyrrolidone, N,N-dimethylacetamide, N,N-dimethylformamide, at a temperature ranging from room temperature to 150° C.

Alternatively, when Q is boronic acid or boronate ester, the reaction can be carried out by employing the proper aryl, heteroaryl or heterocyclyl boronic derivative in the presence of a base such as sodium carbonate, potassium carbonate, potassium acetate, in the presence of a suitable catalyst such as tetrakis(triphenylphosphine)palladium(0), palladium acetate, bis(triphenylphosphine)palladium(II) dichloride, bis (diphenylphosphino)ferrocene-palladium(II) dichloride dichloromethane complex, with or without the presence of lithium chloride, in a suitable solvent such as 1,4-dioxane, mixtures water/1,4-dioxane, tetrahydrofuran, N,N-dimethylformamide, dimethylsulphoxide, toluene or mixtures water/ethanol/toluene, at a temperature ranging from 70 to 160° C., in classical thermal conditions or in a microwave apparatus.

Alternatively, when Q is a stannane, the reaction can be carried out by employing the proper ($C_2$-$C_6$) alkenyl stannane derivative in the presence of tetrabutyl ammonium chloride or bromide or lithium chloride, and in the presence of a catalyst such as palladium acetate, bis(triphenylphosphine)palladium(II) dichloride or (diphenylphosphorylferrocene)palladium(II) dichloride, in a suitable solvent such as N,N-dimethylformamide, ethanol, toluene, at a temperature ranging from room temperature to reflux.

Alternatively, when Q is hydrogen and R3 is a ($C_2$-$C_8$) alkenyl derivative, the reaction can be carried out in the presence of potassium acetate, lithium chloride, triethylamine, tetrabutyl ammonium bromide or chloride, with or without the presence of a phosphine such as triphenylphosphine or tris(o-tolyl) triphenylphosphine, and in the presence of a catalyst such as palladium acetate, in a suitable solvent such as N,N-dimethylformamide or acetonitrile at a temperature ranging from room temperature to reflux.

According to step d) of the present invention, the reaction can be carried out in the presence of N-iodosuccinimide or molecular iodine to obtain the compounds of formula (IIF) wherein Hal is iodine or with N-bromosuccinimide or pyridine hydrobromide perbromide or molecular bromine to obtain the compounds of formula (IIF) wherein Hal is bromine, in a suitable solvent such as 1,4-dioxane, dichloromethane, N,N-dimethylformamide or dimethylacetamide at a temperature ranging from room temperature to 80° C., in classical thermal conditions or in a microwave apparatus.

According to step d''') of the present invention, the reaction can be carried out in the presence of N-iodosuccinimide to obtain the compounds of formula (XXIII) wherein Hal is iodine or in the presence of N-bromosuccinimide to obtain the compounds of formula (XXIII) wherein Hal is bromine, in a suitable solvent such as dichloromethane, N,N-dimethylformamide or N,N-dimethylacetamide at room temperature.

The compounds of formula (III) are commercially available or they are known compounds which can be easily obtained according to known methods, for instance as reported in the experimental section.

The reported Scheme 8 shows the preparation of the compounds of formula (III), wherein R4 is as defined above and R5 is a group -L-R7, wherein L is —NHCO— and R7 is as defined above, as per formula (IIIA).

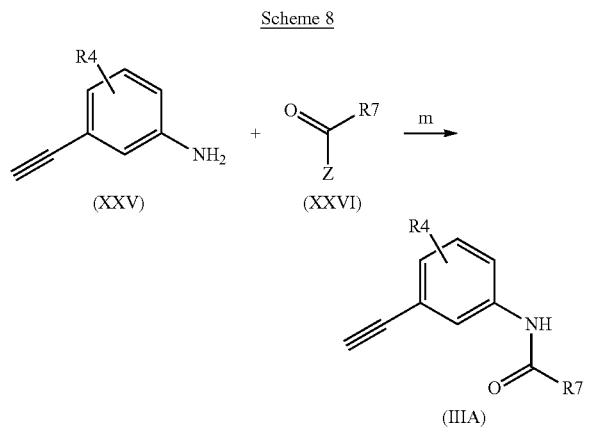

Scheme 8

In the above Scheme 8, R4 and R7 are as defined above and Z is chlorine or hydroxy.

According to Scheme 8, the compounds of formula (IIIA) can be prepared by the following reaction:

Step m) amidation of the compounds of formula (XXV), wherein R4 is as defined above, with the compounds of formula (XXVI) wherein R7 is as defined above and Z is chlorine or hydroxy.

According to step m) of the present invention, the reaction can be carried out by employing a compound of formula (XXVI) wherein Z is chlorine in the presence of a suitable base such as triethylamine, N,N-diisopropyl-N-ethylamine, N-methylmorpholine or pyridine in a suitable solvent such as dichloromethane, chloroform, diethylether, tetrahydrofuran, 1,4-dioxane, toluene, acetonitrile at a temperature ranging from 0° C. to room temperature.

Alternatively the reaction can be carried out by employing a compound of formula (XXVI) wherein Z is hydroxyl, in the presence of a coupling agent such as, for instance, 2-(1H-benzotriazol-1-yl)-1,1,3,3-tetramethyluronium tetrafluoroborate (TBTU), 1,3-dicyclohexylcarbodiimide (DCC), 1,3-diisopropylcarbodiimide (DIC), 1-(3-dimethylaminopropyl)-3-ethylcarbodiimide (EDCI), N-cyclohexylcarbodiimide-N'-propyloxymethyl polystyrene or N-cyclohexylcarbodiimide-N'-methyl polystyrene, 1,1'-carbonyldiimidazole (CDI), benzotriazol-1-yloxytripyrrolidinophosphonium hexafluorophosphate (PyBOP), in a suitable solvent such as, for instance, dichloromethane, chloroform, tetrahydrofuran, diethyl ether, 1,4-dioxane, acetonitrile, toluene, dimethylacetamide (DMA), N-methylpyrrolidone (NMP), or N,N-dimethylformamide (DMF), at a temperature ranging from about −10° C. to reflux and for a suitable time, for instance from about 30 minutes to 96 hours. The said reaction is optionally carried out in the presence of a suitable catalyst, for instance 4-dimethylaminopyridine (DMAP), or in the presence of a further coupling reagent such as N-hydroxybenzotriazole (HOBT), or in the presence of a suitable base such as triethylamine (TEA) or N,N-diisopropyl-N-ethylamine (DIPEA).

Alternatively, this same reaction can be carried out, for example, through a mixed anhydride method, by using an alkyl chloroformate such as ethyl, iso-butyl or iso-propyl chloroformate, in the presence of a tertiary base such as triethylamine, N,N-diisopropyl-N-ethylamine or pyridine, in a suitable solvent such as, for instance, toluene, dichloromethane, chloroform, tetrahydrofuran, acetonitrile, diethyl ether, 1,4-dioxane or N,N-dimethylformamide, at a temperature ranging from about −30° C. to room temperature.

Another embodiment of the present invention is reported in the following Scheme 9 where the preparation of the compounds of formula (III), wherein R4 is as defined above and R5 is a group -L-R7, wherein L is —CON(Y)— and Y and R7 are as defined above, as per formula (IIIB), is shown.

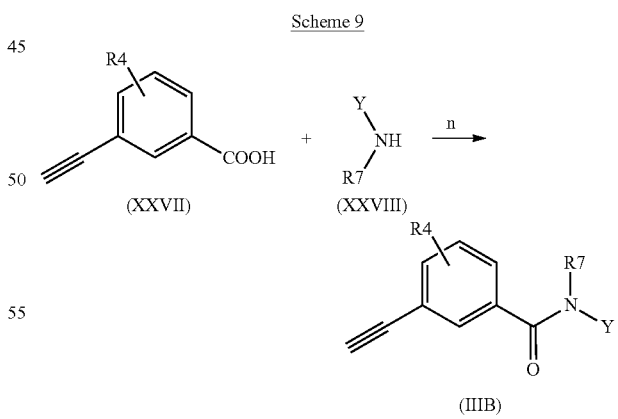

Scheme 9

In the above Scheme 9, R4, Y and R7 are as defined above.

According to Scheme 9, the compounds of formula (IIIB) can be prepared by the following reaction:

Step n) reaction of the compounds of formula (XXVII), wherein R4 is as defined above, with the compounds of formula (XXVIII), wherein Y and R7 are as defined above, to obtain the resultant compounds of formula (IIIB), wherein R4, R7 and Y are as defined above.

According to step n) of the present invention, the reaction can be carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide (DCC), 1,3-diisopropylcarbodiimide (DIC), 1-(3-dimethylaminopropyl)-3-ethylcarbodiimide (EDCI), N-cyclohexylcarbodiimide-N'-propyloxymethyl polystyrene or N-cyclohexylcarbodiimide-N'-methyl polystyrene, 1,1'-carbonyldiimidazole (CDI), benzotriazol-1-yloxytripyrrolidinophosphonium hexafluorophosphate (PyBOP), in a suitable solvent such as, for instance, dichloromethane, chloroform, tetrahydrofuran, diethyl ether, 1,4-dioxane, acetonitrile, toluene, N,N-dimethylacetamide (DMA), N-methylpyrrolidone (NMP), or N,N-dimethylformamide (DMF), at a temperature ranging from about −10° C. to reflux and for a suitable time, for instance from about 30 minutes to 96 hours. The said reaction is optionally carried out in the presence of a suitable catalyst, for instance 4-dimethylaminopyridine (DMAP), or in the presence of a further coupling reagent such as N-hydroxybenzotriazole (HOBT), or in the presence of a suitable base such as triethylamine (TEA) or N,N-diisopropyl-N-ethylamine (DIPEA).

Alternatively, this same reaction can be carried out, for example, through a mixed anhydride method, by using an alkyl chloroformate such as ethyl, iso-butyl, or iso-propyl chloroformate, in the presence of a tertiary base such as triethylamine, N,N-diisopropyl-N-ethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

Another embodiment of the present invention is reported in the following Scheme 10, where the preparation of the compounds of formula (III), wherein R4 is as defined above and R5 is a group -L-R7, wherein L is —CON(Y)— and Y and R7 are as defined above, and n is 0 or 1 as per formula (IIIC), is shown.

In the above Scheme 10, R4, Y and R7 are as defined above, Hal is iodine or bromine and n is 0 or 1.

According to Scheme 10, a process for preparation of the compounds of formula (IIIC) comprises the following steps:

Step n) reaction of the compounds of formula (IXA), wherein R4 is as defined above, Hal is iodine or bromine and n is 0 or 1, with the compounds of formula (XXVIII), wherein R7 and Y are as defined above, thus obtaining the compounds of formula (IXB) wherein Hal, R4, Y and R7 are as defined above;

Step o) submission of the resultant compounds of formula (IXB) to Sonogashira coupling with trimethylsilyl acetylene to afford the compounds of formula (XXIX), wherein R4, R7 and Y are as defined above;

Step p) removal of trimethylsilyl protecting group from the resultant compounds of formula (XXIX) to afford the compounds of formula (IIIC) wherein R4, R7 and Y are as defined above.

According to Step n) of the present invention, the reaction can be carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide (DCC), 1,3-diisopropylcarbodiimide (DIC), 1-(3-dimethylaminopropyl)-3-ethylcarbodiimide (EDCI), N-cyclohexylcarbodiimide-N'-propyloxymethyl polystyrene or N-cyclohexylcarbodiimide-N'-methyl polystyrene, 1,1'-carbonyldiimidazole (CDI), benzotriazol-1-yloxytripyrrolidinophosphonium hexafluorophosphate (PyBOP), in a suitable solvent such as, for instance, dichloromethane, chloroform, tetrahydrofuran, diethyl ether, 1,4-dioxane, acetonitrile, toluene, dimethylacetamide (DMA), N-methylpyrrolidone (NMP), or N,N-dimethylformamide (DMF), at a temperature ranging from about −10° C. to reflux and for a suitable time, for instance from about 30 minutes to 96 hours. The said reaction is optionally carried out in the presence of a suitable catalyst, for instance 4-dimethylaminopyridine (DMAP), or in the presence of a further coupling reagent such as N-hydroxybenzotriazole (HOBT), or in the presence of a suitable base such as triethylamine (TEA) or N,N-diisopropyl-N-ethylamine (DIPEA).

Scheme 10

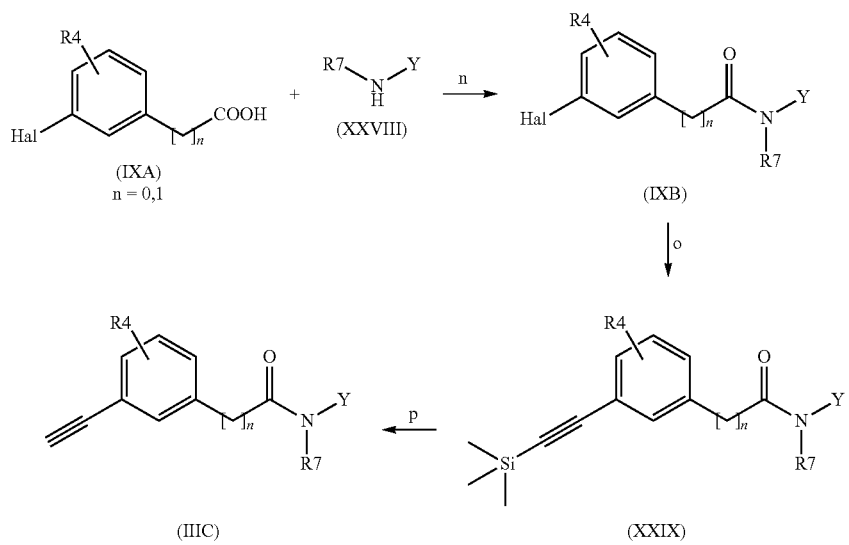

Alternatively, this same reaction can be carried out, for example, through a mixed anhydride method, by using an alkyl chloroformate such as ethyl, iso-butyl or iso-propyl chloroformate, in the presence of a tertiary base such as triethylamine, N,N-diisopropyl-N-ethylamine or pyridine, in a suitable solvent such as, for instance, toluene, dichloromethane, chloroform, tetrahydrofuran, acetonitrile, diethyl ether, 1,4-dioxane or N,N-dimethylformamide, at a temperature ranging from about −30° C. to room temperature.

According to step o) of the present invention, the reaction of the compounds of formula (IXB) with trimethylsilyl acetylene can be carried out in the presence of cuprous iodide, a palladium catalyst such as bis(triphenylphosphine) palladium(II) dichloride, triethylamine, in a suitable solvent such as tetrahydrofuran, acetonitrile or N,N-dimethylformamide, at a temperature ranging from room temperature to 100° C., in classical thermal conditions or in a microwave apparatus.

According to step p) of the present invention, the reaction can be carried out in the presence of a suitable base such as potassium carbonate or potassium hydrate in methanol or ethanol or their mixtures with water or in the presence of DBU in a suitable solvent such as acetonitrile or its mixtures with water, at room temperature. Alternatively the reaction can be carried out with tetrabutylammonium fluoride (TBAF) in a suitable solvent such as dichloromethane, acetonitrile, tetrahydrofuran or 1,4-dioxane at room temperature. Alternatively the reaction can be carried out with silver trifluoromethansulfonate in a suitable solvent such as a mixture of acetone/water/methanol at room temperature.

Another embodiment of the present invention provides the preparation of the compounds of formula (III) wherein R4 is as defined above and R5 is a group -L-R7, wherein R7 is as defined above and L is —NHSO₂—, as per formula (IIID), as shown in the following Scheme 11.

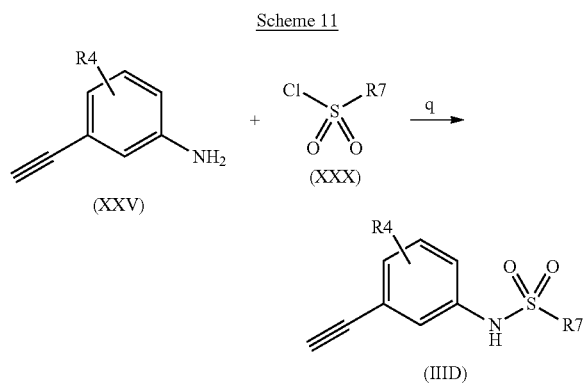

Scheme 11

In the above Scheme 11, R4 and R7 are as defined above.

According to Scheme 11, the compounds of formula (IIID) can be prepared by the following reaction: Step q) reaction of the compounds of formula (XXV), wherein R4 is as defined above, with the compounds of formula (XXX) wherein R7 is as defined above, thus affording the compounds of formula (IIID) wherein R4 and R7 are as defined above.

According to step q) of the present invention, the reaction can be carried out in the presence of a suitable base such as triethylamine, N,N-diisopropyl-N-ethylamine, N-methylmorpholine, 2,6-lutidine or pyridine in a suitable solvent such as diethylether, tetrahydrofuran, 1,4-dioxane at a temperature ranging from 0° C. to reflux.

Another embodiment of the present invention provides the preparation of the compounds of formula (III) wherein R4 is as defined above and R5 is a group -L-R7, wherein R7 is as defined above and L is —SO₂N(Y)—, wherein Y is as defined above, as per formula (IIIE), which is shown in the following Scheme 12.

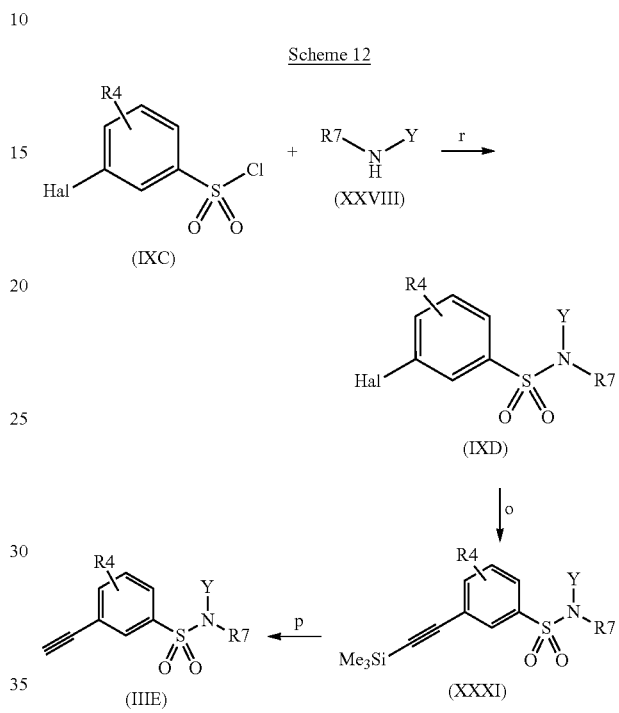

Scheme 12

In the above Scheme 12, R4, Y and R7 are as defined above and Hal is iodine or bromine.

According to Scheme 12, a process for preparation of the compounds of formula (IIIE) comprises the following steps: Step r) reaction of the compounds of formula (IXC), wherein Hal is iodine or bromine and R4 is as defined above, with the compounds of formula (XXVIII) wherein Y and R7 are as defined above, thus obtaining the compounds of formula (IXD) wherein Hal is bromine or iodine and R4, R7 and Y are as defined above;

Step o) submission of the resultant compounds of formula (IXD) to Sonogashira coupling with trimethylsilyl acetylene, thus obtaining the compounds of formula (XXXI) wherein R4, R7 and Y are as defined above;

Step p) removal of trimethylsilyl protecting group from the resultant compounds of formula (XXXI) to afford the compounds of formula (IIIE) wherein R4, R7 and Y are as defined above.

According to step r) of the present invention, the reaction can be carried out in a suitable solvent such as diethylether, tetrahydrofuran, 1,4-dioxane, at a temperature ranging from 0° C. to room temperature.

According to step o) of the present invention, the reaction can be carried out in the presence of cuprous iodide, a palladium catalyst such as bis(triphenylphosphine)palladium(II) dichloride, triethylamine, in suitable solvent such as tetrahydrofuran, acetonitrile or N,N-dimethylformamide, at a temperature ranging from room temperature to 100° C., in classical thermal conditions or in a microwave apparatus.

According to step p) of the present invention, the reaction can be carried out in the presence of a suitable base such as potassium carbonate or potassium hydrate in methanol or ethanol or their mixtures with water or in the presence of DBU in a suitable solvent such as acetonitrile or its mixtures with water, at room temperature. Alternatively the reaction can be carried out with tetrabutylammonium fluoride (TBAF) in a suitable solvent such as dichloromethane, acetonitrile, tetrahydrofuran or 1,4-dioxane at room temperature. Alternatively the reaction can be carried out with silver trifluoromethansulfonate in a suitable solvent such as a mixture of acetone/water/methanol at room temperature.

Another embodiment of the present invention provides the preparation of the compounds of formula (VIII) wherein R1, R2 and R3 are as defined above, as shown in the following Scheme 13.

In the above Scheme 13, R1, R2, R3 and Hal are as defined above.

Scheme 13

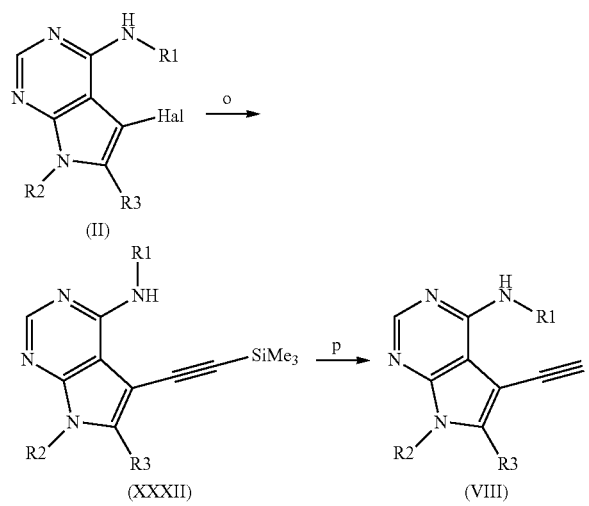

According to Scheme 13, a process for preparation of the compounds of formula (VIII) comprises the following steps:

Step o): Sonogashira coupling of the compounds of formula (II) with trimethylsilylacetylene to obtain the compounds of formula (XXXII), wherein R1, R2 and R3 are as defined above;

Step p): removal of trimethylsilyl group to obtain the compounds of formula (VIII), wherein R1, R2 and R3 are as defined above.

According to Step o) of the present invention, the reaction can be carried out in the presence of cuprous iodide, a palladium catalyst such as bis(triphenylphosphine)palladium(II) dichloride, triethylamine, in suitable solvent such as tetrahydrofuran, acetonitrile or N,N-dimethylformamide, at a temperature ranging from room temperature to 100° C., in classical thermal conditions or in a microwave apparatus.

According to Step p) of the present invention, the reaction can be carried out in the presence of a suitable base such as potassium carbonate or potassium hydrate in methanol or ethanol or their mixtures with water or in the presence of DBU in a suitable solvent such as acetonitrile or its mixtures with water, at room temperature. Alternatively the reaction can be carried out with tetrabutylammonium fluoride (TBAF) in a suitable solvent such as dichloromethane, acetonitrile, tetrahydrofuran or 1,4-dioxane at room temperature. Alternatively the reaction can be carried out with silver trifluoromethansulfonate in a suitable solvent such as a mixture of acetone/water/methanol at room temperature.

When preparing the compounds of formula (I) according to any variants of the process, which are all to be intended as within the scope of the invention, optional functional groups (within the starting materials, the reagents or the intermediates thereof) which could give rise to unwanted side reactions need to be properly protected according to conventional techniques. Likewise, the conversion of these latter into the free deprotected compounds may be carried out according to known procedures.

The compounds of every general formula can be further transformed in other compounds of the same general formula according to methods well known in the literature, as reported in the experimental section.

Some examples of possible transformations may be the followings:

1) transformation of a compound of formula (X) into another compound of formula (X) by introduction of a protecting group, as reported in the Preparation 4;

2) transformation of a compound of formula (XII) into another compound of formula (XII) by protecting group removal and double bond hydrogenation, as reported in the Preparation 7;

3) transformation of a compound of formula (IIB) into another compound of formula (IIB) by acetylation and protecting group removal, as reported in the Preparation 9.

The final compounds may be isolated and purified using conventional procedures, for example chromatography and/or crystallization and salt formation.

The compounds of the formula (I) as defined above can be converted into pharmaceutically acceptable salts. The compounds of the formula (I) as defined above, or the pharmaceutically acceptable salts thereof, can be subsequently formulated with a pharmaceutically acceptable carrier or diluent to provide a pharmaceutical composition.

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resultant from the two or more steps is isolated and purified.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H., —Enantiomers, Racemates, and Resolutions, John Wiley & Sons Inc., New York (N.Y.), 1981.

The starting materials of the process object of the present invention, comprehensive of any possible variant, as well as any reactant thereof, are known compounds and if not commercially available per se may be prepared according to well-known methods or as described in the experimental part below.

PHARMACOLOGY

In Vitro Cell Proliferation Assay

To evaluate the antiproliferative activity of a compound of formula (I) the following human cell lines were used: A2780 ovarian carcinoma; TT and MZ-CRC-1 medullary thyroid carcinoma, harboring a mutated RET-C634W and RET-M918T receptor respectively; LC-2/ad human lung adenocarcinoma, harboring the CCDC6-RET fusion protein. Exponentially growing cells were seeded and incubated at 37° C. in a humidified 5% CO2 atmosphere using appropriate medium supplemented with 10% Fetal Bovine Serum. 24 hours following cell plating, scalar doses of the compounds dissolved in 0.1% DMSO were added to the medium and cells were exposed to drugs for either 72 hours (A2780) or 144 hours (TT, MZ-CRC-1 and LC-2/ad), according to their different proliferation rate. At the end of treatment, cell proliferation was determined by an intracellular ATP monitoring system (CellTiterGlo—Promega), following manufacturer's instructions, and using an Envision instrument (PerkinElmer) as reader. Data obtained from compound versus vehicle treated cells were compared using Assay Explorer (Symyx Technologies Inc) software. IC50 values were calculated using sigmoidal interpolation curve fitting.

In the following Table A the antiproliferative activity of representative compounds of formula (I) on two medullary thyroid carcinoma cell lines expressing the aforementioned mutated forms of RET (TT and MZ-CRC-1) and on one lung adenocarcinoma cell line harboring the aforementioned fusion form of RET (LC-2/ad) is reported. As control, the antiproliferative activity of the same compounds on an unrelated non RET-dependent cell line (A2780) is reported. All these compounds show remarkable activity on RET-driven cellular models with respect to the unrelated ones.

TABLE A

| Cmpd # | A2780 IC$_{50}$ (µM) | TT IC$_{50}$ (µM) (144 h) | LC-2/ad IC$_{50}$ (µM) (144 h) | MZ-CRC-1 IC$_{50}$ (µM) (144 h) |
|---|---|---|---|---|
| 12 | 0.695 | 0.012 | 0.111 | 0.222 |
| 11 | 0.601 | 0.249 | | |
| 59 | 2.141 | 0.036 | 0.048 | 0.040 |
| 36 | 1.728 | 0.053 | 0.058 | 0.166 |
| 31 | 4.453 | 0.111 | | |
| 26 | 3.669 | 0.140 | 0.490 | |
| 24 | 0.137 | 0.003 | 0.066 | 0.024 |
| 9 | 6.905 | 0.865 | | |
| 15 | 4.365 | 0.192 | | |
| 40 | 1.934 | 0.022 | 0.033 | 0.049 |
| 82 | 0.046 | 0.001 | 0.004 | |
| 37 | 6.790 | 0.109 | 0.115 | 0.271 |
| 93 | 4.542 | 0.035 | 0.241 | 0.264 |
| 52 | 3.908 | 0.100 | 0.107 | 0.201 |
| 53 | 0.837 | 0.010 | 0.009 | |
| 51 | 1.591 | 0.016 | 0.019 | |
| 86 | 1.910 | 0.025 | 0.018 | |
| 85 | 1.598 | 0.030 | 0.024 | |
| 88 | 1.519 | 0.052 | 0.048 | |
| 110 | 5.882 | 0.227 | 0.279 | |
| 46 | 4.321 | 0.023 | 0.020 | |
| 89 | 6.690 | 0.136 | 0.127 | |
| 87 | 1.525 | 0.019 | 0.012 | |
| 95 | 2.453 | 0.060 | 0.032 | |
| 99 | 1.795 | 0.017 | 0.019 | |
| 108 | 6.113 | 0.023 | 0.045 | |
| 68 | 7.184 | 0.043 | 0.021 | |
| 70 | >10 | 0.213 | 0.213 | |
| 92 | 4.095 | 0.053 | 0.052 | |
| 54 | 3.292 | 0.020 | 0.053 | 0.068 |
| 58 | 0.539 | 0.004 | 0.004 | |

From all of the above, the novel compounds of formula (I) of the invention appear to be particularly advantageous in the therapy of diseases caused by dysregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g. to humans, can be administered by the usual routes and the dosage level depends upon the age, weight, and conditions of the patient and administration route.

For example, a suitable dosage adopted for oral administration of a compound of formula (I) may range from about 10 to about 1 g per dose, from 1 to 5 times daily. The compounds of the invention can be administered in a variety of dosage forms, e.g. orally, in the form tablets, capsules, sugar or film coated tablets, liquid solutions or suspensions; rectally in the form suppositories; parenterally, e.g. intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g. lactose, dextrose saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine methylcellulose, carboxymethylcellulose or polyvinyl pyrrolidone; disintegrating agents, e.g. starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g. syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g. cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| | |
|---|---|
| g (grams) | mg (milligrams) |
| mL (milliliters) | μL (microliters) |
| mM (millimolar) | mmol (millimoles) |
| μM (micromolar) | $R_t$ (retention time) |
| h (hours) | MHz (Mega-Hertz) |
| mm (millimetres) | Hz (Hertz) |
| M (molar) | min (minutes) |
| mol (moles) | TLC (thin layer chromatography) |
| r.t. (room temperature) | |
| DMAP (dimethylaminopyridine) | TEA (triethylamine) |
| TFA (trifluoroacetic acid) | DME (dimethoxyethane) |
| $Na_2CO_3$ (sodium carbonate) | $Na_2SO_4$ (sodium sulphate) |
| DMF (N,N-dimethylformamide) | $K_2CO_3$ (potassium carbonate) |
| DIPEA (N,N-diisopropyl-N-ethylamine) | DCM (dichloromethane) |
| THF (tetrahydrofuran) | Hex (hexane) |
| MeOH (methanol) | DMSO (dimethylsulfoxide) |
| HOBT (N-hydroxy-benzotriazole) | ESI (electrospray ionization) |
| EDCI (1-ethyl-3-(3-dimethylaminopropyl)carbodiimide hydrochloride) | |
| TBTU (N,N,N',N'-tetramethyl-O-(benzotriazol-1-yl)uronium-tetrafluoroborate) | |

RP-HPLC (reverse phase high performance liquid chromatography) With the aim at better illustrating the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, DCM were obtained from the Aldrich Chemical Company. All reactions involving air- or moisture-sensitive compounds were performed under nitrogen or argon atmosphere. General Purification and Analytical Methods Flash Chromatography was performed on silica gel (Merck grade 9395, 60A).

HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.2 with acetic acid-acetonitrile 95:5), and Mobile phase B was water-acetonitrile (5:95). Gradient from 10 to 90% B in 8 min, hold 90% B 2 min. UV detection at 220 nm and 254 nm. Flow rate 1 mL/min. Injection volume 10 μL. Full scan, mass range from 100 to 800 amu. Capillary voltage was 2.5 KV; source temperature was 120° C.; cone was 10 V. Retention times (HPLC $R_t$) are given in minutes (min) at 220 nm or at 254 nm. Mass are given as m/z ratio.

When necessary, compounds were purified by preparative HPLC on a Waters Symmetry C18 (19×50 mm, 5 μm) column or on a Waters X Terra RP 18 (30×150 mm, 5 μm) column using a Waters preparative HPLC 600 equipped with a 996 Waters PDA detector and a Micromass mod. ZQ single quadrupole mass spectrometer, electron spray ionization, positive mode. Mobile phase A was water/0.1% TFA, and mobile phase B was acetonitrile. Gradient from 10 to 90% B in 8 min, hold 90% B 2 min. Flow rate 20 mL/min. In alternative, mobile phase A was water/0.05% $NH_3$, and mobile phase B was acetonitrile. Gradient from 10 to 100% B in 8 min, hold 100% B 2 min. Flow rate 20 mL/min. $^1$H-NMR spectra were recorded at a constant temperature of 28° C. on a Varian INOVA 400 spectrometer operating at 400.50 MHz and equipped with a 5 mm z-axis PFG Indirect Detection Probe ($^1$H{$^{15}$N-$^{31}$P}).

Chemical shifts were referenced with respect to the residual solvent signals (DMSO-$d_6$: 2.50 ppm for $^1$H, where not otherwise specified). Data are reported as follows: chemical shift (δ), multiplicity (s=singlet, d=doublet, t=triplet, q=quartet, br. s=broad singlet, td=triplet of doublets, dd=doublet of doublets, ddd=doublet of doublets of doublets, m=multiplet, spt=septet), coupling constants (J, Hz) and number of protons.

As formerly reported (M. Colombo, F. R. Sirtori, V. Rizzo, Rapid Commun Mass Spectrom 2004, 18(4), 511-517), ESI(+) high-resolution mass spectra (HRMS) were obtained on a Q-Tof Ultima (Waters, Manchester, UK) mass spectrometer directly connected with an Agilent 1100 micro-HPLC system (Palo Alto, US).

Preparation 1

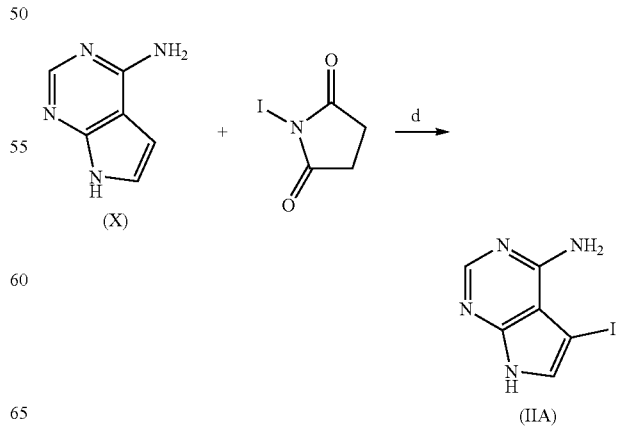

5-iodo-7H-pyrrolo[2,3-d]pyrimidin-4-amine (cmpd (IIA), step d)

Method 1)

100 mg (0.75 mmol) of 7H-pyrrolo[2,3-d]pyrimidin-4-amine were dissolved in 3 mL of DMF and 169 mg (0.75 mmol) of N-iodosuccinimide were added. The solution was stirred at room temperature for 8 h. The solvent was removed under reduced pressure, the residue taken up with dichloromethane and washed with aqueous NaHCO$_3$. The organic layer was dried over Na$_2$SO$_4$ and evaporated to dryness. After a flash-chromatography (DCM/MeOH 95/5) 97 mg (50%) of the title compound were obtained.

Method 2)

1 g (7.46 mmol) of 7H-pyrrolo[2,3-d]pyrimidino-4-amine were dissolved in 15 mL of dry DMF and 1.77 g (7.87 mmol) of N-iodosuccinimide were added in a vial. The mixture was heated at 70° C. for 1 h in a microwave apparatus. After that time the solvent was evaporated and the residue chromatographed on silica gel (DCM/MeOH 95/5), giving, after trituration with diethylether, 1.49 g (77%) of the title compound.

Method 3)

1.3 g (9.7 mmol) of 7H-pyrrolo[2,3-d]pyrimidino-4-amine were suspended in 30 mL of chloroform and 2.18 g (9.7 mmol) of N-iodosuccinimide were added. The reaction mixture was refluxed for 2 hours, then the precipitated collected by filtration. The product was purified by a silica gel column eluted by DCM/MeOH 95/5, affording 2.02 g (80%) of the title compound.

Method 4)

1 g (7.46 mmol) of 7H-pyrrolo[2,3-d]pyrimidino-4-amine were dissolved in 20 mL of dry DMF and 1.25 g (7.46 mmol) of silver acetate followed by 1.8 g (7.46 mmol) of molecular iodine were added. The mixture was stirred at room temperature overnight, then filtered through a celite pad. The filtrate was evaporated and the residue chromatographed on a silica gel column eluted by DCM/MeOH 95/5 affording 970 mg (50%) of the title compound.

$^1$H NMR (600 MHz, DMSO-d$_6$) δ ppm 6.51 (br. s., 2H) 7.35 (s, 1H) 8.05 (s, 1H) 11.93 (br. s., 1H)

HRMS (ESI) calcd for C$_6$H$_5$N$_4$I [M+H]+ 260.9632. found 260.9633.

According to the same methods, but starting from the suitable (XII) derivatives the following compounds (IIB) were prepared:

tert-butyl 4-(4-amino-5-iodo-7H-pyrrolo[2,3-d]pyrimidin-7-yl)piperidine-1-carboxylate (cmpd (IIB), step d')
HPLC-MS: Rt 5.25 min ethyl 4-(4-amino-5-iodo-7H-pyrrolo[2,3-d]pyrimidin-7-yl)piperidine-1-carboxylate (cmpd (IID), step d')
$^1$H NMR (401 MHz, DMSO-d$_6$) ppm 1.18 (t, J=7.08 Hz, 3H) 1.76-1.96 (m, 4H) 2.94 (br. s., 2H) 4.03 (q, J=7.16 Hz, 2H) 4.10 (d, J=11.84 Hz, 2H) 4.61-4.78 (m, 1H) 6.81 (br. s., 2H) 7.63 (s, 1H) 8.11 (s, 1H)
Yield 33%

1-[4-(4-amino-5-iodo-7H-pyrrolo[2,3-d]pyrimidin-7-yl)piperidin-1-yl]ethanone (cmpd (IID), step d')
Yield 22%

5-iodo-7-[1-(methylsulfonyl)piperidin-4-yl]-7H-pyrrolo[2,3-d]pyrimidin-4-amine (cmpd (IID), step d')
Yield 30%.

5-iodo-7-{1-[2-(tetrahydro-2H-pyran-2-yloxy)ethyl]piperidin-4-yl}-7H-pyrrolo[2,3-d]pyrimidin-4-amine (cmpd (IID), step d')

According to the same method, but starting from the suitable (XV) derivatives, the following compounds were prepared:

4-chloro-5-iodo-7-(1-methoxypropan-2-yl)-7H-pyrrolo[2,3-d]pyrimidine (cmpd (XVII, step d)

4-chloro-5-iodo-7-(1,1,1-trifluoropropan-2-yl)-7H-pyrrolo[2,3-d]pyrimidine (cmpd (XVII, step d)

4-chloro-5-iodo-7-(4,4,4-trifluorobutan-2-yl)-7H-pyrrolo[2,3-d]pyrimidine (cmpd (XVII, step d)

tert-butyl 4-(4-chloro-5-iodo-7H-pyrrolo[2,3-d]pyrimidin-7-yl)piperidine-1-carboxylate (cmpd (XVII), step d)

Preparation 2

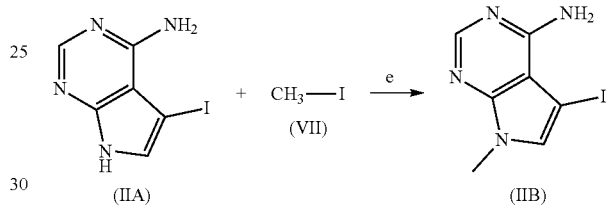

(IIA)     (VII)     (IIB)

7-methyl-7H-pyrrolo[2,3-d]pyrimidin-4-amine (cmpd (IIB), step e)

To a solution of 750 mg (2.88 mmol) of 5-iodo-7H-pyrrolo[2,3-d]pyrimidin-4-amine in 20 mL of dry DMF, 190 µL (3.02 mmol) of methyl iodide and 795 mg (5.76 mmol) of anhydrous potassium carbonate were added. After 8 h the solvent was evaporated, the residue taken up with DCM and washed with water.

The organic layer was dried over anhydrous Na$_2$SO$_4$ and evaporated again to afford 394 mg (50%) of the title compound. HRMS (ESI) calcd for C$_7$H$_7$N$_4$I [M+H]+ 274.9788. found 274.9788.

According to the same method, but employing the suitable alkylating agent and alternatively caesium carbonate as a base, the following compounds were prepared:

5-iodo-7-[2-(tetrahydro-2H-pyran-2-yloxy)ethyl]-7H-pyrrolo[2,3-d]pyrimidin-4-amine (cmpd (IIB), step e)
$^1$H NMR (600 MHz, DMSO-d$_6$) δ ppm 3.64-3.70 (m, 1H) 3.82-3.89 (m, 1H) 4.22-4.37 (m, 2H) 4.52-4.55 (m, 1H) 6.57 (br. s., 2H) 7.44 (s, 1H) 8.08-8.10 (m, 1H)

HRMS (ESI) calcd for C$_{13}$H$_{17}$N$_4$O$_2$I [M+H]+ 389.0469. found 389.0458.
Yield: 82% tert-butyl [2-(4-amino-5-iodo-7H-pyrrolo[2,3-d]pyrimidin-7-yl)ethyl]carbamate (cmpd (IIB), step e)
$^1$H NMR (600 MHz, DMSO-d$_6$) δ ppm 1.33 (s, 10H) 3.26 (q, J=5.62 Hz, 3H) 4.14 (t, J=5.95 Hz, 2H) 6.55 (br. s., 2H) 6.87 (t, J=5.13 Hz, 1H) 7.33 (s, 1H) 8.08 (s, 1H)

HRMS (ESI) calcd for C$_{13}$H$_{18}$N$_5$O$_2$I [M+H]+ 404.0578. found 404.0579.
Yield: 62%

5-iodo-7-(2,2,2-trifluoroethyl)-7H-pyrrolo[2,3-d]pyrimidin-4-amine (cmpd (IIB), step e)

¹H NMR (600 MHz, DMSO-d₆) δ ppm 5.03 (q, J=9.16 Hz, 2H) 6.75 (br. s., 2H) 7.49-7.50 (m, 1H) 8.15 (s, 1H)

HRMS (ESI) calcd for C₈H₆N₄F₃I [M+H]+ 342.9662. found 342.9663.

Yield: 61%

(This compound can be prepared also according to preparation 3, starting from 4-chloro-5-iodo-7-(2,2,2-trifluoroethyl)-7H-pyrrolo[2,3-d]pyrimidine.)

tert-butyl 4-[(4-amino-5-iodo-7H-pyrrolo[2,3-d]pyrimidin-7-yl)methyl]piperidine-1-carboxylate (cmpd (IIB), step e)

¹H NMR (600 MHz, DMSO-d₆) δ ppm 0.98-1.09 (m, 2H) 1.38 (s, 9H) 1.98 (ddt, J=14.95, 7.58, 3.85, 3.85 Hz, 1H) 2.66 (br. s., 1H) 3.89 (d, J=10.07 Hz, 2H) 3.99 (d, J=7.33 Hz, 2H) 6.58 (br. s., 2H) 7.44 (s, 1H) 8.09 (s, 1H)

HRMS (ESI) calcd for C₁₇H₂₄N₅O₂I [M+H]+ 458.1048. found 458.1049.

Yield: 63% tert-butyl [2-(4-{[(E)-(dimethylamino)methylidene]amino}-5-iodo-7H-pyrrolo[2,3-d]pyrimidin-7-yl)ethyl]carbamate (cmpd (IIB), step e)

HRMS (ESI) calcd for C₁₆H₂₃N₆O₂I [M+H]+ 459.1000. found 459.1002.

2-(4-amino-5-iodo-7H-pyrrolo[2,3-d]pyrimidin-7-yl)acetamide (cmpd (IIB), step e)

¹H NMR (401 MHz, DMSO-d₆) δ ppm 4.71-4.75 (m, 2H) 6.57 (br. s., 2H) 7.18 (br. s., 1H) 7.37 (s, 1H) 7.57 (br. s., 1H) 8.07 (s, 1H)

N-[2-(4-amino-5-iodo-7H-pyrrolo[2,3-d]pyrimidin-7-yl)ethyl]formamide (cmpd (IIIB), step e)

¹H NMR (401 MHz, DMSO-d₆) δ ppm 3.46 (q, J=6.10 Hz, 2H) 4.18 (t, J=6.04 Hz, 2H) 6.58 (br. s., 2H) 7.41-7.43 (m, 1H) 7.96 (d, J=1.46 Hz, 1H) 8.05 (br. s., 1H) 8.09 (s, 1H)

According to the same method, but starting from the suitable intermediates (XVI), the following compounds were prepared:

4-chloro-5-iodo-7-(2,2,2-trifluoroethyl)-7H-pyrrolo[2,3-d]pyrimidine (cmpd (XVII), step e)

¹H NMR (401 MHz, DMSO-d₆) δ ppm 5.23 (q, J=9.11 Hz, 2H) 8.05 (s, 1H) 8.74 (s, 1H)

4-chloro-7-(cyclopropylmethyl)-5-iodo-7H-pyrrolo[2,3-d]pyrimidine (cmpd (XVII), step e)

¹H NMR (401 MHz, DMSO-d₆) δ ppm 0.39-0.46 (m, 2H) 0.48-0.55 (m, 2H) 1.27 (d, J=7.81 Hz, 1H) 4.12 (d, J=7.32 Hz, 2H) 8.09 (s, 1H) 8.64 (s, 1H)

4-chloro-5-iodo-7-(2-methoxyethyl)-7H-pyrrolo[2,3-d]pyrimidine (cmpd (XVII), step e)

¹H NMR (401 MHz, DMSO-d₆) δ ppm 3.22 (s, 3H) 3.71 (t, J=5.31 Hz, 2H) 4.40-4.45 (m, 2H) 7.98 (s, 1H) 8.64 (s, 1H)

4-chloro-7-(cyclobutylmethyl)-5-iodo-7H-pyrrolo[2,3-d]pyrimidine (cmpd (XVII), step e)

Yield 94%

4-chloro-7-(cyclohexylmethyl)-5-iodo-7H-pyrrolo[2,3-d]pyrimidine (cmpd (XVII), step e)

Yield 94%

4-chloro-5-iodo-7-methyl-7H-pyrrolo[2,3-d]pyrimidine (cmpd (XVII), step e)

¹H NMR (401 MHz, DMSO-d₆) δ ppm 3.83 (s, 3H) 7.98 (s, 1H) 8.65 (s, 1H)

Yield 63%

4-chloro-7-ethyl-5-iodo-7H-pyrrolo[2,3-d]pyrimidine (cmpd (XVII), step e)

¹H NMR (401 MHz, DMSO-d₆) δ ppm 1.38 (t, J=7.26 Hz, 3H) 4.29 (q, J=7.24 Hz, 2H) 8.06 (s, 1H) 8.64 (s, 1H)

Yield 85%

4-chloro-7-cyclopentyl-5-iodo-7H-pyrrolo[2,3-d]pyrimidine (cmpd (XVII), step e)

¹H NMR (401 MHz, DMSO-d₆) δ ppm 1.61-1.74 (m, 2H) 1.81-2.03 (m, 4H) 2.06-2.22 (m, 2H) 5.04-5.20 (m, 1H) 8.10 (s, 1H) 8.63 (s, 1H)

4-chloro-5-iodo-7-(3,3,3-trifluoropropyl)-7H-pyrrolo[2,3-d]pyrimidine (cmpd (XVII), step e)

4-chloro-7-cyclopropyl-5-iodo-7H-pyrrolo[2,3-d]pyrimidine (cmpd (XVII), step e)

4-chloro-7-cyclobutyl-5-iodo-7H-pyrrolo[2,3-d]pyrimidine (cmpd (XVII), step e)

4-chloro-7-cyclohexyl-5-iodo-7H-pyrrolo[2,3-d]pyrimidine (cmpd (XVII), step e)

2-(4-chloro-5-iodo-7H-pyrrolo[2,3-d]pyrimidin-7-yl)-N,N-dimethylethanamine (cmpd (XVII), step e)

4-chloro-7-(2-chloroethyl)-5-iodo-7H-pyrrolo[2,3-d]pyrimidine (cmpd (XVII), step e)

4-chloro-5-iodo-7-(1-methylpiperidin-3-yl)-7H-pyrrolo[2,3-d]pyrimidine (cmpd (XVII), step e)

4-chloro-5-iodo-7-propyl-7H-pyrrolo[2,3-d]pyrimidine (cmpd (XVII), step e)

¹H NMR (401 MHz, DMSO-d₆) δ ppm 0.81 (t, J=7.45 Hz, 3H) 1.73-1.88 (m, 2H) 4.22 (t, J=7.08 Hz, 2H) 8.04 (s, 1H) 8.63 (s, 1H).

Yield 94%

4-Chloro-5-iodo-7-isobutyl-7H-pyrrolo[2,3-d]pyrimidine (cmpd (XVII), step e)

¹H NMR (401 MHz, DMSO-d₆) δ ppm 0.83 (d, J=6.71 Hz, 6H) 2.09-2.26 (m, 1H) 4.08 (d, J=7.45 Hz, 2H) 8.02 (s, 1H) 8.63 (s, 1H).

Yield 91%

4-Chloro-7-(2-fluoro-ethyl)-5-iodo-7H-pyrrolo[2,3-d]pyrimidine (cmpd (XVII), step e)

¹H NMR (401 MHz, DMSO-d₆) δ ppm 4.49-4.66 (m, 2H) 4.69-4.91 (m, 2H) 8.03 (s, 1H) 8.66 (s, 1H).

Yield 95%.

7-sec-Butyl-4-chloro-5-iodo-7H-pyrrolo[2,3-d]pyrimidine (cmpd (XVII), step e)

¹H NMR (401 MHz, DMSO-d₆) δ ppm 0.67 (t, J=7.38 Hz, 3H) 1.46 (d, J=6.71 Hz, 3H) 1.72-1.98 (m, 2H) 4.62-4.98 (m, 1H) 8.15 (s, 1H) 8.62 (s, 1H).

Yield 88%.

4-Chloro-5-iodo-7-pyridin-4-ylmethyl-7H-pyrrolo[2,3-d]pyrimidine (cmpd (XVII), step e)

¹H NMR (401 MHz, DMSO-d₆) δ ppm 5.54 (s, 2H) 6.93-7.25 (m, 2H) 8.13 (s, 1H) 8.43-8.54 (m, 2H) 8.65 (s, 1H).

Yield 65%.

4-Chloro-5-iodo-7-pyridin-3-ylmethyl-7H-pyrrolo[2,3-d]pyrimidine (cmpd (XVII), step e)

¹H NMR (401 MHz, DMSO-d₆) δ ppm 5.52 (s, 2H) 7.35 (dd, J=7.38, 4.82 Hz, 1H) 7.68 (dt, J=7.93, 1.95 Hz, 1H) 8.15 (s, 1H) 8.48-8.52 (m, 1H) 8.60 (d, J=1.71 Hz, 1H) 8.68 (s, 1H).

Yield 58%

Preparation 3

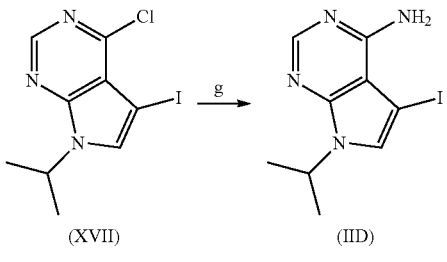

5-iodo-7-(propan-2-yl)-7H-pyrrolo[2,3-d]pyrimidin-4-amine (cmpd (IID), step g)

Method 1)

384 mg (1.2 mmol) of 4-chloro-5-iodo-7-(propan-2-yl)-7H-pyrrolo[2,3-d]pyrimidine were dissolved in 2.80 mL of 1,4-dioxane and 2.31 mL of 30% ammonium hydrate were added. The mixture was stirred in a close bottle at 110° C. overnight, then the solvent evaporated and the residue partitioned between ethyl acetate and water. The organic layer was washed with brine, dried over $Na_2SO_4$ and evaporated again to give 219 mg (60%) of the title compound.

Method 2)

the reaction can be carried out in a microwave apparatus at 100° C. for 4 hours to give the same compound (95%).

Method 3)

The title compound can be prepared also according to preparation 1 starting from of 5-iodo-7H-pyrrolo[2,3-d]pyrimidin-4-amine (87%)

$^1$H NMR (600 MHz, DMSO-$d_6$) δ ppm 1.40 (d, J=6.78 Hz, 6H) 4.89 (quin, J=6.78 Hz, 1H) 6.55 (br. s., 2H) 7.57 (s, 1H) 8.04-8.10 (m, 1H)

HRMS (ESI) calcd for $C_9H_{11}N_4I$ [M+H]+ 303-0101. found 303.0104.

According to the same methods, the following compounds were prepared:

5-iodo-7-(2-methoxyethyl)-7H-pyrrolo[2,3-d]pyrimidin-4-amine (cmpd (IID), step g)

7-(cyclopropylmethyl)-5-iodo-7H-pyrrolo[2,3-d]pyrimidin-4-amine (cmpd (IID), step g)

$^1$H NMR (401 MHz, DMSO-$d_6$) δ ppm 0.35-0.40 (m, 2H) 0.44-0.54 (m, 2H) 1.15-1.29 (m, 1H) 3.95 (d, J=7.08 Hz, 2H) 6.57 (br. s., 2H) 7.52 (s, 1H) 8.09 (s, 1H)

7-(cyclobutylmethyl)-5-iodo-7H-pyrrolo[2,3-d]pyrimidin-4-amine (cmpd (IID), step g)

$^1$H NMR (401 MHz, DMSO-$d_6$) δ ppm 1.59-2.02 (m, 7H) 2.73 (quin, J=7.57 Hz, 1H) 4.12 (d, J=7.45 Hz, 2H) 6.57 (br. s., 2H) 7.39-7.47 (m, 1H) 8.09 (s, 1H)

Yield 71%

7-(cyclohexylmethyl)-5-iodo-7H-pyrrolo[2,3-d]pyrimidin-4-amine (cmpd (IID), step g)

$^1$H NMR (401 MHz, DMSO-$d_6$) δ ppm 0.85-0.99 (m, 2H) 1.00-1.25 (m, 4H) 1.45 (d, J=12.57 Hz, 2H) 1.54-1.68 (m, 3H) 1.79 (ddd, J=11.17, 7.51, 3.78 Hz, 1H) 3.94 (d, J=7.20 Hz, 2H) 6.56 (br. s., 2H) 7.43 (s, 1H) 8.08 (s, 1H)

Yield 74%

5-iodo-7-methyl-7H-pyrrolo[2,3-d]pyrimidin-4-amine (cmpd (IID), step g)

$^1$H NMR (401 MHz, DMSO-$d_6$) δ ppm 3.67 (s, 3H) 6.19-6.84 (m, 2H) 7.41 (s, 1H) 8.10 (s, 1H)

Yield 58%

7-ethyl-5-iodo-7H-pyrrolo[2,3-d]pyrimidin-4-amine (cmpd (IID), step g)

$^1$H NMR (401 MHz, DMSO-$d_6$) δ ppm 1.31 (t, J=7.26 Hz, 3H) 4.13 (d, J=7.20 Hz, 2H) 6.38-6.72 (m, 2H) 7.47-7.50 (m, 1H) 8.09 (s, 1H)

Yield 87%

7-cyclopentyl-5-iodo-7H-pyrrolo[2,3-d]pyrimidin-4-amine (cmpd (IID), step g)

$^1$H NMR (401 MHz, DMSO-$d_6$) δ ppm 1.52-1.73 (m, 2H) 1.75-1.91 (m, 4H) 1.98-2.16 (m, 2H) 4.90-5.06 (m, 1H) 6.55 (br. s., 2H) 7.52 (s, 1H) 8.08 (s, 1H)

5-iodo-7-(3,3,3-trifluoropropyl)-7H-pyrrolo[2,3-d]pyrimidin-4-amine (cmpd (IID), step g)

7-cyclopropyl-5-iodo-7H-pyrrolo[2,3-d]pyrimidin-4-amine (cmpd (IID), step g)

7-cyclobutyl-5-iodo-7H-pyrrolo[2,3-d]pyrimidin-4-amine (cmpd (IID), step g)

7-cyclohexyl-5-iodo-7H-pyrrolo[2,3-d]pyrimidin-4-amine (cmpd (IID), step g)

7-[2-(dimethylamino)ethyl]-5-iodo-7H-pyrrolo[2,3-d]pyrimidin-4-amine (cmpd (IID), step g)

5-iodo-7-(1,1,1-trifluoropropan-2-yl)-7H-pyrrolo[2,3-d]pyrimidin-4-amine (cmpd (IID), step g)

5-iodo-7-(4,4,4-trifluorobutan-2-yl)-7H-pyrrolo[2,3-d]pyrimidin-4-amine (cmpd (IID), step g)

5-iodo-7-(1-methylpiperidin-3-yl)-7H-pyrrolo[2,3-d]pyrimidin-4-amine (cmpd (IID), step g)

5-Iodo-7-propyl-7H-pyrrolo[2,3-d]pyrimidin-4-ylamine (cmpd (IID), step g)

$^1$H NMR (401 MHz, DMSO-$d_6$) δ ppm 0.80 (t, J=7.38 Hz, 3H) 1.74 (sxt, J=7.30 Hz, 2H) 4.06 (t, J=7.08 Hz, 2H) 6.56 (br. s., 2H) 7.47 (s, 1H) 8.08 (s, 1H).

Yield 65%.

5-Iodo-7-isobutyl-7H-pyrrolo[2,3-d]pyrimidin-4-ylamine (cmpd (IID), step g)

$^1$H NMR (401 MHz, DMSO-$d_6$) δ ppm 0.81 (d, J=6.71 Hz, 6H) 2.12 (dt, J=13.70, 7.00 Hz, 1H) 3.91 (d, J=7.32 Hz, 2H) 6.56 (br. s., 2H) 7.45 (s, 1H) 8.08 (s, 1H).

Yield 85%.

7-(2-Fluoro-ethyl)-5-iodo-7H-pyrrolo[2,3-d]pyrimidin-4-ylamine (cmpd (IID), step g)

$^1$H NMR (401 MHz, DMSO-$d_6$) δ ppm 4.34-4.50 (m, 2H) 4.64-4.82 (m, 2H) 6.61 (br. s., 2H) 7.47 (s, 1H) 8.10 (s, 1H).

Yield 80%.

7-sec-Butyl-5-iodo-7H-pyrrolo[2,3-d]pyrimidin-4-ylamine (cmpd (IID), step g)

$^1$H NMR (401 MHz, DMSO-$d_6$) δ ppm 0.67 (t, J=7.38 Hz, 3H) 1.39 (d, J=6.84 Hz, 3H) 1.70-1.88 (m, 2H) 4.66 (dt, J=8.42, 6.53 Hz, 1H) 6.54 (br. s., 2H) 7.55 (s, 1H) 8.07 (s, 1H).

Yield 77%.

5-Iodo-7-(3-methyl-oxetan-3-ylmethyl)-7H-pyrrolo[2,3-d]pyrimidin-4-ylamine (cmpd (IID), step g)

$^1$H NMR (401 MHz, DMSO-$d_6$) δ ppm 1.15 (s, 3H) 4.19 (d, J=5.86 Hz, 2H) 4.32 (s, 2H) 4.59 (d, J=5.98 Hz, 2H) 6.61 (br. s., 2H) 7.44-7.57 (m, 1H) 8.10 (s, 1H).

Yield 62%.

5-Iodo-7-(1-methyl-pyrrolidin-3-yl)-7H-pyrrolo[2,3-d]pyrimidin-4-ylamine (cmpd (IID), step g)

Yield 74%.

5-Iodo-7-pyridin-4-ylmethyl-7H-pyrrolo[2,3-d]pyrimidin-4-ylamine (cmpd (IID), step g)

$^1$H NMR (401 MHz, DMSO-$d_6$) δ ppm 5.37 (s, 2H) 6.67 (br. s., 2H) 7.08-7.14 (m, 2H) 7.57 (s, 1H) 8.10 (s, 1H) 8.46-8.51 (m, 2H).

Yield 93%.

5-Iodo-7-pyridin-3-ylmethyl-7H-pyrrolo[2,3-d]pyrimidin-4-ylamine (cmpd (IID), step g)

$^1$H NMR (401 MHz, DMSO-$d_6$) δ ppm 5.36 (s, 2H) 6.64 (br. s., 2H) 7.34 (dd, J=7.75, 4.82 Hz, 1H) 7.59 (s, 1H) 7.63 (dt, J=7.81, 1.95 Hz, 1H) 8.13 (s, 1H) 8.47 (d, J=3.78 Hz, 1H) 8.54 (s, 1H).

Yield 80%.

5-iodo-7-(1-methoxypropan-2-yl)-7H-pyrrolo[2,3-d]pyrimidin-4-amine (cmpd (IID), step g)

Yield 78%

5-iodo-7-(tetrahydro-2H-pyran-4-yl)-7H-pyrrolo[2,3-d]pyrimidin-4-amine (cmpd (IID), step g)

tert-butyl 4-(4-amino-5-iodo-7H-pyrrolo[2,3-d]pyrimidin-7-yl)piperidine-1-carboxylate (cmpd (IID), step g)
7-ethyl-5-iodo-6-methyl-7H-pyrrolo[2,3-d]pyrimidin-4-amine (cmpd (IID), step g)

$^1$H NMR (401 MHz, DMSO-d$_6$) δ ppm 1.16-1.25 (m, 3H) 2.38 (s, 3H) 4.20 (q, J=7.12 Hz, 2H) 6.49 (br. s., 2H) 8.06 (s, 1H).

According to the same method, but employing methylamine in place of ammonium hydrate, the following compound was prepared:
5-iodo-N-methyl-7-(propan-2-yl)-7H-pyrrolo[2,3-d]pyrimidin-4-amine (cmpd (IID), step g)

$^1$H NMR (401 MHz, DMSO-d$_6$) δ ppm 1.37-1.44 (m, 6H) 3.02 (d, J=4.76 Hz, 3H) 4.82-4.98 (m, 1H) 6.35 (d, J=4.64 Hz, 1H) 7.55 (s, 1H) 8.19 (s, 1H)

Preparation 4

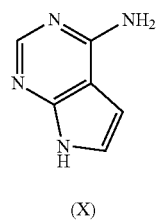 + 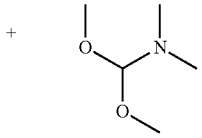 →

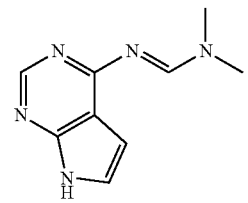

(X)

N,N-dimethyl-N'-7H-pyrrolo[2,3-d]pyrimidin-4-yl-imidoformamide (cmpd (X))

To a solution of 200 mg (1.49 mmol) of 7H-pyrrolo[2,3-d]pyrimidin-4-amine in 4 mL of DMF, 235 μL of dimethylformamide dimethyl acetal were added. The mixture was stirred at room temperature overnight. The solvent was then removed in vacuo and the residue taken up with DCM, washed with brine, dried over anhydrous Na$_2$SO$_4$ and evaporated to dryness. The crude was triturated with diisopropylether and filtered, to afford 204 mg (73%) of the title compound.

$^1$H NMR (600 MHz, DMSO-d$_6$) δ ppm 3.10 (s, 3H) 3.16 (s, 3H) 6.45 (dd, J=3.39, 1.92 Hz, 1H) 7.21 (dd, J=3.11, 2.38 Hz, 1H) 8.28 (s, 1H) 8.79 (s, 1H) 11.60 (br. s., 1H)

HRMS (ESI) calcd for C$_9$H$_{11}$N$_5$ [M+H]+ 190.1087. found 190.1085.

Analogously the following compound was prepared, starting from the corresponding amino derivative:
N'-(5-iodo-7H-pyrrolo[2,3-d]pyrimidin-4-yl)-N,N-dimethylimidoformamide (cmpd (X))

$^1$H NMR (600 MHz, DMSO-d$_6$) δ ppm 3.16-3.19 (m, 3H) 3.22 (s, 3H) 7.41 (s, 1H) 8.27 (s, 1H) 8.80 (s, 1H) 11.96 (br. s., 1H)

HRMS (ESI) calcd for C$_9$H$_{10}$N$_5$I [M+H]+ 316.0054. found 316.0062.

Yield: 84%

Preparation 5

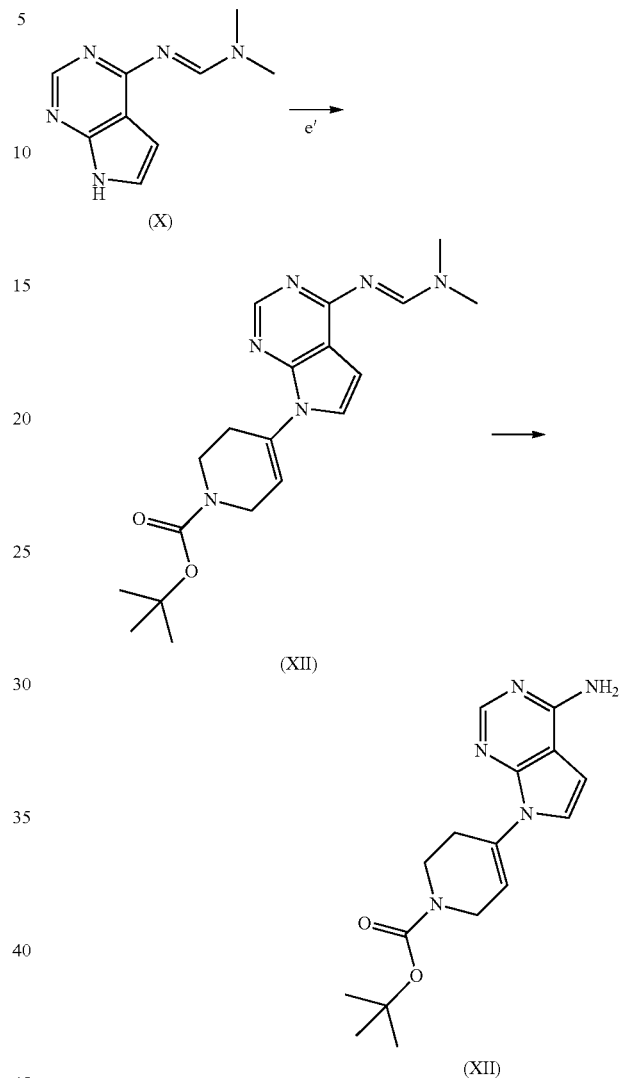

tert-butyl 4-(4-amino-7H-pyrrolo[2,3-d]pyrimidin-7-yl)-3,6-dihydropyridine-1(2H)-carboxylate (cmpd (XII)

To a solution of 100 mg (0.53 mmol) of N,N-dimethyl-N'-7H-pyrrolo[2,3-d]pyrimidin-4-ylimidoformamide in 4 mL of N,N-dimethylacetamide, 198 mg (0.64 mmol) of tert-butyl 4-(4,4,5,5-tetramethyl-1,3,2-dioxaborolan-2-yl)-3,6-dihydropyridine-1(2H)-carboxylate, 103 mg (0.64 mmol) of copper acetate, 100 mg (0.64 mmol) of 2,2'-bipyridyl and 169 mg (1.59 mmol) of anhydrous sodium carbonate were added consecutively. The mixture was stirred at 90° C. for 2 h, then diluted with DCM and washed three times with water. The organic phase was dried over Na$_2$SO$_4$ and evaporated to dryness, giving tert-butyl 4-(4-{[(E)-(dimethylamino)methylidene]amino}-7H-pyrrolo[2,3-d]pyrimidin-7-yl)-3,6-dihydropyridine-1(2H)-carboxylate.

HPLC-MS: R$_t$. 4.70 min

The last intermediate, without any further purification, was dissolved in 4 mL of ethanol and 72 μL (1.06 mmol) of ethylendiamine were added. The resulting solution was refluxed under stirring for 16 h. The solvent was evaporated, the residue re-dissolved in DCM and washed with water. The organic layer was dried over $Na_2SO_4$ and evaporated again. The crude was finally flash-chromatographed on silica gel (DCM-MeOH 95/5) affording, after trituration with diethylether, 80 mg (48% over 2 steps) of the title compound.

$^1$H NMR (600 MHz, DMSO-$d_6$) δ ppm 1.44 (s, 9H) 2.74 (br. s., 2H) 3.61 (t, J=5.68 Hz, 2H) 4.04 (br. s., 2H) 6.22 (br. s., 1H) 6.62 (d, J=3.66 Hz, 1H) 7.03 (br. s., 2H) 7.25 (d, J=3.66 Hz, 1H) 8.06 (s, 1H)

HRMS (ESI) calcd for $C_{16}H_{21}N_5O_2$ [M+H]+ 316.1768. found 316.1765.

The same compound can be prepared starting from non protected 7H-pyrrolo[2,3-d]pyrimidin-4-amine (X).

Analogously, but employing the suitable boronate derivatives as reagents, the following compounds were prepared:
7-(3,6-dihydro-2H-pyran-4-yl)-7H-pyrrolo[2,3-d]pyrimidin-4-amine (cmpd (XII), step e')

$^1$H NMR (401 MHz, DMSO-$d_6$) δ ppm 2.74 (dtd, J=5.49, 2.75, 2.75, 1.46 Hz, 2H) 3.87 (t, J=5.55 Hz, 2H) 4.26 (q, J=2.81 Hz, 2H) 6.32-6.40 (m, 1H) 6.63 (d, J=3.66 Hz, 1H) 7.03 (s, 2H) 7.27 (d, J=3.66 Hz, 1H) 8.07 (s, 1H).

ethyl 4-(4-amino-7H-pyrrolo[2,3-d]pyrimidin-7-yl)-3,6-dihydropyridine-1(2H)-carboxylate (cmpd (XII), step e')

1-[4-(4-amino-7H-pyrrolo[2,3-d]pyrimidin-7-yl)-3,6-dihydropyridin-1(2H)-yl]ethanone (cmpd (XII), step e')

$^1$H NMR (401 MHz, DMSO-$d_6$) δ ppm 2.07 (d, J=11.47 Hz, 3H) 2.68-2.88 (m, 2H) 3.71 (dt, J=12.30, 6.00 Hz, 2H) 4.07-4.21 (m, 2H) 6.15-6.33 (m, 1H) 6.63 (d, J=3.66 Hz, 1H) 7.04 (br. s., 2H) 7.25 (dd, J=6.41, 3.60 Hz, 1H) 8.07 (d, J=2.44 Hz, 1H)

7-[1-(methylsulfonyl)-1,2,3,6-tetrahydropyridin-4-yl]-7H-pyrrolo[2,3-d]pyrimidin-4-amine (cmpd (XII), step e')

$^1$H NMR (401 MHz, DMSO-$d_6$) δ ppm 2.89 (d, J=1.59 Hz, 2H) 2.97 (s, 3H) 3.46 (t, J=5.80 Hz, 2H) 3.91 (q, J=2.73 Hz, 2H) 6.32 (t, J=3.54 Hz, 1H) 6.64 (d, J=3.54 Hz, 1H) 7.05 (s, 2H) 7.27 (d, J=3.54 Hz, 1H) 8.07 (s, 1H)

According to the same method, but employing the suitable boronate derivatives and starting from 5-iodo-7H-pyrrolo[2,3-d]pyrimidin-4-amine, the following compounds were prepared:

5-iodo-7-(pyridin-4-yl)-7H-pyrrolo[2,3-d]pyrimidin-4-amine (cmpd (XII), step e')

5-iodo-7-(pyridin-3-yl)-7H-pyrrolo[2,3-d]pyrimidin-4-amine (cmpd (XII), step e')

5-iodo-7-(3-methoxyphenyl)-7H-pyrrolo[2,3-d]pyrimidin-4-amine (cmpd (XII), step e')

$^1$H NMR (401 MHz, DMSO-$d_6$) δ ppm 3.82 (s, 3H) 6.76 (br. s., 2H) 6.94 (ddd, J=7.93, 2.38, 1.40 Hz, 1H) 7.35-7.39 (m, 2H) 7.40-7.45 (m, 1H) 7.88 (s, 1H) 8.16 (s, 1H)

5-iodo-7-(1-methyl-1H-pyrazol-4-yl)-7H-pyrrolo[2,3-d]pyrimidin-4-amine (cmpd (XII), step e')

$^1$H NMR (401 MHz, DMSO-$d_6$) δ ppm 3.87-3.91 (m, 3H) 6.60-6.83 (m, 2H) 7.81 (s, 1H) 7.94 (s, 1H) 8.17 (s, 1H) 8.31 (s, 1H)

7-(furan-2-yl)-5-iodo-7H-pyrrolo[2,3-d]pyrimidin-4-amine (cmpd (XII), step e')

$^1$H NMR (401 MHz, DMSO-$d_6$) δ ppm 6.76 (d, J=19.77 Hz, 2H) 7.21 (dd, J=2.01, 0.79 Hz, 1H) 7.77 (t, J=1.89 Hz, 1H) 7.89 (s, 1H) 8.21 (s, 1H) 8.38 (dd, J=1.71, 0.85 Hz, 1H)

The boronate derivatives employed in preparation 5 are commercial products or can be prepared according to preparation 6.

Preparation 6

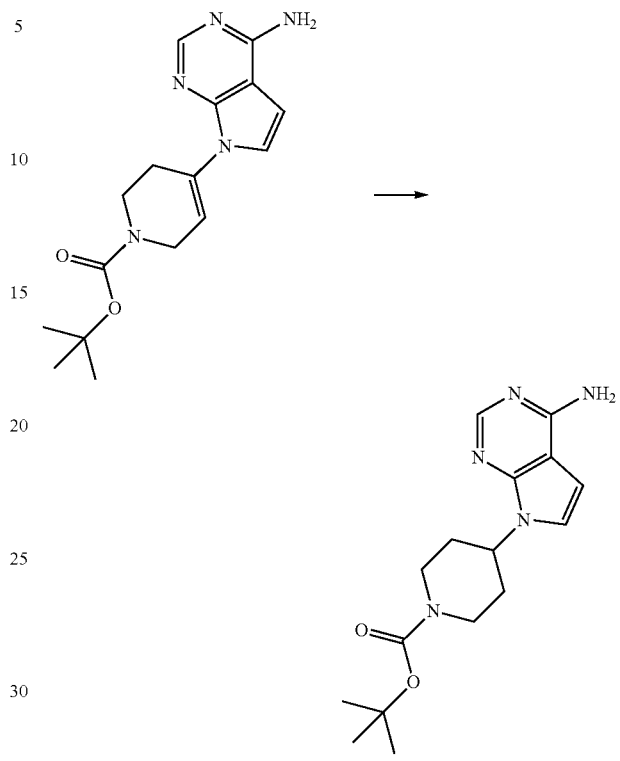

tert-butyl 4-(4-amino-7H-pyrrolo[2,3-d]pyrimidin-7-yl)piperidine-1-carboxylate (cmpd (XII), step e')

To a solution of 80 mg (0.25 mmol) of tert-butyl 4-(4-amino-7H-pyrrolo[2,3-d]pyrimidin-7-yl)-3,6-dihydropyridine-1(2H)-carboxylate in 5 mL of methanol, 158 mg (2.5 mmol) of ammonium formate and 8 mg of palladium on charcoal 10% were added under argon atmosphere. The reaction mixture was refluxed for 8 h, then the same amount of reactant and catalyst were added and the suspension heated for further 4 h. The mixture was then filtered through a celite pad and the solvent evaporated. The residue was partitioned between DCM and water. The organic phase was separated, dried over $Na_2SO_4$ end evaporated again, affording, after trituration with diisopropylether, 60 mg (76%) of the title compound.

$^1$H NMR (600 MHz, DMSO-$d_6$) δ ppm 1.43 (s, 9H) 1.81-1.93 (m, 4H) 2.76-3.01 (m, 2H) 4.10 (br. s., 2H) 4.66 (tt, J=10.69, 5.24 Hz, 1H) 6.52 (d, J=3.48 Hz, 1H) 6.91 (br. s., 2H) 7.26 (d, J=3.66 Hz, 1H) 8.03 (s, 1H)

HRMS (ESI) calcd for $C_{16}H_{23}N_5O_2$ [M+H]+ 318-1925. found 318.1922.

Analogously the following compound was prepared:
7-(tetrahydro-2H-pyran-4-yl)-7H-pyrrolo[2,3-d]pyrimidin-4-amine (cmpd (XII), step e')

$^1$H NMR (600 MHz, DMSO-$d_6$) δ ppm 1.81 (dd, J=12.36, 2.29 Hz, 2H) 1.98-2.10 (m, 2H) 3.50 (t, J=11.26 Hz, 2H) 3.98 (dd, J=11.36, 4.03 Hz, 2H) 4.65-4.79 (m, 1H) 6.54 (d, J=3.48 Hz, 1H) 6.91 (br. s., 2H) 7.27 (d, J=3.48 Hz, 1H) 8.04 (s, 1H)

HRMS (ESI) calcd for $C_{11}H_{14}N_4O$ [M+H]+ 219.1241. found 219.1247.

Yield: 18%.

ethyl 4-(4-amino-7H-pyrrolo[2,3-d]pyrimidin-7-yl)piperidine-1-carboxylate (cmpd (XII), step e')

¹H NMR (401 MHz, DMSO-d₆) δ ppm 1.16-1.24 (m, 3H) 1.75-1.98 (m, 4H) 2.85-3.10 (m, 2H) 4.06 (q, J=7.08 Hz, 2H) 4.14 (d, J=13.30 Hz, 2H) 4.69 (tt, J=10.80, 5.25 Hz, 1H) 6.52 (d, J=3.54 Hz, 1H) 6.91 (s, 2H) 7.26 (d, J=3.54 Hz, 1H) 8.04 (s, 1H)

1-[4-(4-amino-7H-pyrrolo[2,3-d]pyrimidin-7-yl)piperidin-1-yl]ethanone (cmpd (XII), step e')

7-[1-(methylsulfonyl)piperidin-4-yl]-7H-pyrrolo[2,3-d]pyrimidin-4-amine (cmpd (XII), step e')

¹H NMR (401 MHz, DMSO-d₆) δ ppm 1.92-2.01 (m, 2H) 2.08 (qd, J=12.31, 4.09 Hz, 2H) 2.93 (s, 3H) 2.94-3.00 (m, 2H) 3.71 (d, J=12.08 Hz, 2H) 4.55-4.71 (m, 1H) 6.54 (d, J=3.54 Hz, 1H) 6.93 (s, 2H) 7.29 (d, J=3.66 Hz, 1H) 8.04 (s, 1H)

Preparation 7

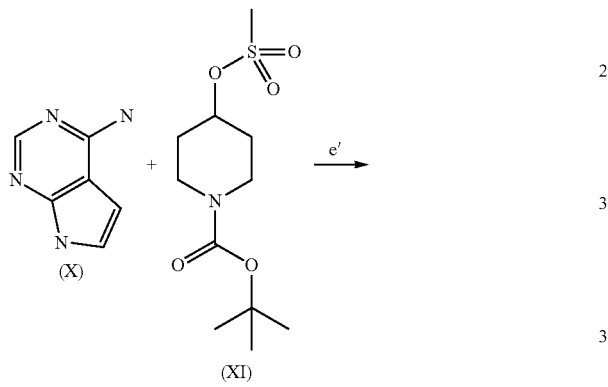

tert-butyl 4-(4-amino-7H-pyrrolo[2,3-d]pyrimidin-7-yl)piperidine-1-carboxylate (cmpd (XII), step e')

500 mg (3.7 mmol) of 7H-pyrrolo[2,3-d]pyrimidin-4-amine were dissolved in 40 mL of dry DMF and 1.03 g (3.7 mmol) of tert-butyl 4-[(methylsulfonyl)oxy]piperidine-1-carboxylate were added, followed by 3.87 g (3.7 mmol) of caesium carbonate, under argon atmosphere. The mixture was heated in a microwave apparatus at 100° C. for 4 hours, then the solvent removed under vacuum. The residue was taken up with dicholomethane and washed with brine. The organic layer was dried over Na₂SO₄ and evaporated to give, after trituration with diethylether, 420 mg of the title compound. (36%)

This compound can also be prepared by a process comprising preparations 5 and 6.

According to the same method, but employing the suitable mesyl or tosyl derivative as reactant and starting from 4-chloro-7H-pyrrolo[2,3-d]pyrimidine, the following compounds were prepared:

4-chloro-7-(1-methoxypropan-2-yl)-7H-pyrrolo[2,3-d]pyrimidine (cmpd (XV), step e)

Yield 58%

According to the same method, but employing the suitable mesilate or tosylate derivatives as alkylating agents, the following compounds were prepared:

tert-butyl 4-(4-chloro-7H-pyrrolo[2,3-d]pyrimidin-7-yl)piperidine-1-carboxylate (cmpd (XV), step e)

4-chloro-7-(1,1,1-trifluoropropan-2-yl)-7H-pyrrolo[2,3-d]pyrimidine (cmpd (XV), step e)

4-chloro-7-(4,4,4-trifluorobutan-2-yl)-7H-pyrrolo[2,3-d]pyrimidine (cmpd (XV), step e)

According to the same method, but starting from 4-chloro-5-iodo-7H-pyrrolo[2,3-d]pyrimidine, the following compounds were prepared:

4-Chloro-5-iodo-7-(3-methyl-oxetan-3-ylmethyl)-7H-pyrrolo[2,3-d]pyrimidine (cmpd (XVII), step e)

¹H NMR (401 MHz, DMSO-d₆) δ ppm 1.10-1.20 (m, 3H) 4.22 (d, J=6.10 Hz, 2H) 4.50 (s, 2H) 4.60 (d, J=6.10 Hz, 2H) 8.05 (s, 1H) 8.65 (s, 1H).

4-Chloro-5-iodo-7-(1-methyl-pyrrolidin-3-yl)-7H-pyrrolo[2,3-d]pyrimidine (cmpd (XVII), step e)

¹H NMR (401 MHz, DMSO-d₆) δ ppm 2.84 (d, J=8.06 Hz, 1H) 3.02 (dt, J=8.48, 4.30 Hz, 1H) 5.38 (td, J=6.23, 3.42 Hz, 1H) 8.04 (s, 1H) 8.63 (s, 1H).

Yield 37%.

4-chloro-5-iodo-7-(tetrahydro-2H-pyran-4-yl)-7H-pyrrolo[2,3-d]pyrimidine (cmpd (XVII), step e)

Preparation 8

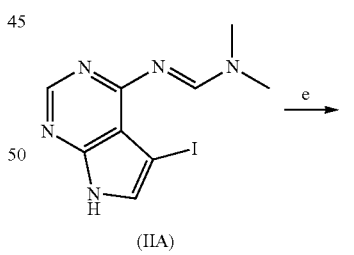

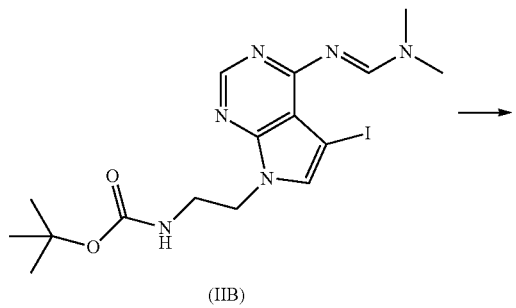

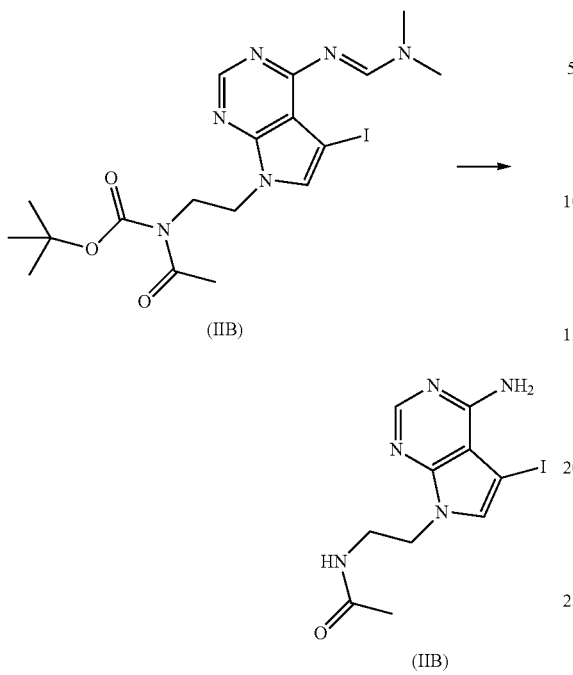

N-[2-(4-amino-5-iodo-7H-pyrrolo[2,3-d]pyrimidin-7-yl)ethyl]acetamide (cmpd (IIB), step e)

To a solution of 242 mg (0.77 mmol) of N'-(5-iodo-7H-pyrrolo[2,3-d]pyrimidin-4-yl)-N,N-dimethylimidoformamide (prepared as described in preparation 3) in 4 mL of dry DMF, 211 mg (1.54 mmol) of anhydrous $K_2CO_3$ and 229 mg (1.03 mmol) of N-tert-butoxycarbonylethyl bromide were added. The mixture was stirred at room temperature for 24 h. The solvent was removed in vacuo, the residue taken up with ethylacetate and washed with water. The organic layer was dried over $Na_2SO_4$ and evaporated, giving tert-butyl [2-(4-{[(E)-(dimethylamino)methylidene]amino}-5-iodo-7H-pyrrolo[2,3-d]pyrimidin-7-yl)ethyl]carbamate, that was used in the next step, without any further purification.

The last intermediate (50 mg, 0.11 mmol) was dissolved in 5 mL of dry THF, under argon atmosphere, and 13 mg (0.13 mmol) of NaH 60% in mineral oil were added. After 15 min. at room temperature 9 µL (0.12 mmol) of acetyl chloride were added to the mixture, that was maintained under stirring for 8 h. Water was then added dropwise and the mixture was partitioned between DCM and water. The organic phase was separated, dried over $Na_2SO_4$ and evaporated, to afford tert-butyl acetyl[2-(4-{[(E)-(dimethylamino)methylidene]amino}-5-iodo-7H-pyrrolo[2,3-d]pyrimidin-7-yl)ethyl]carbamate. The last compound was finally dissolved in 5 mL of dry DCM and 2 mL of TFA were added. The reaction mixture was stirred at room temperature overnight and evaporated to dryness. The residue was re-dissolved in DCM and washed with aqueous $NaHCO_3$. The organic layer was dried over $Na_2SO_4$ and evaporated, to give the title compound (25% over 3 steps).

Preparation 9

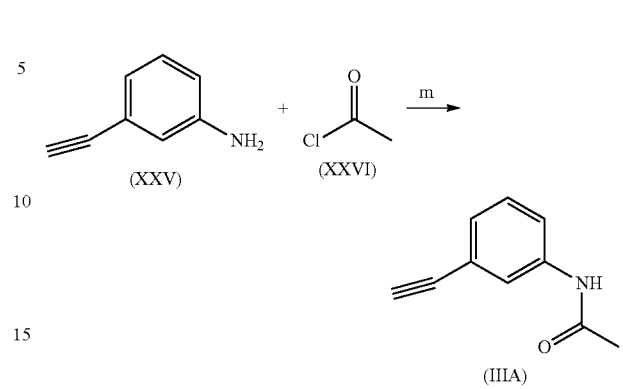

N-(3-ethynylphenyl)acetamide (cmpd (IIIA), step m)

To a solution of 113 µL (1 mmol) of 3-aminophenylacetylene and 150 µL of TEA (10 mmol) in 4 mL of dry DCM, 93 µL (1.3 mmol) of acetyl chloride were added. The mixture was stirred at room temperature for 1 h. The solvent was then evaporated, the residue re-dissolved in ethylacetate and washed with brine. The organic phase was dried over $Na_2SO_4$ and evaporated to give, after trituration with diisopropylether, 150 mg (94%) of the title compound.
$^1$H NMR (600 MHz, DMSO-$d_6$) δ ppm 2.04 (s, 3H) 4.14 (s, 1H) 7.13 (d, J=7.69 Hz, 1H) 7.30 (t, J=7.88 Hz, 1H) 7.53 (d, J=8.06 Hz, 1H) 7.76 (s, 1H) 10.01 (br. s., 1H)
HRMS (ESI) calcd for $C_{10}H_9NO$ [M+H]+ 160.0757. found 160.0755.

Analogously the following compounds were prepared:
N-(3-ethynylphenyl)cyclopropanecarboxamide (cmpd (IIIA), step m)
$^1$H NMR (600 MHz, DMSO-$d_6$) δ ppm 0.76-0.83 (m, 4H) 1.71-1.80 (m, 1H) 4.14 (s, 1H) 7.12 (dt, J=7.60, 1.14 Hz, 1H) 7.30 (t, J=7.97 Hz, 1H) 7.56 (dd, J=8.24, 1.10 Hz, 1H) 7.77 (s, 1H) 10.27 (s, 1H)
HRMS (ESI) calcd for $C_{12}H_{11}NO$ [M+H]+ 186.0914. found 186.0914.
Yield: 70%

N-(3-ethynylphenyl)benzamide (cmpd (IIIA), step m)
$^1$H NMR (600 MHz, DMSO-$d_6$) δ ppm 4.18 (s, 1H) 7.21 (d, J=7.69 Hz, 1H) 7.37 (t, J=7.88 Hz, 1H) 7.52-7.56 (m, 2H) 7.59-7.63 (m, 1H) 7.80 (dd, J=8.33, 1.01 Hz, 1H) 7.91-7.98 (m, 3H) 10.32 (s, 1H)
HRMS (ESI) calcd for $C_{15}H_{11}NO$ [M+H]+ 222.0914. found 222.0910.
Yield: 95%

N-(3-ethynylphenyl)-3-(trifluoromethyl)benzamide (cmpd (IIIA), step m)
$^1$H NMR (600 MHz, DMSO-$d_6$) δ ppm 4.20 (s, 1H) 7.24 (dt, J=7.69, 1.19 Hz, 1H) 7.40 (t, J=7.97 Hz, 1H) 7.75-7.83 (m, 2H) 7.92-7.94 (m, 1H) 7.98 (d, J=7.69 Hz, 1H) 8.26 (d, J=7.88 Hz, 1H) 8.29 (s, 1H) 10.53 (s, 1H)
HRMS (ESI) calcd for $C_{16}H_{10}NOF_3$ [M+H]+ 290.0787. found 290.0788.
Yield: 85%

N-(3-ethynylphenyl)-4-(trifluoromethyl)benzamide (cmpd (IIIA), step m)
$^1$H NMR (600 MHz, DMSO-$d_6$) δ ppm 4.20 (s, 1H) 7.24 (dt, J=7.69, 1.19 Hz, 1H) 7.39 (t, J=7.88 Hz, 1H) 7.80 (dd, J=8.24, 1.10 Hz, 1H) 7.91-7.96 (m, 3H) 8.15 (d, J=8.06 Hz, 2H) 10.53 (s, 1H)

HRMS (ESI) calcd for $C_{16}H_{10}NOF_3$ [M+H]+ 290.0787. found 290.0789.

Yield: 90%

3-chloro-N-(3-ethynylphenyl)benzamide (cmpd (IIIA), step m)

$^1$H NMR (600 MHz, DMSO-$d_6$) δ ppm 4.19 (s, 1H) 7.23 (dt, J=7.69, 1.19 Hz, 1H) 7.38 (t, J=7.97 Hz, 1H) 7.56-7.60 (m, 1H) 7.68 (ddd, J=8.06, 2.11, 1.01 Hz, 1H) 7.79 (dt, J=7.23, 1.05 Hz, 1H) 7.91 (dq, J=7.72, 0.91 Hz, 1H) 7.93 (t, J=1.65 Hz, 1H) 8.00 (t, J=1.74 Hz, 1H) 10.41 (s, 1H)

HRMS (ESI) calcd for $C_{15}H_{10}NOCl$ [M+H]+ 256.0524. found 256.0522.

Yield: 90%

4-chloro-N-(3-ethynylphenyl)benzamide (cmpd (IIIA), step m)

$^1$H NMR (600 MHz, DMSO-$d_6$) δ ppm 4.18 (s, 1H) 7.22 (dt, J=7.65, 1.21 Hz, 1H) 7.38 (t, J=7.97 Hz, 1H) 7.59-7.63 (m, 2H) 7.76-7.79 (m, 1H) 7.93 (t, J=1.65 Hz, 1H) 7.96-8.00 (m, 2H) 10.38 (s, 1H)

HRMS (ESI) calcd for $C_{15}H_{10}NOCl$ [M+H]+ 256.0524. found 256.0531.

Yield: 88%

N-(3-ethynylphenyl)-3-methylbenzamide (cmpd (IIIA), step m)

$^1$H NMR (600 MHz, DMSO-$d_6$) δ ppm 2.40 (s, 3H) 4.17 (s, 1H) 7.20 (dt, J=7.65, 1.21 Hz, 1H) 7.37 (t, J=7.97 Hz, 1H) 7.40-7.45 (m, 2H) 7.72-7.75 (m, 1H) 7.76 (s, 1H) 7.79-7.81 (m, 1H) 7.95 (t, J=1.74 Hz, 1H) 10.27 (s, 1H)

HRMS (ESI) calcd for $C_{16}H_{13}NO$ [M+H]+ 236.1070. found 236.1071.

Yield: 85%

N-(3-ethynylphenyl)-4-methylbenzamide (cmpd (IIIA), step m)

$^1$H NMR (600 MHz, DMSO-$d_6$) δ ppm 2.39 (s, 3H) 4.17 (s, 1H) 7.20 (dt, J=7.65, 1.21 Hz, 1H) 7.32-7.38 (m, 3H) 7.78-7.81 (m, 1H) 7.87 (d, J=8.24 Hz, 2H) 7.95 (t, J=1.74 Hz, 1H) 10.22 (s, 1H)

HRMS (ESI) calcd for $C_{16}H_{13}NO$ [M+H]+ 236.1070. found 236.1073.

Yield: 89%

N-(3-ethynylphenyl)-3-methoxybenzamide (cmpd (IIIA), step m)

$^1$H NMR (600 MHz, DMSO-$d_6$) δ ppm 3.84 (s, 3H) 4.18 (s, 1H) 7.17 (ddd, J=8.20, 2.61, 0.92 Hz, 1H) 7.21 (dt, J=7.69, 1.19 Hz, 1H) 7.37 (t, J=7.97 Hz, 1H) 7.45 (t, J=7.97 Hz, 1H) 7.47-7.49 (m, 1H) 7.51-7.54 (m, 1H) 7.78-7.81 (m, 1H) 7.94 (t, J=1.74 Hz, 1H) 10.28 (s, 1H)

HRMS (ESI) calcd for $C_{16}H_{13}NO_2$ [M+H]+ 252.1019. found 252.1015.

Yield: 92%

N-(3-ethynylphenyl)-4-methoxybenzamide (cmpd (IIIA), step m)

$^1$H NMR (600 MHz, DMSO-$d_6$) δ ppm 3.84 (s, 3H) 4.17 (s, 1H) 7.05-7.09 (m, 2H) 7.19 (dt, J=7.65, 1.21 Hz, 1H) 7.35 (t, J=7.88 Hz, 1H) 7.77-7.81 (m, 1H) 7.92-7.98 (m, 3H) 10.15 (s, 1H)

HRMS (ESI) calcd for $C_{16}H_{13}NO_2$ [M+H]+ 252.1019. found 252.1024.

Yield: 88%

N-(3-ethynylphenyl)-3-fluorobenzamide (cmpd (IIIA), step m)

$^1$H NMR (600 MHz, DMSO-$d_6$) δ ppm 4.19 (s, 1H) 7.23 (dt, J=7.65, 1.21 Hz, 1H) 7.38 (t, J=7.97 Hz, 1H) 7.44-7.49 (m, 1H) 7.60 (td, J=7.97, 5.86 Hz, 1H) 7.73-7.83 (m, 3H) 7.94 (t, J=1.74 Hz, 1H) 10.38 (s, 1H)

HRMS (ESI) calcd for $C_{15}H_{10}NOF$ [M+H]+ 240.0819. found 240.0817.

Yield: 94%

N-(3-ethynylphenyl)-4-fluorobenzamide (cmpd (IIIA), step m)

$^1$H NMR (600 MHz, DMSO-$d_6$) δ ppm 4.18 (s, 1H) 7.21 (dt, J=7.69, 1.19 Hz, 1H) 7.34-7.41 (m, 2H) 7.77-7.80 (m, 1H) 7.93 (t, J=1.74 Hz, 1H) 8.00-8.07 (m, 2H) 10.33 (s, 1H)

HRMS (ESI) calcd for $C_{15}H_{10}NOF$ [M+H]+ 240.0819. found 240.0820.

Yield: 84%

N-(3-ethynylphenyl)-3-(trifluoromethoxy)benzamide (cmpd (IIIA), step m)

$^1$H NMR (600 MHz, DMSO-$d_6$) δ ppm 4.19 (s, 1H) 7.24 (dt, J=7.65, 1.21 Hz, 1H) 7.39 (t, J=7.97 Hz, 1H) 7.62 (dt, J=8.38, 1.12 Hz, 1H) 7.68-7.72 (m, 1H) 7.77-7.81 (m, 1H) 7.91 (s, 1H) 7.93 (t, J=1.65 Hz, 1H) 8.01 (dt, J=7.97, 1.14 Hz, 1H) 10.44 (s, 1H)

HRMS (ESI) calcd for $C_{16}H_{10}NO_2F_3$ [M+H]+ 306.0737. found 306.0739.

Yield: 82%

N-(3-ethynylphenyl)-1,3-benzodioxole-5-carboxamide (cmpd (IIIA), step m)

$^1$H NMR (600 MHz, DMSO-$d_6$) δ ppm 4.17 (s, 1H) 6.13 (s, 2H) 7.06 (d, J=8.06 Hz, 1H) 7.19 (dt, J=7.65, 1.21 Hz, 1H) 7.32-7.37 (m, 1H) 7.50 (d, J=1.65 Hz, 1H) 7.57 (dd, J=8.06, 1.83 Hz, 1H) 7.76-7.79 (m, 1H) 7.92 (t, J=1.65 Hz, 1H) 10.12 (s, 1H)

HRMS (ESI) calcd for $C_{16}H_{11}NO_3$ [M+H]+ 266.0812. found 266.0915.

Yield: 50%

Preparation 10

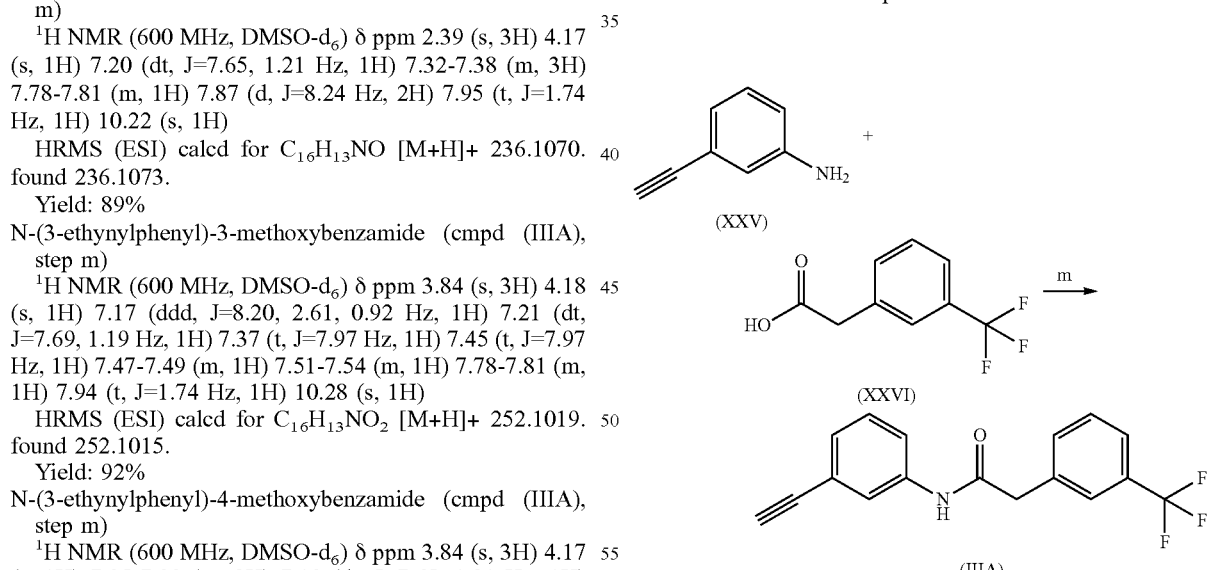

N-(3-ethynylphenyl)-2-[3-(trifluoromethyl)phenyl] acetamide (cmpd (IIIA), step m)

A mixture of 150 mg (1.28 mmol) of 3-aminophenylacetylene, 261 mg (1.28 mmol) of 3-trifluoromethylphenylacetic acid, 452 mg (1.41 mmol) of TBTU and 0.28 mL (1.66 mmol) of DIPEA in 5 mL of dry DMF was stirred at room temperature for 3 h. The solution was then diluted with ethylacetate, washed with hydrochloric acid 1N, a saturated solution of NaHCO$_3$, water and brine. The organic layer was dried over Na$_2$SO$_4$ and evaporated to give 298 mg (77%) of the title compound.

$^1$H NMR (600 MHz, DMSO-d$_6$) δ ppm 3.79 (s, 2H) 4.15 (s, 1H) 7.15 (d, J=7.51 Hz, 1H) 7.32 (t, J=7.88 Hz, 1H) 7.52-7.66 (m, 4H) 7.69 (s, 1H) 7.78 (s, 1H) 10.32 (s, 1H) HRMS (ESI) calcd for C$_{17}$H$_{12}$NOF$_3$ [M+H]+ 304.0944. found 304.0945.

Preparation 11

Method 1)

3-ethynyl-N-methylbenzamide (cmpd (IIIB), step n)

To a solution of 146 mg (1 mmol) of 3-ethynyl benzoic acid in 4 mL of dry DMF and 667 μL (4 mmol) of DIPEA, 406 mg (3 mmol) of HOBT and 574 mg (2 mmol) of EDCI were added consecutively. After 1 h under stirring at room temperature, 2 mL of methylamine 2M in THF (4 mmol) were added and the mixture stirred overnight. The solvent was then removed in vacuo and the residue taken up with dichloromethane, washed with aqueous NaHCO$_3$, with hydrochloric acid 0.5 M and finally with water. The organic layer was dried over Na$_2$SO$_4$ and evaporated to dryness, affording, after trituration with diisopropylether, 83 mg (52%) of the title compound.

$^1$H NMR (600 MHz, DMSO-d$_6$) δ ppm 2.78 (d, J=4.58 Hz, 3H) 4.25 (s, 1H) 7.45-7.51 (m, 1H) 7.61 (dt, J=7.69, 1.28 Hz, 1H) 7.85 (dt, J=7.83, 1.40 Hz, 1H) 7.91 (t, J=1.47 Hz, 1H) 8.52 (d, J=3.66 Hz, 1H) HRMS (ESI) calcd for C$_{10}$H$_9$NO [M+H]+ 160.0757. found 160.0755.

According to the same method, but employing the suitable amine derivative, the following compounds were prepared:

3-ethynylbenzamide (cmpd (IIIB), step n)

$^1$H NMR (600 MHz, DMSO-d$_6$) δ ppm 7.45 (br. s., 1H) 7.46-7.50 (m, 1H) 7.62 (dt, J=7.69, 1.28 Hz, 1H) 7.89 (dt, J=7.88, 1.37 Hz, 1H) 7.94-7.98 (m, 1H) 8.05 (br. s., 1H)

HRMS (ESI) calcd for C$_9$H$_7$NO [M+H]+ 160.0757. found 160.0755.

Yield: 55%

3-ethynyl-N-phenylbenzamide (cmpd (IIIB), step n)

$^1$H NMR (600 MHz, DMSO-d$_6$) δ ppm 4.31 (s, 1H) 7.08-7.15 (m, 1H) 7.33-7.39 (m, 2H) 7.54-7.58 (m, 1H) 7.66-7.71 (m, 1H) 7.74-7.79 (m, 2H) 7.95-8.00 (m, 1H) 8.03-8.09 (m, 1H) 10.31 (s, 1H)

HRMS (ESI) calcd for C$_{15}$H$_{11}$NO [M+H]+ 222.0914. found 222.0919.

Yield: 68%

N-cyclopropyl-3-ethynylbenzamide (cmpd (IIIB), step n)

$^1$H NMR (600 MHz, DMSO-d$_6$) δ ppm 0.54-0.61 (m, 2H) 0.66-0.71 (m, 2H) 2.85 (td, J=7.37, 3.94 Hz, 1H) 4.25 (s, 1H) 7.45-7.50 (m, 1H) 7.60 (dt, J=7.69, 1.28 Hz, 1H) 7.82-7.85 (m, 1H) 7.90 (s, 1H) 8.50 (d, J=3.30 Hz, 1H)

HRMS (ESI) calcd for C$_{12}$H$_{11}$NO [M+H]+ 186.0914. found 186.0916.

Yield: 46%

N-cyclopentyl-3-ethynylbenzamide (cmpd (IIIB), step n)

$^1$H NMR (600 MHz, DMSO-d$_6$) δ ppm 1.44-1.59 (m, 4H) 1.65-1.74 (m, 2H) 1.83-1.93 (m, 2H) 4.18-4.25 (m, 1H) 4.26 (s, 1H) 7.47 (t, J=7.78 Hz, 1H) 7.60 (dt, J=7.69, 1.28 Hz, 1H) 7.86 (dt, J=7.88, 1.37 Hz, 1H) 7.92-7.96 (m, 1H) 8.37 (d, J=6.96 Hz, 1H)

HRMS (ESI) calcd for C$_{14}$H$_{15}$NO [M+H]+ 214.1227. found 214.1231.

Yield: 70%

3-ethynyl-N-(propan-2-yl)benzamide (cmpd (IIIB), step n)

$^1$H NMR (600 MHz, DMSO-d$_6$) δ ppm 1.16 (d, J=6.59 Hz, 6H) 4.08 (dq, J=13.92, 6.78 Hz, 1H) 4.26 (s, 1H) 7.47 (t, J=7.78 Hz, 1H) 7.58-7.62 (m, 1H) 7.85-7.87 (m, 1H) 7.95 (s, 1H) 8.31 (d, J=7.51 Hz, 1H)

HRMS (ESI) calcd for C$_{12}$H$_{13}$NO [M+H]+ 188.1070. found 188.1070.

Yield: 68%

N-tert-butyl-3-ethynylbenzamide (cmpd (IIIB), step n)

$^1$H NMR (600 MHz, DMSO-d$_6$) δ ppm 1.37 (s, 9H) 4.24 (s, 1H) 7.45 (t, J=7.69 Hz, 1H) 7.59 (dt, J=7.69, 1.28 Hz, 1H) 7.81 (dt, J=7.88, 1.37 Hz, 1H) 7.86 (s, 1H) 7.90 (s, 1H)

HRMS (ESI) calcd for C$_{13}$F$_{15}$NO [M+H]+ 202.1227. found 202.1229.

Yield: 67%

(3-ethynylphenyl)(pyrrolidin-1-yl)methanone (cmpd (IIIB), step n)

$^1$H NMR (600 MHz, DMSO-d$_6$) δ ppm 1.76-1.91 (m, 4H) 3.35-3.37 (m, 2H) 3.45 (t, J=6.96 Hz, 2H) 4.23-4.25 (m, 1H) 7.43-7.47 (m, 1H) 7.51-7.57 (m, 3H) HRMS (ESI) calcd for C$_{13}$H$_{13}$NO [M+H]+ 200.1070. found 200.1076.

Yield: 60%

Method 2)

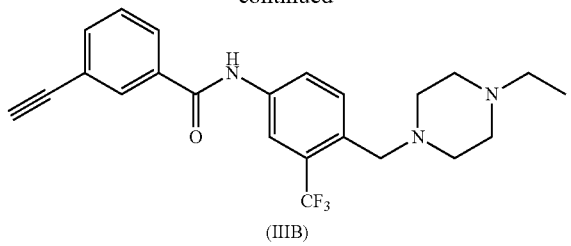

(IIIB)

N-{4-[(4-ethylpiperazin-1-yl)methyl]-3-(trifluoromethyl)phenyl}-3-ethynylbenzamide (cmpd (IIIB), step n)

To a solution of 100 mg (0.69 mmol) of 3-ethynyl benzoic acid in 5 mL of dry N,N-dimethylformamide, 164 mg (0.57 mmol) of 4-[(4-ethylpiperazin-1-yl)methyl]-3-(trifluoromethyl)aniline (prepared as described in J. Med. Chem., (2010) 53, 4701-4719) 242 mg (0.75 mmol) of TBTU and 0.14 mL (0.82 mmol) of DIPEA were added consecutively. After 15 h under stirring at room temperature the mixture was poured into aqueous NaHCO₃ and extracted twice with ethylacetate. The organic phase was then washed with brine, dried over Na₂SO₄ and evaporated to dryness. A flash-chromatography on silica gel (DCM-MeOH—NH₃ 7N in methanol 9/1/0.04), afforded 149 mg of the title compound (63%).

$^1$H NMR (600 MHz, DMSO-$d_6$) δ ppm 0.99 (t, J=7.14 Hz, 3H) 2.19-2.46 (m, 10H) 3.57 (s, 3H) 6.61 (br. s., 2H) 7.60 (t, J=7.88 Hz, 1H) 7.64 (d, J=2.20 Hz, 1H) 7.72 (d, J=8.61 Hz, 1H) 7.80 (dt, J=7.83, 1.21 Hz, 1H) 7.91-7.98 (m, 1H) 8.05 (dd, J=8.52, 1.92 Hz, 1H) 8.12 (s, 1H) 8.16 (t, J=1.47 Hz, 1H) 8.21 (d, J=2.20 Hz, 1H) 10.59 (s, 1H) 12.08 (br. s., 1H)

HRMS (ESI) calcd for $C_{29}H_{28}N_7OF_3$ [M+H]+ 548.2380. found 548.2392.

Preparation 12

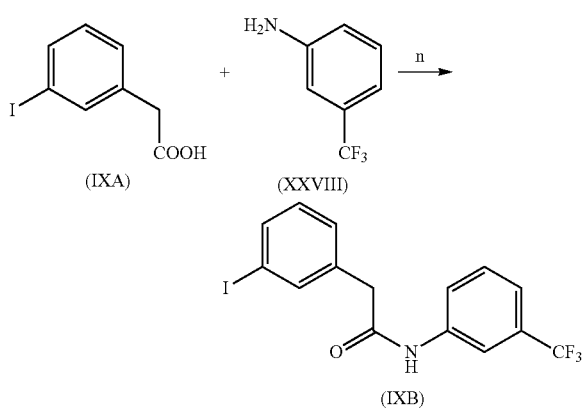

2-(3-iodophenyl)-N-[3-(trifluoromethyl)phenyl]acetamide (cmpd (IXB), step n)

200 mg (0.73 mmol) of (3-iodophenyl)acetic acid were dissolved in 4 mL of N,N dimethylacetamide and 244 mg (0.76 mmol) of TBTU, followed by 150 μL (0.80 mmol) of N-diisopropyl-N'-ethyl amine and 177 mg (1.1 mmol) of 3-(trifluoromethyl)aniline were added. The mixture was maintained at room temperature for 2 hours, then diluted with ethylacetate, washed with aqueous NaHCO₃, HCl 2N, water and brine. The crude was triturated with a mixture diisopropyl ether-hexane affording, after filtration, 200 mg of the title compound as a white solid (68%).

$^1$H NMR (401 MHz, DMSO-$d_6$) δ ppm 7.14 (t, J=7.75 Hz, 1H) 7.35 (d, J=7.69 Hz, 1H) 7.40 (d, J=7.81 Hz, 1H) 7.55 (t, J=7.99 Hz, 1H) 7.63 (dt, J=7.84, 1.39 Hz, 1H) 7.73 (t, J=1.59 Hz, 1H) 7.77 (d, J=8.30 Hz, 1H) 8.08 (s, 1H) 10.50 (s, 1H)

2-(3-Iodo-phenyl)-N-(4-trifluoromethyl-phenyl)acetamide (cmpd (IXB), step n)

$^1$H NMR (401 MHz, DMSO-$d_6$) δ ppm 3.67 (s, 2H) 7.14 (t, J=7.81 Hz, 1H) 7.35 (d, J=7.69 Hz, 1H) 7.63 (dt, J=7.81, 1.40 Hz, 1H) 7.67 (d, J=8.54 Hz, 2H) 7.73 (t, J=1.59 Hz, 1H) 7.79 (d, J=8.42 Hz, 2H) 10.51 (s, 1H)

2-(3-Iodo-phenyl)-N-phenyl-acetamide (cmpd (IXB), step n)

$^1$H NMR (401 MHz, DMSO-$d_6$) δ ppm 3.61 (s, 2H) 7.01-7.07 (m, 1H) 7.14 (t, J=7.75 Hz, 1H) 7.26-7.32 (m, 2H) 7.35 (d, J=7.81 Hz, 1H) 7.57 (dd, J=8.61, 1.04 Hz, 2H) 7.61-7.64 (m, 1H) 7.72 (t, J=1.53 Hz, 1H) 10.15 (s, 1H)

N-Cyclopropyl-3-iodo-4-methyl-benzamide (cmpd (IXB), step n)

$^1$H NMR (401 MHz, DMSO-$d_6$) δ ppm 0.52-0.60 (m, 2H) 0.64-0.73 (m, 2H) 2.39 (s, 3H) 2.82 (tq, J=7.38, 3.95 Hz, 1H) 7.39 (d, J=7.93 Hz, 1H) 7.74 (dd, J=7.87, 1.77 Hz, 1H) 8.24 (d, J=1.83 Hz, 1H) 8.44 (d, J=3.91 Hz, 1H)

N-cyclopropyl-5-bromo-2-methylbenzamide (cmpd (IXB), step n)

$^1$H NMR (600 MHz, DMSO-$d_6$) δ ppm 0.50-0.55 (m, 2H) 0.65-0.70 (m, 2H) 2.26 (s, 3H) 2.80 (td, J=7.37, 3.94 Hz, 1H) 7.19 (d, J=8.24 Hz, 1H) 7.42 (d, J=2.01 Hz, 1H) 7.48-7.50 (m, 1H) 8.37 (br. s., 1H)

3-bromo-N-cyclopropyl-4-fluorobenzamide (cmpd (IXB), step n)

$^1$H NMR (401 MHz, DMSO-$d_6$) δ ppm 0.51-0.59 (m, 2H) 0.67-0.74 (m, 2H) 2.83 (td, J=7.29, 3.97 Hz, 1H) 7.46 (t, J=8.67 Hz, 1H) 7.88 (ddd, J=8.64, 4.85, 2.26 Hz, 1H) 8.14 (dd, J=6.71, 2.20 Hz, 1H) 8.53 (d, J=3.42 Hz, 1H)

3-bromo-N-cyclopropyl-5-fluorobenzamide (cmpd (IXB), step n)

$^1$H NMR (401 MHz, DMSO-$d_6$) δ ppm 0.53-0.61 (m, 2H) 0.67-0.74 (m, 2H) 2.79-2.89 (m, 1H) 7.61-7.66 (m, 1H) 7.71-7.76 (m, 1H) 7.86 (t, J=1.46 Hz, 1H) 8.60 (d, J=3.66 Hz, 1H)

5-Bromo-N-cyclopropyl-2-fluoro-benzamide (cmpd (IXB), step n)

$^1$H NMR (600 MHz, DMSO-$d_6$) δ ppm 0.50-0.56 (m, 2H) 0.66-0.72 (m, 2H) 2.81 (td, J=7.42, 3.85 Hz, 1H) 7.27 (t, J=9.25 Hz, 1H) 7.65-7.71 (m, 2H) 8.47 (br. s., 1H)

N-[4-(4-Ethyl-piperazin-1-ylmethyl)-3-trifluoromethyl-phenyl]-3-iodo-benzamide (cmpd (IXB), step n)

$^1$H NMR (401 MHz, DMSO-$d_6$) δ ppm 0.98 (t, 3H) 2.18-2.46 (m, 10H) 3.56 (s, 2H) 7.36 (t, J=7.81 Hz, 1H) 7.71 (d, J=8.42 Hz, 1H) 7.94-7.99 (m, 2H) 8.02 (dd, J=8.61, 2.01 Hz, 1H) 8.17 (d, J=2.07 Hz, 1H) 8.31 (t, J=1.65 Hz, 1H) 10.54 (s, 1H)

N-[4-(4-Ethyl-piperazin-1-ylmethyl)-3-trifluoromethyl-phenyl]-3-iodo-4-methyl-benzamide (cmpd (IXB), step n)

$^1$H NMR (401 MHz, DMSO-$d_6$) δ ppm 0.98 (t, 3H) 2.40 (br. s., 10H) 2.45 (s, 3H) 3.56 (s, 2H) 7.47-7.52 (m, 1H) 7.70 (d, J=8.42 Hz, 1H) 7.91 (dd, J=7.87, 1.89 Hz, 1H) 8.02 (dd, J=8.61, 2.01 Hz, 1H) 8.17 (d, J=2.20 Hz, 1H) 8.42 (d, J=1.83 Hz, 1H) 10.48 (s, 1H)

N-{4-[(4-ethylpiperazin-1-yl)methyl]-3-(trifluoromethyl)phenyl}-2-(3-iodophenyl)acetamide (cmpd (IXB), step n).

$^1$H NMR (600 MHz, DMSO-d$_6$) δ ppm 0.97 (t, J=7.14 Hz, 3H) 2.27-2.32 (m, 2H) 2.32-2.46 (m, 4H) 3.52 (s, 2H) 3.64 (s, 2H) 7.14 (t, J=7.78 Hz, 1H) 7.34 (d, J=7.69 Hz, 1H) 7.64 (dd, J=16.48, 8.24 Hz, 2H) 7.72 (s, 1H) 7.76 (d, J=8.43 Hz, 1H) 8.03 (d, J=1.83 Hz, 1H) 10.44 (s, 1H)

HRMS (ESI) calcd for C$_{22}$H$_{25}$N$_3$OF$_3$I [M+H]+ 532.1067. found 532.1057.

Yield 87%

3-bromo-4-cyano-N-cyclopropylbenzamide (cmpd (IXB), step n)

$^1$H NMR (401 MHz, DMSO-d$_6$) δ ppm 0.55-0.63 (m, 2H) 0.69-0.76 (m, 2H) 2.86 (td, J=7.29, 4.09 Hz, 1H) 7.95 (dd, J=8.18, 1.59 Hz, 1H) 8.05 (d, J=8.06 Hz, 1H) 8.23 (d, J=1.47 Hz, 1H) 8.74 (d, J=4.39 Hz, 1H)

Preparation 13

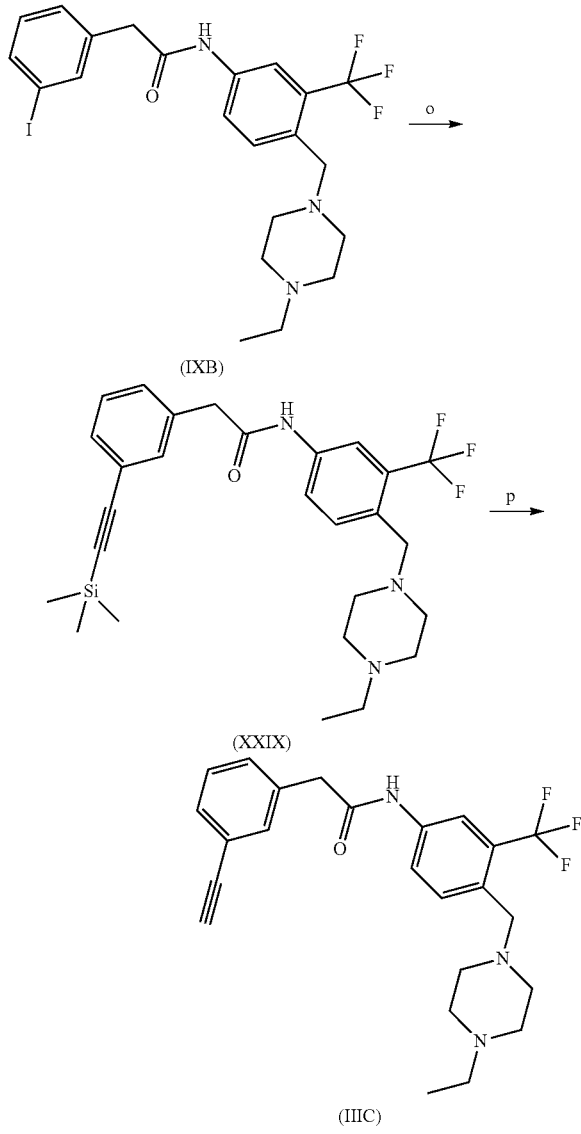

N-{4-[(4-ethylpiperazin-1-yl)methyl]-3-(trifluoromethyl)phenyl}-2-(3-ethynylphenyl)acetamide (cmpd (IIIC), Steps o and p)

To a solution of 241 mg (0.45 mmol) of N-{4-[(4-ethylpiperazin-1-yl)methyl]-3-(trifluoromethyl)phenyl}-2-(3-iodophenyl)acetamide in 5 mL of dry DMF, degassed under an argon stream for 30 minutes, 0.13 mL (0.91 mmol) of trimethylsilyl acetylene, 9 mg (0.045 mmol) of cuprous iodide, 0.62 mL (4.54 mmol) of triethylamine and 32 mg (0.045 mmol) of palladium chloride bis(triphenylphosphine) were added. The mixture was stirred at room temperature for 2 h, then poured into water and extracted twice with ethylacetate. The organic phase was then washed with brine, dried over Na$_2$SO$_4$ and evaporated. The crude was finally chromatographed on silica gel (DCM-MeOH—NH$_3$ 9/1/0.04) to afford 193 mg (85%) of N-{4-[(4-ethylpiperazin-1-yl)methyl]-3-(trifluoromethyl)phenyl}-2-{3-[(trimethylsilyl)ethynyl]phenyl}acetamide (cmpd of formula (XXIX), step o), as a thick oil.

$^1$H NMR (600 MHz, DMSO-d$_6$) δ ppm 0.22-0.23 (m, 10H) 0.97 (t, J=7.14 Hz, 3H) 2.27-2.32 (m, 3H) 2.30-2.45 (m, 5H) 3.52 (s, 2H) 3.66 (s, 2H) 7.31-7.38 (m, 3H) 7.43 (s, 1H) 7.65 (d, J=8.43 Hz, 1H) 7.74-7.78 (m, 1H) 8.03 (d, J=1.83 Hz, 1H) 10.43 (s, 1H).

HRMS (ESI) calcd for C$_{27}$H$_{34}$N$_3$OF$_3$Si [M+H]+ 502.2496. found 502.2485.

193 mg (0.39 mmol) of N-{4-[(4-ethylpiperazin-1-yl)methyl]-3-(trifluoromethyl)phenyl}-2-{3-[(trimethylsilyl)ethynyl]phenyl}acetamide were dissolved in 5 mL of methanol and the solution was degassed under an argon stream for 10 minutes. 56 mg (0.4 mmol) of dry potassium carbonate were added and the mixture stirred at room temperature for 45 minutes. The reaction mixture was then poured into water and extracted twice with ethylacetate. The organic layer was washed with brine, dried over Na$_2$SO$_4$ and evaporated, to give 152 mg (92%) of the title compound as an oil (cmpd IIIC, step p).

$^1$H NMR (600 MHz, DMSO-d$_6$) δ ppm 0.97 (t, J=7.23 Hz, 3H) 2.28-2.32 (m, 2H) 2.33-2.46 (m, 6H) 3.52 (s, 2H) 3.65-3.69 (m, 2H) 4.17 (s, 1H) 7.31-7.40 (m, 3H) 7.44 (s, 1H) 7.65 (d, J=8.43 Hz, 1H) 7.76 (dd, J=8.43, 1.83 Hz, 1H) 8.03 (d, J=2.01 Hz, 1H) 10.45 (s, 1H).

HRMS (ESI) calcd for C$_{24}$H$_{26}$N$_3$OF$_3$ [M+H]+ 430.2101. found 430.2096.

According to the same method, but employing the suitable intermediates, the following compounds were prepared:

N-cyclopropyl-5-ethynyl-2-methylbenzamide (cmpd (IIIC), steps o and p)

N-cyclopropyl-3-ethynyl-4-methylbenzamide (cmpd (IIIC), steps o and p)

N-cyclopropyl-5-ethynyl-2-fluorobenzamide (cmpd (IIIC), steps o and p)

$^1$H NMR (600 MHz, DMSO-d$_6$) δ ppm 0.49-0.59 (m, 2H) 0.65-0.73 (m, 2H) 2.82 (td, J=7.28, 3.94 Hz, 1H) 7.30 (t, J=9.62 Hz, 1H) 7.58-7.63 (m, 2H) 8.45 (br. s., 1H)

HRMS (ESI) calcd for C$_{12}$H$_{10}$NOF [M+H]+ 204.0819. found 204.0819.

N-cyclopropyl-3-ethynyl-4-fluorobenzamide (cmpd (IIIC), steps o and p)

$^1$H NMR (600 MHz, DMSO-d$_6$) δ ppm 0.52-0.59 (m, 2H) 0.66-0.73 (m, 2H) 2.83 (tq, J=7.44, 3.89 Hz, 1H) 4.57 (s, 1H) 7.39 (t, J=9.07 Hz, 1H) 7.88-7.92 (m, 1H) 8.01 (dd, J=6.87, 2.29 Hz, 1H) 8.51 (d, J=3.66 Hz, 1H)

HRMS (ESI) calcd for C$_{12}$H$_{10}$NOF [M+H]+ 204.0819. found 204.0820.

N-cyclopropyl-3-ethynyl-5-fluorobenzamide (cmpd (IIIC), steps o and p)

$^1$H NMR (600 MHz, DMSO-$d_6$) δ ppm 0.54-0.61 (m, 2H) 0.68-0.74 (m, 2H) 2.85 (qt, J=7.45, 3.66 Hz, 1H) 4.40 (s, 1H) 7.52 (dd, J=7.69, 1.10 Hz, 1H) 7.65 (dd, J=9.25, 1.92 Hz, 1H) 7.77-7.79 (m, 1H) 8.58 (d, J=3.66 Hz, 1H)

HRMS (ESI) calcd for $C_{12}H_{10}NOF$ [M+H]+ 204.0819. found 204.0826.

N-cyclopropyl-4-ethynylbenzamide (cmpd (IIIC), steps o and p)

N-(cyclopropylmethyl)-3-ethynylbenzamide (cmpd (IIIC), steps o and p)

N-cyclopropyl-2-(3-ethynylphenyl)acetamide (cmpd (IIIC), steps o and p)

4-cyano-N-cyclopropyl-3-ethynylbenzamide (cmpd (IIIC), steps o and p)

Preparation 14

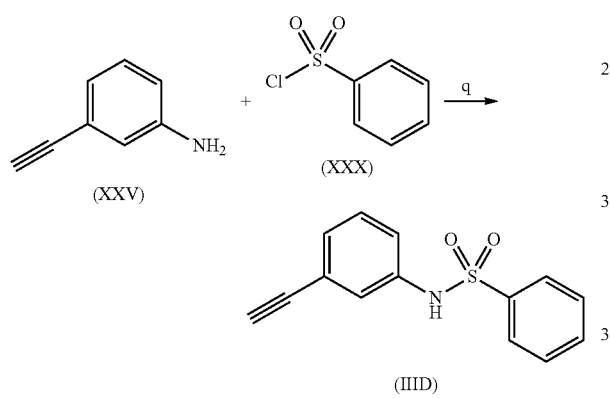

N-(3-ethynylphenyl)benzenesulfonamide (cmpd (IIID), step q)

To a solution of 150 mg (1.28 mmol) of 3-aminophenylacetylene and 0.3 mL (2.56 mmol) of 2,6-lutidine in 4 mL of dry THF, 136 μL (1.07 mmol) of benzensulfonyl chloride were added. The solution was stirred at room temperature for 3 h and another amount of 0.3 mL of 2,6-lutidine was added to the reaction mixture. The solution was stirred overnight and heated at 60° C. for further 8 h, then was diluted with ethylacetate and washed successively with hydrochloric acid 1 M, a saturated solution of NaHCO$_3$, water and brine. The organic layer was then dried over anhydrous Na$_2$SO$_4$ and evaporated to dryness, affording 230 mg (96%) of the title compound.

$^1$H NMR (600 MHz, DMSO-$d_6$) δ ppm 4.17 (s, 1H) 7.07-7.16 (m, 3H) 7.19-7.27 (m, 1H) 7.54-7.58 (m, 2H) 7.61-7.64 (m, 1H) 7.74-7.78 (m, 2H) 10.45 (s, 1H)

HRMS (ESI) calcd for $C_{14}H_{11}NO_2S$ [M+H]+ 258.0583. found 258.0577.

According to the same method but employing the suitable sulfonyl chloride the following intermediates were prepared:

N-(3-ethynylphenyl)methanesulfonamide (cmpd (IIID), step q)

N-(3-ethynylphenyl)cyclopropanesulfonamide (cmpd (IIID), step q)

Preparation 15

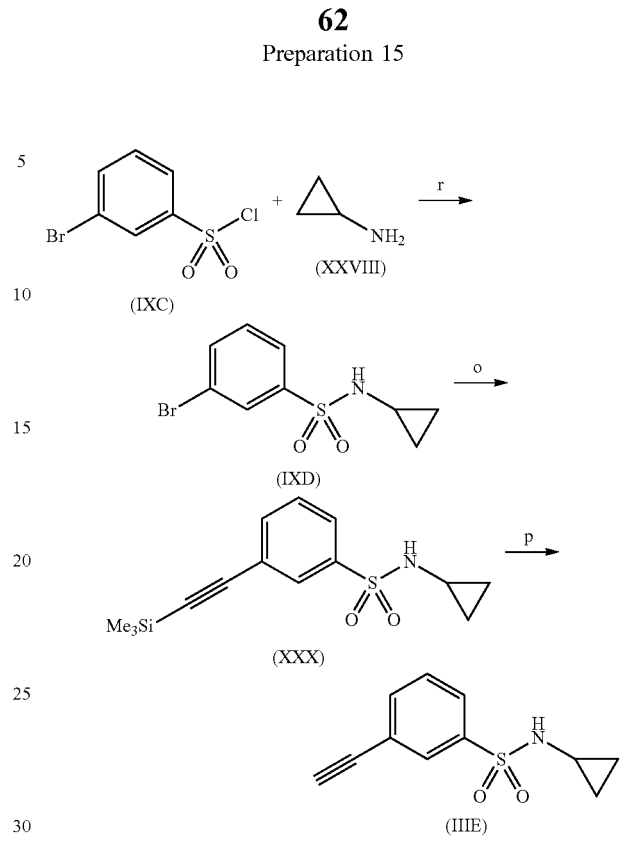

N-cyclopropyl-3-ethynylbenzenesulfonamide (cmpd (IIIE), Steps r, o, p)

200 mg (0.78 mmol) of m-bromosulfonyl chloride were dissolved in 5 mL of dry THF and 152 μL 2.34 mmol) of cyclopropylamine were added under stirring. The resulting solution was maintained at room temperature for 3 h. The solvent was removed under reduced pressure, the residue taken up with DCM and washed with water. The organic layer was dried over Na$_2$SO$_4$ and evaporated to give, after trituration with petroleum ether, 145 mg (67%) of 3-bromo-N-cyclopropylbenzenesulfonamide (cmpd of formula (cmpd (IXD)), step r).

The latter was dissolved in 5 mL of dry DMF in a microwave vial and 28 mg (0.12 mmol) of cupreous iodide, 84 mg (0.12 mmol) of palladium dichloride bis (triphenylphosphine), 81 μL of trimethylsilylacetylene, and 763 μL of TEA were added consecutively. The solvent was degassed under argon stream for 10 minutes and the mixture submitted to microwave irradiation at 60° C. for 1 h. The mixture was then filtered through a celite pad and the filtrate evaporated to dryness. The residue was re-dissolved in DCM and washed with KHSO$_4$ 5%. The organic layer was dried over Na$_2$SO$_4$ and evaporated to afford N-cyclopropyl-3-[(trimethylsilyl)ethynyl]benzenesulfonamide (cmpd (XXX), step o). This intermediate was dissolved in 10 mL of methanol, 88 mg (0.64 mmol) of dry K$_2$CO$_3$ were added and the reaction mixture was stirred at room temperature for 2 h.

The solvent was removed in vacuo, the residue taken up with DCM and washed with aqueous KHSO$_4$ 5%. The organic phase was dried over Na$_2$SO$_4$ and evaporated, to give the title compound (cmpd (IIIE), step p).

According to the same method, but employing the suitable amine derivative, the following intermediates were prepared:

3-ethynyl-N-methylbenzenesulfonamide (cmpd (IIIE), steps r, o, p)
3-ethynyl-N-phenylbenzenesulfonamide (cmpd (IIIE), steps r, o, p)

Preparation 16

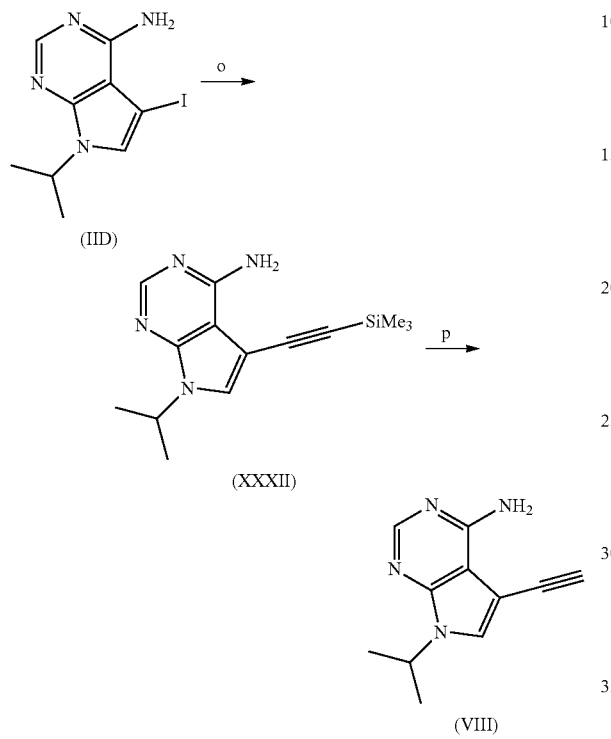

5-ethynyl-7-(propan-2-yl)-7H-pyrrolo[2,3-d]pyrimidin-4-amine (cmpd (VIII), steps o and p)

455 mg (1.51 mmol) of 5-iodo-7-(propan-2-yl)-7H-pyrrolo[2,3-d]pyrimidin-4-amine were dissolved in 15 mL of dry DMF, degassed under argon stream. 52 mg (0.074 mmol) of palladium dichloride bis(triphenylphosphine), 21 mg (0.116 mmol) of cuprous iodide, 2 mL (14.89 mmol) of triethylamine and 424 µL of trimethylsilylacetylene were added consecutively. The mixture was stirred at room temperature for 1.5 hours, then poured into water and extracted twice with ethylacetate. The organic phase was then washed with brine, dried over $Na_2SO_4$ and evaporated to give, after flash-chromatography on silica gel (ethylacetate/hexane, from 1/1 to 7/3), 419 mg of 7-(propan-2-yl)-5-[(trimethylsilyl)ethynyl]-7H-pyrrolo[2,3-d]pyrimidin-4-amine (cmpd (XXXII), step o).

This intermediate (415 mg (1.52 mmol) was dissolved in methanol, degassed under argon stream (15 mL) and potassium carbonate (1.05 g, 7.61 mmol) was added. The reaction mixture was stirred at room temperature for 2 h. The solvent was then removed in vacuo, the residue taken up with DCM and washed with aqueous $KHSO_4$ 5%. The organic phase was dried over $Na_2SO_4$ and evaporated, to give the title compound (cmpd (VIII), step p).

$^1$H NMR (401 MHz, DMSO-$d_6$) δ ppm 1.43 (d, J=6.84 Hz, 6H) 4.27 (s, 1H) 4.84-4.94 (m, 1H) 6.98 (br. s., 2H) 7.83 (s, 1H) 8.19 (s, 1H)

Preparation 17

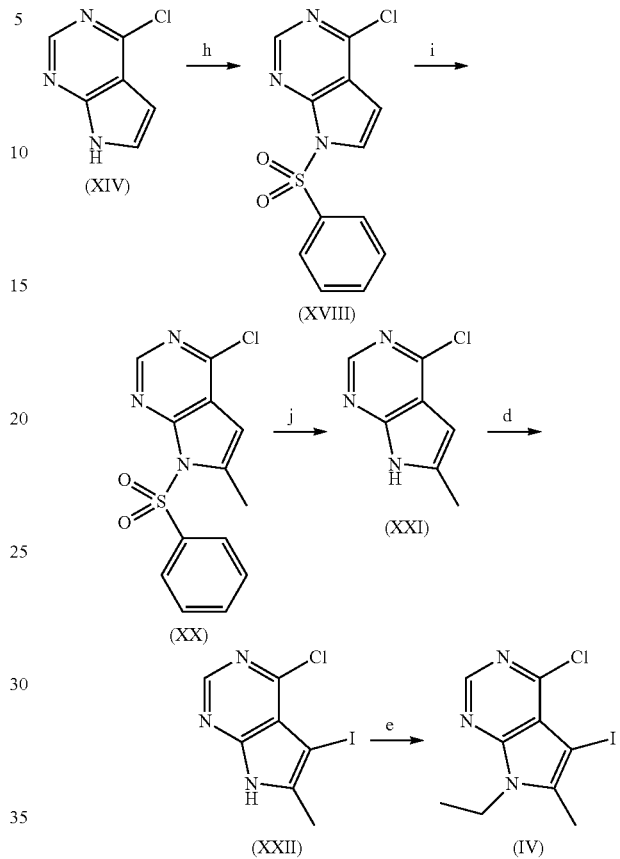

4-chloro-7-ethyl-5-iodo-6-methyl-7H-pyrrolo[2,3-d]pyrimidine (cmpd (IV), steps h, l, j, d, e)

To a solution of 4-chloro-7H-pyrrolo[2,3-d]pyrimidine (500 mg, 3.27 mmol) in DMF (5 mL) caesium carbonate (2.13 g, 6.54 mmol) and benzensulfonyl chloride (417 µL, 3.27 mmol) were added. The mixture was stirred at room temperature for 1.5 hours, then diluted with ethylacetate and washed with water and brine. The organic layer was dried over $Na_2SO_4$ and evaporated to dryness. The residue was chromatographed on a silica gel column eluted with dichloroethane/ethylacetate 7/3 affording 761 mg (79%) of 4-chloro-7-(phenylsulfonyl)-7H-pyrrolo[2,3-d]pyrimidine (cmpd (XVIII), step h).

To a solution of 2M in THF lithium diisopropylamide (0.83 mL, 1.65 mmol) in dry THF (5 mL) cooled to −78° C., under argon atmosphere, the last intermediate (400 mg, 1.37 mmol) dissolved in 5 mL of dry THF, was added dropwise during 10 minutes. The mixture was maintained in these conditions for 1 hour and then methyl iodide was added (0.11 mL, 1.78 mmol). The mixture was stirred 2 hours and during this time further 0.21 mL of methyl iodide were added. After 4 hours the temperature was driven to −10° C. and a saturated aqueous solution of ammonium chloride was added. The product was then extracted with ethylacetate, the organic layer dried over $Na_2SO_4$ and evaporated affording 4-chloro-6-methyl-7-(phenylsulfonyl)-7H-pyrrolo[2,3-d]pyrimidine (cmpd (XX), step i).

This intermediate (1.37 mmol) was dissolved in 10 mL of THF and 5 mL of methanol and 0.5 g of sodium hydrate were added. The mixture was stirred at room temperature for 1 hour, then the solvent removed in vacuo. The residue was taken up with ethylacetate and washed with a saturated aqueous solution of ammonium chloride and extracted again with ethylacetate. The organic layer was washed with brine, dried over $Na_2SO_4$ and evaporated, giving 223 mg of 4-chloro-6-methyl-7H-pyrrolo[2,3-d]pyrimidine (cmpd (XXI), step j).

This intermediate (1.37 mmol) was dissolved in chloroform (10 mL) and N-iodo succinimide (308 mg, 1.37 mmol) was added. The mixture was refluxed for 1.5 hours, cooled to room temperature, diluted with dichloromethane, washed with aqueous $Na_2S_2O_3$ and ammonium chloride. The organic layer was dried over $Na_2SO_4$ and evaporated. The residue was chromatographed on a silica gel column 1,2-dichloroethane/ethylacetate 6/4, giving 110 mg of 4-chloro-5-iodo-6-methyl-7H-pyrrolo[2,3-d]pyrimidine (cmpd (XXII), step d).

The last intermediate (0.39 mmol) was dissolved in DMF (3 mL) and additioned with caesium carbonate (257 mg, 0.79 mmol) and iodoethane (47 µL, 0.59 mmol). The mixture was stirred at room temperature for 2 hours, then poured into water and extracted twice with ethylacetate. The organic layer was washed with brine, dried over $Na_2SO_4$ and evaporated. The residue was finally purified by chromatography on a silica gel column eluted with dichloromethane/ethylacetate giving 51 mg of 4-chloro-7-ethyl-5-iodo-6-methyl-7H-pyrrolo[2,3-d]pyrimidine (cmpd (IV), step e).

$^1$H NMR (401 MHz, DMSO-$d_6$) δ ppm 1.24-1.32 (m, 3H) 2.54 (s, 3H) 4.36 (q, J=7.16 Hz, 2H) 8.58 (s, 1H)

Example 1

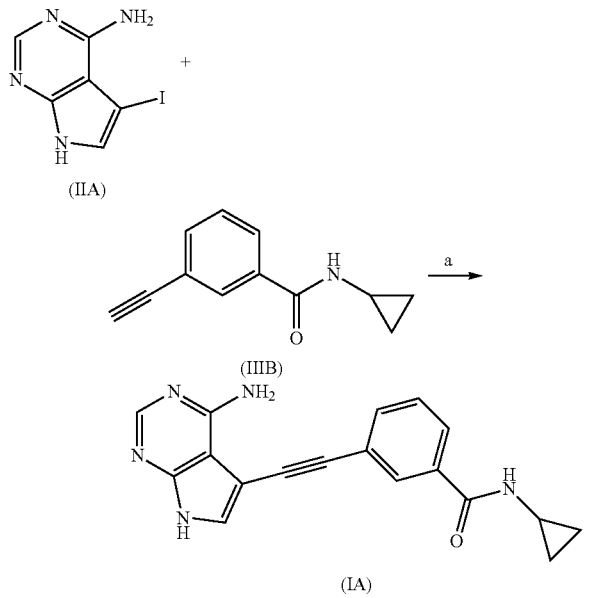

3-[(4-amino-7H-pyrrolo[2,3-d]pyrimidin-5-yl)ethynyl]-N-cyclopropylbenzamide (cmpd 15).
[R1=R2=R3=R4=R6=H, A=triple bond, L=CONH, R7=cyclopropyl]

60 mg (0.245 mmol) of 5-iodo-7H-pyrrolo[2,3-d]pyrimidin-4-amine (prepared as described in preparation 1) were dissolved in a microwave vial in 4 mL of dry DMF. 10 mg (0.048 mmol) of cupreous iodide, 48 mg (0.26 mmol) of N-cyclopropyl-3-ethynylbenzamide (prepared as described in preparation 8), 34 mg (0.048 mmol) of palladium dichloride bis(triphenylphosphine) and 346 µL of TEA were added to the reaction medium. The solvent was degassed under an argon stream for 10 minutes and the mixture submitted to microwave irradiation at 60° C. for 30 minutes and then filtered through a celite pad and evaporated to dryness. The residue was dissolved in DCM and washed with brine. The organic layer was dried over $Na_2SO_4$ and evaporated. The crude was purified by flash-chromatography (DCM/MeOH 95/5) affording 23 mg (30%) of the title compound.

$^1$H NMR (600 MHz, DMSO-$d_6$) δ ppm 0.53-0.62 (m, 2H) 0.68-0.74 (m, 2H) 2.86 (tq, J=7.44, 3.89 Hz, 1H) 2.82-2.90 (m, 1H) 6.58 (br. s., 2H) 7.44-7.53 (m, 1H) 7.61 (s, 1H) 7.70 (d, J=7.88 Hz, 1H) 7.80 (d, J=7.88 Hz, 1H) 7.98 (s, 1H) 8.11 (s, 1H) 8.52 (d, J=4.21 Hz, 1H) 12.06 (br. s., 1H)

HRMS (ESI) calcd for $C_{18}H_{15}N_5O$ [M+H]+ 318.1350. found 318.1346.

According to the same method, but employing the suitable iodo intermediate and acetylene derivative, the following compounds were prepared:

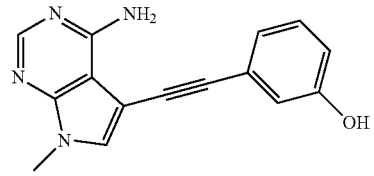 [SMILES: Cn1cc(C#Cc2cccc(O)c2)c2c(N)ncnc21]

3-[(4-amino-7-methyl-7H-pyrrolo[2,3-d]pyrimidin-5-yl)ethynyl]phenol trifluoroacetate (cmpd 1).
[R1=R3=R5=R6=H, A=triple bond, R2=methyl, R4=hydroxyl]

$^1$H NMR (600 MHz, DMSO-$d_6$) δ ppm 3.89 (s, 3H) 6.71-6.77 (m, 1H) 6.87-6.91 (m, 1H) 6.94 (d, J=7.88 Hz, 1H) 7.17 (t, J=7.88 Hz, 1H) 7.50 (d, J=6.59 Hz, 1H) 8.30 (s, 1H) 9.56 (s, 1H)

HRMS (ESI) calcd for $C_{15}H_{12}N_4O$ [M+H]+ 265.1084. found 265.1093.

3-[(4-chloro-7H-pyrrolo[2,3-d]pyrimidin-5-yl)ethynyl]phenol (cmpd (V), step a)

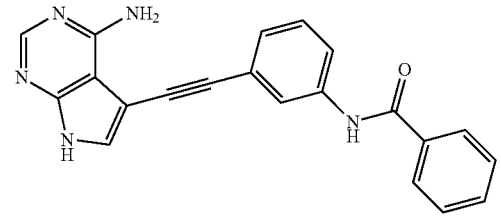 [SMILES: Nc1ncnc2[nH]cc(C#Cc3cccc(NC(=O)c4ccccc4)c3)c12]

N-{3-[(4-amino-7H-pyrrolo[2,3-d]pyrimidin-5-yl)ethynyl]phenyl}benzamide (cmpd 9).
[R1=R2=R3=R4=R6=H, A=triple bond, L=NHCO, R7=phenyl]

$^1$H NMR (600 MHz, DMSO-$d_6$) δ ppm 6.57 (br. s., 2H) 7.31 (d, J=7.69 Hz, 1H) 7.40 (t, J=7.97 Hz, 1H) 7.53-7.57

(m, 2H) 7.59-7.64 (m, 2H) 7.77 (d, J=8.24 Hz, 1H) 7.97 (d, J=7.14 Hz, 2H) 8.01 (s, 1H) 8.11 (s, 1H) 10.34 (s, 1H) 12.05 (br. s., 1H)

HRMS (ESI) calcd for $C_{21}H_{15}N_5O$ [M+H]+ 354.1350. found 354.1350.

Yield: 36%

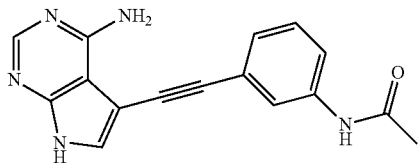 [SMILES: CC(=O)Nc1cccc(C#Cc2c[nH]c3ncnc(N)c23)c1]

N-{3-[(4-amino-7H-pyrrolo[2,3-d]pyrimidin-5-yl) ethynyl]phenyl}acetamide (cmpd 14).
[R1=R2=R3=R4=R6=H, A=triple bond, L=NHCO, R7=methyl]

$^1$H NMR (600 MHz, DMSO-$d_6$) δ ppm 2.02-2.09 (m, 3H) 6.15-6.74 (m, 2H) 7.22 (d, J=7.51 Hz, 1H) 7.33 (t, J=7.97 Hz, 1H) 7.51 (d, J=8.06 Hz, 1H) 7.61 (d, J=2.38 Hz, 1H) 7.82 (s, 1H) 8.11 (s, 1H) 10.04 (s, 1H) 12.03 (br. s., 1H)

HRMS (ESI) calcd for $C_{16}H_{13}N_5O$ [M+H]+ 292.1193. found 292.1191.

Yield: 29%

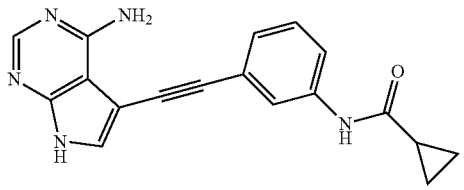 [SMILES: Nc1ncnc2[nH]cc(C#Cc3cccc(NC(=O)C4CC4)c3)c12]

N-{3-[(4-amino-7H-pyrrolo[2,3-d]pyrimidin-5-yl) ethynyl]phenyl}cyclopropanecarboxamide (cmpd 13). [R1=R2=R3=R4=R6=H, A=triple bond, L=NHCO, R7=cyclopropyl]

$^1$H NMR (600 MHz, DMSO-$d_6$) δ ppm 0.77-0.85 (m, 4H) 1.71-1.83 (m, 1H) 6.55 (br. s., 2H) 7.22 (d, J=7.69 Hz, 1H) 7.33 (t, J=7.97 Hz, 1H) 7.51-7.55 (m, 1H) 7.60 (s, 1H) 7.83 (s, 1H) 8.11 (s, 1H) 10.29 (s, 1H) 12.03 (br. s., 1H)

HRMS (ESI) calcd for $C_{18}H_{15}N_5O$ [M+H]+ 318.1350. found 318.1352.

Yield: 24%

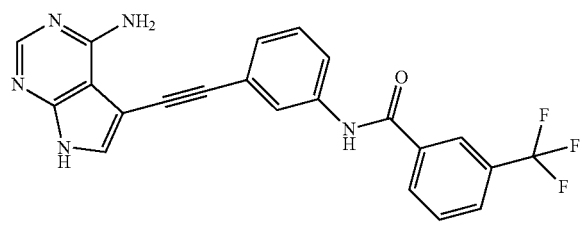 [SMILES: Nc1ncnc2[nH]cc(C#Cc3cccc(NC(=O)c4cccc(C(F)(F)F)c4)c3)c12]

N-{3-[(4-amino-7H-pyrrolo[2,3-d]pyrimidin-5-yl) ethynyl]phenyl}-3-(trifluoromethyl)benzamide (cmpd 24). [R1=R2=R3=R4=R6=H, A=triple bond, L=NHCO, R7=3-(trifluoromethyl)phenyl]

$^1$H NMR (600 MHz, DMSO-$d_6$) δ ppm 6.58 (br. s., 2H) 7.34 (d, J=7.88 Hz, 1H) 7.43 (t, J=7.97 Hz, 1H) 7.63 (s, 1H) 7.77-7.79 (m, 1H) 7.81 (t, J=7.88 Hz, 1H) 7.96-8.02 (m, 2H) 8.12 (s, 1H) 8.28 (d, J=7.88 Hz, 1H) 8.31 (s, 1H) 10.56 (s, 1H) 12.05 (br. s., 1H)

HRMS (ESI) calcd for $C_{22}H_{14}N_5OF_3$ [M+H]+ 422.1223. found 422.1223.

Yield: 12%

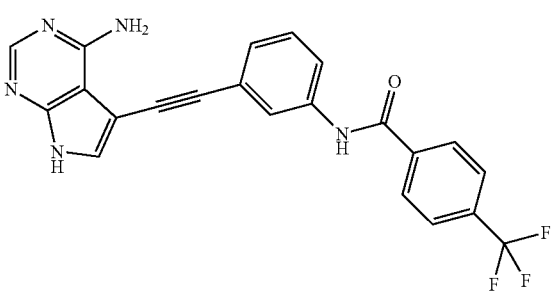 [SMILES: Nc1ncnc2[nH]cc(C#Cc3cccc(NC(=O)c4ccc(C(F)(F)F)cc4)c3)c12]

N-{3-[(4-amino-7H-pyrrolo[2,3-d]pyrimidin-5-yl) ethynyl]phenyl}-4-(trifluoromethyl)benzamide (cmpd 25). [R1=R2=R3=R4=R6=H, A=triple bond, L=NHCO, R7=4-(trifluoromethyl)phenyl]

$^1$H NMR (600 MHz, DMSO-$d_6$) δ ppm 6.52 (br. s., 2H) 7.31-7.36 (m, 1H) 7.43 (t, J=7.97 Hz, 1H) 7.63 (s, 1H) 7.76-7.79 (m, 1H) 7.93 (d, J=8.24 Hz, 2H) 8.01 (s, 1H) 8.12 (s, 1H) 8.16 (d, J=8.24 Hz, 2H) 10.56 (s, 1H) 12.05 (br. s., 1H)

HRMS (ESI) calcd for $C_{22}H_{14}N_5OF_3$ [M+H]+ 422.1223. found 422.1221.

Yield: 16%

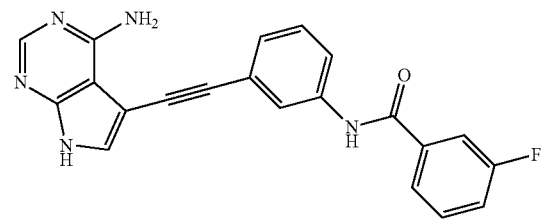 [SMILES: Nc1ncnc2[nH]cc(C#Cc3cccc(NC(=O)c4cccc(F)c4)c3)c12]

N-{3-[(4-amino-7H-pyrrolo[2,3-d]pyrimidin-5-yl) ethynyl]phenyl}-3-fluorobenzamide (cmpd 26). [R1=R2=R3=R4=R6=H, A=triple bond, L=NHCO, R7=3-fluorophenyl]

$^1$H NMR (600 MHz, DMSO-$d_6$) δ ppm 6.58 (br. s., 2H) 7.31-7.35 (m, 1H) 7.41 (t, J=7.88 Hz, 1H) 7.47 (td, J=8.43, 2.01 Hz, 1H) 7.58-7.65 (m, 3H) 7.78 (t, J=9.71 Hz, 3H) 7.83 (d, J=7.69 Hz, 1H) 8.00 (s, 1H) 8.12 (s, 1H) 10.40 (s, 1H) 12.05 (br. s., 1H)

HRMS (ESI) calcd for $C_{21}H_{14}N_5OF$ [M+H]+ 372.1255. found 372.1255.

Yield: 11%

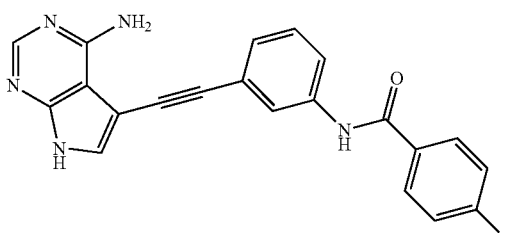

N-{3-[(4-amino-7H-pyrrolo[2,3-d]pyrimidin-5-yl)ethynyl]phenyl}-4-fluorobenzamide (cmpd 27).
[R1=R2=R3=R4=R6=H, A=triple bond, L=NHCO, R7=4-fluorophenyl]

$^1$H NMR (600 MHz, DMSO-d$_6$) δ ppm 6.21-6.81 (m, 2H) 7.31 (d, J=7.69 Hz, 1H) 7.34-7.45 (m, 4H) 7.63 (d, J=2.38 Hz, 1H) 7.76 (dd, J=8.24, 1.10 Hz, 1H) 8.00 (t, J=1.65 Hz, 1H) 8.03-8.07 (m, 2H) 8.12 (s, 1H) 10.35 (s, 1H) 12.05 (br. s., 1H)

HRMS (ESI) calcd for C$_{21}$H$_{14}$N$_5$OF [M+H]+ 372.1255. found 372.1263.

Yield: 22%

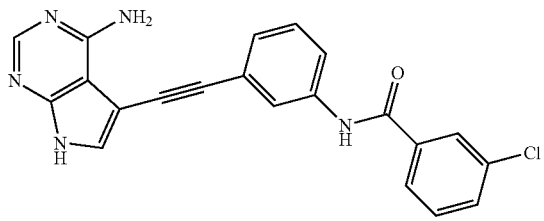 [SMILES: Nc1ncnc2[nH]cc(C#Cc3cccc(NC(=O)c4cccc(Cl)c4)c3)c12]

N-{3-[(4-amino-7H-pyrrolo[2,3-d]pyrimidin-5-yl)ethynyl]phenyl}-3-chlorobenzamide (cmpd 28).
[R1=R2=R3=R4=R6=H, A=triple bond, L=NHCO, R7=3-chlorophenyl]

$^1$H NMR (600 MHz, DMSO-d$_6$) δ ppm 7.30-7.36 (m, 1H) 7.41 (t, J=7.97 Hz, 1H) 7.56-7.61 (m, 1H) 7.63 (d, J=2.38 Hz, 1H) 7.66-7.70 (m, 1H) 7.74-7.78 (m, 1H) 7.77 (d, J=8.06 Hz, 1H) 7.93 (d, J=7.51 Hz, 1H) 8.00 (s, 1H) 8.02 (s, 1H) 8.13 (br. s., 1H) 12.02-12.09 (m, 1H)

HRMS (ESI) calcd for C$_{21}$H$_{14}$N$_5$OCl [M+H]+ 388.0960. found 388.0957.

Yield: 20%

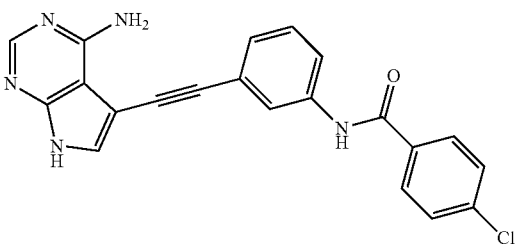 [SMILES: Nc1ncnc2[nH]cc(C#Cc3cccc(NC(=O)c4ccc(Cl)cc4)c3)c12]

N-{3-[(4-amino-7H-pyrrolo[2,3-d]pyrimidin-5-yl)ethynyl]phenyl}-4-chlorobenzamide (cmpd 29).
[R1=R2=R3=R4=R6=H, A=triple bond, L=NHCO, R7=4-chlorophenyl]

$^1$H NMR (600 MHz, DMSO-d$_6$) δ ppm 6.55 (d, J=6.41 Hz, 2H) 7.32 (d, J=7.88 Hz, 1H) 7.41 (t, J=7.97 Hz, 1H) 7.56-7.65 (m, 3H) 7.76 (dd, J=8.24, 1.10 Hz, 1H) 7.96-8.03 (m, 3H) 8.12 (s, 1H) 10.40 (s, 1H) 12.05 (br. s., 1H)

HRMS (ESI) calcd for C$_{21}$H$_{14}$N$_5$OCl [M+H]+ 388.0960. found 388.0961.

Yield: 27%

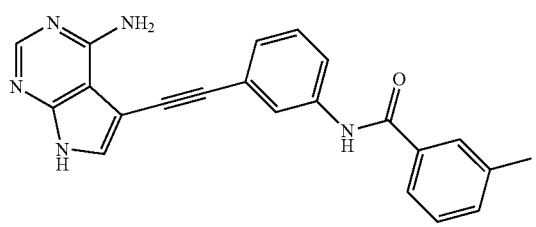 [SMILES: Cc1cccc(C(=O)Nc2cccc(C#Cc3c[nH]c4ncnc(N)c34)c2)c1]

N-{3-[(4-amino-7H-pyrrolo[2,3-d]pyrimidin-5-yl)ethynyl]phenyl}-3-methylbenzamide (cmpd 30).
[R1=R2=R3=R4=R6=H, A=triple bond, L=NHCO, R7=3-methylphenyl]

$^1$H NMR (600 MHz, DMSO-d$_6$) δ ppm 6.53 (br. s., 2H) 7.30 (d, J=7.88 Hz, 1H) 7.38-7.47 (m, 3H) 7.63 (d, J=2.38 Hz, 1H) 7.72-7.80 (m, 3H) 8.01 (s, 1H) 8.12 (s, 1H) 10.29 (s, 1H) 12.05 (br. s., 1H)

HRMS (ESI) calcd for C$_{22}$H$_{17}$N$_5$O [M+H]+ 368.1506. found 368.1510.

Yield: 15%

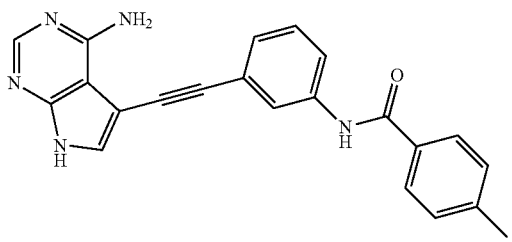 [SMILES: Cc1ccc(C(=O)Nc2cccc(C#Cc3c[nH]c4ncnc(N)c34)c2)cc1]

N-{3-[(4-amino-7H-pyrrolo[2,3-d]pyrimidin-5-yl)ethynyl]phenyl}-4-methylbenzamide (cmpd 31).
[R1=R2=R3=R4=R6=H, A=triple bond, L=NHCO, R7=4-methylphenyl]

$^1$H NMR (600 MHz, DMSO-d$_6$) δ ppm 2.39 (s, 3H) 6.52 (br. s., 2H) 7.30 (d, J=7.69 Hz, 1H) 7.33-7.37 (m, 2H) 7.39 (t, J=7.88 Hz, 1H) 7.63 (d, J=2.38 Hz, 1H) 7.72-7.79 (m, 1H) 7.86-7.92 (m, 2H) 8.01 (d, J=1.65 Hz, 1H) 8.12 (s, 1H) 10.02-10.42 (m, 1H) 11.73-12.20 (m, 1H)

HRMS (ESI) calcd for C$_{22}$H$_{17}$N$_5$O [M+H]+ 368.1506. found 368.1511.

Yield: 18%

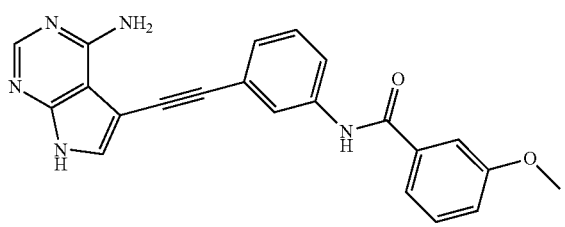 [SMILES: COc1cccc(C(=O)Nc2cccc(C#Cc3c[nH]c4ncnc(N)c34)c2)c1]

N-{3-[(4-amino-7H-pyrrolo[2,3-d]pyrimidin-5-yl)ethynyl]phenyl}-3-methoxybenzamide (cmpd 32). [R1=R2=R3=R4=R6=H, A=triple bond, L=NHCO, R7=3-methoxyphenyl]

$^1$H NMR (600 MHz, DMSO-d$_6$) δ ppm 3.85 (s, 3H) 6.55 (br. s., 2H) 7.14-7.21 (m, 1H) 7.31 (d, J=7.69 Hz, 1H) 7.40 (t, J=7.97 Hz, 1H) 7.46 (t, J=7.97 Hz, 1H) 7.49-7.51 (m, 1H) 7.55 (d, J=7.69 Hz, 1H) 7.63 (d, J=2.56 Hz, 1H) 7.77 (dd, J=8.06, 1.10 Hz, 1H) 8.00 (d, J=1.65 Hz, 1H) 8.12 (s, 1H) 10.30 (s, 1H) 11.47-12.31 (m, 1H)

HRMS (ESI) calcd for C$_{22}$H$_{17}$N$_5$O$_2$ [M+H]+ 384.1455. found 384.1459.

Yield: 25%

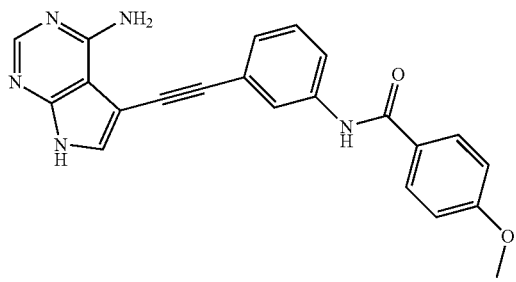 [SMILES: COc1ccc(C(=O)Nc2cccc(C#Cc3c[nH]c4ncnc(N)c34)c2)cc1]

N-{3-[(4-amino-7H-pyrrolo[2,3-d]pyrimidin-5-yl)ethynyl]phenyl}-4-methoxybenzamide (cmpd 33). [R1=R2=R3=R4=R6=H, A=triple bond, L=NHCO, R7=4-methoxyphenyl]

$^1$H NMR (600 MHz, DMSO-d$_6$) δ ppm 3.85 (s, 3H) 6.55 (br. s., 2H) 7.08 (d, J=8.79 Hz, 2H) 7.29 (d, J=7.88 Hz, 1H) 7.39 (t, J=7.88 Hz, 1H) 7.62 (d, J=2.38 Hz, 1H) 7.76 (dd, J=8.15, 1.01 Hz, 1H) 7.94-7.99 (m, 2H) 8.00-8.01 (m, 1H) 8.12 (s, 1H) 10.17 (s, 1H) 12.04 (br. s., 1H)

HRMS (ESI) calcd for C$_{22}$H$_{17}$N$_5$O$_2$ [M+H]+ 384.1455. found 384.1452.

Yield: 21%

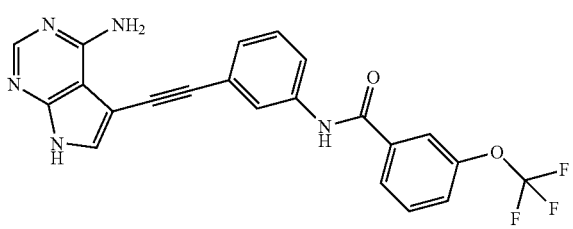 [SMILES: Nc1ncnc2[nH]cc(C#Cc3cccc(NC(=O)c4cccc(OC(F)(F)F)c4)c3)c12]

N-{3-[(4-amino-7H-pyrrolo[2,3-d]pyrimidin-5-yl)ethynyl]phenyl}-3-(trifluoromethoxy)benzamide (cmpd 34). [R1=R2=R3=R4=R6=H, A=triple bond, L=NHCO, R7=3-(trifluoromethoxy)phenyl]

$^1$H NMR (600 MHz, DMSO-d$_6$) δ ppm 6.58 (d, J=9.71 Hz, 2H) 7.34 (d, J=8.06 Hz, 1H) 7.42 (t, J=7.88 Hz, 1H) 7.59-7.65 (m, 2H) 7.69-7.72 (m, 1H) 7.77 (dd, J=8.24, 1.10 Hz, 1H) 7.93 (s, 1H) 7.99 (s, 1H) 8.03 (d, J=8.06 Hz, 1H) 8.12 (s, 1H) 10.47 (s, 1H) 12.05 (br. s., 1H)

HRMS (ESI) calcd for C$_{22}$H$_{14}$N$_5$O$_2$F$_3$ [M+H]+ 438.1173. found 438.1169.

Yield: 17%

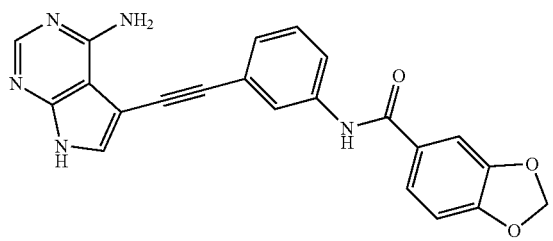 [SMILES: Nc1ncnc2[nH]cc(C#Cc3cccc(NC(=O)c4ccc5c(c4)OCO5)c3)c12]

N-{3-[(4-amino-7H-pyrrolo[2,3-d]pyrimidin-5-yl)ethynyl]phenyl}-1,3-benzodioxole-5-carboxamide (cmpd 35). [R1=R2=R3=R4=R6=H, A=triple bond, L=NHCO, R7=5-(1,3-benzodioxolyl)phenyl]

$^1$H NMR (600 MHz, DMSO-d$_6$) δ ppm 6.14 (s, 2H) 6.57 (br. s., 2H) 7.07 (d, J=8.24 Hz, 1H) 7.29 (d, J=7.69 Hz, 1H) 7.39 (t, J=7.88 Hz, 1H) 7.52 (d, J=1.83 Hz, 1H) 7.59 (dd, J=8.15, 1.74 Hz, 1H) 7.62 (s, 1H) 7.71-7.77 (m, 1H) 7.99 (s, 1H) 8.12 (s, 1H) 10.15 (s, 1H) 12.04 (br. s., 1H)

HRMS (ESI) calcd for C$_{22}$H$_{15}$N$_5$O$_3$ [M+H]+ 398.1248. found 398.1245.

Yield: 8%

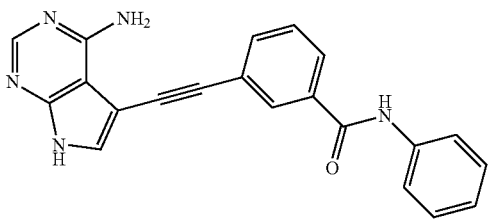 [SMILES: Nc1ncnc2[nH]cc(C#Cc3cccc(C(=O)Nc4ccccc4)c3)c12]

3-[(4-amino-7H-pyrrolo[2,3-d]pyrimidin-5-yl)ethynyl]-N-phenylbenzamide (cmpd 16). [R1=R2=R3=R4=R6=H, A=triple bond, L=NHCO, R7=phenyl]

$^1$H NMR (600 MHz, DMSO-d$_6$) δ ppm 6.63 (br. s., 1H) 7.12 (t, J=7.42 Hz, 1H) 7.36 (t, J=7.97 Hz, 2H) 7.58 (t, J=7.69 Hz, 1H) 7.63 (s, 1H) 7.78 (d, J=7.69 Hz, 3H) 7.93 (d, J=8.06 Hz, 1H) 8.12 (s, 1H) 8.14 (s, 1H) 10.34 (s, 1H) 12.08 (br. s., 1H)

HRMS (ESI) calcd for C$_{21}$H$_{15}$N$_5$O [M+H]+ 354.1350. found 354.1355.

Yield: 12%

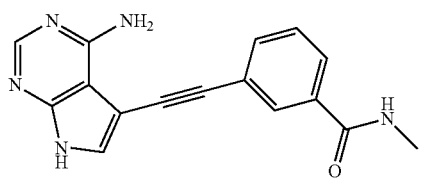 [SMILES: CNC(=O)c1cccc(C#Cc2c[nH]c3ncnc(N)c23)c1]

3-[(4-amino-7H-pyrrolo[2,3-d]pyrimidin-5-yl)ethy-nyl]-N-methylbenzamide (cmpd 17).
[R1=R2=R3=R4=R6=H, A=triple bond, L=CONH, R7=methyl]

$^1$H NMR (600 MHz, DMSO-$d_6$) δ ppm 2.79 (d, J=4.58 Hz, 3H) 6.24-6.90 (m, 2H) 7.48-7.52 (m, 1H) 7.61 (d, J=2.20 Hz, 1H) 7.70 (d, J=7.69 Hz, 1H) 7.81 (d, J=7.88 Hz, 1H) 8.00 (s, 1H) 8.11 (s, 1H) 8.53 (d, J=4.40 Hz, 1H) 12.06 (br. s., 1H)
HRMS (ESI) calcd for $C_{16}H_{13}N_5O$ [M+H]+ 292.1193. found 292.1192.
Yield: 67%

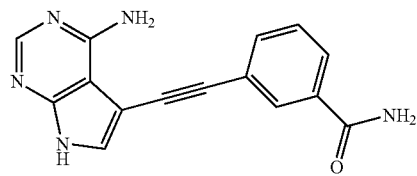 [SMILES: NC(=O)c1cccc(C#Cc2c[nH]c3ncnc(N)c23)c1]

3-[(4-amino-7H-pyrrolo[2,3-d]pyrimidin-5-yl)ethy-nyl]benzamide (cmpd 18).
[R1=R2=R3=R4=R6=R7=H, A=triple bond, L=CONH]

$^1$H NMR (600 MHz, DMSO-$d_6$) δ ppm 6.60 (br. s., 2H) 7.43-7.46 (m, 1H) 7.48-7.52 (m, 3H) 7.61 (s, 1H) 7.71 (d, J=7.69 Hz, 1H) 7.85-7.88 (m, 1H) 8.05 (d, J=1.65 Hz, 2H) 8.11 (s, 1H) 11.92-12.20 (m, 1H)
HRMS (ESI) calcd for $C_{15}H_{11}N_5O$ [M+H]+ 278.1037. found 278.1037.

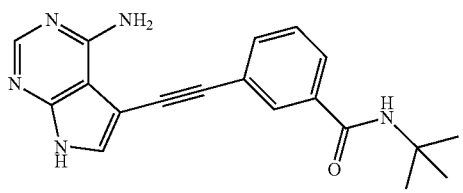 [SMILES: CC(C)(C)NC(=O)c1cccc(C#Cc2c[nH]c3ncnc(N)c23)c1]

3-[(4-amino-7H-pyrrolo[2,3-d]pyrimidin-5-yl)ethy-nyl]-N-tert-butylbenzamide (cmpd 20).
[R1=R2=R3=R4=R6=H, A=triple bond, L=CONH, R7=tertbutyl]

$^1$H NMR (600 MHz, DMSO-$d_6$) δ ppm 1.39 (s, 10H) 6.22-6.85 (m, 2H) 7.45-7.50 (m, 1H) 7.61 (d, J=2.38 Hz, 1H) 7.68 (d, J=7.51 Hz, 1H) 7.78 (d, J=7.88 Hz, 1H) 7.87 (s, 1H) 7.97 (s, 1H) 8.12 (br. s, 1H) 12.05 (br. s., 1H)
HRMS (ESI) calcd for $C_{19}H_{19}N_5O$ [M+H]+ 334.1663. found 334.1667.

Yield: 19%

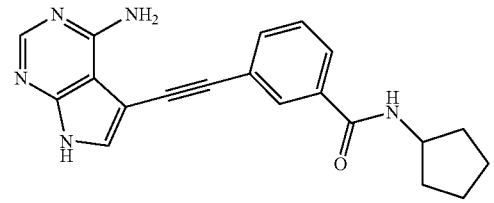 [SMILES: Nc1ncnc2[nH]cc(C#Cc3cccc(C(=O)NC4CCCC4)c3)c12]

3-[(4-amino-7H-pyrrolo[2,3-d]pyrimidin-5-yl)ethy-nyl]-N-cyclopentylbenzamide (cmpd 21).
[R1=R2=R3=R4=R6=H, A=triple bond, L=CONH, R7=cyclopentyl]

$^1$H NMR (600 MHz, DMSO-$d_6$) δ ppm 1.54 (br. s., 6H) 1.70 (br. s., 3H) 1.78-1.95 (m, 3H) 4.17-4.29 (m, 1H) 6.60 (br. s., 2H) 7.45-7.52 (m, 1H) 7.61 (d, J=1.83 Hz, 1H) 7.70 (d, J=7.51 Hz, 1H) 7.82 (d, J=7.69 Hz, 1H) 8.02 (s, 1H) 8.12 (s, 1H) 8.38 (d, J=6.96 Hz, 1H) 12.06 (br. s., 1H)
HRMS (ESI) calcd for $C_{20}H_{19}N_5O$ [M+H]+ 346.1663. found 346.1675.
Yield: 9%

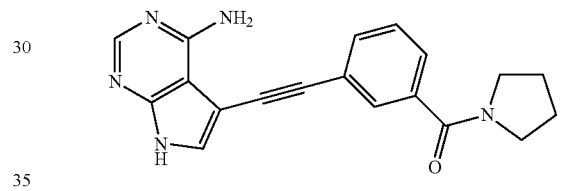

{3-[(4-amino-7H-pyrrolo[2,3-d]pyrimidin-5-yl)ethy-nyl]phenyl}(pyrrolidin-1-yl)methanone (cmpd 22).
[R1=R2=R3=R4=R6=H, A=triple bond, L=CON(Y), Y and R7 together=pyrrolidinyl]

$^1$H NMR (600 MHz, DMSO-$d_6$) δ ppm 1.78-1.91 (m, 5H) 3.39 (t, J=6.50 Hz, 3H) 3.47 (t, J=6.87 Hz, 2H) 6.45-6.73 (m, 2H) 7.45-7.52 (m, 2H) 7.58-7.64 (m, 2H) 7.67-7.69 (m, 1H) 8.11 (s, 1H) 12.05 (br. s., 1H)
HRMS (ESI) calcd for $C_{19}H_{17}N_5O$ [M+H]+ 332.1506. found 332.1516.
Yield: 43%

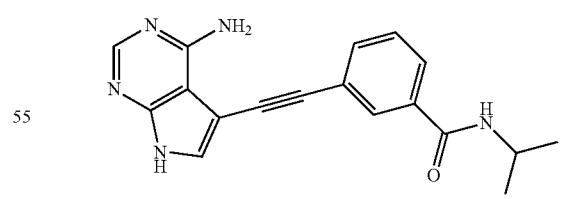

3-[(4-amino-7H-pyrrolo[2,3-d]pyrimidin-5-yl)ethy-nyl]-N-(propan-2Il)benzamide (cmpd 23).
[R1=R2=R3=R4=R6=H, A=triple bond, L=CONH, R7=propan-2-yl]

$^1$H NMR (600 MHz, DMSO-$d_6$) δ ppm 1.17 (d, J=6.59 Hz, 7H) 4.02-4.15 (m, 1H) 6.61 (br. s., 2H) 7.47-7.52 (m, 1H) 7.61 (d, J=2.38 Hz, 1H) 7.68-7.72 (m, 1H) 7.81-7.85 (m, 1H) 8.02 (s, 1H) 8.12 (s, 1H) 8.32 (d, J=7.51 Hz, 1H) 12.06 (br. s., 1H)

HRMS (ESI) calcd for $C_{18}H_{17}N_5O$ [M+H]+ 320.1506. found 320.1502.

Yield: 20%

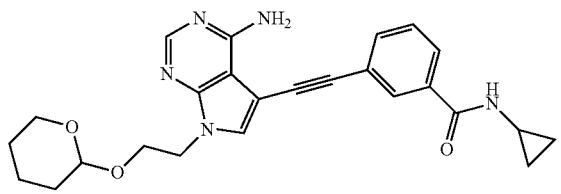 [SMILES: Nc1ncnc2c1c(C#Cc1cccc(C(=O)NC3CC3)c1)cn2CCOC1CCCCO1]

3-({4-amino-7-[2-(tetrahydro-2H-pyran-2-yloxy) ethyl]-7H-pyrrolo[2,3-d]pyrimidin-5-yl}ethynyl)-N-cyclopropyl benzamide (cmpd (IA))
[R1=R3=R4=R6=H, R2=2-(tetrahydro-2H-pyran-2-yloxy)ethyl, A=triple bond, L=CONH, R7=cyclopropyl]

$^1$H NMR (600 MHz, DMSO-$d_6$) δ ppm 0.55-0.61 (m, 2H) 0.68-0.73 (m, 2H) 1.30-1.48 (m, 6H) 1.49-1.58 (m, 1H) 1.59-1.68 (m, 1H) 2.86 (tq, J=7.44, 3.95 Hz, 2H) 3.52 (ddd, J=11.26, 8.43, 3.02 Hz, 1H) 3.73 (dt, J=10.71, 5.27 Hz, 1H) 3.93 (ddd, J=10.94, 6.73, 4.67 Hz, 1H) 4.26-4.33 (m, 1H) 4.34-4.41 (m, 2H) 4.56 (t, J=3.30 Hz, 1H) 6.65 (br. s., 2H) 7.48-7.51 (m, 1H) 7.69 (s, 1H) 7.70-7.73 (m, 1H) 7.80 (d, J=7.88 Hz, 1H) 7.99 (s, 1H) 8.18 (br. s., 1H) 8.52 (d, J=4.03 Hz, 1H)

HRMS (ESI) calcd for $C_{25}H_{27}N_5O_3$ [M+H]+ 444.2187. found 444.2177.

Yield: 67%

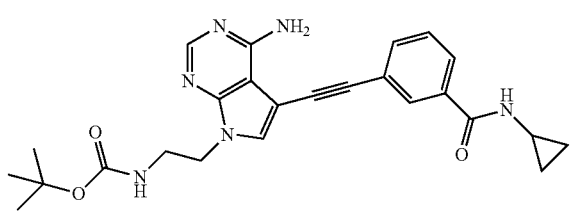 [SMILES: CC(C)(C)OC(=O)NCCn1cc(C#Cc2cccc(C(=O)NC3CC3)c2)c2c(N)ncnc21]

tert-butyl [2-(4-amino-5-{[3-(cyclopropylcarbamoyl)phenyl]ethynyl}-7H-pyrrolo[2,3-d]pyrimidin-7-yl)ethyl]carbamate (cmpd (IA))
[R1=R3=R4=R6=H,
R2=tertbutoxycarbonylaminoethyl, A=triple bond, L=CONH, R7=cyclopropyl]

$^1$H NMR (600 MHz, DMSO-$d_6$) δ ppm 0.56-0.62 (m, 2H) 0.67-0.76 (m, 2H) 1.32 (s, 9H) 2.86 (td, J=7.37, 3.94 Hz, 1H) 4.18 (t, J=5.86 Hz, 2H) 6.29-6.77 (m, 1H) 6.91 (t, J=5.49 Hz, 1H) 7.40-7.54 (m, 1H) 7.59 (s, 1H) 7.70 (d, J=7.88 Hz, 1H) 7.80 (d, J=7.88 Hz, 1H) 7.98 (s, 1H) 8.15 (s, 1H) 8.52 (d, J=4.21 Hz, 1H)

HRMS (ESI) calcd for $C_{25}H_{28}N_6O_3$ [M+H]+ 461.2296. found 461.2295.

Yield: 55%

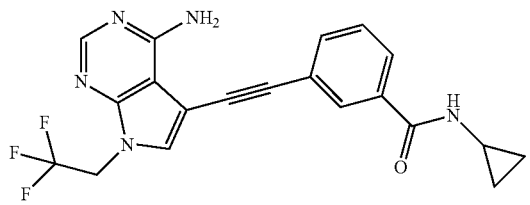 [SMILES: Nc1ncnc2c1c(C#Cc1cccc(C(=O)NC3CC3)c1)cn2CC(F)(F)F]

3-{[4-amino-7-(2,2,2-trifluoroethyl)-7H-pyrrolo[2,3-d]pyrimidin-5-yl]ethynyl}-N-cyclopropylbenzamide (cmpd 36). [R1=R3=R4=R6=H, R2=2,2,2-trifluoroethyl, A=triple bond, L=CONH, R7=cyclopropyl]

$^1$H NMR (600 MHz, DMSO-$d_6$) δ ppm 0.50-0.64 (m, 2H) 0.65-0.76 (m, 2H) 2.86 (tq, J=7.45, 3.95 Hz, 1H) 5.10 (q, J=9.10 Hz, 2H) 6.24-7.06 (m, 2H) 7.51 (t, J=7.88 Hz, 1H) 7.69-7.77 (m, 2H) 7.82 (d, J=7.88 Hz, 1H) 8.02 (s, 1H) 8.22 (s, 1H) 8.52 (d, J=4.03 Hz, 1H)

HRMS (ESI) calcd for $C_{20}H_{16}N_5OF_3$ [M+H]+ 400.1380. found 400.1381.

Yield: 78%

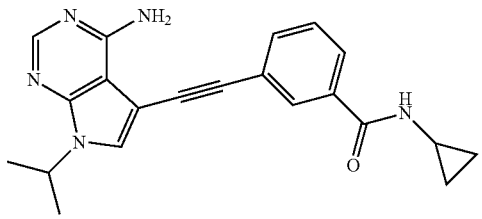 [SMILES: CC(C)n1cc(C#Cc2cccc(C(=O)NC3CC3)c2)c2c(N)ncnc21]

3-{[4-amino-7-(propan-2-yl)-7H-pyrrolo[2,3-d]pyrimidin-5-yl]ethynyl}-N-cyclopropylbenzamide (cmpd 40). [R1=R3=R4=R6=H, R2=propan-2-yl, A=triple bond, L=CONH, R7=cyclopropyl]

$^1$H NMR (600 MHz, DMSO-$d_6$) δ ppm 0.55-0.60 (m, 2H) 0.67-0.74 (m, 2H) 1.45 (d, J=6.78 Hz, 6H) 2.86 (td, J=7.37, 3.75 Hz, 2H) 4.88-4.95 (m, 1H) 6.66 (s, 2H) 7.46-7.52 (m, 1H) 7.68-7.71 (m, 1H) 7.80 (d, J=7.88 Hz, 1H) 7.84 (s, 1H) 7.98 (s, 1H) 8.18 (br. s., 1H) 8.52 (d, J=4.21 Hz, 1H)

HRMS (ESI) calcd for $C_{21}H_{21}N_5O$ [M+H]+ 360.1819. found 360.1819.

Yield: 22%

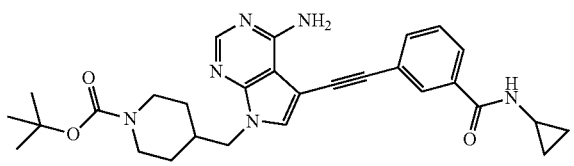 [SMILES: CC(C)(C)OC(=O)N1CCC(Cn2cc(C#Cc3cccc(C(=O)NC4CC4)c3)c3c(N)ncnc32)CC1]

tert-butyl 4-[(4-amino-5-{[3-(cyclopropylcarbamoyl)phenyl]ethynyl}-7H-pyrrolo[2,3-d]pyrimidin-7-yl)methyl]piperidine-1-carboxylate (cmpd (IA))
[R1=R3=R4=R6=H, R2=N-(tert-butoxycarbonyl) piperidin-4-yl]methyl, A=triple bond, L=CONH, R7=cyclopropyl]

$^1$H NMR (600 MHz, DMSO-$d_6$) δ ppm 0.56-0.61 (m, 2H) 0.68-0.73 (m, 2H) 1.04-1.12 (m, 2H) 1.38 (s, 9H) 1.43 (m, J=11.54 Hz, 1H) 1.95-2.08 (m, 1H) 2.59-2.73 (m, 1H) 2.86 (tq, J=7.50, 3.98 Hz, 1H) 3.91 (m, J=11.36 Hz, 1H) 4.05 (d, J=7.14 Hz, 1H) 6.65 (br. s., 2H) 7.48-7.51 (m, 1H) 7.69 (s, 1H) 7.71 (s, 0H) 7.81 (d, J=7.88 Hz, 1H) 7.99 (s, 1H) 8.18 (br. s., 1H) 8.52 (d, J=4.03 Hz, 1H)

HRMS (ESI) calcd for $C_{29}H_{34}N_6O_3$ [M+H]+ 515.2765. found 515.2758.

Yield: 37%

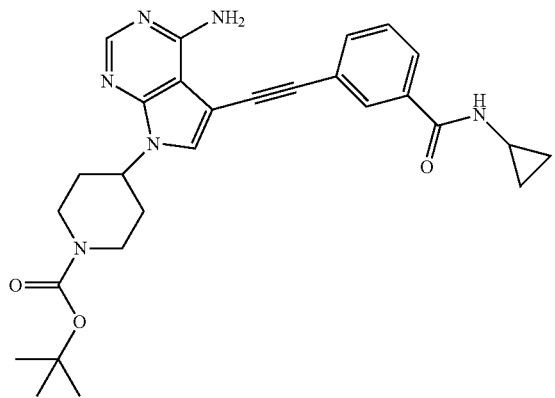 [SMILES: CC(C)(C)OC(=O)N1CCC(n2cc(C#Cc3cccc(C(=O)NC4CC4)c3)c3c(N)ncnc32)CC1]

tert-butyl 4-(4-amino-5-{[3-(cyclopropylcarbamoyl) phenyl]ethynyl}-7H-pyrrolo[2,3-d]pyrimidin-7-yl) piperidine-1-carboxylate (cmpd (IA))
[R1=R3=R4=R6=H, R2=N-(tert-butoxycarbonyl) piperidin-4-yl, A=triple bond, L=CONH, R7=cyclopropyl]

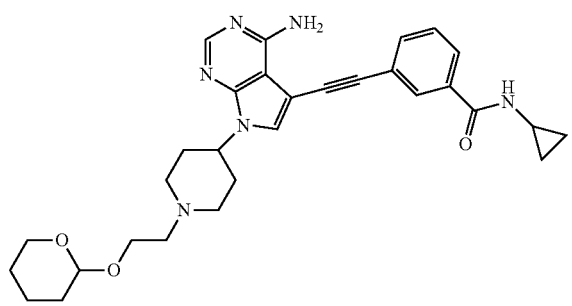 [SMILES: Nc1ncnc2c1c(C#Cc1cccc(C(=O)NC3CC3)c1)cn2C1CCN(CCOC2CCCCO2)CC1]

3-[(4-amino-7-{1-[2-(tetrahydro-2H-pyran-2-yloxy) ethyl]piperidin-4-yl}-7H-pyrrolo[2,3-d]pyrimidin-5-yl)ethynyl]-N-cyclopropylbenzamide (cmpd (IA) R1=R3=R4=R6=H, R2=1-[2-(tetrahydro-2H-pyran-2-yloxy)ethyl), A=triple bond, L=CONH, R7=cyclopropyl]

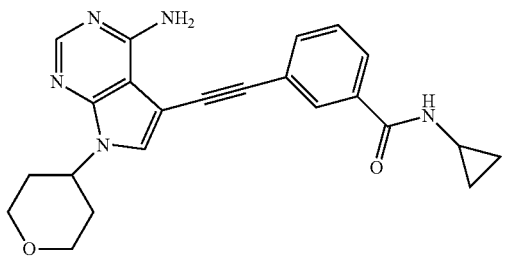 [SMILES: Nc1ncnc2c1c(C#Cc1cccc(C(=O)NC3CC3)c1)cn2C1CCOCC1]

3-{[4-amino-7-(tetrahydro-2H-pyran-4-yl)-7H-pyrrolo[2,3-d]pyrimidin-5-yl]ethynyl}-N-cyclopropylbenzamide (cmpd 47). [R1=R3=R4=R6=H, R2=tetrahydro-2H-pyran-4-yl, A=triple bond, L=CONH, R7=cyclopropyl]

$^1$H NMR (401 MHz, DMSO-$d_6$) δ ppm 0.54-0.62 (m, 2H) 0.67-0.74 (m, 2H) 1.86 (dd, J=12.27, 2.26 Hz, 2H) 2.09 (qd, J=12.23, 4.46 Hz, 2H) 2.81-2.91 (m, 1H) 3.47-3.58 (m, 2H) 4.00 (dd, J=11.35, 3.91 Hz, 2H) 4.71-4.85 (m, 1H) 6.68 (br. s., 2H) 7.45-7.53 (m, 1H) 7.70 (dt, J=7.78, 1.30 Hz, 1H) 7.81 (dt, J=7.81, 1.46 Hz, 1H) 7.84-7.90 (m, 1H) 7.99 (t, J=1.53 Hz, 1H) 8.15 (s, 1H) 8.52 (d, J=4.15 Hz, 1H)

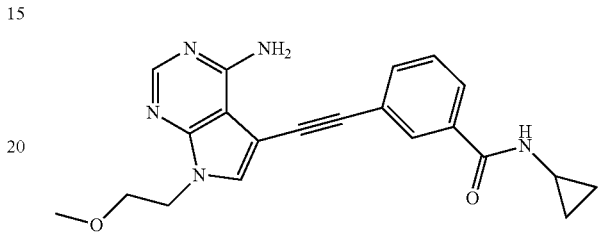

3-{[4-amino-7-(2-methoxyethyl)-7H-pyrrolo[2,3-d] pyrimidin-5-yl]ethynyl}-N-cyclopropylbenzamide (cmpd 48). [R1=R3=R4=R6=H, R2=2-methoxyethyl, A=triple bond, L=CONH, R7=cyclopropyl]

$^1$H NMR (401 MHz, DMSO-$d_6$) δ ppm 0.55-0.62 (m, 2H) 0.67-0.74 (m, 2H) 2.86 (td, J=7.29, 4.09 Hz, 1H) 3.19-3.26 (m, 3H) 3.68 (t, J=5.31 Hz, 2H) 4.27-4.35 (m, 2H) 6.66 (br. s., 2H) 7.44-7.53 (m, 1H) 7.67 (s, 1H) 7.71 (dt, J=7.81, 1.34 Hz, 1H) 7.80 (dt, J=7.87, 1.43 Hz, 1H) 7.99 (t, J=1.53 Hz, 1H) 8.15 (s, 1H) 8.51 (d, J=4.15 Hz, 1H)

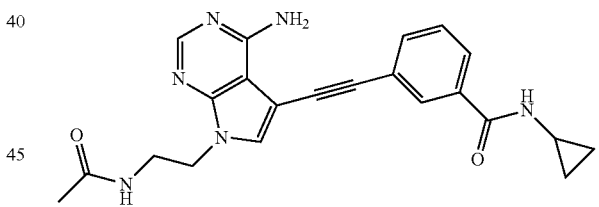

3-({7-[2-(acetylamino)ethyl]-4-amino-7H-pyrrolo[2,3-d]pyrimidin-5-yl}ethynyl)-N-cyclopropylbenzamide (cmpd 49). [R1=R3=R4=R6=H, R2=2-(acetylaminoethyl), A=triple bond, L=CONH, R7=cyclopropyl]

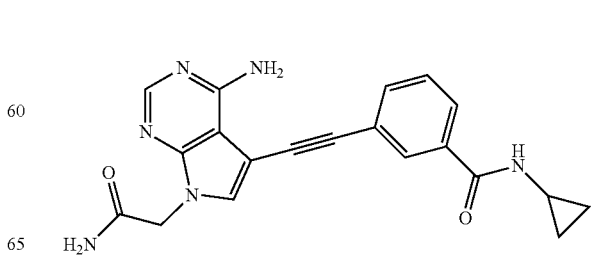

3-{[4-amino-7-(2-amino-2-oxoethyl)-7H-pyrrolo[2,3-d]pyrimidin-5-yl]ethynyl}-N-cyclopropylbenzamide (cmpd 50). [R1=R3=R4=R6=H, R2=2-amino-2-oxoethyl, A=triple bond, L=CONH, R7=cyclopropyl]

$^1$H NMR (401 MHz, DMSO-d$_6$) δ ppm 0.52-0.63 (m, 2H) 0.66-0.75 (m, 2H) 2.86 (tq, J=7.38, 3.95 Hz, 1H) 4.79 (s, 2H) 6.66 (br. s., 2H) 7.23 (s, 1H) 7.43-7.54 (m, 1H) 7.60-7.62 (m, 1H) 7.63 (br. s., 1H) 7.72 (dt, J=7.87, 1.31 Hz, 1H) 7.81 (dt, J=7.84, 1.45 Hz, 1H) 8.00 (t, J=1.53 Hz, 1H) 8.13 (s, 1H) 8.52 (d, J=4.03 Hz, 1H)

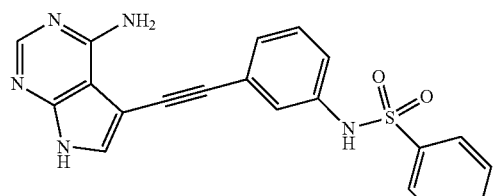

N-{3-[(4-amino-7H-pyrrolo[2,3-d]pyrimidin-5-yl)ethynyl]phenyl}benzenesulfonamide (cmpd 3). [R1=R2=R3=R4=R6=H, A=triple bond, L=NHSO$_2$, R7=phenyl]

$^1$H NMR (600 MHz, DMSO-d$_6$) δ ppm 6.54 (br. s., 2H) 7.09-7.12 (m, 1H) 7.19-7.23 (m, 2H) 7.25-7.29 (m, 1H) 7.55-7.59 (m, 2H) 7.61 (d, J=2.38 Hz, 1H) 7.62-7.65 (m, 1H) 7.77-7.80 (m, 2H) 8.11 (s, 1H) 10.44 (s, 1H) 12.04 (br. s., 1H)

HRMS (ESI) calcd for C$_{20}$H$_{15}$N$_5$O$_2$S [M+H]+ 390.1019. found 390.1027.

Yield: 41%

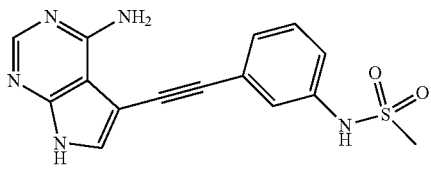 [SMILES: CS(=O)(=O)Nc1cccc(C#Cc2c[nH]c3ncnc(N)c23)c1]

N-{3-[(4-amino-7H-pyrrolo[2,3-d]pyrimidin-5-yl)ethynyl]phenyl}methanesulfonamide (cmpd 4). [(R1=R2=R3=R4=R6=H, A=triple bond, L=NHSO$_2$, R7=methyl]

$^1$H NMR (600 MHz, DMSO-d$_6$) δ ppm 3.03 (s, 3H) 6.30-6.72 (m, 2H) 7.20-7.24 (m, 1H) 7.29-7.32 (m, 1H) 7.34 (t, J=1.65 Hz, 1H) 7.36-7.40 (m, 1H) 7.62 (d, J=2.38 Hz, 1H) 8.11 (s, 1H) 9.87 (br. s., 1H) 12.05 (br. s., 1H)

HRMS (ESI) calcd for C$_{15}$H$_{13}$N$_5$O$_2$S [M+H]+ 328.0863. found 328.0862.

Yield: 29%

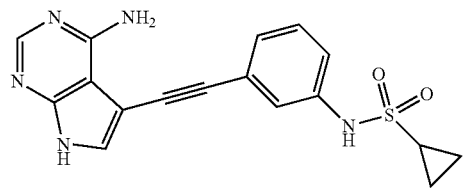 [SMILES: Nc1ncnc2[nH]cc(C#Cc3cccc(NS(=O)(=O)C4CC4)c3)c12]

N-{3-[(4-amino-7H-pyrrolo[2,3-d]pyrimidin-5-yl)ethynyl]phenyl}cyclopropanesulfonamide (cmpd 5). [R1=R2=R3=R4=R6=H, A=triple bond, L=NHSO$_2$, R7=cyclopropyl]

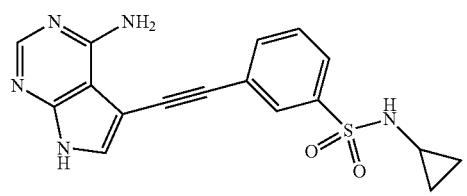 [SMILES: Nc1ncnc2[nH]cc(C#Cc3cccc(S(=O)(=O)NC4CC4)c3)c12]

3-[(4-amino-7H-pyrrolo[2,3-d]pyrimidin-5-yl)ethynyl]-N-cyclopropylbenzenesulfonamide (cmpd 6). [R1=R2=R3=R4=R6=H, A=triple bond, L=SO$_2$NH, R7=cyclopropyl]

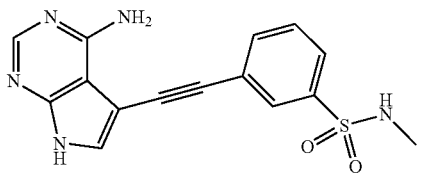 [SMILES: CNS(=O)(=O)c1cccc(C#Cc2c[nH]c3ncnc(N)c23)c1]

3-[(4-amino-7H-pyrrolo[2,3-d]pyrimidin-5-yl)ethynyl]-N-methylbenzenesulfonamide (cmpd 7). [R1=R2=R3=R4=R6=H, A=triple bond, L=SO$_2$NH, R7=methyl]

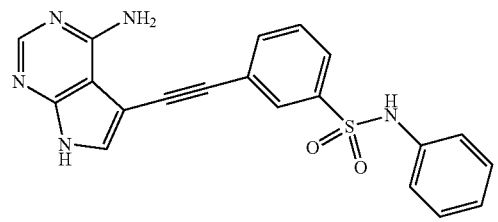 [SMILES: Nc1ncnc2[nH]cc(C#Cc3cccc(S(=O)(=O)Nc4ccccc4)c3)c12]

3-[(4-amino-7H-pyrrolo[2,3-d]pyrimidin-5-yl)ethy-nyl]-N-phenylbenzenesulfonamide (cmpd 8).
[R1=R2=R3=R4=R6=H, A=triple bond, L=SO₂NH, R7=phenyl]

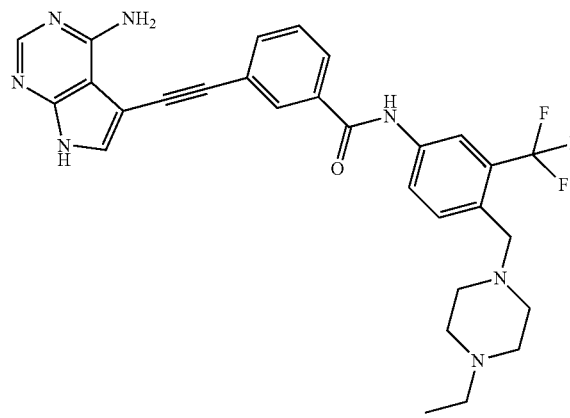

3-[(4-amino-7H-pyrrolo[2,3-d]pyrimidin-5-yl)ethy-nyl]-N-{4-[(4-ethylpiperazin-1-yl)methyl]-3-(trifluo-romethyl)phenyl}benzamide (cmpd 19).
[R1=R2=R3=R4=R6=H, A=triple bond, L=CONH, R7=4-[(4-ethylpiperazin-1-yl)methyl-3-(trifluorom-ethyl) phenyl]

$^1$H NMR (600 MHz, DMSO-d$_6$) δ ppm 0.99 (t, J=7.14 Hz, 3H) 2.19-2.46 (m, 10H) 3.57 (s, 3H) 6.61 (br. s., 2H) 7.60 (t, J=7.88 Hz, 1H) 7.64 (d, J=2.20 Hz, 1H) 7.72 (d, J=8.61 Hz, 1H) 7.80 (dt, J=7.83, 1.21 Hz, 1H) 7.91-7.98 (m, 1H) 8.05 (dd, J=8.52, 1.92 Hz, 1H) 8.12 (s, 1H) 8.16 (t, J=1.47 Hz, 1H) 8.21 (d, J=2.20 Hz, 1H) 10.59 (s, 1H) 12.08 (br. s., 1H)
HRMS (ESI) calcd for C$_{29}$H$_{28}$N$_7$OF$_3$ [M+H]+ 548.2380. found 548.2392.
Yield: 21%

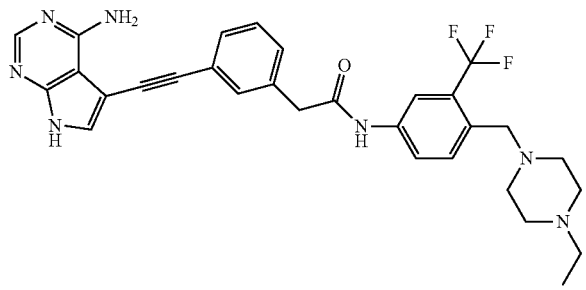 [SMILES: CCN1CCN(Cc2ccc(NC(=O)Cc3cccc(C#Cc4c[nH]c5ncnc(N)c45)c3)cc2C(F)(F)F)CC1]

2-{3-[(4-amino-7H-pyrrolo[2,3-d]pyrimidin-5-yl) ethynyl]phenyl}-N-{4-[(4-ethylpiperazin-1-yl) methyl]-3-(trifluoro methyl)phenyl}acetamide (cmpd 12). [R1=R2=R3=R4=R6=H, A=triple bond, L=CH₂CONH, R7=4-[(4-ethylpiperazin-1-yl) methyl-3-(trifluoromethyl) phenyl]

$^1$H NMR (600 MHz, DMSO-d$_6$) δ ppm 0.97 (t, J=7.05 Hz, 3H) 1.95-2.47 (m, 9H) 3.53 (s, 2H) 3.69 (s, 2H) 6.18-6.76 (m, 2H) 7.30-7.36 (m, 1H) 7.36-7.39 (m, 1H) 7.46 (d, J=7.51 Hz, 1H) 7.53 (s, 1H) 7.59 (d, J=2.56 Hz, 1H) 7.66 (d, J=8.43 Hz, 1H) 7.78 (dd, J=8.52, 1.74 Hz, 1H) 8.05 (d, J=2.01 Hz, 1H) 8.11 (s, 1H) 10.47 (s, 1H) 12.03 (br. s., 1H)
HRMS (ESI) calcd for C$_{30}$H$_{30}$N$_7$OF$_3$ [M+H]+ 562.2537. found 562.2537.
Yield: 22%

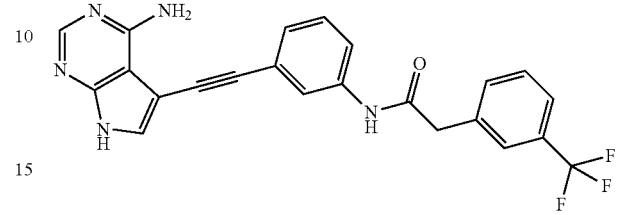

N-{3-[(4-amino-7H-pyrrolo[2,3-d]pyrimidin-5-yl) ethynyl]phenyl}-2-[3-(trifluoromethyl)phenyl]acet-amide (cmpd 11). [R1=R2=R3=R4=R6=H, A=triple bond, L=NHCOCH₂, R7=3-(trifluoromethyl)phenyl]

$^1$H NMR (600 MHz, DMSO-d$_6$) δ ppm 3.80 (s, 2H) 6.53 (br. s., 2H) 7.25 (d, J=7.69 Hz, 1H) 7.35 (t, J=7.97 Hz, 1H) 7.52-7.55 (m, 1H) 7.56-7.66 (m, 5H) 7.71 (s, 1H) 7.84 (s, 1H) 8.11 (s, 1H) 10.34 (s, 1H)
HRMS (ESI) calcd for C$_{23}$H$_{16}$N$_5$OF$_3$ [M+H]+ 436.1380. found 436.1380
Yield: 20%

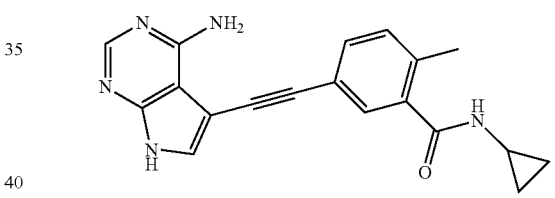

5-[(4-amino-7H-pyrrolo[2,3-d]pyrimidin-5-yl)ethy-nyl]-N-cyclopropyl-2-methylbenzamide (cmpd 41).
[R1=R2=R3=R6=H, R4=2-methyl, A=triple bond, L=CONH, R7=cyclopropyl]

$^1$H NMR (600 MHz, DMSO-d$_6$) δ ppm 0.50-0.58 (m, 2H) 0.66-0.72 (m, 2H) 2.31-2.37 (m, 3H) 2.83 (tq, J=7.44, 3.89 Hz, 1H) 6.29-6.77 (m, 2H) 7.27 (d, J=7.88 Hz, 1H) 7.46-7.48 (m, 1H) 7.50 (d, J=1.65 Hz, 1H) 7.57 (d, J=2.38 Hz, 1H) 8.11 (s, 1H) 8.36 (d, J=4.21 Hz, 1H) 12.02 (br. s., 1H)
HRMS (ESI) calcd for C$_{19}$H$_{17}$N$_5$O [M+H]+ 332.1506. found 332.1503.
Yield: 6%

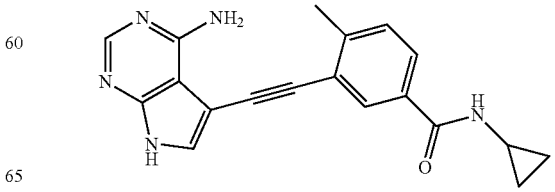

3-[(4-amino-7H-pyrrolo[2,3-d]pyrimidin-5-yl)ethynyl]-N-cyclopropyl-4-methylbenzamide (cmpd 42).
[R1=R2=R3=R6=H, R4=4-methyl, A=triple bond, L=CONH, R7=cyclopropyl]

¹H NMR (600 MHz, DMSO-d₆) δ ppm 0.54-0.61 (m, 2H) 0.67-0.73 (m, 2H) 2.85 (tq, J=7.51, 3.91 Hz, 1H) 6.57 (br. s., 2H) 7.39 (d, J=8.06 Hz, 1H) 7.62 (s, 1H) 7.72 (d, J=8.42 Hz, 1H) 7.97 (s, 1H) 8.11 (s, 1H) 8.46 (d, J=4.03 Hz, 1H) 12.08 (br. s., 1H)

HRMS (ESI) calcd for $C_{19}H_{17}N_5O$ [M+H]+ 332.1506. found 332.1497.

Yield: 4%.

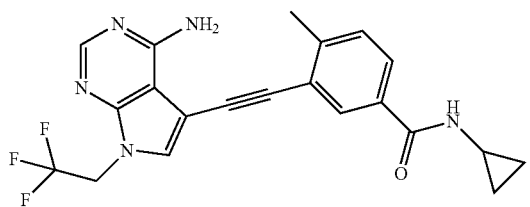 [SMILES: Cc1ccc(C(=O)NC2CC2)cc1C#Cc1cn(CC(F)(F)F)c2ncnc(N)c12]

3-{[4-amino-7-(2,2,2-trifluoroethyl)-7H-pyrrolo[2,3-d]pyrimidin-5-yl]ethynyl}-N-cyclopropyl-4-methylbenzamide (cmpd 52). [R1=R3=R6=H, R2=2,2,2-trifluoroethyl, R4=4-methyl, A=triple bond, L=CONH, R7=cyclopropyl]

¹H NMR (401 MHz, DMSO-d₆) δ ppm 0.54-0.61 (m, 2H) 0.66-0.74 (m, 2H) 2.85 (tq, J=7.44, 3.91 Hz, 1H) 5.10 (q, J=9.28 Hz, 2H) 6.81 (br. s., 2H) 7.40 (d, J=8.18 Hz, 1H) 7.70-7.77 (m, 2H) 8.01 (d, J=1.59 Hz, 1H) 8.22 (s, 1H) 8.45 (d, J=4.15 Hz, 1H)

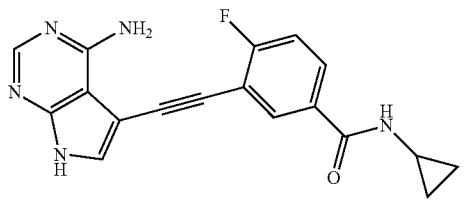 [SMILES: Nc1ncnc2[nH]cc(C#Cc3cc(C(=O)NC4CC4)ccc3F)c12]

3-[(4-amino-7H-pyrrolo[2,3-d]pyrimidin-5-yl)ethynyl]-N-cyclopropyl-4-fluorobenzamide (cmpd 43).
[R1=R2=R3=R6=H, R4=4-fluoro, A=triple bond, L=CONH, R7=cyclopropyl]

¹H NMR (600 MHz, DMSO-d₆) δ ppm 0.55-0.61 (m, 2H) 0.68-0.73 (m, 2H) 2.85 (tq, J=7.39, 3.86 Hz, 1H) 6.64 (br. s., 2H) 7.42 (t, J=9.07 Hz, 1H) 7.66 (s, 1H) 7.82-7.91 (m, 1H) 8.07 (dd, J=6.87, 2.11 Hz, 1H) 8.12 (s, 1H) 8.54 (d, J=4.40 Hz, 1H) 12.15 (br. s., 1H)

HRMS (ESI) calcd for $C_{18}H_{14}N_5OF$ [M+H]+ 336.1255. found 336.1252.

Yield: 7%

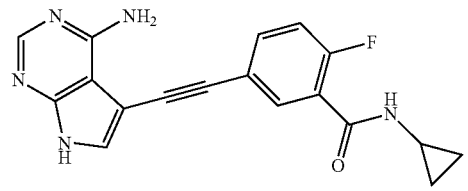 [SMILES: Nc1ncnc2[nH]cc(C#Cc3ccc(F)c(C(=O)NC4CC4)c3)c12]

5-[(4-amino-7H-pyrrolo[2,3-d]pyrimidin-5-yl)ethynyl]-N-cyclopropyl-2-fluorobenzamide (cmpd 44).
[R1=R2=R3=R6=H, R4=2-fluoro, A=triple bond, L=CONH, R7=cyclopropyl]

¹H NMR (600 MHz, DMSO-d₆) δ ppm 0.53-0.56 (m, 2H) 0.70 (t, J=5.86 Hz, 2H) 2.82-2.86 (m, 1H) 6.46-6.70 (m, 1H) 7.32 (t, J=9.34 Hz, 1H) 7.59 (s, 1H) 7.67-7.71 (m, 2H) 7.73 (dd, J=6.69, 2.11 Hz, 1H) 8.10 (s, 1H) 8.47 (d, J=3.85 Hz, 1H) 12.05 (br. s., 1H)

HRMS (ESI) calcd for $C_{18}H_{14}N_5OF$ [M+H]+ 336.1255. found 336.1256.

Yield: 2%

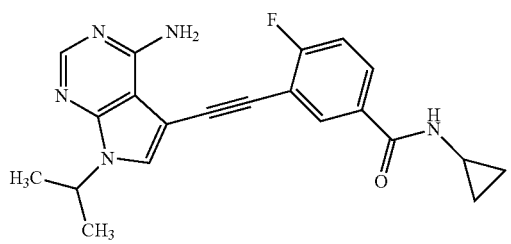 [SMILES: CC(C)n1cc(C#Cc2cc(C(=O)NC3CC3)ccc2F)c2c(N)ncnc21]

3-{[4-amino-7-(propan-2-yl)-7H-pyrrolo[2,3-d]pyrimidin-5-yl]ethynyl}-N-cyclopropyl-4-fluorobenzamide (cmpd 53). [R1=R3=R6=H, R2=propan-2-yl, R4=4-fluoro, A=triple bond, L=CONH, R7=cyclopropyl]

¹H NMR (401 MHz, DMSO-d₆) δ ppm 0.55-0.61 (m, 2H) 0.68-0.74 (m, 2H) 1.45 (d, J=6.71 Hz, 6H) 2.79-2.90 (m, 1H) 4.92 (quin, J=6.77 Hz, 1H) 6.49-6.95 (m, 1H) 7.42 (t, J=9.09 Hz, 1H) 7.82-7.90 (m, 2H) 8.07 (dd, J=7.02, 2.26 Hz, 1H) 8.16 (s, 1H) 8.54 (d, J=4.03 Hz, 1H)

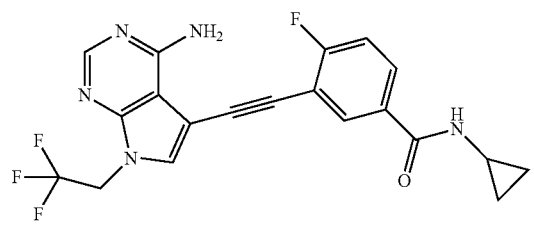 [SMILES: Nc1ncnc2c1c(C#Cc1cc(C(=O)NC3CC3)ccc1F)cn2CC(F)(F)F]

3-{[4-amino-7-(2,2,2-trifluoroethyl)-7H-pyrrolo[2,3-d]pyrimidin-5-yl]ethynyl}-N-cyclopropyl-4-fluorobenzamide (cmpd 54). [R1=R3=R6=H, R2=2,2,2-trifluoroethyl, R4=4-fluoro, A=triple bond, L=CONH, R7=cyclopropyl]

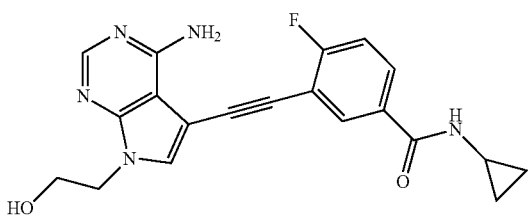 [SMILES: Nc1ncnc2c1c(C#Cc1cc(C(=O)NC3CC3)ccc1F)cn2CCO]

3-{[4-amino-7-(2-hydroxyethyl)-7H-pyrrolo[2,3-d]pyrimidin-5-yl]ethynyl}-N-cyclopropyl-4-fluorobenzamide (cmpd 55). [R1=R3=R6=H, R2=2-hydroxyethyl, R4=4-fluoro, A=triple bond, L=CONH, R7=cyclopropyl]

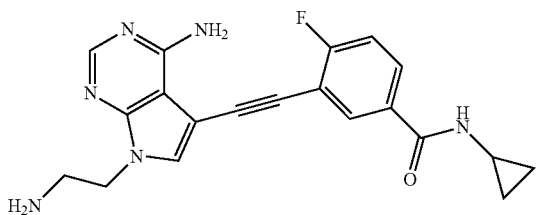 [SMILES: NCCn1cc(C#Cc2cc(C(=O)NC3CC3)ccc2F)c2c(N)ncnc21]

3-{[4-amino-7-(2-aminoethyl)-7H-pyrrolo[2,3-d]pyrimidin-5-yl]ethynyl}-N-cyclopropyl-4-fluorobenzamide (cmpd 56). [R1=R3=R6=H, R2=2-aminoethyl, R4=4-fluoro, A=triple bond, L=CONH, R7=cyclopropyl]

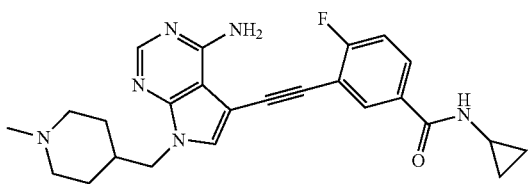 [SMILES: CN1CCC(Cn2cc(C#Cc3cc(C(=O)NC4CC4)ccc3F)c3c(N)ncnc32)CC1]

3-({4-amino-7-[(1-methylpiperidin-4-yl)methyl]-7H-pyrrolo[2,3-d]pyrimidin-5-yl}ethynyl)-N-cyclopropyl-4-fluorobenzamide (cmpd 57). [R1=R3=R6=H, R2=(1-methylpiperidin-4-yl)methyl, R4=4-fluoro, A=triple bond, L=CONH, R7=cyclopropyl]

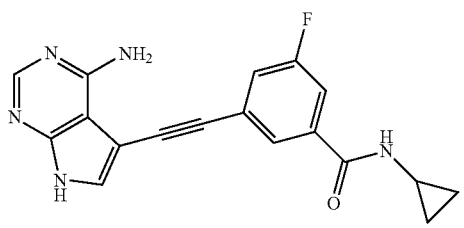 [SMILES: Nc1ncnc2[nH]cc(C#Cc3cc(F)cc(C(=O)NC4CC4)c3)c12]

3-[(4-amino-7H-pyrrolo[2,3-d]pyrimidin-5-yl)ethynyl]-N-cyclopropyl-5-fluorobenzamide (cmpd 45). [R1=R2=R3=R6=H, R4=5-fluoro, A=triple bond, L=CONH, R7=cyclopropyl]

$^1$H NMR (600 MHz, DMSO-d$_6$) δ ppm 0.56-0.61 (m, 2H) 0.69-0.74 (m, 2H) 2.86 (tq, J=7.49, 3.92 Hz, 1H) 6.61 (br. s., 2H) 7.60 (m, J=9.71, 1.28 Hz, 1H) 7.64 (s, 1H) 7.65 (m, J=9.20, 1.17, 1.17 Hz, 1H) 7.84 (t, J=1.28 Hz, 1H) 8.11 (s, 1H) 8.60 (d, J=4.03 Hz, 1H) 12.10 (br. s., 1H)

HRMS (ESI) calcd for C$_{18}$H$_{14}$N$_5$OF [M+H]+ 336.1255. found 336.1255.

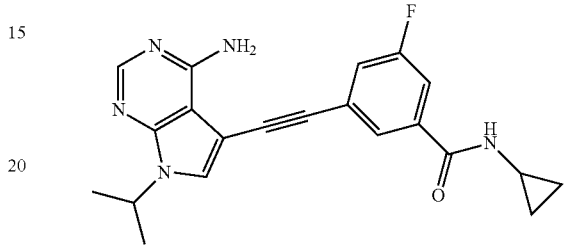

3-{[4-amino-7-(propan-2-yl)-7H-pyrrolo[2,3-d]pyrimidin-5-yl]ethynyl}-N-cyclopropyl-5-fluorobenzamide (cmpd 58). [R1=R3=R6=H, R2=propan-2-yl, R4=5-fluoro, A=triple bond, L=CONH, R7=cyclopropyl]

$^1$H NMR (401 MHz, DMSO-d$_6$) δ ppm 0.52-0.63 (m, 2H) 0.69-0.75 (m, 2H) 1.45 (d, J=6.71 Hz, 6H) 2.82-2.91 (m, 1H) 4.92 (quin, J=6.74 Hz, 1H) 6.67 (br. s., 2H) 7.63 (m, J=17.00, 9.50, 2.50, 1.50 Hz, 2H) 7.84 (t, J=1.40 Hz, 1H) 7.86 (s, 1H) 8.15 (s, 1H) 8.59 (d, J=4.15 Hz, 1H)

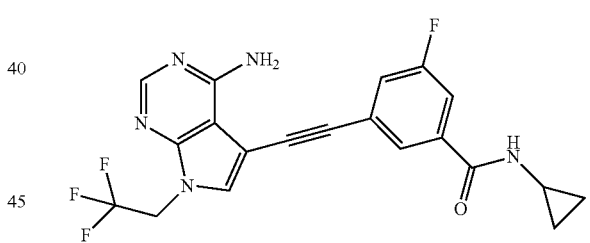

3-{[4-amino-7-(2,2,2-trifluoroethyl)-7H-pyrrolo[2,3-d]pyrimidin-5-yl]ethynyl}-N-cyclopropyl-5-fluorobenzamide (cmpd 59). [R1=R3=R6=H, R2=2,2,2-trifluoroethyl, R4=5-fluoro, A=triple bond, L=CONH, R7=cyclopropyl]

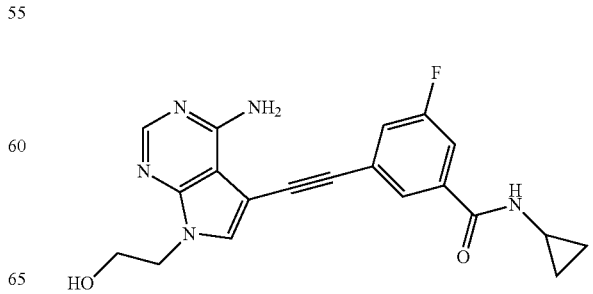

3-{[4-amino-7-(2-hydroxyethyl)-7H-pyrrolo[2,3-d]pyrimidin-5-yl]ethynyl}-N-cyclopropyl-5-fluorobenzamide (cmpd 60). [R1=R3=R6=H, R2=2-hydroxyethyl, R4=5-fluoro, A=triple bond, L=CONH, R7=cyclopropyl]

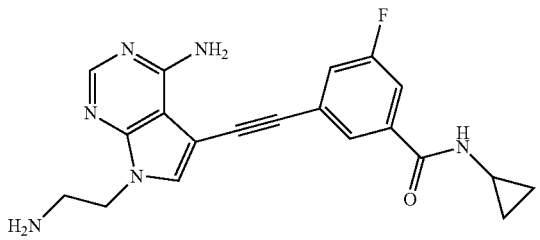 [SMILES: NCCn1cc(C#Cc2cc(F)cc(C(=O)NC3CC3)c2)c2c(N)ncnc21]

3-{[4-amino-7-(2-aminoethyl)-7H-pyrrolo[2,3-d]pyrimidin-5-yl]ethynyl}-N-cyclopropyl-5-fluorobenzamide (cmpd 61). [R1=R3=R6=H, R2=2-aminoethyl, R4=5-fluoro, A=triple bond, L=CONH, R7=cyclopropyl]

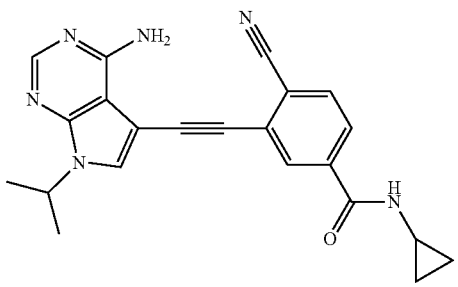 [SMILES: CC(C)n1cc(C#Cc2cc(C(=O)NC3CC3)ccc2C#N)c2c(N)ncnc21]

3-{[4-amino-7-(propan-2-yl)-7H-pyrrolo[2,3-d]pyrimidin-5-yl]ethynyl}-4-cyano-N-cyclopropylbenzamide (cmpd 108). [R1=R3=R6=H, R2=propan-2-yl, R4=4-cyano, A=triple bond, L=CONH, R7=cyclopropyl]

$^1$H NMR (401 MHz, DMSO-$d_6$) δ ppm 0.55-0.64 (m, 2H) 0.70-0.77 (m, 2H) 1.47 (d, J=6.71 Hz, 6H) 2.84-2.93 (m, 1H) 4.94 (quin, J=6.74 Hz, 1H) 6.78 (br. s., 2H) 7.90 (dd, J=8.06, 1.71 Hz, 1H) 7.94 (s, 1H) 8.02 (d, J=8.18 Hz, 1H) 8.14 (d, J=1.34 Hz, 1H) 8.17 (s, 1H) 8.75 (d, J=4.03 Hz, 1H)

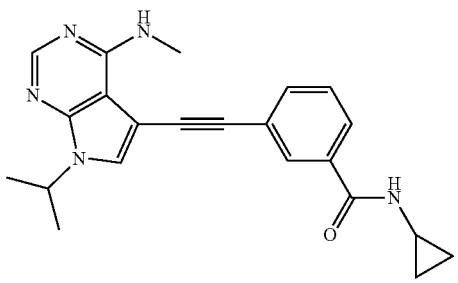 [SMILES: CNc1ncnc2c1c(C#Cc1cccc(C(=O)NC3CC3)c1)cn2C(C)C]

N-cyclopropyl-3-{[4-(methylamino)-7-(propan-2-yl)-7H-pyrrolo[2,3-d]pyrimidin-5-yl]ethynyl}benzamide (cmpd 63). [R1=methylamino, R3=R4=R6=H, R2=isopropyl, H, A=triple bond, L=CONH, R7=cyclopropyl]

$^1$H NMR (401 MHz, DMSO-$d_6$) δ ppm 0.51-0.60 (m, 2H) 0.65-0.74 (m, 2H) 1.42 (d, J=6.71 Hz, 6H) 2.84 (tq, J=7.37, 3.92 Hz, 1H) 3.04 (d, J=4.76 Hz, 3H) 4.91 (quin, J=6.74 Hz, 1H) 6.51 (br. s., 1H) 7.43-7.52 (m, 1H) 7.70 (dt, J=7.84, 1.21 Hz, 1H) 7.78 (dt, J=7.99, 1.37 Hz, 1H) 7.83 (s, 1H) 7.98 (t, J=1.53 Hz, 1H) 8.23 (s, 1H) 8.49 (d, J=4.39 Hz, 1H)

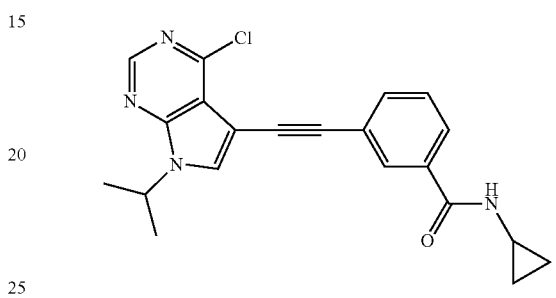

3-{[4-chloro-7-(propan-2-yl)-7H-pyrrolo[2,3-d]pyrimidin-5-yl]ethynyl}-N-cyclopropylbenzamide (cmpd (V)) [R1=chloro, R3=R4=R6=H, R2=isopropyl, H, A=triple bond, L=CONH, R7=cyclopropyl]

$^1$H NMR (401 MHz, DMSO-$d_6$) δ ppm 0.55-0.61 (m, 2H) 0.67-0.76 (m, 2H) 1.51 (d, J=6.84 Hz, 6H) 2.86 (td, J=7.26, 4.03 Hz, 1H) 5.07 (quin, J=6.74 Hz, 1H) 7.51 (t, J=7.75 Hz, 1H) 7.66 (dt, J=7.75, 1.31 Hz, 1H) 7.83 (dt, J=7.87, 1.43 Hz, 1H) 7.94 (t, J=1.53 Hz, 1H) 8.38 (s, 1H) 8.56 (d, J=4.03 Hz, 1H) 8.70 (s, 1H)

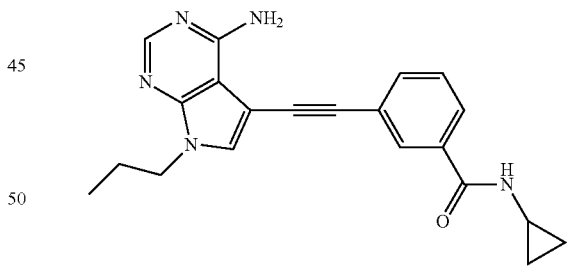

3-[(4-amino-7-propyl-7H-pyrrolo[2,3-d]pyrimidin-5-yl)ethynyl]-N-cyclopropylbenzamide (cmpd 66). [R1=R3=R4=R6=H, R2=propyl, A=triple bond, L=CONH, R7=cyclopropyl]

$^1$H NMR (401 MHz, DMSO-$d_6$) δ ppm 0.54-0.64 (m, 2H) 0.67-0.75 (m, 2H) 0.83 (t, J=7.38 Hz, 3H) 1.79 (sxt, J=7.25 Hz, 2H) 2.86 (td, J=7.23, 4.09 Hz, 1H) 4.11 (t, J=7.02 Hz, 2H) 6.64 (br. s., 1H) 7.47-7.52 (m, 1H) 7.68-7.72 (m, 2H) 7.80 (dt, J=8.06, 1.34 Hz, 1H) 7.99 (t, J=1.46 Hz, 1H) 8.15 (s, 1H) 8.52 (d, J=4.27 Hz, 1H)

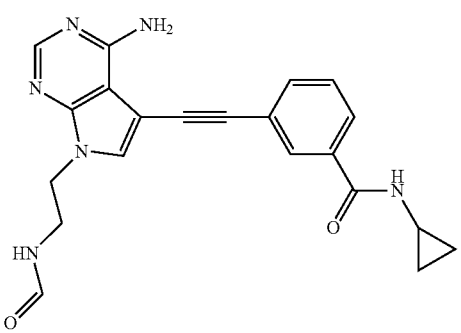 [SMILES: Nc1ncnc2c1c(C#Cc1cccc(C(=O)NC3CC3)c1)cn2CCNC=O]

3-({4-amino-7-[2-(formylamino)ethyl]-7H-pyrrolo[2,3-d]pyrimidin-5-yl}ethynyl)-N-cyclopropylbenzamide (cmpd 67). [R1=R3=R4=R6=H, R2=formylaminoethyl, A=triple bond, L=CONH, R7=cyclopropyl]

$^1$H NMR (401 MHz, DMSO-d$_6$) δ ppm 0.54-0.62 (m, 2H) 0.67-0.75 (m, 2H) 2.86 (tq, J=7.40, 3.90 Hz, 1H) 3.51 (q, J=6.10 Hz, 2H) 4.23 (t, J=5.98 Hz, 2H) 6.67 (br. s., 2H) 7.47-7.52 (m, 1H) 7.66 (s, 1H) 7.71 (d, J=7.81 Hz, 1H) 7.81 (d, J=8.30 Hz, 1H) 7.96-8.01 (m, 2H) 8.08 (br. s., 1H) 8.16 (s, 1H) 8.52 (d, J=3.91 Hz, 1H)

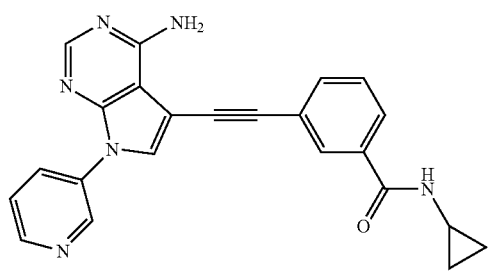 [SMILES: Nc1ncnc2c1c(C#Cc1cccc(C(=O)NC3CC3)c1)cn2-c1cccnc1]

3-{[4-amino-7-(pyridin-3-yl)-7H-pyrrolo[2,3-d]pyrimidin-5-yl]ethynyl}-N-cyclopropylbenzamide (cmpd 68). [R1=R3=R4=R6=H, R2=pyridin-3-yl, A=triple bond, L=CONH, R7=cyclopropyl]

$^1$H NMR (401 MHz, DMSO-d$_6$) δ ppm 0.48-0.62 (m, 2H) 0.68-0.77 (m, 2H) 2.87 (td, J=7.29, 3.97 Hz, 1H) 6.91 (br. s., 2H) 7.52 (t, J=7.87 Hz, 1H) 7.59-7.64 (m, 1H) 7.76 (dt, J=7.78, 1.30 Hz, 1H) 7.84 (dt, J=7.84, 1.45 Hz, 1H) 8.04 (t, J=1.53 Hz, 1H) 8.20 (s, 1H) 8.24 (s, 1H) 8.31 (ddd, J=8.27, 2.65, 1.53 Hz, 1H) 8.54 (d, J=4.15 Hz, 1H) 8.60-8.62 (m, 1H) 9.09 (d, J=2.20 Hz, 1H)

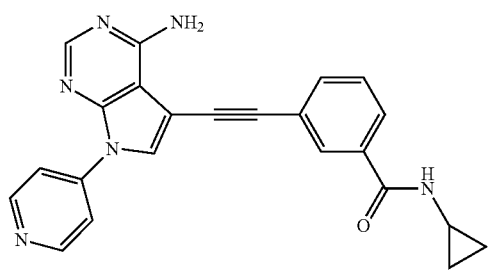 [SMILES: Nc1ncnc2c1c(C#Cc1cccc(C(=O)NC3CC3)c1)cn2-c1ccncc1]

3-{[4-amino-7-(pyridin-4-yl)-7H-pyrrolo[2,3-d]pyrimidin-5-yl]ethynyl}-N-cyclopropylbenzamide (cmpd 69). [R1=R3=R4=R6=H, R2=pyridin-4-yl, A=triple bond, L=CONH, R7=cyclopropyl]

$^1$H NMR (401 MHz, DMSO-d$_6$) δ ppm 0.56-0.61 (m, 2H) 0.68-0.74 (m, 2H) 2.87 (tq, J=7.45, 3.90 Hz, 1H) 6.95 (br. s., 2H) 7.53 (t, J=7.75 Hz, 1H) 7.77 (dd, J=7.75, 1.28 Hz, 1H) 7.83-7.87 (m, 1H) 8.03-8.07 (m, 1H) 8.13-8.17 (m, 2H) 8.30 (s, 1H) 8.35 (s, 1H) 8.55 (d, J=4.03 Hz, 1H) 8.71 (d, J=5.86 Hz, 2H)

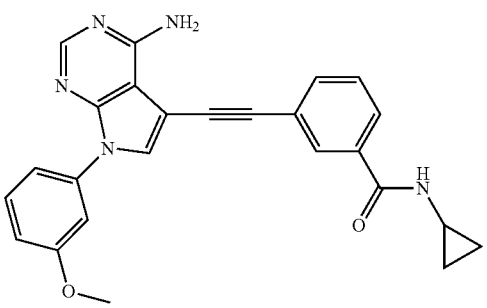 [SMILES: COc1cccc(-n2cc(C#Cc3cccc(C(=O)NC4CC4)c3)c3c(N)ncnc32)c1]

3-{[4-amino-7-(3-methoxyphenyl)-7H-pyrrolo[2,3-d]pyrimidin-5-yl]ethynyl}-N-cyclopropylbenzamide (cmpd 70). [R1=R3=R4=R6=H, R2=3-methoxyphenyl, A=triple bond, L=CONH, R7=cyclopropyl]

$^1$H NMR (401 MHz, DMSO-d$_6$) δ ppm 0.53-0.64 (m, 2H) 0.68-0.75 (m, 2H) 2.87 (td, J=7.29, 3.97 Hz, 1H) 3.84 (s, 3H) 6.58-6.91 (m, 1H) 6.96-7.03 (m, 1H) 7.43-7.47 (m, 3H) 7.52 (t, J=7.75 Hz, 1H) 7.75 (dt, J=7.84, 1.33 Hz, 1H) 7.84 (dt, J=7.75, 1.43 Hz, 1H) 8.03 (t, J=1.53 Hz, 1H) 8.13 (s, 1H) 8.22 (s, 1H) 8.55 (d, J=4.39 Hz, 1H).

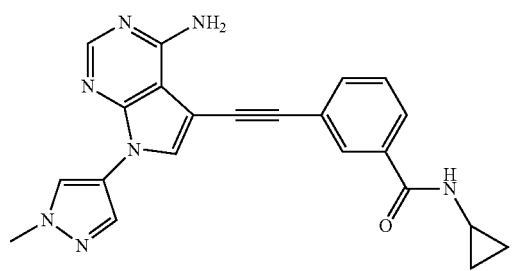 [SMILES: Cn1cc(-n2cc(C#Cc3cccc(C(=O)NC4CC4)c3)c3c(N)ncnc32)cn1]

3-{[4-amino-7-(1-methyl-1H-pyrazol-4-yl)-7H-pyrrolo[2,3-d]pyrimidin-5-yl]ethynyl}-N-cyclopropylbenzamide (cmpd 71). [R1=R3=R4=R6=H, R2=1-methyl-1H-pyrazol-4-yl, A=triple bond, L=CONH, R7=cyclopropyl]

$^1$H NMR (401 MHz, DMSO-d$_6$) δ ppm 0.55-0.63 (m, 2H) 0.67-0.77 (m, 2H) 2.87 (td, J=7.32, 3.78 Hz, 1H) 3.92 (s, 3H) 6.46-7.00 (m, 2H) 7.49-7.54 (m, 2H) 7.74 (d, J=7.69 Hz, 1H) 7.83 (d, J=7.81 Hz, 1H) 8.00-8.03 (m, 2H) 8.05 (s, 1H) 8.24 (s, 1H) 8.39 (s, 1H) 8.53 (d, J=3.91 Hz, 1H)

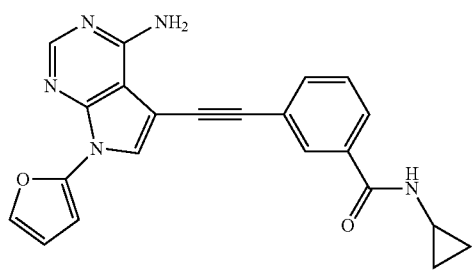 [SMILES: Nc1ncnc2c1c(C#Cc1cccc(C(=O)NC3CC3)c1)cn2-c1ccco1]

3-{[4-amino-7-(furan-2-yl)-7H-pyrrolo[2,3-d]pyrimidin-5-yl]ethynyl}-N-cyclopropylbenzamide (cmpd 72) [R1=R3=R4=R6=H, R2=furan-2-yl, A=triple bond, L=CONH, R7=cyclopropyl]

$^1$H NMR (401 MHz, DMSO-d$_6$) δ ppm 0.55-0.63 (m, 2H) 0.67-0.75 (m, 2H) 2.87 (tq, J=7.38, 3.95 Hz, 1H) 6.85 (br. s., 2H) 7.52 (t, J=7.81 Hz, 1H) 7.74 (d, J=7.93 Hz, 1H) 7.81 (t, J=1.83 Hz, 1H) 7.84 (s, 1H) 8.03 (s, 1H) 8.14 (s, 1H) 8.27 (s, 1H) 8.45-8.47 (m, 1H) 8.53 (d, J=4.03 Hz, 1H)

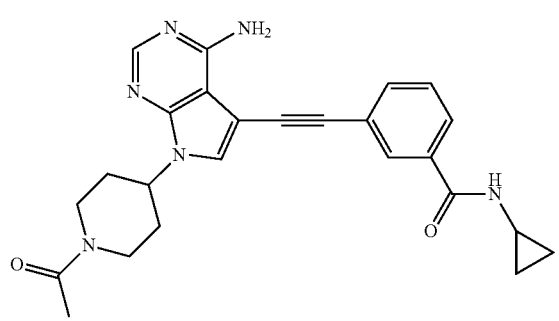 [SMILES: CC(=O)N1CCC(n2cc(C#Cc3cccc(C(=O)NC4CC4)c3)c3c(N)ncnc32)CC1]

3-{[7-(1-acetylpiperidin-4-yl)-4-amino-7H-pyrrolo[2,3-d]pyrimidin-5-yl]ethynyl}-N-cyclopropylbenzamide (cmpd 76). [R1=R3=R4=R6=H, R2=1-acetylpiperidin-4-yl, A=triple bond, L=CONH, R7=cyclopropyl]

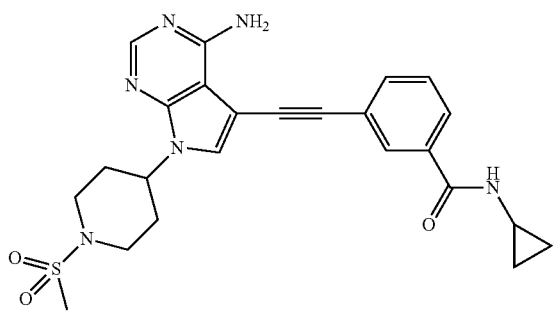 [SMILES: CS(=O)(=O)N1CCC(n2cc(C#Cc3cccc(C(=O)NC4CC4)c3)c3c(N)ncnc32)CC1]

3-({4-amino-7-[1-(methylsulfonyl)piperidin-4-yl]-7H-pyrrolo[2,3-d]pyrimidin-5-yl}ethynyl)-N-cyclopropyl benzamide (cmpd 77). [R1=R3=R4=R6=H, R2=1-(methylsulfonyl)piperidin-4-yl, A=triple bond, L=CONH, R7=cyclopropyl]

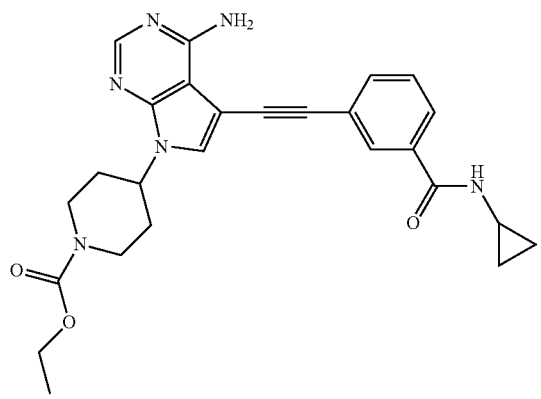 [SMILES: CCOC(=O)N1CCC(n2cc(C#Cc3cccc(C(=O)NC4CC4)c3)c3c(N)ncnc32)CC1]

ethyl 4-(4-amino-5-{[3-(cyclopropylcarbamoyl)phenyl]ethynyl}-7H-pyrrolo[2,3-d]pyrimidin-7-yl)piperidine-1-carboxylate (cmpd 78).
[R1=R3=R4=R6=H, R2=1-carbetoxypiperidin-4-yl, A=triple bond, L=CONH, R7=cyclopropyl]

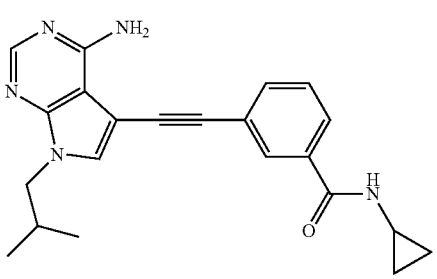 [SMILES: CC(C)Cn1cc(C#Cc2cccc(C(=O)NC3CC3)c2)c2c(N)ncnc21]

3-{[4-amino-7-(2-methylpropyl)-7H-pyrrolo[2,3-d]pyrimidin-5-yl]ethynyl}-N-cyclopropylbenzamide (cmpd 84). [R1=R3=R4=R6=H, R2=2-methylpropyl, A=triple bond, L=CONH, R7=cyclopropyl]

$^1$H NMR (401 MHz, DMSO-d$_6$) δ ppm 0.50-0.63 (m, 2H) 0.66-0.74 (m, 2H) 0.84 (d, J=6.71 Hz, 6H) 2.17 (dt, J=13.73, 6.93 Hz, 1H) 2.73-2.96 (m, 1H) 3.96 (d, J=7.45 Hz, 2H) 6.65 (br. s., 2H) 7.44-7.53 (m, 1H) 7.65-7.73 (m, 2H) 7.80 (dt, J=8.06, 1.34 Hz, 1H) 7.99 (t, J=1.53 Hz, 1H) 8.14 (s, 1H) 8.52 (d, J=4.27 Hz, 1H)

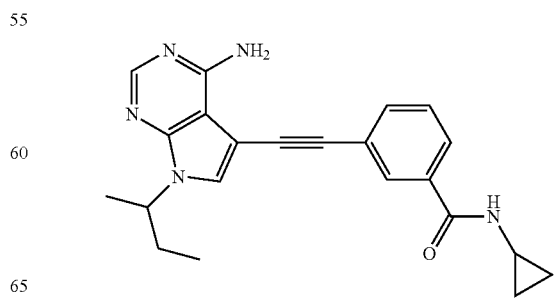

3-{[4-amino-7-(butan-2-yl)-7H-pyrrolo[2,3-d]pyrimidin-5-yl]ethynyl}-N-cyclopropylbenzamide (cmpd 85). [R1=R3=R4=R6=H, R2=butan-2-yl, A=triple bond, L=CONH, R7=cyclopropyl]

¹H NMR (401 MHz, DMSO-d₆) δ ppm 0.55-0.62 (m, 2H) 0.65-0.77 (m, 5H) 1.44 (d, J=6.84 Hz, 3H) 1.73-1.94 (m, 2H) 2.81-2.92 (m, 1H) 4.60-4.78 (m, 1H) 6.62 (br. s., 2H) 7.46-7.53 (m, 1H) 7.70 (dt, J=7.75, 1.37 Hz, 1H) 7.79-7.83 (m, 2H) 7.99 (t, J=1.53 Hz, 1H) 8.19 (br. s., 1H) 8.52 (d, J=4.15 Hz, 1H)

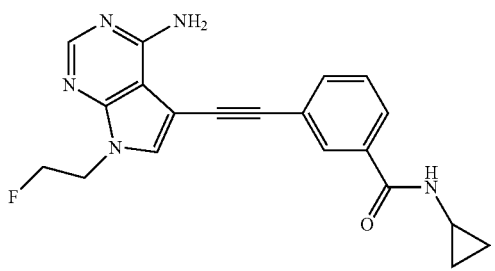 [SMILES: Nc1ncnc2c1c(C#Cc1cccc(C(=O)NC3CC3)c1)cn2CCF]

3-{[4-amino-7-(2-fluoroethyl)-7H-pyrrolo[2,3-d]pyrimidin-5-yl]ethynyl}-N-cyclopropylbenzamide (cmpd 86). [R1=R3=R4=R6=H, R2=fluoroethyl, A=triple bond, L=CONH, R7=cyclopropyl]

¹H NMR (401 MHz, DMSO-d₆) δ ppm 0.55-0.63 (m, 2H) 0.67-0.75 (m, 2H) 2.86 (tq, J=7.42, 3.97 Hz, 1H) 4.40-4.55 (m, 2H) 4.70-4.86 (m, 2H) 6.36-7.00 (m, 2H) 7.47-7.52 (m, 1H) 7.69-7.74 (m, 2H) 7.81 (dt, J=8.06, 1.34 Hz, 1H) 8.00 (t, J=1.53 Hz, 1H) 8.17 (s, 1H) 8.52 (d, J=4.27 Hz, 1H)

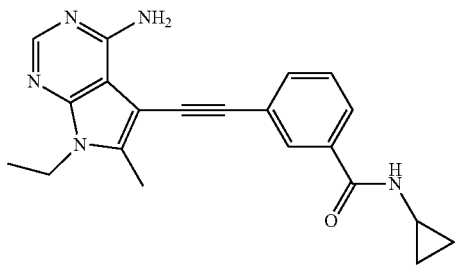 [SMILES: CCn1c(C)c(C#Cc2cccc(C(=O)NC3CC3)c2)c2c(N)ncnc21]

3-[(4-amino-7-ethyl-6-methyl-7H-pyrrolo[2,3-d]pyrimidin-5-yl)ethynyl]-N-cyclopropylbenzamide (cmpd 87). [R1=R4=R6=H, R2=ethyl, R3=methyl, A=triple bond, L=CONH, R7=cyclopropyl]

¹H NMR (401 MHz, DMSO-d₆) δ ppm 0.51-0.62 (m, 2H) 0.67-0.75 (m, 2H) 1.27 (t, J=7.14 Hz, 3H) 2.55 (s, 3H) 2.78-2.92 (m, 1H) 4.09-4.26 (m, 2H) 6.57 (br. s., 2H) 7.45-7.51 (m, 1H) 7.72 (dt, J=7.84, 1.27 Hz, 1H) 7.79 (dt, J=7.81, 1.46 Hz, 1H) 7.98 (t, J=1.53 Hz, 1H) 8.13 (s, 1H) 8.52 (d, J=4.15 Hz, 1H)

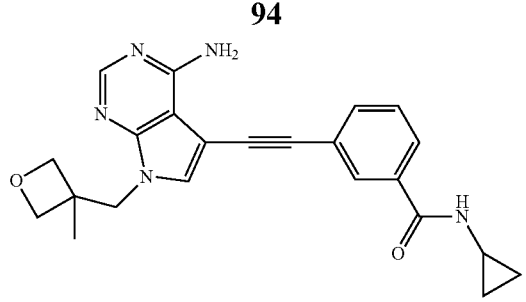

3-({4-amino-7-[(3-methyloxetan-3-yl)methyl]-7H-pyrrolo[2,3-d]pyrimidin-5-yl}ethynyl)-N-cyclopropyl benzamide (cmpd 88). [R1=R3=R4=R6=H, R2=3-methyloxetan-3-yl, A=triple bond, L=CONH, R7=cyclopropyl]

¹H NMR (401 MHz, DMSO-d₆) δ ppm 0.53-0.62 (m, 2H) 0.67-0.74 (m, 2H) 1.18 (s, 3H) 2.82-2.91 (m, 1H) 4.23 (d, J=5.98 Hz, 3H) 4.38 (s, 2H) 4.63 (d, J=5.98 Hz, 2H) 6.69 (br. s., 2H) 7.46-7.56 (m, 1H) 7.70-7.73 (m, 1H) 7.73 (s, 1H) 7.81 (dt, J=8.06, 1.28 Hz, 1H) 8.00 (t, J=1.46 Hz, 1H) 8.16 (s, 1H) 8.51 (d, J=4.03 Hz, 1H)

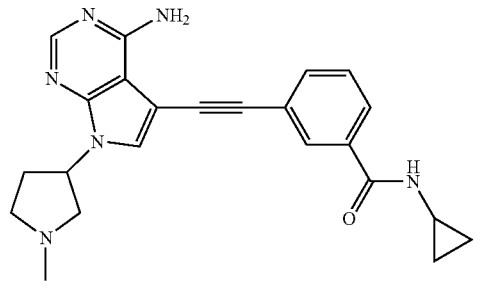 [SMILES: CN1CCC(n2cc(C#Cc3cccc(C(=O)NC4CC4)c3)c3c(N)ncnc32)C1]

3-{[4-amino-7-(1-methylpyrrolidin-3-yl)-7H-pyrrolo[2,3-d]pyrimidin-5-yl]ethynyl}-N-cyclopropylbenzamide (cmpd 89). [R1=R3=R4=R6=H, R2=1-methylpyrrolidin-3-yl, A=triple bond, L=CONH, R7=cyclopropyl]

¹H NMR (401 MHz, DMSO-d₆) δ ppm 0.53-0.62 (m, 2H) 0.67-0.76 (m, 2H) 1.77-2.08 (m, 1H) 2.11-2.47 (m, 5H) 2.65-2.94 (m, 3H) 3.03 (br. s., 1H) 5.29 (dd, J=8.73, 6.29 Hz, 1H) 6.68 (br. s., 2H) 7.47-7.52 (m, 1H) 7.72 (dt, J=7.81, 1.34 Hz, 1H) 7.78-7.83 (m, 2H) 8.00 (t, J=1.53 Hz, 1H) 8.15 (s, 1H) 8.51 (d, J=4.15 Hz, 1H)

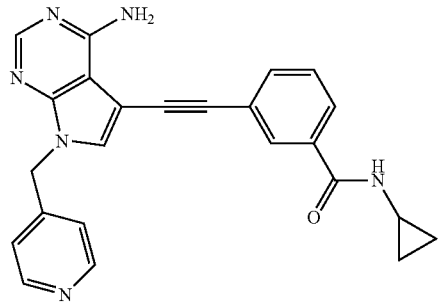 [SMILES: Nc1ncnc2c1c(C#Cc1cccc(C(=O)NC3CC3)c1)cn2Cc1ccncc1]

3-{[4-amino-7-(pyridin-4-ylmethyl)-7H-pyrrolo[2,3-d]pyrimidin-5-yl]ethynyl}-N-cyclopropylbenzamide (cmpd 90). [R1=R3=R4=R6=H, R2=pyridin-4-ylmethyl, A=triple bond, L=CONH, R7=cyclopropyl]

¹H NMR (401 MHz, DMSO-d₆) δ ppm 0.53-0.63 (m, 2H) 0.68-0.74 (m, 2H) 2.86 (td, J=7.35, 3.97 Hz, 1H) 5.43 (s, 2H) 6.75 (br. s., 2H) 7.14 (d, J=5.61 Hz, 1H) 7.46-7.52 (m, 1H) 7.72 (d, J=7.81 Hz, 1H) 7.79-7.83 (m, 1H) 8.00 (s, 1H) 8.15 (s, 1H) 8.51 (d, J=4.03 Hz, 2H)

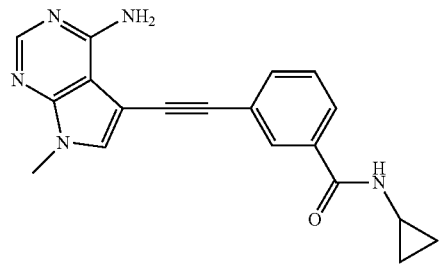

3-[(4-amino-7-methyl-7H-pyrrolo[2,3-d]pyrimidin-5-yl)ethynyl]-N-cyclopropylbenzamide (cmpd 93). [R1=R3=R4=R6=H, R2=methyl, A=triple bond, L=CONH, R7=cyclopropyl]

¹H NMR (401 MHz, DMSO-d₆) δ ppm 0.50-0.62 (m, 2H) 0.67-0.74 (m, 2H) 2.86 (td, J=7.26, 4.15 Hz, 1H) 3.67-3.76 (m, 3H) 6.64 (br. s., 2H) 7.66 (s, 1H) 7.71 (dt, J=7.87, 1.31 Hz, 1H) 7.80 (dt, J=8.09, 1.33 Hz, 1H) 7.98 (t, J=1.46 Hz, 1H) 8.16 (s, 1H) 8.52 (d, J=4.03 Hz, 1H)

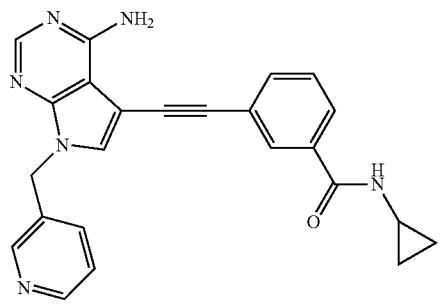 [SMILES: Nc1ncnc2c1c(C#Cc1cccc(C(=O)NC3CC3)c1)cn2Cc1cccnc1]

3-{[4-amino-7-(pyridin-3-ylmethyl)-7H-pyrrolo[2,3-d]pyrimidin-5-yl]ethynyl}-N-cyclopropylbenzamide (cmpd 91). [R1=R3=R4=R6=H, R2=pyridin-3-ylmethyl, A=triple bond, L=CONH, R7=cyclopropyl]

¹H NMR (401 MHz, DMSO-d₆) δ ppm 0.53-0.62 (m, 2H) 0.67-0.74 (m, 2H) 2.86 (tq, J=7.42, 3.97 Hz, 1H) 5.41 (s, 2H) 6.72 (br. s., 2H) 7.37 (dd, J=7.69, 4.52 Hz, 1H) 7.46-7.53 (m, 1H) 7.67 (d, J=7.93 Hz, 1H) 7.71 (dt, J=7.81, 1.28 Hz, 1H) 7.80 (dt, J=7.87, 1.37 Hz, 1H) 7.84 (s, 1H) 7.99 (t, J=1.46 Hz, 1H) 8.18 (s, 1H) 8.51 (d, J=4.03 Hz, 2H)

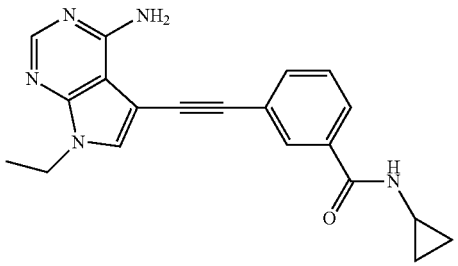

3-[(4-amino-7-ethyl-7H-pyrrolo[2,3-d]pyrimidin-5-yl)ethynyl]-N-cyclopropylbenzamide (cmpd 94). [R1=R3=R4=R6=H, R2=ethyl, A=triple bond, L=CONH, R7=cyclopropyl]

¹H NMR (401 MHz, DMSO-d₆) δ ppm 0.55-0.62 (m, 2H) 0.67-0.74 (m, 2H) 1.36 (t, J=7.26 Hz, 3H) 2.80-2.91 (m, 1H) 4.18 (q, J=7.20 Hz, 2H) 6.65 (br. s., 2H) 7.46-7.52 (m, 1H) 7.70 (dt, J=7.75, 1.31 Hz, 1H) 7.74 (s, 1H) 7.80 (dt, J=7.99, 1.31 Hz, 1H) 7.98 (t, J=1.46 Hz, 1H) 8.15 (s, 1H) 8.52 (d, J=4.27 Hz, 1H)

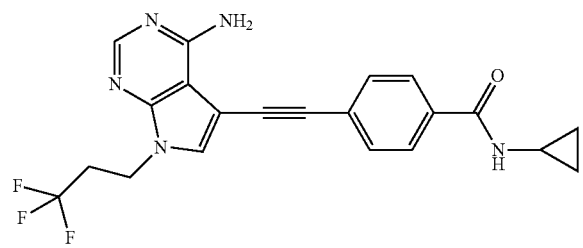 [SMILES: Nc1ncnc2c1c(C#Cc1ccc(C(=O)NC3CC3)cc1)cn2CCC(F)(F)F]

2-(4-{[4-amino-7-(2,2,2-trifluoroethyl)-7H-pyrrolo[2,3-d]pyrimidin-5-yl]ethynyl}phenyl)-N-cyclopropyl acetamide (cmpd 92). [R1=R3=R4=R6=H, R2=2,2,2-trifluoroethyl, A=triple bond, L=CONH, R7=cyclopropyl]

¹H NMR (401 MHz, DMSO-d₆) δ ppm 0.55-0.62 (m, 2H) 0.67-0.74 (m, 2H) 2.82-3.00 (m, 3H) 4.43 (t, J=6.90 Hz, 2H) 6.71 (br. s., 2H) 7.47-7.52 (m, 1H) 7.72 (dt, J=7.78, 1.30 Hz, 1H) 7.77 (s, 1H) 7.80-7.83 (m, 1H) 8.00 (t, J=1.53 Hz, 1H) 8.18 (s, 1H) 8.51 (d, J=4.03 Hz, 1H)

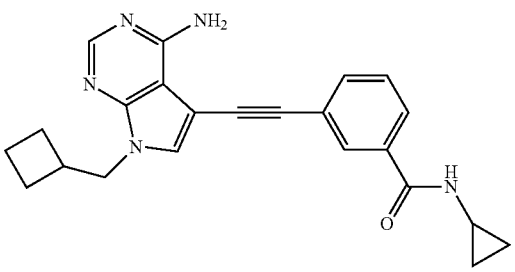 [SMILES: Nc1ncnc2c1c(C#Cc1cccc(C(=O)NC3CC3)c1)cn2CC1CCC1]

3-{[4-amino-7-(cyclobutylmethyl)-7H-pyrrolo[2,3-d]pyrimidin-5-yl]ethynyl}-N-cyclopropylbenzamide (cmpd 95). [R1=R3=R4=R6=H, R2=cyclobutylmethyl, A=triple bond, L=CONH, R7=cyclopropyl]

¹H NMR (401 MHz, DMSO-d₆) δ ppm 0.55-0.61 (m, 2H) 0.67-0.74 (m, 2H) 1.70-2.00 (m, 6H) 2.74-2.82 (m, 1H) 2.86 (td, J=7.29, 3.97 Hz, 1H) 4.17 (d, J=7.32 Hz, 2H) 6.65 (d, J=8.79 Hz, 2H) 7.46-7.52 (m, 1H) 7.67-7.74 (m, 2H) 7.80 (dt, J=7.84, 1.45 Hz, 1H) 7.99 (t, J=1.46 Hz, 1H) 8.15 (s, 1H) 8.51 (d, J=4.15 Hz, 1H)

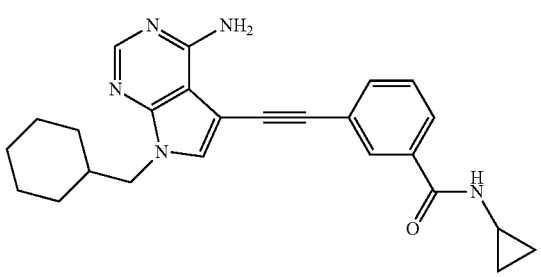 [SMILES: Nc1ncnc2c1c(C#Cc1cccc(C(=O)NC3CC3)c1)cn2CC1CCCCC1]

3-{[4-amino-7-(cyclohexylmethyl)-7H-pyrrolo[2,3-d]pyrimidin-5-yl]ethynyl}-N-cyclopropylbenzamide (cmpd 96). [R1=R3=R4=R6=H, R2=cyclohexylmethyl, A=triple bond, L=CONH, R7=cyclopropyl]

¹H NMR (401 MHz, DMSO-d₆) δ ppm 0.55-0.63 (m, 2H) 0.65-0.74 (m, 2H) 0.85-1.05 (m, 2H) 1.09-1.26 (m, 3H) 1.42-1.55 (m, 2H) 1.55-1.72 (m, 3H) 1.85 (ddd, J=11.02, 7.48, 3.60 Hz, 1H) 2.86 (td, J=7.29, 3.84 Hz, 1H) 3.99 (d, J=7.32 Hz, 1H) 6.66 (br. s., 2H) 7.45-7.53 (m, 1H) 7.68 (s, 1H) 7.70-7.72 (m, 1H) 7.80 (dt, J=7.84, 1.45 Hz, 1H) 7.99 (t, J=1.53 Hz, 1H) 8.14 (s, 1H) 8.51 (d, J=4.15 Hz, 1H)

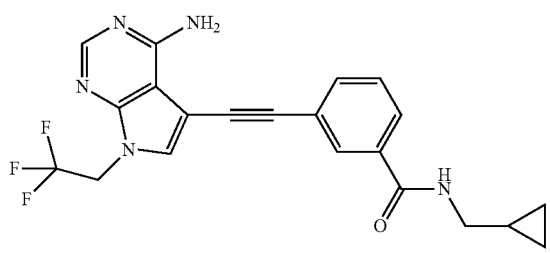 [SMILES: Nc1ncnc2c1c(C#Cc1cccc(C(=O)NCC3CC3)c1)cn2CC(F)(F)F]

3-{[4-amino-7-(2,2,2-trifluoroethyl)-7H-pyrrolo[2,3-d]pyrimidin-5-yl]ethynyl}-N-(cyclopropylmethyl)benzamide (cmpd 97). [R1=R3=R4=R6=H, R2=2,2,2-trifluoroethyl, A=triple bond, L=CONH, R7=cyclopropylmethyl]

¹H NMR (401 MHz, DMSO-d₆) δ ppm 0.38-0.47 (m, 2H) 0.97-1.11 (m, 1H) 3.16 (t, J=6.23 Hz, 2H) 5.10 (q, J=9.20 Hz, 2H) 6.82 (br. s., 2H) 7.50-7.56 (m, 1H) 7.71-7.77 (m, 2H) 7.86 (dt, J=7.90, 1.36 Hz, 1H) 8.05-8.09 (m, 1H) 8.21 (s, 1H) 8.66 (t, J=5.68 Hz, 1H)

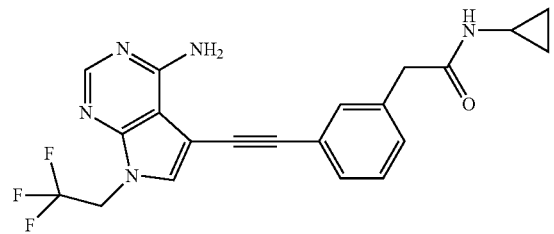 [SMILES: Nc1ncnc2c1c(C#Cc1cccc(CC(=O)NC3CC3)c1)cn2CC(F)(F)F]

2-(3-{[4-amino-7-(2,2,2-trifluoroethyl)-7H-pyrrolo[2,3-d]pyrimidin-5-yl]ethynyl}phenyl)-N-cyclopropyl acetamide (cmpd 113). [R1=R3=R4=R6=H, R2=2,2,2-trifluoroethyl, A=triple bond, L=CH₂CONH, R7=cyclopropyl]

¹H NMR (401 MHz, DMSO-d₆) δ ppm 0.32-0.45 (m, 2H) 0.56-0.73 (m, 2H) 2.62 (tq, J=7.41, 3.85 Hz, 1H) 5.09 (q, J=9.11 Hz, 2H) 6.76 (br. s., 2H) 7.23-7.31 (m, 1H) 7.32-7.39 (m, 1H) 7.43-7.49 (m, 2H) 7.72 (s, 1H) 8.14 (d, J=3.54 Hz, 1H) 8.21 (s, 1H)

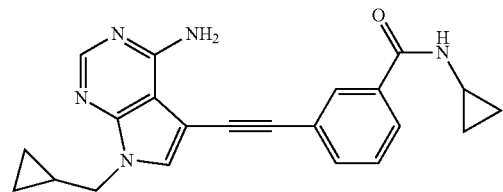 [SMILES: Nc1ncnc2c1c(C#Cc1cccc(C(=O)NC3CC3)c1)cn2CC1CC1]

3-{[4-amino-7-(cyclopropylmethyl)-7H-pyrrolo[2,3-d]pyrimidin-5-yl]ethynyl}-N-cyclopropylbenzamide (cmpd 99). [R1=R3=R4=R6=H, R2=cyclopropylmethyl, A=triple bond, L=CONH, R7=cyclopropyl]

¹H NMR (401 MHz, DMSO-d₆) δ ppm 0.38-0.45 (m, 2H) 0.48-0.54 (m, 2H) 0.56-0.61 (m, 2H) 0.67-0.74 (m, 2H) 1.20-1.34 (m, 1H) 2.87 (td, J=7.42, 3.97 Hz, 1H) 4.01 (d, J=7.20 Hz, 2H) 6.65 (br. s., 2H) 7.47-7.53 (m, 1H) 7.69-7.73 (m, 1H) 7.78 (s, 1H) 7.80 (dd, J=8.12, 1.40 Hz, 1H) 7.98-8.01 (m, 1H) 8.15 (s, 1H) 8.52 (d, J=4.03 Hz, 1H)

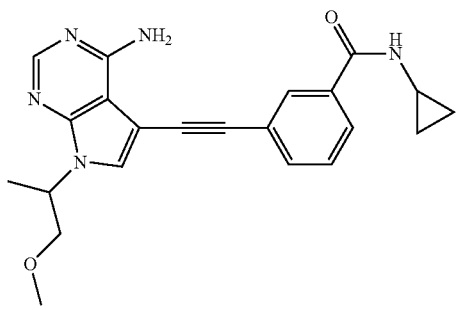 [SMILES: COCC(C)n1cc(C#Cc2cccc(C(=O)NC3CC3)c2)c2c(N)ncnc21]

3-{[4-amino-7-(1-methoxypropan-2-yl)-7H-pyrrolo[2,3-d]pyrimidin-5-yl]ethynyl}-N-cyclopropylbenzamide (cmpd 100). [R1=R3=R4=R6=H, R2=1-methoxypropan-2-yl, A=triple bond, L=CONH, R7=cyclopropyl]

$^1$H NMR (401 MHz, DMSO-d$_6$) δ ppm 0.55-0.64 (m, 2H) 0.68-0.75 (m, 2H) 1.42 (d, J=7.08 Hz, 3H) 2.78-2.93 (m, 1H) 3.18-3.24 (m, 3H) 3.59 (dd, J=10.25, 4.76 Hz, 1H) 3.75 (dd, J=10.25, 7.69 Hz, 1H) 4.98 (td, J=7.29, 4.70 Hz, 1H) 6.64 (br. s., 2H) 7.46-7.52 (m, 1H) 7.70 (dt, J=7.87, 1.31 Hz, 1H) 7.77-7.83 (m, 2H) 7.99 (t, J=1.53 Hz, 1H) 8.15 (s, 1H) 8.52 (d, J=4.15 Hz, 1H)

3-[(4-amino-7-cyclohexyl-7H-pyrrolo[2,3-d]pyrimidin-5-yl)ethynyl]-N-cyclopropylbenzamide (cmpd 101). [R1=R3=R4=R6=H, R2=cyclohexyl, A=triple bond, L=CONH, R7=cyclopropyl]

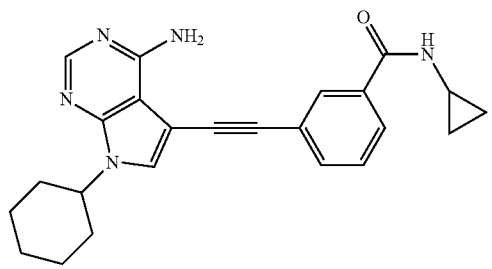 [SMILES: Nc1ncnc2c1c(C#Cc1cccc(C(=O)NC3CC3)c1)cn2C1CCCCC1]

3-[(4-amino-7-cyclobutyl-7H-pyrrolo[2,3-d]pyrimidin-5-yl)ethynyl]-N-cyclopropylbenzamide (cmpd 102). [R1=R3=R4=R6=H, R2=cyclobutyl, A=triple bond, L=CONH, R7=cyclopropyl]

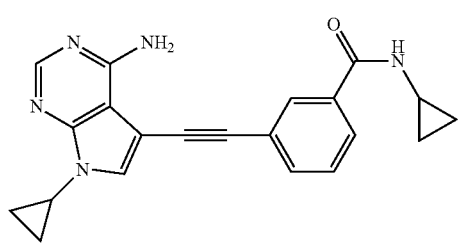 [SMILES: Nc1ncnc2c1c(C#Cc1cccc(C(=O)NC3CC3)c1)cn2C1CC1]

3-[(4-amino-7-cyclopropyl-7H-pyrrolo[2,3-d]pyrimidin-5-yl)ethynyl]-N-cyclopropylbenzamide (cmpd 103). [R1=R3=R4=R6=H, R2=cyclopropyl, A=triple bond, L=CONH, R7=cyclopropyl]

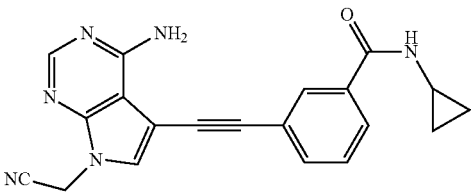 [SMILES: N#CCn1cc(C#Cc2cccc(C(=O)NC3CC3)c2)c2c(N)ncnc21]

3-{[4-amino-7-(cyanomethyl)-7H-pyrrolo[2,3-d]pyrimidin-5-yl]ethynyl}-N-cyclopropylbenzamide (cmpd 104). [R1=R3=R4=R6=H, R2=cyanomethyl, A=triple bond, L=CONH, R7=cyclopropyl]

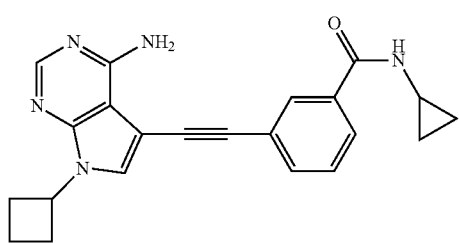

3-({4-amino-7-[2-(dimethylamino)ethyl]-7H-pyrrolo[2,3-d]pyrimidin-5-yl}ethynyl)-N-cyclopropylbenzamide (cmpd 105). [R1=R3=R4=R6=H, R2=2-(dimethylamino)ethyl, A=triple bond, L=CONH, R7=cyclopropyl]

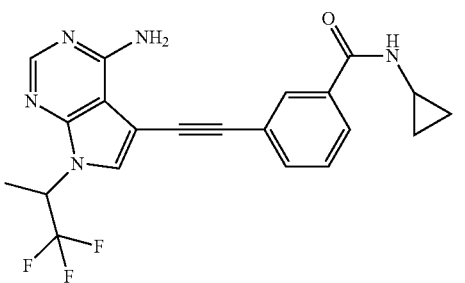 [SMILES: CC(n1cc(C#Cc2cccc(C(=O)NC3CC3)c2)c2c(N)ncnc21)C(F)(F)F]

3-{[4-amino-7-(1,1,1-trifluoropropan-2-yl)-7H-pyrrolo[2,3-d]pyrimidin-5-yl]ethynyl}-N-cyclopropyl-benzamide (cmpd 106). [R1=R3=R4=R6=H, R2=1,1,1-trifluoropropan-2-yl, A=triple bond, L=CONH, R7=cyclopropyl]

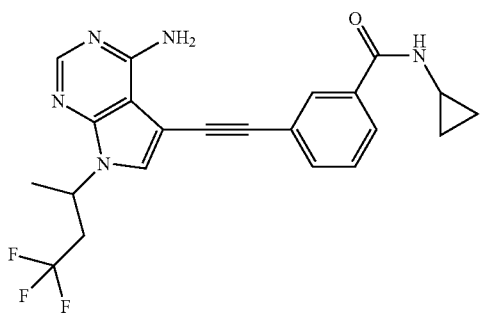 [SMILES: CC(CC(F)(F)F)n1cc(C#Cc2cccc(C(=O)NC3CC3)c2)c2c(N)ncnc21]

3-{[4-amino-7-(4,4,4-trifluorobutan-2-yl)-7H-pyrrolo[2,3-d]pyrimidin-5-yl]ethynyl}-N-cyclopropyl-benzamide (cmpd 107). [R1=R3=R4=R6=H, R2=4,4,4-trifluorobutan-2-yl, A=triple bond, L=CONH, R7=cyclopropyl]

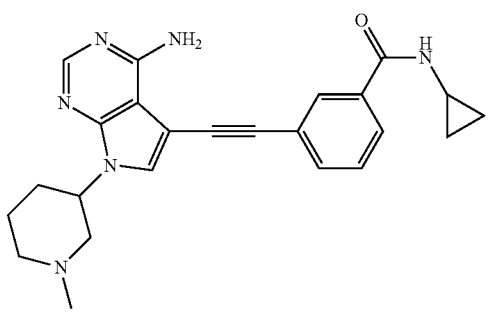 [SMILES: CN1CCCC(n2cc(C#Cc3cccc(C(=O)NC4CC4)c3)c3c(N)ncnc32)C1]

3-{[4-amino-7-(1-methylpiperidin-3-yl)-7H-pyrrolo[2,3-d]pyrimidin-5-yl]ethynyl}-N-cyclopropylbenzamide (cmpd 109). [R1=R3=R4=R6=H, R2=-methylpiperidin-3-yl, A=triple bond, L=CONH, R7=cyclopropyl]

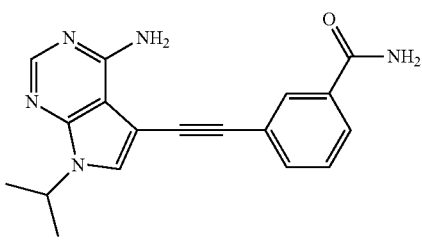 [SMILES: CC(C)n1cc(C#Cc2cccc(C(N)=O)c2)c2c(N)ncnc21]

3-{[4-amino-7-(propan-2-yl)-7H-pyrrolo[2,3-d]pyrimidin-5-yl]ethynyl}benzamide (cmpd 110). [R1=R3=R4=R6=H, R2=-propan-2-yl, A=triple bond, L=CONH, R7=hydrogen]

$^1$H NMR (401 MHz, DMSO-d$_6$) δ ppm 1.45 (d, J=6.71 Hz, 6H) 4.92 (quin, J=6.71 Hz, 1H) 6.63 (br. s., 2H) 7.45 (br. s., 1H) 7.48-7.54 (m, 1H) 7.70 (dt, J=7.78, 1.30 Hz, 1H) 7.84 (s, 1H) 7.85-7.88 (m, 1H) 7.99-8.25 (m, 3H)

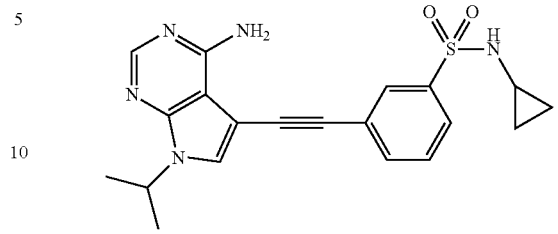

3-{[4-amino-7-(propan-2-yl)-7H-pyrrolo[2,3-d]pyrimidin-5-yl]ethynyl}-N-cyclopropylbenzenesulfonamide (cmpd 111). [R1=R3=R4=R6=H, R2=-methylpiperidin-3-yl, A=triple bond, L=SO$_2$NH, R7=cyclopropyl]

$^1$H NMR (401 MHz, DMSO-d$_6$) δ ppm 0.37-0.43 (m, 2H) 0.48-0.55 (m, 2H) 1.45 (d, J=6.71 Hz, 7H) 2.15 (td, J=6.71, 3.30 Hz, 1H) 4.92 (quin, J=6.71 Hz, 1H) 6.69 (br. s., 2H) 7.62-7.69 (m, 1H) 7.76-7.81 (m, 1H) 7.85 (dt, J=7.75, 1.31 Hz, 1H) 7.90 (s, 1H) 7.96 (t, J=1.53 Hz, 1H) 7.99 (d, J=2.56 Hz, 1H) 8.15 (s, 1H)

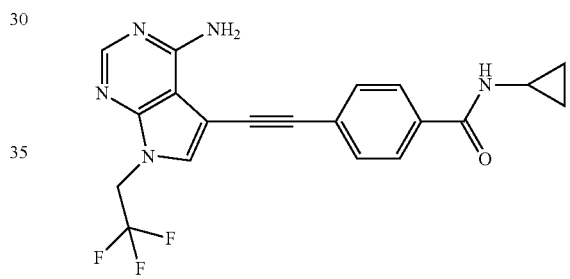

4-{[4-amino-7-(2,2,2-trifluoroethyl)-7H-pyrrolo[2,3-d]pyrimidin-5-yl]ethynyl}-N-cyclopropylbenzamide (cmpd 98). [R1=R3=R4=R6=H, R2=2,2,2-trifluoroethyl, A=triple bond, L=para-CONH, R7=cyclopropyl]

$^1$H NMR (401 MHz, DMSO-d$_6$) δ ppm 0.53-0.62 (m, 2H) 0.66-0.74 (m, 2H) 2.86 (tq, J=7.46, 3.86 Hz, 1H) 5.10 (q, J=9.32 Hz, 2H) 6.83 (br. s., 2H) 7.65-7.70 (m, 2H) 7.75 (s, 1H) 7.86 (d, J=8.42 Hz, 2H) 8.21 (s, 1H) 8.50 (d, J=4.27 Hz, 1H)

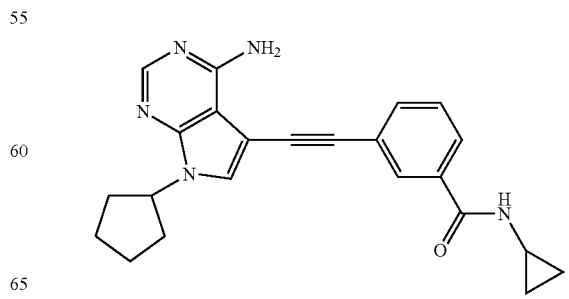

3-[(4-amino-7-cyclopentyl-7H-pyrrolo[2,3-d]pyrimidin-5-yl)ethynyl]-N-cyclopropylbenzamide (cmpd 112). [R1=R3=R4=R6=H, R2=cyclopentyl, A=triple bond, L=CONH, R7=cyclopropyl]

¹H NMR (401 MHz, DMSO-d₆) δ ppm 0.55-0.61 (m, 2H) 0.67-0.74 (m, 2H) 1.60-1.76 (m, 2H) 1.79-1.95 (m, 4H) 2.04-2.18 (m, 2H) 2.80-2.94 (m, 1H) 5.03 (quin, J=7.45 Hz, 1H) 6.66 (d, J=18.68 Hz, 1H) 7.45-7.53 (m, 1H) 7.70 (dt, J=7.75, 1.25 Hz, 1H) 7.76-7.83 (m, 2H) 7.98 (t, J=1.46 Hz, 1H) 8.15 (s, 1H) 8.52 (d, J=4.03 Hz, 1H)

Example 2

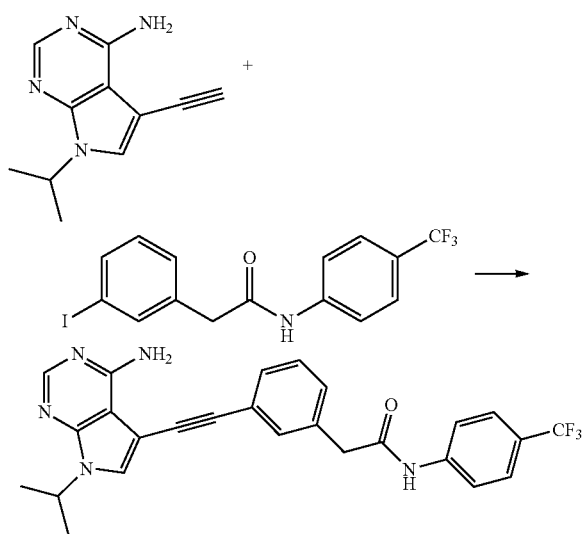

+

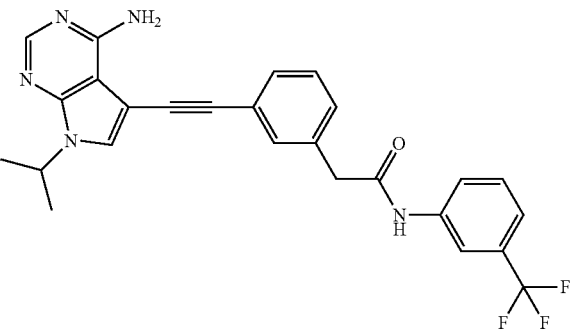 [SMILES: CC(C)n1cc(C#Cc2cccc(CC(=O)Nc3cccc(C(F)(F)F)c3)c2)c2c(N)ncnc21]

2-(3-{[4-amino-7-(propan-2-yl)-7H-pyrrolo[2,3-d]pyrimidin-5-yl]ethynyl}phenyl)-N-[4-(trifluoromethyl)phenyl]acetamide (cmpd 80). [R1=R3=R4=R6=H, R2=propan-2-yl, A=triple bond, L=CH₂CONH, R7=4-trifluoromethylphenyl]

37 mg (0.184 mmol) of 5-ethynyl-7-(propan-2-yl)-7H-pyrrolo[2,3-d]pyrimidin-4-amine were dissolved in 5 mL of dry DMF and degassed under argon stream for 30 minutes. 26 mg (0.0138 mmol) of cupreous iodide, 247 μL of triethylamine, 75 mg (0.184 mmol) of 2-(3-iodophenyl)-N-[4-(trifluoromethyl)phenyl]acetamide and 6.5 mg (0.0092 mmol) of palladium dichloride bis(triphenylphosphine) were added consecutively under argon atmosphere. The mixture was stirred at room temperature for 2 hours, then diluted with DCM and washed with diluted 5% NH₄OH, water and brine. The organic layer was dried over Na₂SO₄ and evaporated. The residue was finally purified by flash-chromatography on a silica gel column eluted by hexane/ethylacetate, from 1/1 to 3/7 to 0/1, affording 50 mg (57%) of the title compound.

¹H NMR (401 MHz, DMSO-d₆) δ ppm 3.73 (s, 2H) 4.91 (quin, J=6.77 Hz, 1H) 6.59 (br. s., 2H) 7.32-7.41 (m, 2H) 7.44-7.48 (m, 1H) 7.53 (s, 1H) 7.65-7.69 (m, 2H) 7.78-7.84 (m, 3H) 8.14 (s, 1H) 10.55 (s, 1H)

According to the same method the following compounds were prepared:

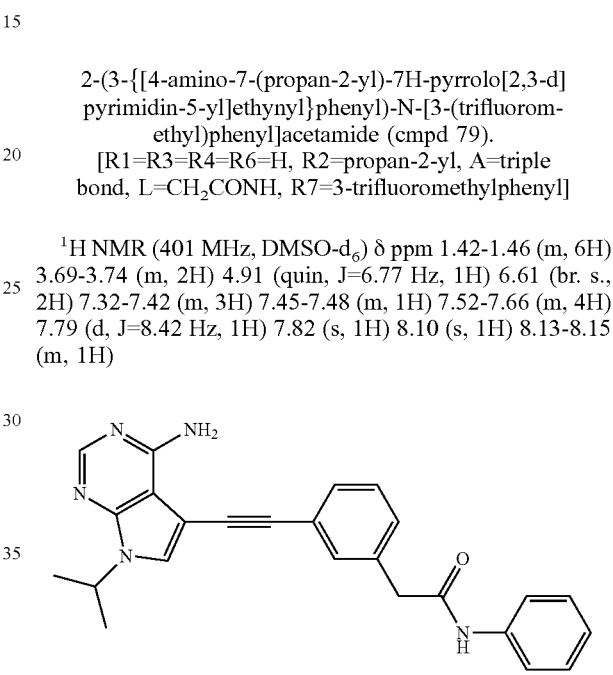

2-(3-{[4-amino-7-(propan-2-yl)-7H-pyrrolo[2,3-d]pyrimidin-5-yl]ethynyl}phenyl)-N-[3-(trifluoromethyl)phenyl]acetamide (cmpd 79). [R1=R3=R4=R6=H, R2=propan-2-yl, A=triple bond, L=CH₂CONH, R7=3-trifluoromethylphenyl]

¹H NMR (401 MHz, DMSO-d₆) δ ppm 1.42-1.46 (m, 6H) 3.69-3.74 (m, 2H) 4.91 (quin, J=6.77 Hz, 1H) 6.61 (br. s., 2H) 7.32-7.42 (m, 3H) 7.45-7.48 (m, 1H) 7.52-7.66 (m, 4H) 7.79 (d, J=8.42 Hz, 1H) 7.82 (s, 1H) 8.10 (s, 1H) 8.13-8.15 (m, 1H)

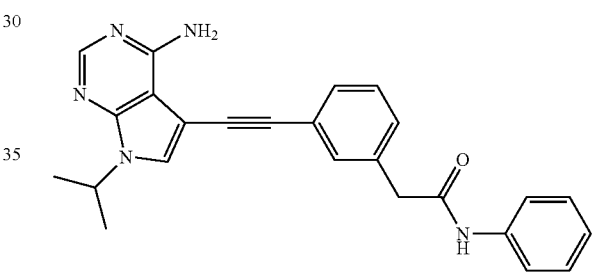

2-(3-{[4-amino-7-(propan-2-yl)-7H-pyrrolo[2,3-d]pyrimidin-5-yl]ethynyl}phenyl)-N-phenylacetamide (cmpd 65). [R1=R3=R4=R6=H, R2=propan-2-yl, A=triple bond, L=CH₂CONH, R7=phenyl]

¹H NMR (401 MHz, DMSO-d₆) δ ppm 1.39-1.47 (m, 6H) 3.67 (s, 2H) 4.91 (quin, J=6.74 Hz, 1H) 6.60 (br. s., 2H) 7.00-7.07 (m, 1H) 7.27-7.33 (m, 2H) 7.33-7.41 (m, 2H) 7.43-7.48 (m, 1H) 7.52 (s, 1H) 7.57-7.62 (m, 2H) 7.83 (s, 1H) 8.14 (s, 1H) 10.18 (s, 1H)

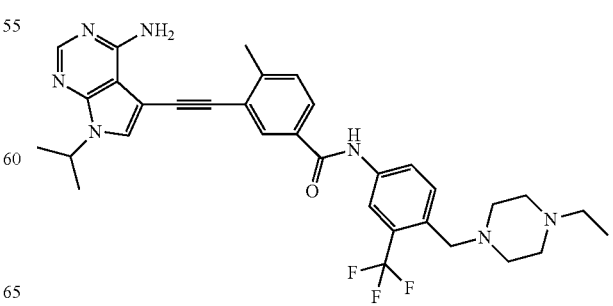

3-{[4-amino-7-(propan-2-yl)-7H-pyrrolo[2,3-d]pyrimidin-5-yl]ethynyl}-N-{4-[(4-ethylpiperazin-1-yl)methyl]-3-(trifluoromethyl)phenyl}-4-methylbenzamide (cmpd 81). [R1=R3=R6=H, R2=propan-2-yl, R4=4-methyl, A=triple bond, L=CONH, R7=3-trifluoromethyl-4-ethylpiperazin-1-yl)methyl phenyl]

$^1$H NMR (401 MHz, DMSO-d$_6$) δ ppm 0.98 (t, J=7.20 Hz, 3H) 1.46 (d, J=6.71 Hz, 6H) 2.28-2.34 (m, 3H) 2.35-2.47 (m, 6H) 2.55 (s, 3H) 3.57 (s, 2H) 4.93 (quin, J=6.77 Hz, 1H) 6.65 (br. s., 2H) 7.51 (s, 1H) 7.71 (d, J=8.42 Hz, 1H) 7.85-7.90 (m, 2H) 8.05 (dd, J=8.54, 2.08 Hz, 1H) 8.14-8.17 (m, 2H) 8.20 (d, J=2.08 Hz, 1H) 10.52 (s, 1H)

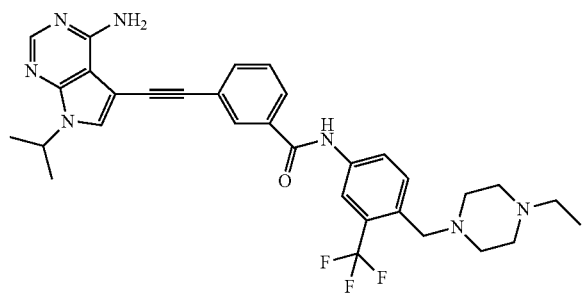 [SMILES: CCN1CCN(Cc2ccc(NC(=O)c3cccc(C#Cc4cn(C(C)C)c5ncnc(N)c45)c3)cc2C(F)(F)F)CC1]

3-{[4-amino-7-(propan-2-yl)-7H-pyrrolo[2,3-d]pyrimidin-5-yl]ethynyl}-N-{4-[(4-ethylpiperazin-1-yl)methyl]-3-(trifluoromethyl)phenyl}benzamide (cmpd 82). [R1=R3=R4=R6=H, R2=propan-2-yl, A=triple bond, L=CONH, R7=3-trifluoromethyl-4-ethylpiperazin-1-yl)methyl phenyl]

$^1$H NMR (401 MHz, DMSO-d$_6$) δ ppm 0.98 (t, J=7.20 Hz, 3H) 1.46 (d, J=6.84 Hz, 6H) 2.28-2.34 (m, 3H) 2.33-2.48 (m, 6H) 3.57 (s, 2H) 4.93 (quin, J=6.77 Hz, 1H) 6.63 (br. s., 2H) 7.60 (t, J=7.81 Hz, 1H) 7.72 (d, J=8.42 Hz, 1H) 7.80 (dt, J=7.75, 1.25 Hz, 1H) 7.86 (s, 1H) 7.95 (dt, J=8.00, 1.31 Hz, 1H) 8.05 (dd, J=8.54, 1.95 Hz, 1H) 8.14-8.17 (m, 2H) 8.21 (d, J=2.20 Hz, 1H) 10.59 (s, 1H).

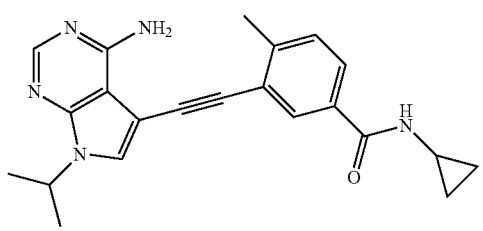 [SMILES: Cc1ccc(C(=O)NC2CC2)cc1C#Cc1cn(C(C)C)c2ncnc(N)c12]

3-{[4-amino-7-(propan-2-yl)-7H-pyrrolo[2,3-d]pyrimidin-5-yl]ethynyl}-N-cyclopropyl-4-methylbenzamide (cmpd 51). [R1=R3=R6=H, R2=propan-2-yl, R4=4-methyl, A=triple bond, L=CONH, R7=cyclopropyl]

$^1$H NMR (401 MHz, DMSO-d$_6$) δ ppm 0.51-0.62 (m, 2H) 0.65-0.76 (m, 2H) 1.45 (d, J=6.71 Hz, 6H) 2.77-2.91 (m, 1H) 4.92 (quin, J=6.74 Hz, 1H) 6.63 (br. s., 2H) 7.39 (d, J=8.06 Hz, 1H) 7.72 (dd, J=8.00, 1.89 Hz, 1H) 7.84 (s, 1H) 7.97 (d, J=1.83 Hz, 1H) 8.15 (s, 1H) 8.45 (d, J=4.39 Hz, 1H)

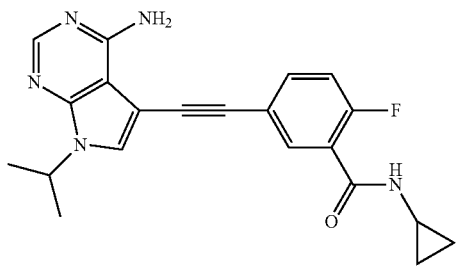 [SMILES: CC(C)n1cc(C#Cc2ccc(F)c(C(=O)NC3CC3)c2)c2c(N)ncnc21]

5-{[4-amino-7-(propan-2-yl)-7H-pyrrolo[2,3-d]pyrimidin-5-yl]ethynyl}-N-cyclopropyl-2-fluorobenzamide (cmpd 83). [R1=R3=R6=H, R2=propan-2-yl, R4=2-fluoro, A=triple bond, L=CONH, R7=cyclopropyl]

$^1$H NMR (401 MHz, DMSO-d$_6$) δ ppm 0.51-0.59 (m, 2H) 0.66-0.75 (m, 2H) 1.40-1.50 (m, 7H) 2.79-2.90 (m, 1H) 4.91 (quin, J=6.80 Hz, 1H) 6.64 (br. s., 2H) 7.32 (dd, J=10.07, 8.61 Hz, 1H) 7.68 (ddd, J=8.51, 4.91, 2.32 Hz, 1H) 7.74 (dd, J=6.77, 2.26 Hz, 1H) 7.82 (s, 1H) 8.14 (s, 1H) 8.47 (d, J=4.15 Hz, 1H)

Example 3

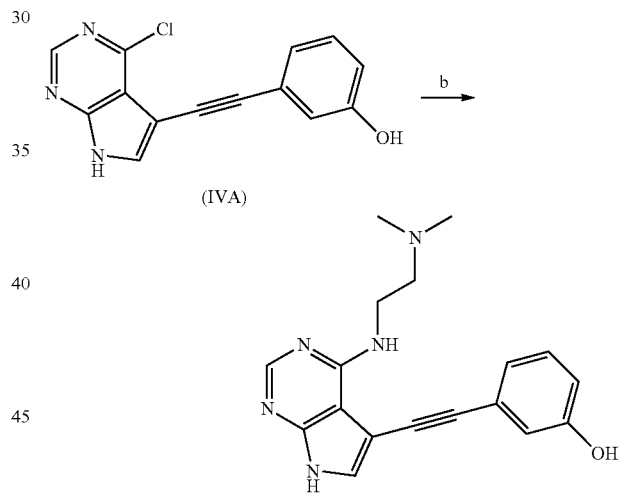

3-[(4-{[2-(dimethylamino)ethyl]amino}-7H-pyrrolo[2,3-d]pyrimidin-5-yl)ethynyl]phenol (cmpd 2). [R2=R3=R4=R6=H, R1=[2-(dimethylamino)ethyl]amino, A=triple bond, L-R7=hydroxyl]

2 mL of dimethylaminoethylamine were added to 10 mg (0.037 mmol) of 3-[(4-chloro-7H-pyrrolo[2,3-d]pyrimidin-5-yl)ethynyl]phenol (prepared as described in example 1) and the reaction heated at 100° C. for 1 h. The reaction mixture was poured into a saturated aqueous solution of NaHCO$_3$ and extracted twice with ethylacetate. The organic layer was dried over Na$_2$SO$_4$ and evaporated to afford, after trituration with DCM, 7 mg (59%) of the title compound as a yellowish solid.

$^1$H NMR (600 MHz, DMSO-d$_6$) δ ppm 2.13 (s, 6H) 3.57-3.62 (m, 2H) 6.56 (t, J=4.49 Hz, 1H) 6.80 (ddd, J=8.24, 2.38, 0.92 Hz, 1H) 6.91-6.94 (m, 1H) 6.98-7.02 (m, 1H) 7.22 (t, J=7.88 Hz, 1H) 7.56 (s, 1H) 8.17 (s, 1H) 9.64 (br. s., 1H) 12.02 (br. s., 1H)

HRMS (ESI) calcd for $C_{18}H_{19}N_6O$ [M+H]+ 322.1663. found 322.1671.

Example 4

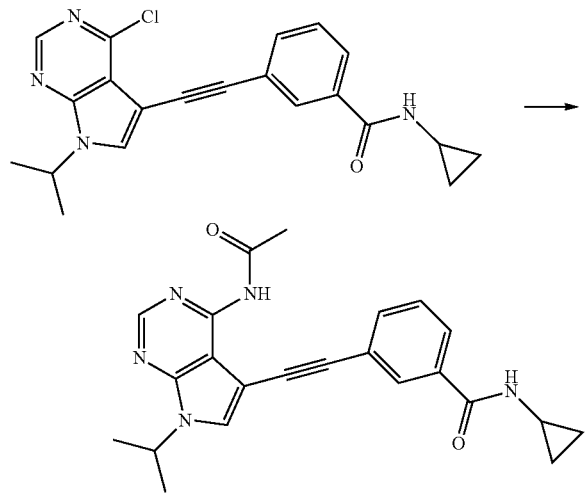

3-{[4-(acetylamino)-7-(propan-2-yl)-7H-pyrrolo[2,3-d]pyrimidin-5-yl]ethynyl}-N-cyclopropylbenzamide (cmpd 64). [R1=COR6, R2=propan-2-yl, R3=R4, R6=methyl, A=triple bond, L=CONH, 7=cyclopropyl]

To a solution of 50 mg (0.13 mmol) of 3-{[4-chloro-7-(propan-2-yl)-7H-pyrrolo[2,3-d]pyrimidin-5-yl]ethynyl}-N-cyclopropylbenzamide in 5 mL of dry THF degassed under argon stream, 85 mg (0.26 mmol) of caesium carbonate, 8 mg (0.013 mmol) of Xantphos, 2 mg (0.007 mmol) of palladium acetate and 15 mg (0.26 mmol) of acetamide were added consecutively. The mixture was heated at 100° C. for 1 hour in a microwave oven. The mixture was then filtered through a celite pad and the filtrate evaporated. The residue was re-dissolved in dichloromethane and washed with brine. The product was purified by flash-chromatography on a silica gel column eluted by cyclohexane/ethylacetate 1/1, affording 20 mg of the title compound (38%).

$^1$H NMR (401 MHz, DMSO-d$_6$) δ ppm 0.50-0.63 (m, 2H) 0.64-0.80 (m, 2H) 1.50 (d, J=6.71 Hz, 6H) 2.21 (s, 1H) 2.87 (td, J=7.29, 3.97 Hz, 1H) 5.05 (quin, J=6.74 Hz, 1H) 7.40-7.55 (m, 1H) 7.61 (dt, J=7.72, 1.39 Hz, 1H) 7.80 (dt, J=7.81, 1.46 Hz, 1H) 7.94 (t, J=1.46 Hz, 1H) 8.16 (s, 1H) 8.52 (d, J=4.27 Hz, 1H) 8.63 (s, 1H) 10.22 (s, 1H)

Example 5

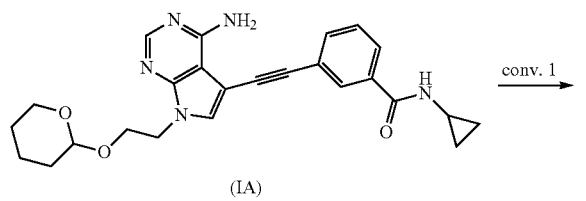

(IA)

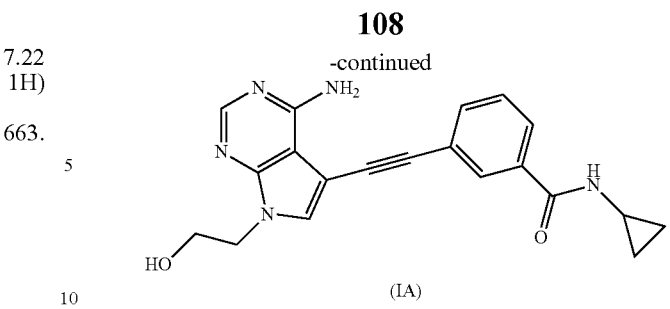

(IA)

3-{[4-amino-7-(2-hydroxyethyl)-7H-pyrrolo[2,3-d]pyrimidin-5-yl]ethynyl}-N-cyclopropylbenzamide) (cmpd 37). [R1=R3=R4=R6=H, R2=2-hydroxyethyl, A=triple bond, L=CONH, R7=cyclopropyl]

To a solution of 60 mg (0.13 mmol) of 3-({4-amino-7-[2-(tetrahydro-2H-pyran-2-yloxy)ethyl]-7H-pyrrolo[2,3-d]pyrimidin-5-yl}ethynyl)-N-cyclopropylbenzamide (prepared as described in example 1) in 5 mL of dry DCM, 2.5 mL of TFA were added in a close bottle. The reaction mixture was stirred at room temperature for 2 h. The solvent was then removed in vacuo and the residue partitioned between DCM and sodium hydrate 1N. The organic phase was separated, dried over $Na_2SO_4$ and evaporated. The crude was finally purified by flash-chromatography (DCM/MeOH 95/5) giving 12 mg (26%) of the title compound.

$^1$H NMR (600 MHz, DMSO-d$_6$) δ ppm 0.57-0.61 (m, 1H) 0.68-0.73 (m, 1H) 2.84-2.90 (m, 1H) 3.72 (q, J=5.49 Hz, 1H) 4.20 (t, J=5.68 Hz, 1H) 4.95 (t, J=5.40 Hz, 1H) 6.66 (br. s., 2H) 7.47-7.52 (m, 1H) 7.67 (s, 1H) 7.71 (d, J=7.88 Hz, 1H) 7.80 (d, J=7.88 Hz, 1H) 7.99 (s, 1H) 8.15 (s, 1H) 8.52 (d, J=4.03 Hz, 1H)

HRMS (ESI) calcd for $C_{20}H_{19}N_6O_2$ [M+H]+ 362.1612. found 362.1617.

According to the same method the following compound were prepared:

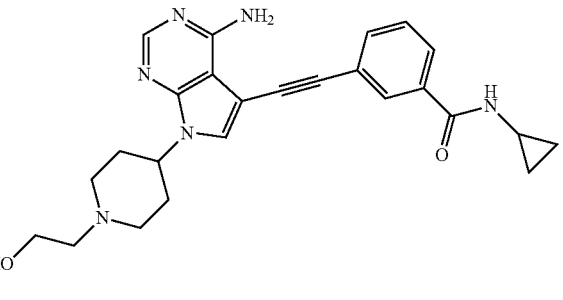

3-({4-amino-7-[1-(2-hydroxyethyl)piperidin-4-yl]-7H-pyrrolo[2,3-d]pyrimidin-5-yl}ethynyl)-N-cyclopropyl benzamide (cmpd 75). [R1=R3=R4=R6=H, R2=1-(2-hydroxyethyl)piperidin-4-yl, A=triple bond, L=CONH, R7=cyclopropyl]

According to the same method, but starting from the corresponding tert-butoxycarbonyl derivatives (prepared as described in example 1) the following compounds were prepared:

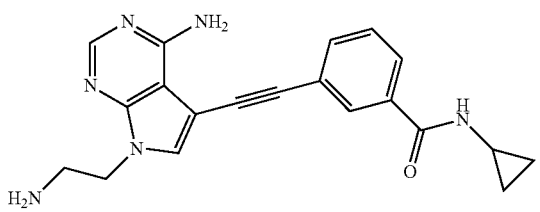 [SMILES: NCCn1cc(C#Cc2cccc(C(=O)NC3CC3)c2)c2c(N)ncnc21]

3-{[4-amino-7-(2-aminoethyl)-7H-pyrrolo[2,3-d]
pyrimidin-5-yl]ethynyl}-N-cyclopropylbenzamide
(cmpd 38). [R1=R3=R4=R6=H, R2=2-aminoethyl,
A=triple bond, L=CONH, R7=cyclopropyl]

$^1$H NMR (600 MHz, DMSO-$d_6$) δ ppm 0.59 (br. s., 2H) 0.65-0.76 (m, 2H) 2.86-3.06 (m, 2H) 4.13 (br. s., 2H) 6.66 (d, J=12.82 Hz, 2H) 7.45-7.55 (m, 1H) 7.65-7.73 (m, 2H) 7.80 (d, J=7.88 Hz, 1H) 7.98 (s, 1H) 8.15 (br. s., 1H) 8.52 (d, J=3.30 Hz, 1H)

HRMS (ESI) calcd for $C_{20}H_{20}N_6O$ [M+H]+ 361.1772. found 361.1767.

Yield: 25%

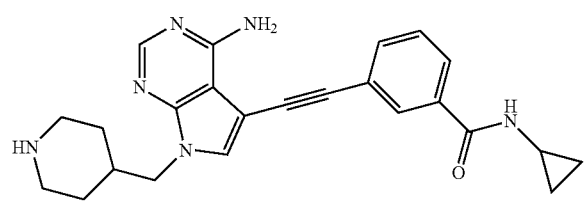 [SMILES: Nc1ncnc2c1c(C#Cc1cccc(C(=O)NC3CC3)c1)cn2CC1CCNCC1]

3-{[4-amino-7-(piperidin-4-yl)-7H-pyrrolo[2,3-d]
pyrimidin-5-yl]ethynyl}-N-cyclopropylbenzamide
(cmpd (IA)) [R1=R3=R4=R6=H, R2=(piperidin-4-
yl)methyl, A=triple bond, L=CONH,
R7=cyclopropyl]

$^1$H NMR (600 MHz, DMSO-$d_6$) δ ppm 0.56-0.61 (m, 2H) 0.68-0.73 (m, 2H) 1.10-1.18 (m, 2H) 1.38-1.45 (m, 2H) 1.91-2.01 (m, 1H) 2.41-2.49 (m, 2H) 2.83-2.88 (m, 1H) 2.97 (m, J=12.27 Hz, 2H) 4.03 (d, J=7.33 Hz, 2H) 6.64 (br. s., 2H) 7.47-7.52 (m, 1H) 7.68-7.72 (m, 2H) 7.81 (d, J=7.51 Hz, 1H) 7.99 (s, 1H) 8.15 (s, 1H) 8.52 (d, J=4.21 Hz, 1H)

HRMS (ESI) calcd for $C_{24}H_{26}N_6O$ [M+H]+ 415.2241. found 415.2229.

Yield: 91%

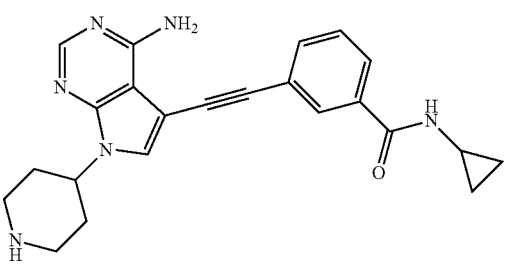 [SMILES: Nc1ncnc2c1c(C#Cc1cccc(C(=O)NC3CC3)c1)cn2C1CCNCC1]

3-{[4-amino-7-(piperidin-4-yl)-7H-pyrrolo[2,3-d]
pyrimidin-5-yl]ethynyl}-N-cyclopropylbenzamide
(cmpd (IA)) [R1=R3=R4=R6=H, R2=piperidin-4-
yl, A=triple bond, L=CONH, R7=cyclopropyl]

$^1$H NMR (401 MHz, DMSO-$d_6$) δ ppm 0.56-0.62 (m, 2H) 0.68-0.74 (m, 2H) 1.75-1.97 (m, 4H) 2.60-2.70 (m, 2H) 2.86 (tq, J=7.43, 3.92 Hz, 1H) 3.08 (d, J=12.33 Hz, 2H) 4.54-4.65 (m, 1H) 6.66 (br. s., 2H) 7.46-7.53 (m, 1H) 7.70 (dt, J=7.75, 1.31 Hz, 1H) 7.78-7.82 (m, 2H) 7.98 (t, J=1.53 Hz, 1H) 8.14 (s, 1H) 8.52 (d, J=4.15 Hz, 1H)

Example 6

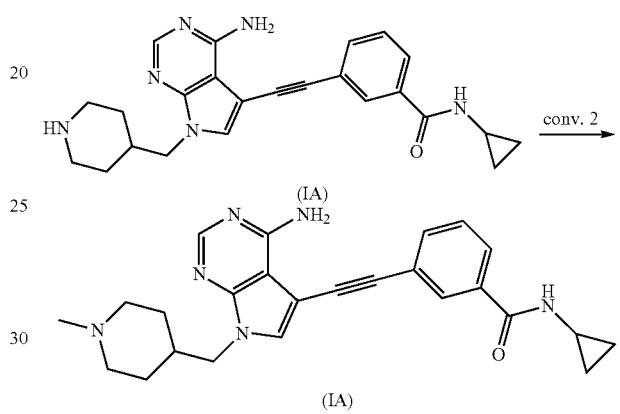

3-({4-amino-7-[(1-methylpiperidin-4-yl)methyl]-7H-
pyrrolo[2,3-d]pyrimidin-5-yl}ethynyl)-N-cyclopro-
pyl benzamide (cmpd 39). [R1=R3=R4=R6=H,
R2=(1-methylpiperidin-4-yl)methyl, A=triple bond,
L=CONH, R7=cyclopropyl]

To a solution of 30 mg (0.07 mmol) of 3-{[4-amino-7-(piperidin-4-ylmethyl)-7H-pyrrolo[2,3-d]pyrimidin-5-yl]ethynyl}-N- cyclopropylbenzamide (prepared as described in example 2) in 4 mL of methanol, 12 μL of glacial acetic acid, 6 μL (0.11 mmol) of aqueous formaldehyde 37% and 7 mg (0.14 mmol) of sodium cyanoborohydride were added consecutively. The reaction mixture was stirred at room temperature for 2 h and then evaporated in vacuo. The residue was partitioned between DCM and aqueous NaHCO$_3$. The organic phase was separated, dried over Na$_2$SO$_4$ and evaporated. The crude was purified by flash-chromatography on silica gel (DCM/MeOH 95/5) affording the title compound (14 mg, 47%).

$^1$H NMR (600 MHz, DMSO-$d_6$) δ ppm 0.56-0.61 (m, 2H) 0.68-0.74 (m, 2H) 1.16-1.28 (m, 3H) 1.40 (d, J=11.90 Hz, 2H) 1.75 (t, J=10.81 Hz, 2H) 1.79 (br. s., 1H) 2.11 (s, 3H) 2.71 (d, J=11.36 Hz, 2H) 2.86 (dd, J=7.42, 3.57 Hz, 1H) 4.03 (d, J=7.33 Hz, 2H) 7.49 (t, J=7.78 Hz, 1H) 7.67-7.73 (m, 2H) 7.80 (d, J=7.88 Hz, 1H) 7.99 (s, 1H) 8.15 (s, 1H) 8.52 (d, J=4.03 Hz, 1H)

HRMS (ESI) calcd for $C_{25}H_{28}N_6O$ [M+H]+ 429.2398. found 429.2389.

According to the same method, the following compound was prepared:

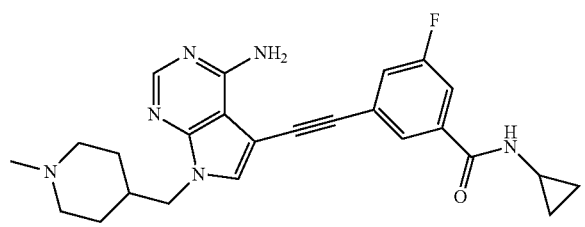 [SMILES: CN1CCC(Cn2cc(C#Cc3cc(F)cc(C(=O)NC4CC4)c3)c3c(N)ncnc32)CC1]

3-({4-amino-7-[(1-methylpiperidin-4-yl)methyl]-7H-pyrrolo[2,3-d]pyrimidin-5-yl}ethynyl)-N-cyclopropyl-5-fluorobenzamide (cmpd 62). [R1=R3=R6=H, R2=(1-methylpiperidin-4-yl)methyl, R4=5-fluoro, A=triple bond, L=CONH, R7=cyclopropyl]

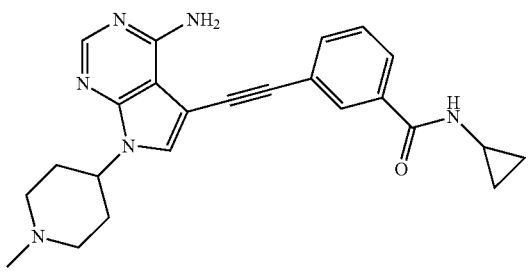 [SMILES: CN1CCC(n2cc(C#Cc3cccc(C(=O)NC4CC4)c3)c3c(N)ncnc32)CC1]

3-{[4-amino-7-(1-methylpiperidin-4-yl)-7H-pyrrolo[2,3-d]pyrimidin-5-yl]ethynyl}-N-cyclopropylbenzamide (cmpd 46). [R1=R3=R4=R6=H, R2=1-methylpiperidin-4-yl, A=triple bond, L=CONH, R7=cyclopropyl]

$^1$H NMR (401 MHz, DMSO-$d_6$) δ ppm 0.59 (br. s., 2H) 0.72 (m, J=5.98 Hz, 2H) 1.86 (br. s., 2H) 2.06 (br. s., 4H) 2.22 (s, 3H) 2.78-3.02 (m, 3H) 4.49 (br. s., 1H) 6.66 (br. s., 2H) 7.41-7.58 (m, 1H) 7.70 (d, J=7.32 Hz, 1H) 7.75-7.88 (m, 2H) 7.98 (br. s., 1H) 8.14 (s, 1H) 8.52 (br. s., 1H)

According to the same method but employing acetone as carbonyl derivative, the following compound was prepared:

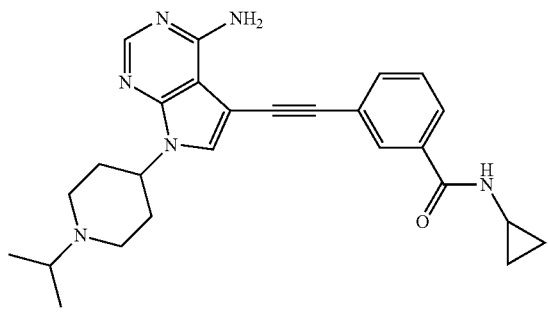 [SMILES: CC(C)N1CCC(n2cc(C#Cc3cccc(C(=O)NC4CC4)c3)c3c(N)ncnc32)CC1]

3-({4-amino-7-[1-(propan-2-yl)piperidin-4-yl]-7H-pyrrolo[2,3-d]pyrimidin-5-yl}ethynyl)-N-cyclopropyl benzamide (cmpd 74). [R1=R3=R4=R6=H, R2=1-isopropylpiperidin-4-yl, A=triple bond, L=CONH, R7=cyclopropyl]

According to the same method but employing [(1-ethoxycyclopropyl)oxy](trimethyl)silane as synthetic equivalent of cyclopropyl ketone, the following compound was prepared:

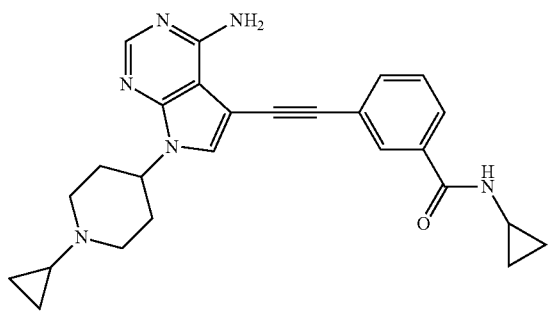 [SMILES: Nc1ncnc2c1c(C#Cc1cccc(C(=O)NC3CC3)c1)cn2C1CCN(C2CC2)CC1]

3-{[4-amino-7-(1-cyclopropylpiperidin-4-yl)-7H-pyrrolo[2,3-d]pyrimidin-5-yl]ethynyl}-N-cyclopropylbenzamide (cmpd 73). [R1=R3=R4=R6=H, R2=1-cyclopropylpiperidin-4-yl, A=triple bond, L=CONH, R7=cyclopropyl]

Example 7

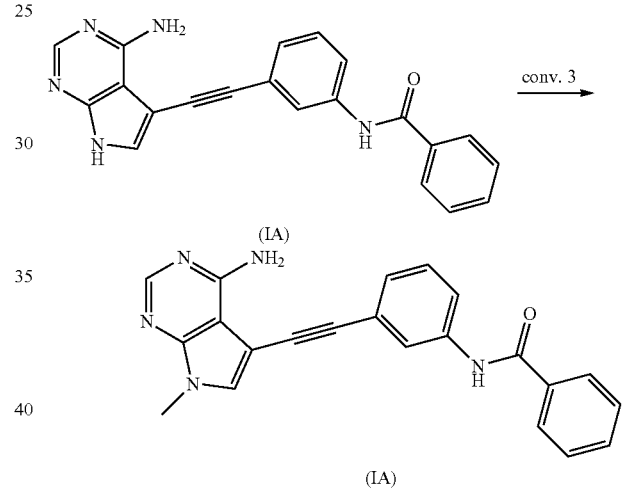

N-{3-[(4-amino-7-methyl-7H-pyrrolo[2,3-d]pyrimidin-5-yl)ethynyl]phenyl}benzamide (cmpd 10). [R1=R3=R4=R6=H, R2=methyl, A=triple bond, L=NHCO, R7=phenyl]

To a solution of 30 mg (0.09 mmol) of N-{3-[(4-amino-7H-pyrrolo[2,3-d]pyrimidin-5-yl)ethynyl]phenyl}benzamide (prepared as described in example 1) in 3 mL of dry DMF, 25 mg (0.18 mmol) of anhydrous potassium carbonate and 9 μL of methyl iodide were added. The reaction mixture was stirred at room temperature for 4 h, then poured into water and extracted with DCM. The organic phase was separated, washed with brine, dried over Na$_2$SO$_4$ and evaporated. The residue was purified by flash-chromatography on silica gel (DCM/MeOH 97/3) affording 10 mg (30%) of the title compound, after trituration with diisopropylether and filtration.

$^1$H NMR (600 MHz, DMSO-$d_6$) δ ppm 3.72 (s, 3H) 6.37-6.97 (m, 2H) 7.29-7.35 (m, 1H) 7.37-7.44 (m, 1H) 7.52-7.57 (m, 2H) 7.59-7.64 (m, 1H) 7.68 (s, 1H) 7.78 (dd, J=8.33, 1.01 Hz, 1H) 7.93-7.99 (m, 2H) 8.01 (t, J=1.74 Hz, 1H) 8.17 (s, 1H) 10.34 (s, 1H)

HRMS (ESI) calcd for $C_{22}H_{17}N_6O$ [M+H]+ 368.1506. found 368.1506.

The invention claimed is:
1. A compound of formula (I),

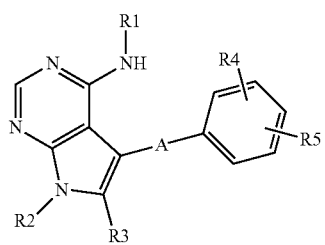

wherein
R1 is hydrogen, methyl, cyclopropyl or COR6, wherein R6 is methyl,
R2 is hydrogen or an optionally substituted group selected from straight or branched ($C_1$-$C_8$) alkyl, ($C_3$-$C_8$) cycloalkyl, aryl, heteroaryl, a 3- to 4- or a 6- to 7-membered heterocyclyl ring, where one or more carbon atoms are replaced by nitrogen, sulfur or oxygen, and a 5-membered heterocyclyl ring where one or more carbon atoms are replaced by nitrogen or sulfur;
R3 is hydrogen, ($C_1$-$C_8$) alkyl, ($C_2$-$C_8$) alkenyl, aryl, heteroaryl or heterocyclyl,
A is C≡C,
R4 is hydrogen, halogen, hydroxyl, cyano or optionally substituted ($C_1$-$C_3$) alkyl,
R5 is a group -L-R7, wherein:
R7 is hydrogen or an optionally substituted group selected from straight or branched ($C_1$-$C_8$) alkyl, ($C_3$-$C_8$) cycloalkyl and aryl, and
L is —CON(Y)—, NHCO—, —CH₂CONH—, —NHCOCH₂—, —SO₂NH—, —NHSO₂—, wherein Y is hydrogen or, taken together with the nitrogen atom to which they are bonded, Y and R7 may form an optionally substituted 3 to 6 membered heterocyclyl, optionally containing one additional heteroatom selected from nitrogen, sulfur or oxygen;
or pharmaceutically acceptable salts thereof, with the proviso that when L is —CH₂CONH—, then R2 is different from hydrogen, and wherein R2 can never be (C5) cycloalkyl.
2. A compound of formula (I), according to claim 1, wherein
R1 and R3 are hydrogen,
R2 is hydrogen or an optionally substituted group selected from straight or branched (C1-C8) alkyl, (C3-C8) cycloalkyl, a 3- to 4- or a 6- to 7-membered heterocyclyl ring, where one or more carbon atoms are replaced by nitrogen, sulfur or oxygen, and a 5-membered heterocyclyl ring where one or more carbon atoms are replaced by nitrogen or sulfur;
R4 is hydrogen, halogen, hydroxyl, cyano or methyl,
R5 is a group -L-R7, wherein:
R7 is hydrogen or an optionally substituted group selected from (C3-C8) cycloalkyl and aryl, and
L is —CON(Y)—, NHCO—, —CH2CONH—, —NHCOCH2-, —SO2NH—, —NHSO2-, wherein Y is as defined in claim 1
or pharmaceutically acceptable salts thereof, with the proviso that when L is —CH₂CONH—, then R2 is different from hydrogen, and wherein R2 can never be ($C_5$) cycloalkyl.
3. A compound according to claim 1, or a pharmaceutical acceptable salt thereof, which is selected from the group consisting of:
N-[3-(4-Amino-7H-pyrrolo[2,3-d]pyrimidin-5-ylethynyl)-phenyl]-benzenesulfonamide (cmpd 3),
N-[3-(4-Amino-7H-pyrrolo[2,3-d]pyrimidin-5-ylethynyl)-phenyl]-methanesulfonamide (cmpd 4),
N-{3-[(4-amino-7H-pyrrolo[2,3-d]pyrimidin-5-yl)ethynyl]phenyl}cyclopropanesulfonamide (cmpd 5),
3-[(4-amino-7H-pyrrolo[2,3-d]pyrimidin-5-yl)ethynyl]-N-cyclopropylbenzenesulfonamide (cmpd 6),
3-[(4-amino-7H-pyrrolo[2,3-d]pyrimidin-5-yl)ethynyl]-N-methylbenzenesulfonamide (cmpd 7),
3-[(4-amino-7H-pyrrolo[2,3-d]pyrimidin-5-yl)ethynyl]-N-phenylbenzenesulfonamide (cmpd 8),
N-{3-[(4-amino-7H-pyrrolo[2,3-d]pyrimidin-5-yl)ethynyl]phenyl}benzamide (cmpd 9),
N-{3-[(4-amino-7-methyl-7H-pyrrolo[2,3-d]pyrimidin-5-yl)ethynyl]phenyl}benzamide (cmpd 10),
N-[3-(4-Amino-7H-pyrrolo[2,3-d]pyrimidin-5-ylethynyl)-phenyl]-2-(3-trifluoromethyl-phenyl)-acetamide (cmpd 11),
2-[3-(4-Amino-7H-pyrrolo[2,3-d]pyrimidin-5-ylethynyl)-phenyl]-N-[4-(4-ethyl-piperazin-1-ylmethyl)-3-trifluoromethyl-phenyl]-acetamide (cmpd 12),
N-{3-[(4-amino-7H-pyrrolo[2,3-d]pyrimidin-5-yl)ethynyl]phenyl}cyclopropanecarboxamide (cmpd 13),
N-{3-[(4-amino-7H-pyrrolo[2,3-d]pyrimidin-5-yl)ethynyl]phenyl}acetamide (cmpd 14),
3-[(4-amino-7H-pyrrolo[2,3-d]pyrimidin-5-yl)ethynyl]-N-cyclopropylbenzamide (cmpd 15),
3-[(4-amino-7H-pyrrolo[2,3-d]pyrimidin-5-yl)ethynyl]-N-phenylbenzamide (cmpd 16),
3-[(4-amino-7H-pyrrolo[2,3-d]pyrimidin-5-yl)ethynyl]-N-methylbenzamide (cmpd 17),
3-[(4-amino-7H-pyrrolo[2,3-d]pyrimidin-5-yl)ethynyl]benzamide (cmpd 18),
3-(4-Amino-7H-pyrrolo[2,3-d]pyrimidin-5-ylethynyl)-N-[4-(4-ethyl-piperazin-1-ylmethyl)-3-trifluoromethyl-phenyl]-benzamide (cmpd 19),
3-[(4-amino-7H-pyrrolo[2,3-d]pyrimidin-5-yl)ethynyl]-N-tert-butylbenzamide (cmpd 20),
3-[(4-amino-7H-pyrrolo[2,3-d]pyrimidin-5-yl)ethynyl]-N-cyclopentylbenzamide (cmpd 21),
{3-[(4-amino-7H-pyrrolo[2,3-d]pyrimidin-5-yl)ethynyl]phenyl}(pyrrolidin-1-yl)methanone (cmpd 22),
3-[(4-amino-7H-pyrrolo[2,3-d]pyrimidin-5-yl)ethynyl]-N-(propan-2-yl)benzamide (cmpd 23),
N-{3-[(4-amino-7H-pyrrolo[2,3-d]pyrimidin-5-yl)ethynyl]phenyl}-3-(trifluoromethyl)benzamide (cmpd 24),
N-{3-[(4-amino-7H-pyrrolo[2,3-d]pyrimidin-5-yl)ethynyl]phenyl}-4-(trifluoromethyl)benzamide (cmpd 25),
N-{3-[(4-amino-7H-pyrrolo[2,3-d]pyrimidin-5-yl)ethynyl]phenyl}-3-fluorobenzamide (cmpd 26),
N-{3-[(4-amino-7H-pyrrolo[2,3-d]pyrimidin-5-yl)ethynyl]phenyl}-4-fluorobenzamide (cmpd 27),
N-{3-[(4-amino-7H-pyrrolo[2,3-d]pyrimidin-5-yl)ethynyl]phenyl}-3-chlorobenzamide (cmpd 28),
N-{3-[(4-amino-7H-pyrrolo[2,3-d]pyrimidin-5-yl)ethynyl]phenyl}-4-chlorobenzamide (cmpd 29),
N-{3-[(4-amino-7H-pyrrolo[2,3-d]pyrimidin-5-yl)ethynyl]phenyl}-3-methylbenzamide (cmpd 30), N-{3-[(4-amino-7H-pyrrolo[2,3-d]pyrimidin-5-yl)ethynyl]phenyl}-4-methylbenzamide (cmpd 31),
N-{3-[(4-amino-7H-pyrrolo[2,3-d]pyrimidin-5-yl)ethynyl]phenyl}-3-methoxybenzamide (cmpd 32),
N-{3-[(4-amino-7H-pyrrolo[2,3-d]pyrimidin-5-yl)ethynyl]phenyl}-4-methoxybenzamide (cmpd 33),
N-{3-[(4-amino-7H-pyrrolo[2,3-d]pyrimidin-5-yl)ethynyl]phenyl}-3-(trifluoromethoxy)benzamide (cmpd 34),
N-{3-[(4-amino-7H-pyrrolo[2,3-d]pyrimidin-5-yl)ethynyl]phenyl}-1,3-benzodioxole-5-carboxamide (cmpd 35),
3-{[4-amino-7-(2,2,2-trifluoroethyl)-7H-pyrrolo[2,3-d]pyrimidin-5-yl]ethynyl}-N-cyclopropylbenzamide (cmpd 36),
3-{[4-amino-7-(2-hydroxyethyl)-7H-pyrrolo[2,3-d]pyrimidin-5-yl]ethynyl}-N-cyclopropylbenzamide (cmpd 37),
3-{[4-amino-7-(2-aminoethyl)-7H-pyrrolo[2,3-d]pyrimidin-5-yl]ethynyl}-N-cyclopropylbenzamide (cmpd 38),
3-({4-amino-7-[(1-methylpiperidin-4-yl)methyl]-7H-pyrrolo[2,3-d]pyrimidin-5-yl}ethynyl)-N-cyclopropylbenzamide (cmpd 39),
3-{[4-amino-7-(propan-2-yl)-7H-pyrrolo[2,3-d]pyrimidin-5-yl]ethynyl}-N-cyclopropylbenzamide (cmpd 40),
5-[(4-amino-7H-pyrrolo[2,3-d]pyrimidin-5-yl)ethynyl]-N-cyclopropyl-2-methylbenzamide (cmpd 41),
3-[(4-amino-7H-pyrrolo[2,3-d]pyrimidin-5-yl)ethynyl]-N-cyclopropyl-4-methylbenzamide (cmpd 42),
3-[(4-amino-7H-pyrrolo[2,3-d]pyrimidin-5-yl)ethynyl]-N-cyclopropyl-4-fluorobenzamide (cmpd 43),
5-[(4-amino-7H-pyrrolo[2,3-d]pyrimidin-5-yl)ethynyl]-N-cyclopropyl-2-fluorobenzamide (cmpd 44),
3-[(4-amino-7H-pyrrolo[2,3-d]pyrimidin-5-yl)ethynyl]-N-cyclopropyl-5-fluorobenzamide (cmpd 45),
3-{[4-amino-7-(1-methylpiperidin-4-yl)-7H-pyrrolo[2,3-d]pyrimidin-5-yl]ethynyl}-N-cyclopropylbenzamide (cmpd 46),
3-{[4-amino-7-(tetrahydro-2H-pyran-4-yl)-7H-pyrrolo[2,3-d]pyrimidin-5-yl]ethynyl}-N-cyclopropylbenzamide (cmpd 47),
3-{[4-amino-7-(2-methoxyethyl)-7H-pyrrolo[2,3-d]pyrimidin-5-yl]ethynyl}-N-cyclopropylbenzamide (cmpd 48),
3-({7-[2-(acetylamino)ethyl]-4-amino-7H-pyrrolo[2,3-d]pyrimidin-5-yl}ethynyl)-N-cyclopropylbenzamide (cmpd 49),
3-{[4-amino-7-(2-amino-2-oxoethyl)-7H-pyrrolo[2,3-d]pyrimidin-5-yl]ethynyl}-N-cyclopropylbenzamide (cmpd 50),
3-{[4-amino-7-(propan-2-yl)-7H-pyrrolo[2,3-d]pyrimidin-5-yl]ethynyl}-N-cyclopropyl-4-methylbenzamide (cmpd 51),
3-{[4-amino-7-(2,2,2-trifluoroethyl)-7H-pyrrolo[2,3-d]pyrimidin-5-yl]ethynyl}-N-cyclopropyl-4-methylbenzamide (cmpd 52),
3-{[4-amino-7-(propan-2-yl)-7H-pyrrolo[2,3-d]pyrimidin-5-yl]ethynyl}-N-cyclopropyl-4-fluorobenzamide (cmpd 53),
3-{[4-amino-7-(2,2,2-trifluoroethyl)-7H-pyrrolo[2,3-d]pyrimidin-5-yl]ethynyl}-N-cyclopropyl-4-fluorobenzamide (cmpd 54),
3-{[4-amino-7-(2-hydroxyethyl)-7H-pyrrolo[2,3-d]pyrimidin-5-yl]ethynyl}-N-cyclopropyl-4-fluorobenzamide (cmpd 55),
3-{[4-amino-7-(2-aminoethyl)-7H-pyrrolo[2,3-d]pyrimidin-5-yl]ethynyl}-N-cyclopropyl-4-fluorobenzamide (cmpd 56),
3-({4-amino-7-[(1-methylpiperidin-4-yl)methyl]-7H-pyrrolo[2,3-d]pyrimidin-5-yl}ethynyl)-N-cyclopropyl-4-fluorobenzamide (cmpd 57),
3-{[4-amino-7-(propan-2-yl)-7H-pyrrolo[2,3-d]pyrimidin-5-yl]ethynyl}-N-cyclopropyl-5-fluorobenzamide (cmpd 58),
3-{[4-amino-7-(2,2,2-trifluoroethyl)-7H-pyrrolo[2,3-d]pyrimidin-5-yl]ethynyl}-N-cyclopropyl-5-fluorobenzamide (cmpd 59),
3-{[4-amino-7-(2-hydroxyethyl)-7H-pyrrolo[2,3-d]pyrimidin-5-yl]ethynyl}-N-cyclopropyl-5-fluorobenzamide (cmpd 60),
3-{[4-amino-7-(2-aminoethyl)-7H-pyrrolo[2,3-d]pyrimidin-5-yl]ethynyl}-N-cyclopropyl-5-fluorobenzamide (cmpd 61),
3-({4-amino-7-[(1-methylpiperidin-4-yl)methyl]-7H-pyrrolo[2,3-d]pyrimidin-5-yl}ethynyl)-N-cyclopropyl-5-fluorobenzamide (cmpd 62),
N-cyclopropyl-3-{[4-(methylamino)-7-(propan-2-yl)-7H-pyrrolo[2,3-d]pyrimidin-5-yl]ethynyl}benzamide (cmpd 63),
3-{[4-(acetylamino)-7-(propan-2-yl)-7H-pyrrolo[2,3-d]pyrimidin-5-yl]ethynyl}-N-cyclopropylbenzamide (cmpd 64),
2-(3-{[4-amino-7-(propan-2-yl)-7H-pyrrolo[2,3-d]pyrimidin-5-yl]ethynyl}phenyl)-N-phenylacetamide (cmpd 65),
3-[(4-amino-7-propyl-7H-pyrrolo[2,3-d]pyrimidin-5-yl)ethynyl]-N-cyclopropylbenzamide (cmpd 66),
3-({4-amino-7-[2-(formylamino)ethyl]-7H-pyrrolo[2,3-d]pyrimidin-5-yl}ethynyl)-N-cyclopropylbenzamide (cmpd 67),
3-{[4-amino-7-(pyridin-3-yl)-7H-pyrrolo[2,3-d]pyrimidin-5-yl]ethynyl}-N-cyclopropylbenzamide (cmpd 68),
3-{[4-amino-7-(pyridin-4-yl)-7H-pyrrolo[2,3-d]pyrimidin-5-yl]ethynyl}-N-cyclopropylbenzamide (cmpd 69),
3-{[4-amino-7-(3-methoxyphenyl)-7H-pyrrolo[2,3-d]pyrimidin-5-yl]ethynyl}-N-cyclopropylbenzamide (cmpd 70),
3-{[4-amino-7-(1-methyl-1H-pyrazol-4-yl)-7H-pyrrolo[2,3-d]pyrimidin-5-yl]ethynyl}-N-cyclopropylbenzamide (cmpd 71),
3-{[4-amino-7-(furan-2-yl)-7H-pyrrolo[2,3-d]pyrimidin-5-yl]ethynyl}-N-cyclopropylbenzamide (cmpd 72),
3-{[4-amino-7-(1-cyclopropylpiperidin-4-yl)-7H-pyrrolo[2,3-d]pyrimidin-5-yl]ethynyl}-N-cyclopropylbenzamide (cmpd 73),
3-({4-amino-7-[1-(propan-2-yl)piperidin-4-yl]-7H-pyrrolo[2,3-d]pyrimidin-5-yl}ethynyl)-N-cyclopropylbenzamide (cmpd 74),
3-({4-amino-7-[1-(2-hydroxyethyl)piperidin-4-yl]-7H-pyrrolo[2,3-d]pyrimidin-5-yl}ethynyl)-N-cyclopropylbenzamide (cmpd 75),
3-{[7-(1-acetylpiperidin-4-yl)-4-amino-7H-pyrrolo[2,3-d]pyrimidin-5-yl]ethynyl}-N-cyclopropylbenzamide (cmpd 76),
3-({4-amino-7-[1-(methylsulfonyl)piperidin-4-yl]-7H-pyrrolo[2,3-d]pyrimidin-5-yl}ethynyl)-N-cyclopropylbenzamide (cmpd 77),
ethyl 4-(4-amino-5-{[3-(cyclopropylcarbamoyl)phenyl]ethynyl}-7H-pyrrolo[2,3-d]pyrimidin-7-yl)piperidine-1-carboxylate (cmpd 78), 2-(3-{[4-amino-7-(propan-2-yl)-7H-pyrrolo[2,3-d]py-rimidin-5-yl]ethynyl}phenyl)-N-[3-(trifluoromethyl) phenyl]acetamide (cmpd 79),
2-(3-{[4-amino-7-(propan-2-yl)-7H-pyrrolo[2,3-d]py-rimidin-5-yl]ethynyl}phenyl)-N-[4-(trifluoromethyl) phenyl]acetamide (cmpd 80),
3-{[4-amino-7-(propan-2-yl)-7H-pyrrolo[2,3-d]pyrimi-din-5-yl]ethynyl}-N-{4-[(4-ethylpiperazin-1-yl) methyl]-3-(trifluoromethyl)phenyl}-4-methylbenz-amide (cmpd 81),
3-{[4-amino-7-(propan-2-yl)-7H-pyrrolo[2,3-d]pyrimi-din-5-yl]ethynyl}-N-{4-[(4-ethylpiperazin-1-yl) methyl]-3-(trifluoromethyl)phenyl}benzamide (cmpd 82),
5-{[4-amino-7-(propan-2-yl)-7H-pyrrolo[2,3-d]pyrimi-din-5-yl]ethynyl}-N-cyclopropyl-2-fluorobenzamide (cmpd 83),
3-{[4-amino-7-(2-methylpropyl)-7H-pyrrolo[2,3-d]py-rimidin-5-yl]ethynyl}-N-cyclopropylbenzamide (cmpd 84),
3-{[4-amino-7-(butan-2-yl)-7H-pyrrolo[2,3-d]pyrimidin-5-yl]ethynyl}-N-cyclopropylbenzamide (cmpd 85),
3-{[4-amino-7-(2-fluoroethyl)-7H-pyrrolo[2,3-d]pyrimi-din-5-yl]ethynyl}-N-cyclopropylbenzamide (cmpd 86),
3-[(4-amino-7-ethyl-6-methyl-7H-pyrrolo[2,3-d]pyrimi-din-5-yl)ethynyl]-N-cyclopropylbenzamide (cmpd 87),
3-({4-amino-7-[(3-methyloxetan-3-yl)methyl]-7H-pyr-rolo[2,3-d]pyrimidin-5-yl}ethynyl)-N-cyclopropylben-zamide (cmpd 88),
3-{[4-amino-7-(1-methylpyrrolidin-3-yl)-7H-pyrrolo[2, 3-d]pyrimidin-5-yl]ethynyl}-N-cyclopropylbenzamide (cmpd 89),
3-{[4-amino-7-(pyridin-4-ylmethyl)-7H-pyrrolo[2,3-d] pyrimidin-5-yl]ethynyl}-N-cyclopropylbenzamide (cmpd 90),
3-{[4-amino-7-(pyridin-3-ylmethyl)-7H-pyrrolo[2,3-d] pyrimidin-5-yl]ethynyl}-N-cyclopropylbenzamide (cmpd 91),
3-{[4-amino-7-(3,3,3-trifluoropropyl)-7H-pyrrolo[2,3-d] pyrimidin-5-yl]ethynyl}-N-cyclopropylbenzamide (cmpd 92),
3-[(4-amino-7-methyl-7H-pyrrolo[2,3-d]pyrimidin-5-yl) ethynyl]-N-cyclopropylbenzamide (cmpd 93),
3-[(4-amino-7-ethyl-7H-pyrrolo[2,3-d]pyrimidin-5-yl) ethynyl]-N-cyclopropylbenzamide (cmpd 94),
3-{[4-amino-7-(cyclobutylmethyl)-7H-pyrrolo[2,3-d]py-rimidin-5-yl]ethynyl}-N-cyclopropylbenzamide (cmpd 95),
3-{[4-amino-7-(cyclohexylmethyl)-7H-pyrrolo[2,3-d]py-rimidin-5-yl]ethynyl}-N-cyclopropylbenzamide (cmpd 96),
3-{[4-amino-7-(2,2,2-trifluoroethyl)-7H-pyrrolo[2,3-d] pyrimidin-5-yl]ethynyl}-N-(cyclopropylmethyl)benz-amide (cmpd 97),
4-{[4-amino-7-(2,2,2-trifluoroethyl)-7H-pyrrolo[2,3-d] pyrimidin-5-yl]ethynyl}-N-cyclopropylbenzamide (cmpd 98),
3-{[4-amino-7-(cyclopropylmethyl)-7H-pyrrolo[2,3-d] pyrimidin-5-yl]ethynyl}-N-cyclopropylbenzamide (cmpd 99),
3-{[4-amino-7-(1-methoxypropan-2-yl)-7H-pyrrolo[2,3-d]pyrimidin-5-yl]ethynyl}-N-cyclopropylbenzamide (cmpd 100),
3-[(4-amino-7-cyclohexyl-7H-pyrrolo[2,3-d]pyrimidin-5-yl)ethynyl]-N-cyclopropylbenzamide (cmpd 101),
3-[(4-amino-7-cyclobutyl-7H-pyrrolo[2,3-d]pyrimidin-5-yl)ethynyl]-N-cyclopropylbenzamide (cmpd 102),
3-[(4-amino-7-cyclopropyl-7H-pyrrolo[2,3-d]pyrimidin-5-yl)ethynyl]-N-cyclopropylbenzamide (cmpd 103),
3-{[4-amino-7-(cyanomethyl)-7H-pyrrolo[2,3-d]pyrimi-din-5-yl]ethynyl}-N-cyclopropylbenzamide (cmpd 104),
3-({4-amino-7-[2-(dimethylamino)ethyl]-7H-pyrrolo[2, 3-d]pyrimidin-5-yl}ethynyl)-N-cyclopropylbenzamide (cmpd 105),
3-{[4-amino-7-(1,1,1-trifluoropropan-2-yl)-7H-pyrrolo [2,3-d]pyrimidin-5-yl]ethynyl}-N-cyclopropylbenz-amide (cmpd 106),
3-{[4-amino-7-(4,4,4-trifluorobutan-2-yl)-7H-pyrrolo[2, 3-d]pyrimidin-5-yl]ethynyl}-N-cyclopropylbenzamide (cmpd 107),
3-{[4-amino-7-(propan-2-yl)-7H-pyrrolo[2,3-d]pyrimi-din-5-yl]ethynyl}-4-cyano-N-cyclopropylbenzamide (cmpd 108),
3-{[4-amino-7-(1-methylpiperidin-3-yl)-7H-pyrrolo[2,3-d]pyrimidin-5-yl]ethynyl}-N-cyclopropylbenzamide (cmpd 109),
3-{[4-amino-7-(propan-2-yl)-7H-pyrrolo[2,3-d]pyrimi-din-5-yl]ethynyl}benzamide (cmpd 110),
3-{[4-amino-7-(propan-2-yl)-7H-pyrrolo[2,3-d]pyrimi-din-5-yl]ethynyl}-N-cyclopropylbenzenesulfonamide (cmpd 111),
and
2-(3-{[4-amino-7-(2,2,2-trifluoroethyl)-7H-pyrrolo[2,3-d]pyrimidin-5-yl]ethynyl}phenyl)-N-cyclopropylacet-amide (cmpd 113).

4. A process for preparing a compound of formula (I), as defined in claim 1, or the pharmaceutically acceptable salts thereof, which comprises the following steps:

Step a) reaction of a derivative of formula (II)

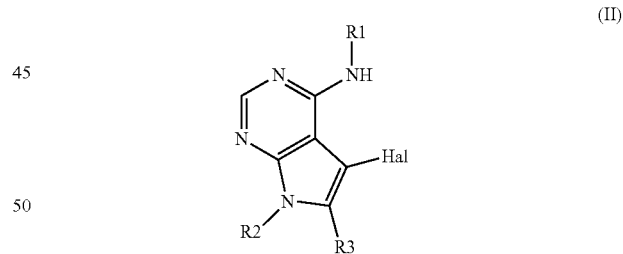

wherein R1, R2 and R3 are as defined in claim 1 and Hal is iodine or bromine, with a compound of formula (III)

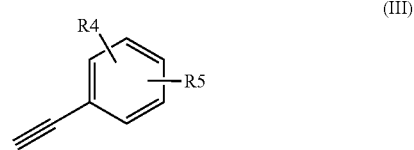

wherein R4 and R5 are as defined in claim 1, to obtain a compound of formula (IA)

(IA)

[structure: pyrrolopyrimidine with R1-NH, R2, R3, and alkyne-phenyl with R4, R5]

wherein R1, R2, R3, R4 and R5 are as defined above;
alternatively:
Step a') reaction of a compound of formula (IV)

(IV)

[structure: 4-chloro-pyrrolopyrimidine with R2, R3, Hal]

wherein R2, R3 and Hal are as defined above, with a compound of formula (III), as defined above, to obtain a compound of formula (V)

(V)

[structure: 4-chloro-pyrrolopyrimidine with R2, R3 and alkyne-phenyl with R4, R5]

wherein R2, R3, R4 and R5 are as defined above; and
Step b) reaction of the resultant compound of formula (V) with a compound of formula (VI), $$H_2N-R1 \quad (VI)$$

wherein R1 is hydrogen methyl or cyclopropyl, to obtain a compound of formula (IA), wherein R1 is methyl or cyclopropyl and R2, R3, R4 and R5 are as defined above; or
Step b') reaction of the resultant compound of formula (V) with a compound of formula (VII)

$$H_2N-COR_6 \quad (VII)$$

wherein R6 is as defined in claim 1, to obtain a compound of formula (IA) wherein R1, R2, R3, R4 and R5 are as defined above;
optionally converting a compound of formula (IA) into another compound of formula (IA), and, if desired, converting a compound of formula (IA) into a pharmaceutically acceptable salt thereof or converting a salt into the free compound (IA).

5. A pharmaceutical composition comprising a compound of formula (I) or a pharmaceutically acceptable salt thereof, as defined in claim 1, and at least one pharmaceutically acceptable excipient, carrier and/or diluent.

6. A pharmaceutical composition, according to claim 5, further comprising one or more chemotherapeutic agents.

7. A product comprising a compound of formula (I) or a pharmaceutically acceptable salt thereof, as defined in claim 1, and one or more chemotherapeutic agents, as a combined preparation for simultaneous, separate or sequential use in anticancer therapy.

* * * * *